(12) United States Patent
Chen et al.

(10) Patent No.: US 10,968,193 B2
(45) Date of Patent: Apr. 6, 2021

(54) ANTIDIABETIC BICYCLIC COMPOUNDS

(71) Applicant: Merck Sharp & Dohme Corp., Rahway, NJ (US)

(72) Inventors: Helen Chen, Marlboro, NJ (US); Steven L. Colletti, Princeton, NJ (US); Duane DeMong, Hanover, MA (US); Yan Guo, Westfield, NJ (US); Michael Miller, Scotch Plains, NJ (US); Anilkumar Nair, Edison, NJ (US); Christopher W. Plummer, Hoboken, NJ (US); Dong Xiao, Warren, NJ (US); De-Yi Yang, Morris Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 15 days.

(21) Appl. No.: 15/328,735

(22) PCT Filed: Aug. 6, 2015

(86) PCT No.: PCT/US2015/043903
§ 371 (c)(1),
(2) Date: Jan. 24, 2017

(87) PCT Pub. No.: WO2016/022742
PCT Pub. Date: Feb. 11, 2016

(65) Prior Publication Data
US 2017/0217918 A1    Aug. 3, 2017

Related U.S. Application Data

(60) Provisional application No. 62/034,820, filed on Aug. 8, 2014.

(51) Int. Cl.
| | |
|---|---|
| *C07D 491/06* | (2006.01) |
| *C07D 311/60* | (2006.01) |
| *C07D 405/14* | (2006.01) |
| *C07D 491/08* | (2006.01) |
| *C07D 405/10* | (2006.01) |
| *C07D 487/04* | (2006.01) |
| *C07D 487/08* | (2006.01) |
| *C07D 491/048* | (2006.01) |
| *C07D 491/107* | (2006.01) |
| *A61K 31/4985* | (2006.01) |
| *C07D 451/02* | (2006.01) |
| *A61K 31/397* | (2006.01) |
| *A61K 45/06* | (2006.01) |
| *A61K 31/366* | (2006.01) |
| *C07D 413/14* | (2006.01) |
| *C07D 413/12* | (2006.01) |
| *C07D 471/08* | (2006.01) |

(52) U.S. Cl.
CPC ......... *C07D 311/60* (2013.01); *A61K 31/366* (2013.01); *A61K 31/397* (2013.01); *A61K 31/4985* (2013.01); *A61K 45/06* (2013.01); *C07D 405/10* (2013.01); *C07D 405/14* (2013.01); *C07D 413/12* (2013.01); *C07D 413/14* (2013.01); *C07D 451/02* (2013.01); *C07D 471/08* (2013.01); *C07D 487/04* (2013.01); *C07D 487/08* (2013.01); *C07D 491/048* (2013.01); *C07D 491/08* (2013.01); *C07D 491/107* (2013.01)

(58) Field of Classification Search
CPC .................................................. C07D 491/06
See application file for complete search history.

(56) References Cited

U.S. PATENT DOCUMENTS

| | | | |
|---|---|---|---|
| 3,812,150 A | 5/1974 | Wasson et al. | |
| 8,030,354 B2 | 10/2011 | Brown et al. | |
| 8,450,522 B2 | 5/2013 | Brown et al. | |

FOREIGN PATENT DOCUMENTS

| | | |
|---|---|---|
| CN | 103012343 A | 4/2013 |
| CN | 103030646 A | 4/2013 |

(Continued)

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.
Brown, S. P. et al., Discovery of AM-1638: A Potent and Orally Bioavailable GPR40/FFA1 Full Agonist, American Chemical Society, 2012, p. 726-730, vol. 3.
Du, Xiaohui, et al., Improving the Pharmacokinetics of GPR40/FFA1 Full Agonists, ACS Medicinal Chemistry Letters, 2014, p. 384-389, vol. 5, No. 4.

(Continued)

*Primary Examiner* — John S Kenyon
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

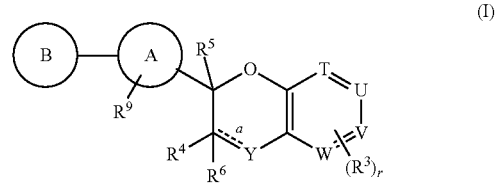

(I)

11 Claims, No Drawings

(56) References Cited

FOREIGN PATENT DOCUMENTS

| | | |
|---|---|---|
| EP | 0283036 A1 | 9/1988 |
| GB | 2498976 A | 7/2013 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO-2009079011 A1 * | 6/2009 ........... C07D 471/04 |
| WO | WO2009111056 A1 | 9/2009 |
| WO | WO2010004347 A1 | 1/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2012011125 A1 | 1/2012 |
| WO | WO2012072691 A1 | 6/2012 |
| WO | WO2013104257 A1 | 7/2013 |
| WO | WO2013122028 A1 | 8/2013 |
| WO | WO2013122029 A1 | 8/2013 |
| WO | WO2013128378 A1 | 9/2013 |
| WO | WO2013131901 A1 | 9/2013 |
| WO | WO 2013131901 A1 * | 9/2013 ........... A61K 31/436 |
| WO | WO2013170147 A1 | 11/2013 |
| WO | WO2013178575 A1 | 12/2013 |
| WO | WO2014073904 A1 | 5/2014 |
| WO | WO2014078608 A1 | 5/2014 |
| WO | WO2014078609 A1 | 5/2014 |
| WO | WO2014078610 A1 | 5/2014 |
| WO | WO2014078611 A1 | 5/2014 |
| WO | WO2014086632 A1 | 6/2014 |
| WO | WO2014130608 A1 | 8/2014 |
| WO | WO-2014130608 A1 * | 8/2014 ........... A61K 31/352 |
| WO | WO2016019587 A1 | 2/2016 |
| WO | WO2016019863 A1 | 2/2016 |
| WO | WO2016022446 A1 | 2/2016 |
| WO | WO2016022448 A1 | 2/2016 |
| WO | WO2016022742 A1 | 2/2016 |

OTHER PUBLICATIONS

Executive Summary, Detection, Evaluation, and Treatment of High Blood Cholesterol in Adults (Adult Treatment Pane III), National Institutes of Health, 2001, pp. 1-40, NIH Publication No. 01-3670.

Ford, Earl, S. et al, Prevalence of the Metabolic Syndrome Amonh US Adults, JAMA, 2002, p. 356-359, vol. 287, No. 3.

Houze, J. B. et al., 265-AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.

Houze, J. B. et al., AMG 837: A potent, orally bioavailable GPR40 agonist, Bioorganic & Medicinal Chemistry Letters, 2012, p. 1267-1270, vol. 22.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS ONE, 2011, p. 1-10, vol. 6, No. 11.

Lou, J. et al., A Potent Class of GPR40 Full Agonist Engages the EnteroInsular Axis to Promote Glucose Control in Rodents, Plos ONE, 2012, p. 6-12, vol. 7, Issue 10.

Lu, H. et al., Discovery of novel orally bioavailable GPR40 agonists, Bioorganic & Medicinal Chemistry Letters, 2013, p. 2920-2924, vol. 23.

Negoro, Nobuyuki, et al., Discovery of TAK-875: A Potent, Selective, and Orally Bioavailable GPR40 Agonist, ACS Medicinal Chemistry Letters, 2010, p. 290-294, vol. 1, No. 6.

Takano, Rieko, et al., Discovery of 3-aryl-3-ethoxypropanoic acids as orally acitve GPR40 Agonists, Bioorganic & Medicinal Chemistry Letters, 2014, p. 2949-2953, vol. 24.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Wang, Y. et al., Discoveryand Optimization of Potent GPR40 Full Agonists Containing Tricyclic Spirocycles, ACS Medicinal Chemistry Letters, 2013, p. 551-555, vol. 4.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

* cited by examiner

ANTIDIABETIC BICYCLIC COMPOUNDS

CROSS-REFERENCE TO RELATED APPLICATIONS

This application is a U.S. National Phase application under 35 U.S.C. § 371 of PCT Application No. PCT/US15/043903, filed on Aug. 6, 2015, which claims priority from and the benefit of U.S. Patent Application Ser. No. 62/034,820, filed Aug. 8, 2014.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body, however patients have a resistance to the effects of insulin in stimulating glucose and lipid metabolism in the insulin-sensitive muscle, liver and adipose tissues. Type 2 diabetes patients often have normal levels of insulin, and may have hyperinsulinemia (elevated plasma insulin levels), as they compensate for the reduced effectiveness of insulin by secreting increased amounts of insulin. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia is associated with increased and premature morbidity and mortality. Abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have Metabolic Syndrome (as defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670). Patients with Metabolic Syndrome have an increased risk of developing the macrovascular and microvascular complications that occur with Type 2 diabetes, such as atherosclerosis and coronary heart disease.

There are several available treatments for Type 2 diabetes. Physical exercise and a reduction in dietary intake of calories are the recommended first-line treatment of Type 2 diabetes and of pre-diabetic conditions associated with insulin resistance, however compliance is generally poor. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The two best known biguanides, phenformin and metformin, cause some correction of hyperglycemia, but can also induce lactic acidosis and nausea/diarrhea. PPAR gamma agonists, such as rosiglitazone and pioglitazone, are modestly effective in reducing plasma glucose and Hemoglobin A1C. However, the currently marketed glitazones do not greatly improve lipid metabolism and may negatively effect on the lipid profile. The administration of insulin secretagogues, such as the sulfonylureas (e.g. tolbutamide, glipizide, and glimepiride) can result in hypoglycemia; their administration must therefore be carefully controlled.

There has been a renewed focus on pancreatic islet-based insulin secretion that is controlled by glucose-dependent insulin secretion. This approach has the potential for stabilization and restoration of β-cell function. Several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be advantageous, because long term diabetes therapy often leads to the gradual diminution of islet activity; after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/011125, WO 2012/072691, WO2013/104257, WO 2013/122028, WO 2013/122029, WO 2013/128378, WO 2013/178575, WO 2014/073904, WO 2014/078608, WO 2014/078609, WO 2014/078610, WO 2014/078611, U.S. Pat. Nos. 8,030,354, 8,450, 522, CN 103030646, CN 103012343, and GB 2498976.

GPR40 agonists are also disclosed in Negoro et al., ACS Medicinal Chemistry Letters (2010), 1(6), 290-294; Walsh et al., Bioorganic & Medicinal Chemistry Letters (2011), 21(11), 3390-3394; Zhou et al., Bioorganic & Medicinal Chemistry Letters (2010), 20(3), 1298-1301; Houze et al., Bioorganic & Medicinal Chemistry Letters (2012), 22(2), 1267-1270; Lu et al., Bioorganic & Medicinal Chemistry Letters (2013), 23(10), 2920-2924; Takano et al., Bioorganic & Medicinal Chemistry Letters (2014), 24(13), 2949-2953; Tan et al., Diabetes (2008), 57(8), 2211-2219; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; Houze et al., Abstracts of Papers, 243rd ACS National Meeting & Exposition, San Diego, Calif., USA Mar. 25-29, 2012, MEDI-265; Wang et al., ACS Medicinal Chemistry Letters (2013), 4(6), 551-555; and Du et al., ACS Medicinal Chemistry Letters (2014), 5(4), 384-389.

SUMMARY OF THE INVENTION

The present invention relates to novel substituted compounds of structural formula I:

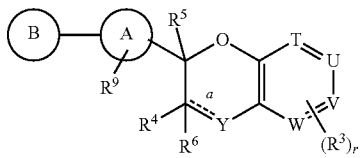

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

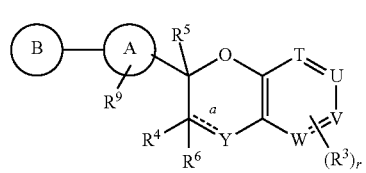

or a pharmaceutically acceptable salt thereof; wherein "a" is a single bond or a double bond, provided that if "a" is a double bond, then $R^6$ is absent and Y is selected from the group consisting of: C—$R^g$, —C—O$C_{1-6}$alkyl, CF and N, and further provided that if "a" is a single bond, then $R^6$ is present and Y is selected from the group consisting of:
 (1) oxygen,
 (2) sulfur,
 (3) —$CR^gR^g$,
 (4) C=O,
 (5) —C($R^g$)O$C_{1-6}$alkyl,
 (6) —$CF_2$, and
 (7) —$NR^e$;
T is selected from the group consisting of:
 (1) CH,
 (2) N, and
 (3) N-oxide;
U is selected from the group consisting of:
 (1) $CR^1$,
 (2) N, and
 (3) N-oxide;
V is selected from the group consisting of:
 (1) $CR^2$,
 (2) N, and
 (3) N-oxide;
W is selected from the group consisting of:
 (1) CH,
 (2) N, and
 (3) N-oxide, provided that no more than two of T, U, V and W are selected from N and N-oxide, further provided that if both T and W are N or N-oxide, then $R^3$ is absent, and further provided that both U and V are not N or N-oxide;

A is selected from the group consisting of:
(1) aryl,
(2) heteroaryl,
(3) $C_{3-6}$cycloalkyl, and
(4) $C_{2-5}$ cycloheteroalkyl,
wherein A is unsubstituted or substituted with one to five substituents selected from $R^a$;

B is selected from the group consisting of:
(1) hydrogen,
(2) aryl,
(3) aryl-O—,
(4) aryl-$C_{1-10}$ alkyl-,
(5) aryl-$C_{1-10}$ alkyl-O—,
(6) $C_{3-6}$cycloalkyl,
(7) $C_{3-6}$cycloalkyl-$C_{1-10}$alkyl-,
(8) $C_{3-6}$cycloalkyl-$C_{1-10}$alkyl-O—,
(9) $C_{3-6}$cycloalkenyl,
(10) $C_{3-6}$cycloalkenyl-$C_{1-10}$alkyl-,
(11) $C_{3-6}$cycloalkenyl-$C_{1-10}$alkyl-O—,
(12) $C_{2-5}$cycloheteroalkyl,
(13) $C_{3-6}$cycloheteroalkyl-$C_{1-10}$alkyl-,
(14) $C_{3-6}$cycloheteroalkyl-$C_{1-10}$alkyl-O—,
(15) heteroaryl,
(16) heteroaryl-O—,
(17) heteroaryl-$C_{1-10}$ alkyl-, and
(18) heteroaryl-$C_{1-10}$ alkyl-O—,
wherein B is unsubstituted or substituted with one to five substituents selected from $R^b$;

$R^1$ and $R^2$ are each independently selected from:
(1) a bond,
(2) hydrogen,
(3) halogen,
(4) —$OR^k$,
(5) —CN,
(6) —$C_{1-6}$alkyl,
(7) —$C_{3-6}$cycloalkyl,
(8) $C_{3-6}$cycloalkyl-$C_{1-3}$alkyl-,
(9) —$C_{2-6}$cycloheteroalkyl, and
(10) $C_{2-6}$cycloheteroalkyl-$C_{1-3}$alkyl-,
wherein each alkyl, cycloalkyl and cycloheteroalkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$;

$R^3$ is absent or when present is selected from the group consisting of:
(1) hydrogen,
(2) halogen,
(3) —$OR^e$,
(4) —CN,
(5) —$C_{1-6}$alkyl,
(6) —$C_{3-6}$cycloalkyl, and
(7) $C_{3-6}$cycloalkyl-$C_{1-3}$alkyl-,
wherein each alkyl and cycloalkyl is unsubstituted or substituted with one to three substituents selected from $R^i$;

$R^4$ is selected from the group consisting of:
(1) hydrogen,
(2) halogen,
(3) $OR^e$,
(4) $C_{1-6}$alkyl,
(5) $C_{1-6}$alkyl-O—,
(6) $C_{3-6}$cycloalkyl,
(7) $C_{3-6}$cycloalkyl-O—,
(8) $C_{3-6}$cycloalkyl-$C_{1-10}$alkyl-,
(9) $C_{3-6}$cycloalkyl-$C_{1-10}$alkyl-O—,
(10) $C_{2-5}$cycloheteroalkyl,
(11) $C_{2-5}$cycloheteroalkyl-O—,
(12) $C_{2-5}$cycloheteroalkyl-$C_{1-10}$alkyl-,
(13) $C_{2-5}$cycloheteroalkyl-$C_{1-10}$alkyl-O—,
(14) aryl,
(15) aryl-O—,
(16) aryl-$C_{1-10}$alkyl-,
(17) heteroaryl,
(18) heteroaryl-O—, and
(19) heteroaryl-$C_{1-10}$alkyl-,
wherein each alkyl, cycloalkyl, cycloheteroalkyl, aryl and heteroaryl is unsubstituted or substituted with one to three substituents selected from $R^j$,
provided that when $R^4$ is:
(1) $OR^e$,
(2) $C_{1-6}$alkyl-O—,
(3) $C_{3-6}$cycloalkyl-O—,
(4) $C_{3-6}$cycloalkyl-$C_{1-10}$alkyl-O—,
(5) $C_{2-5}$ cycloheteroalkyl-O—,
(6) $C_{2-5}$cycloheteroalkyl-$C_{1-10}$alkyl-O—,
(7) aryl-O—, or
(8) heteroaryl-O—,
then Y is selected from the group consisting of:
(1) —$CR^gR^g$,
(2) C=O,
(3) —$C(R^g)OC_{1-6}$alkyl, and
(4) —$CF_2$;

$R^5$ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;

$R^6$ is absent or when present is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;

$R^7$ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$alkyl-$SO_2NHCOR^m$,
(5) —$C_{1-6}$alkyl-tetrazolyl, and
(6) a cycloheteroalkyl selected from the group consisting of:

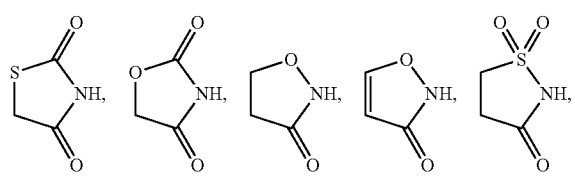

-continued

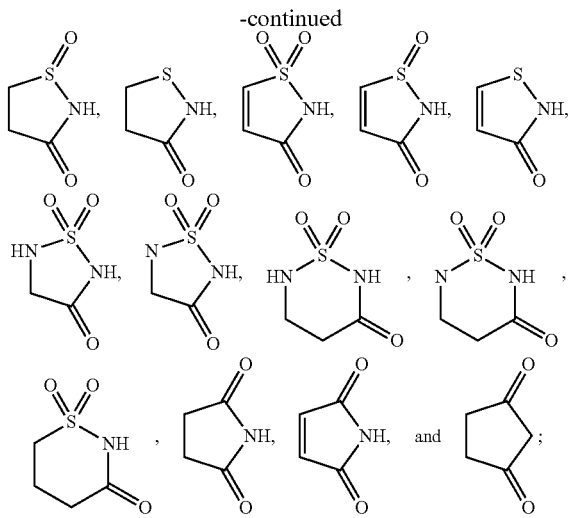

R⁸ is selected from the group consisting of:
(1) hydrogen,
(2) —C$_{1-6}$alkyl,
(3) —C$_{3-6}$cycloalkyl, and
(4) aryl-C$_{1-6}$alkyl,
wherein each alkyl, cycloalkyl and aryl is unsubstituted or substituted with one to three substituents selected from R$^j$;
R⁹ is selected from the group consisting of:
(1) —C$_{1-6}$alkyl-NR$^c$S(O)$_n$R$^e$,
(2) —C$_{1-6}$alkyl-S(O)$_n$R$^e$,
(3) —C$_{1-6}$alkyl-S(O)$_n$NR$^c$R$^d$,
(4) —C$_{1-6}$alkyl-NR$^c$R$^d$,
(5) —C$_{1-6}$alkyl-C(O)NR$^c$R$^d$,
(6) —C$_{1-6}$alkyl-NR$^c$C(O)R$^e$,
(7) —C$_{1-6}$alkyl-NR$^c$C(O)OR$^e$,
(8) —C$_{1-6}$alkyl-NR$^c$C(O)NR$^c$R$^d$,
(9) —C$_{1-6}$alkyl-aryl,
(10) —C$_{1-6}$alkyl-heteroaryl,
(11) —C$_{1-6}$alkyl-C$_{3-10}$cycloalkyl,
(12) —C$_{1-6}$alkyl-C$_{3-10}$cycloalkenyl, and
(13) —C$_{1-6}$alkyl-C$_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —C$_{1-6}$alkyl, halogen, OH, —O—C$_{1-6}$alkyl, —C$_{1-6}$alkyl-O—C$_{1-6}$alkyl, —S(O)$_2$—C$_{1-4}$alkyl, —CN, —OCHF$_2$, —OCF$_3$, —CF$_3$, —C$_{0-6}$alkyl-NR$^c$R$^d$, and —C(O)NH$_2$;
R$^a$ is selected from the group consisting of:
(1) —C$_{1-6}$alkyl,
(2) halogen,
(3) —C$_{0-6}$alkyl-OR$^e$,
(4) —C$_{0-6}$alkyl-NR$^c$S(O)$_n$R$^e$,
(5) —C$_{0-6}$alkyl-S(O)$_n$R$^e$,
(6) —C$_{0-6}$alkyl-S(O)$_n$NR$^c$R$^d$,
(7) —C$_{0-6}$alkyl-NR$^c$R$^d$,
(8) —C$_{0-6}$alkyl-C(O)R$^e$,
(9) —C$_{0-6}$alkyl-OC(O)R$^e$,
(10) —C$_{0-6}$alkyl-CO$_2$R$^e$,
(11) —C$_{0-6}$alkyl-CN,
(12) —C$_{0-6}$alkyl-C(O)NR$^c$R$^d$,
(13) —C$_{0-6}$alkyl-NR$^c$C(O)R$^e$,
(14) —C$_{0-6}$alkyl-NR$^c$C(O)OR$^e$,
(15) —C$_{0-6}$alkyl-NR$^c$C(O)NR$^c$R$^d$,
(16) —CF$_3$,
(17) —OCF$_3$,
(18) —OCHF$_2$,
(19) —C$_{0-6}$alkyl-aryl,
(20) —C$_{0-6}$alkyl-heteroaryl,
(21) —C$_{0-6}$alkyl-C$_{3-10}$cycloalkyl,
(22) —C$_{0-6}$alkyl-C$_{3-10}$ cycloalkenyl, and
(23) —C$_{0-6}$alkyl-C$_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —C$_{1-6}$alkyl, halogen, OH, —O—C$_{1-6}$alkyl, —S(O)$_2$—C$_{1-4}$alkyl, —CN, —OCHF$_2$, —OCF$_3$, —CF$_3$, and —C$_{0-6}$alkyl-NR$^c$R$^d$;
R$^b$ is independently selected from the group consisting of:
(1) —C$_{1-10}$alkyl,
(2) —C$_{2-10}$alkenyl,
(3) —CF$_3$,
(4) halogen,
(5) —CN,
(6) —OH,
(7) —OC$_{1-10}$alkyl,
(8) —OC$_{2-10}$alkenyl,
(9) —O(CH$_2$)$_p$OC$_{1-10}$alkyl,
(10) —O(CH$_2$)$_p$C$_{3-6}$cycloalkyl,
(11) —O(CH$_2$)$_p$C$_{3-6}$ cycloalkyl-C$_{1-10}$alkyl,
(12) —O(CH$_2$)$_p$C$_{2-5}$cycloheteroalkyl,
(13) —O(CH$_2$)$_p$C$_{2-5}$cycloheteroalkyl-C$_{1-10}$alkyl,
(14) —O-aryl,
(15) —O-heteroaryl,
(16) —O-aryl-C$_{1-10}$alkyl,
(17) —O-heteroaryl-C$_{1-10}$alkyl,
(18) —O(CH$_2$)$_p$NR$^c$S(O)$_m$R$^e$,
(19) —O(CH$_2$)$_p$S(O)$_m$R$^e$,
(20) —O(CH$_2$)$_p$S(O)$_m$NR$^c$R$^d$,
(21) —O(CH$_2$)$_p$NR$^c$R$^d$,
(22) —C(O)R$^e$,
(23) —OC(O)R$^e$,
(24) —CO$_2$R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH$_2$)$_p$O—C$_{3-6}$cycloalkyl,
(30) —O(CH$_2$)$_p$O—C$_{2-5}$cycloheteroalkyl,
(31) —OCF$_3$,
(32) —OCHF$_2$,
(33) —(CH$_2$)$_p$C$_{3-6}$cycloalkyl,
(34) —(CH$_2$)$_p$C$_{2-5}$cycloheteroalkyl,
(35) aryl,
(36) heteroaryl,
(37) aryl-C$_{1-10}$alkyl-, and
(38) heteroaryl-C$_{1-10}$alkyl-,
wherein each CH, CH$_2$, alkyl, alkenyl, cycloalkyl, cycloheteroalkyl, aryl and heteroaryl is unsubstituted or substituted with one to five substituents selected from: —C$_{1-6}$alkyl, halogen, —O—C$_{1-6}$alkyl and —CF$_3$;
R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$ cycloheteroalkyl,
(7) C$_{2-5}$ cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-10}$cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$;

each $R^e$ is independently selected from the group consisting of:
  (1) hydrogen,
  (2) —$C_{1-10}$alkyl,
  (3) —$C_{2-10}$ alkenyl,
  (4) —$C_{3-6}$ cycloalkyl,
  (5) $C_{3-6}$ cycloalkyl-$C_{1-10}$alkyl-,
  (6) —$C_{2-5}$cycloheteroalkyl,
  (7) $C_{2-5}$cycloheteroalkyl-$C_{1-10}$alkyl-,
  (8) aryl,
  (9) aryl-$C_{1-10}$alkyl-,
  (10) heteroaryl, and
  (11) heteroaryl-$C_{1-10}$alkyl-,
wherein each alkyl, alkenyl, cycloalkyl, cycloheteroalkyl, aryl and heteroaryl is unsubstituted or substituted with one to three substituents selected from $R^h$;

each $R^f$ is selected from the group consisting of:
  (1) halogen,
  (2) $C_{1-10}$alkyl,
  (3) —$C_{0-6}$alkyl-OH,
  (4) —O—$C_{1-6}$alkyl,
  (5) oxo,
  (6) —$S(O)_m$—$C_{1-4}$alkyl,
  (7) —CN,
  (8) —$CF_3$,
  (9) —$OCHF_2$, and
  (10) —$OCF_3$,
wherein each alkyl is unsubstituted or substituted with one to three substituents independently selected from: —OH, halogen, $C_{1-6}$alkyl, cyano and $S(O)_2C_{1-6}$alkyl;

each $R^g$ is selected from the group consisting of:
  (1) hydrogen,
  (2) —C(O)$R^e$, and
  (3) —$C_{1-10}$alkyl,
wherein alkyl is unsubstituted or substituted with one to five halogens;

each $R^h$ is selected from the group consisting of:
  (1) halogen,
  (2) $C_{1-10}$alkyl,
  (3) —OH,
  (4) —O—$C_{1-4}$alkyl,
  (5) —$S(O)_m$—$C_{1-4}$alkyl,
  (6) —CN,
  (7) —$CF_3$,
  (8) —$OCHF_2$, and
  (9) —$OCF_3$,
wherein each alkyl is unsubstituted or substituted with one to three substituents independently selected from: —OH, halogen, $C_{1-6}$alkyl, cyano and —$S(O)_2C_{1-6}$alkyl;

$R^i$ is selected from the group consisting of:
  (1) —$C_{1-6}$alkyl,
  (2) —$OR^e$,
  (3) —$NR^cS(O)_mR^e$,
  (4) halogen,
  (5) —$S(O)_mR^e$,
  (6) —$S(O)_mNR^cR^d$,
  (7) —$NR^cR^d$,
  (8) —C(O)$R^e$,
  (9) —OC(O)$R^e$,
  (10) —$CO_2R^e$,
  (11) —CN,
  (12) —C(O)$NR^cR^d$,
  (13) —$NR^cC(O)R^e$,
  (14) —$NR^cC(O)OR^e$,
  (15) —$NR^cC(O)NR^cR^d$,
  (16) —$CF_3$,
  (17) —$OCF_3$,
  (18) —$OCHF_2$,
  (19) —$C_{3-6}$cycloalkyl, and
  (20) —$C_{2-5}$cycloheteroalkyl;

each $R^j$ is selected from the group consisting of:
  (1) —$C_{1-6}$alkyl,
  (2) —$OR^e$,
  (3) —$NR^cS(O)_mR^e$,
  (4) halogen,
  (5) —$S(O)_mR^e$,
  (6) —$S(O)_mNR^cR^d$,
  (7) —$NR^cR^d$,
  (8) —C(O)$R^e$,
  (9) —OC(O)$R^e$,
  (10) —$CO_2R^e$,
  (11) —CN,
  (12) —C(O)$NR^cR^d$,
  (13) —$NR^cC(O)R^e$,
  (14) —$NR^cC(O)OR^e$,
  (15) —$NR^cC(O)NR^cR^d$,
  (16) —$CF_3$,
  (17) —$OCF_3$,
  (18) —$OCHF_2$,
  (19) —$C_{3-6}$cycloalkyl, and
  (20) —$C_{2-5}$ cycloheteroalkyl;

$R^k$ is selected from the group consisting of:
  (1) hydrogen,
  (2) —$C_{1-6}$ alkyl,
  (3) —$C_{1-6}$alkyl-$SO_2C_{1-6}$alkyl,
  (4) —$CF_3$, and
  (5) —$CHF_2$,
wherein each alkyl is unsubstituted or substituted with one to three substituents independently selected from: —OH, —$OC_{1-6}$alkyl, halogen, cyano, and —$S(O)_2C_{1-6}$alkyl;

each $R^L$ is independently selected from the group consisting of:
  (1) —$CO_2C_{1-6}$alkyl,
  (2) —$C_{1-10}$alkyl,
  (3) —$C_{2-10}$ alkenyl,
  (4) —$C_{2-10}$alkynyl,
  (5) —$C_{3-6}$cycloalkyl,
  (6) —$C_{2-6}$cycloheteroalkyl,
  (7) aryl, and
  (8) heteroaryl,
wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;

each $R^m$ is independently selected from the group consisting of:
  (1) —$C_{1-10}$alkyl,
  (2) —$C_{2-10}$ alkenyl,
  (3) —$C_{3-6}$ cycloalkyl,
  (4) $C_{3-6}$ cycloalkyl-$C_{1-10}$alkyl-,
  (5) —$C_{2-5}$cycloheteroalkyl,
  (6) $C_{2-5}$cycloheteroalkyl-$C_{1-10}$alkyl-,
  (7) aryl,
  (8) heteroaryl,
  (9) aryl-$C_{1-10}$alkyl-, and
  (10) heteroaryl-$C_{1-10}$alkyl-;

each n is independently selected from: 0, 1 or 2;
each m is independently selected from: 0, 1 or 2;
each p is independently selected from: 0, 1, 2, 3, 4, 5 or 6; and
each r is independently selected from: 0, 1, 2 or 3.

The present invention is also concerned with novel compounds of structural Formula I:

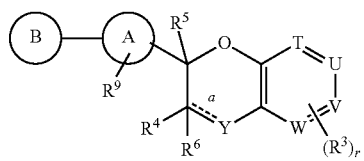

I or a pharmaceutically acceptable salt thereof; wherein
"a" is a single bond or a double bond, provided that if "a" is a double bond, then $R^6$ is absent and Y is selected from the group consisting of: C—$R^g$, —C—$OC_{1-6}$alkyl, CF and N, and further provided that
if "a" is a single bond, then $R^6$ is present and Y is selected from the group consisting of:
  (1) oxygen,
  (2) sulfur,
  (3) —$CR^gR^g$,
  (4) C=O,
  (5) —C($R^g$)$OC_{1-6}$alkyl,
  (6) —$CF_2$, and
  (7) —$NR^c$;
T is selected from the group consisting of:
  (1) CH,
  (2) N, and
  (3) N-oxide;
U is selected from the group consisting of:
  (1) $CR^1$,
  (2) N, and
  (3) N-oxide;
V is selected from the group consisting of:
  (1) $CR^2$,
  (2) N, and
  (3) N-oxide;
W is selected from the group consisting of:
  (1) CH,
  (2) N, and
  (3) N-oxide,
provided that no more than two of T, U, V and W are selected from N and N-oxide, further provided that if both T and W are N or N-oxide, then $R^3$ is absent, and further provided that both U and V are not N or N-oxide;
A is selected from the group consisting of:
  (1) aryl,
  (2) heteroaryl,
  (3) $C_{3-6}$cycloalkyl, and
  (4) $C_{2-5}$ cycloheteroalkyl,
wherein A is unsubstituted or substituted with one to five substituents selected from $R^a$;
B is selected from the group consisting of:
  (1) hydrogen,
  (2) aryl,
  (3) aryl-O—,
  (4) aryl-$C_{1-10}$ alkyl-,
  (5) aryl-$C_{1-10}$ alkyl-O—,
  (6) $C_{3-6}$cycloalkyl,
  (7) $C_{3-6}$cycloalkyl-$C_{1-10}$alkyl-,
  (8) $C_{3-6}$cycloalkyl-$C_{1-10}$alkyl-O—,
  (9) $C_{3-6}$cycloalkenyl,
  (10) $C_{3-6}$cycloalkenyl-$C_{1-10}$alkyl-,
  (11) $C_{3-6}$cycloalkenyl-$C_{1-10}$alkyl-O—,
  (12) $C_{2-5}$cycloheteroalkyl,
  (13) $C_{3-6}$cycloheteroalkyl-$C_{1-10}$alkyl-,
  (14) $C_{3-6}$cycloheteroalkyl-$C_{1-10}$alkyl-O—,
  (15) heteroaryl,
  (16) heteroaryl-O—,
  (17) heteroaryl-$C_{1-10}$ alkyl-, and
  (18) heteroaryl-$C_{1-10}$ alkyl-O—,
wherein B is unsubstituted or substituted with one to five substituents selected from $R^b$;
$R^1$ and $R^2$ are each independently selected from:
  (1) a bond,
  (2) hydrogen,
  (3) halogen,
  (4) —$OR^k$,
  (5) —CN,
  (6) —$C_{1-6}$alkyl,
  (7) —$C_{3-6}$cycloalkyl,
  (8) $C_{3-6}$cycloalkyl-$C_{1-3}$alkyl-,
  (9) —$C_{2-6}$cycloheteroalkyl, and
  (10) $C_{2-6}$cycloheteroalkyl-$C_{1-3}$alkyl-,
wherein each alkyl, cycloalkyl and cycloheteroalkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$;
$R^3$ is absent or when present is selected from the group consisting of:
  (1) hydrogen,
  (2) halogen,
  (3) —$OR^e$,
  (4) —CN,
  (5) —$C_{1-6}$alkyl,
  (6) —$C_{3-6}$cycloalkyl, and
  (7) $C_{3-6}$cycloalkyl-$C_{1-3}$alkyl-,
wherein each alkyl and cycloalkyl is unsubstituted or substituted with one to three substituents selected from $R^i$;
$R^4$ is selected from the group consisting of:
  (1) hydrogen,
  (2) halogen,
  (3) $OR^e$,
  (4) $C_{1-6}$alkyl,
  (5) $C_{1-6}$alkyl-O—,
  (6) $C_{3-6}$cycloalkyl,
  (7) $C_{3-6}$cycloalkyl-O—,
  (8) $C_{3-6}$cycloalkyl-$C_{1-10}$alkyl-,
  (9) $C_{3-6}$cycloalkyl-$C_{1-10}$alkyl-O—,
  (10) $C_{2-5}$cycloheteroalkyl,
  (11) $C_{2-5}$cycloheteroalkyl-O—,
  (12) $C_{2-5}$cycloheteroalkyl-$C_{1-10}$alkyl-,
  (13) $C_{2-5}$cycloheteroalkyl-$C_{1-10}$alkyl-O—,
  (14) aryl,
  (15) aryl-O—,
  (16) aryl-$C_{1-10}$alkyl-,
  (17) heteroaryl,
  (18) heteroaryl-O—, and
  (19) heteroaryl-$C_{1-10}$alkyl-, wherein each alkyl, cycloalkyl, cycloheteroalkyl, aryl and heteroaryl is unsubstituted or substituted with one to three substituents selected from $R^j$,
provided that when $R^4$ is:
(1) $OR^e$,
(2) $C_{1-6}$alkyl-O—,
(3) $C_{3-6}$cycloalkyl-O—,
(4) $C_{3-6}$cycloalkyl-$C_{1-10}$alkyl-O—,
(5) $C_{2-5}$ cycloheteroalkyl-O—,
(6) $C_{2-5}$cycloheteroalkyl-$C_{1-10}$alkyl-O—,
(7) aryl-O—, or
(8) heteroaryl-O—,
then Y is selected from the group consisting of:
(1) —$CR^gR^g$,
(2) C=O,
(3) —$C(R^g)OC_{1-6}$alkyl, and
(4) —$CF_2$;
$R^5$ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
$R^6$ is absent or when present is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
$R^7$ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$-alkyl-$SO_2NHCOR^m$,
(5) —$C_{1-6}$alkyl-tetrazolyl, and
(6) a cycloheteroalkyl selected from the group consisting of:

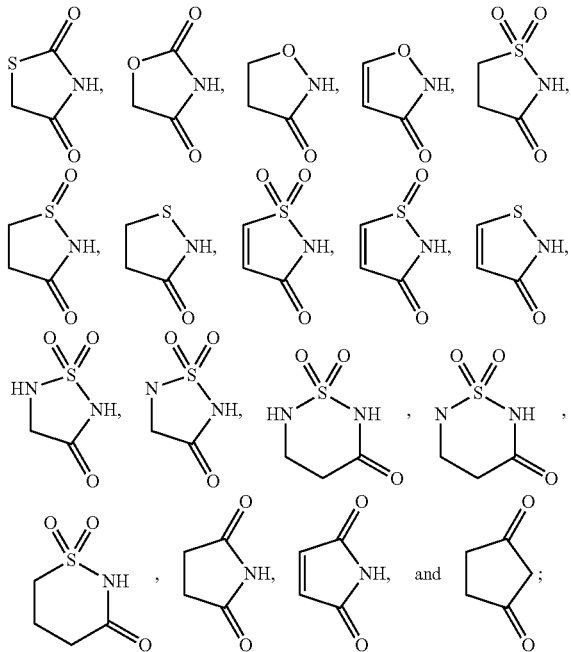

$R^8$ is selected from the group consisting of:
(1) hydrogen,
(2) —$C_{1-6}$alkyl,
(3) —$C_{3-6}$cycloalkyl, and
(4) aryl-$C_{1-6}$alkyl,
wherein each alkyl, cycloalkyl and aryl is unsubstituted or substituted with one to three substituents selected from $R^j$;
$R^9$ is selected from the group consisting of:
(1) —$C_{1-6}$alkyl-$NR^cS(O)_nR^e$,
(2) —$C_{1-6}$alkyl-$S(O)_nR^e$,
(3) —$C_{1-6}$alkyl-$S(O)_nNR^cR^d$,
(4) —$C_{1-6}$alkyl-$NR^cR^d$,
(5) —$C_{1-6}$alkyl-$C(O)NR^cR^d$,
(6) —$C_{1-6}$alkyl-$NR^cC(O)R^e$,
(7) —$C_{1-6}$alkyl-$NR^cC(O)OR^e$,
(8) —$C_{1-6}$alkyl-$NR^cC(O)NR^cR^d$,
(9) —$C_{1-6}$alkyl-aryl,
(10) —$C_{1-6}$alkyl-heteroaryl,
(11) —$C_{1-6}$alkyl-$C_{3-10}$cycloalkyl,
(12) —$C_{1-6}$alkyl-$C_{3-10}$cycloalkenyl, and
(13) —$C_{1-6}$alkyl-$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;
$R^a$ is selected from the group consisting of:
(1) —$C_{1-6}$alkyl,
(2) halogen,
(3) —$C_{0-6}$alkyl-$OR^e$,
(4) —$C_{0-6}$alkyl-$NR^cS(O)_nR^e$,
(5) —$C_{0-6}$alkyl-$S(O)_nR^e$,
(6) —$C_{0-6}$alkyl-$S(O)_nNR^cR^d$,
(7) —$C_{0-6}$alkyl-$NR^cR^d$,
(8) —$C_{0-6}$alkyl-$C(O)R^e$,
(9) —$C_{0-6}$alkyl-$OC(O)R^e$,
(10) —$C_{0-6}$alkyl-$CO_2R^e$,
(11) —$C_{0-6}$alkyl-CN,
(12) —$C_{0-6}$alkyl-$C(O)NR^cR^d$,
(13) —$C_{0-6}$alkyl-$NR^cC(O)R^e$,
(14) —$C_{0-6}$alkyl-$NR^cC(O)OR^e$,
(15) —$C_{0-6}$alkyl-$NR^cC(O)NR^cR^d$,
(16) —$CF_3$,
(17) —$OCF_3$,
(18) —$OCHF_2$,
(19) —$C_{0-6}$alkyl-aryl,
(20) —$C_{0-6}$alkyl-heteroaryl,
(21) —$C_{0-6}$alkyl-$C_{3-10}$cycloalkyl,
(22) —$C_{0-6}$alkyl-$C_{3-10}$cycloalkenyl, and
(23) —$C_{0-6}$alkyl-$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;
$R^b$ is independently selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)_pOC_{1-10}$alkyl,
(10) —$O(CH_2)_pC_{3-6}$cycloalkyl,
(11) —$O(CH_2)_pC_{3-6}$ cycloalkyl-$C_{1-10}$alkyl,
(12) —$O(CH_2)_pC_{2-5}$cycloheteroalkyl,

(13) —O(CH$_2$)$_p$C$_{2-5}$cycloheteroalkyl-C$_{1-10}$alkyl,
(14) —O-aryl,
(15) —O-heteroaryl,
(16) —O-aryl-C$_{1-10}$alkyl,
(17) —O-heteroaryl-C$_{1-10}$alkyl,
(18) —O(CH$_2$)$_p$NR$^c$S(O)$_m$R$^e$,
(19) —O(CH$_2$)$_p$S(O)$_m$R$^e$,
(20) —O(CH$_2$)$_p$S(O)$_m$NR$^c$R$^d$,
(21) —O(CH$_2$)$_p$NR$^c$R$^d$,
(22) —C(O)R$^e$,
(23) —OC(O)R$^e$,
(24) —CO$_2$R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH$_2$)$_p$O—C$_{3-6}$cycloalkyl,
(30) —O(CH$_2$)$_p$O—C$_{2-5}$cycloheteroalkyl,
(31) —OCF$_3$,
(32) —OCHF$_2$,
(33) —(CH$_2$)$_p$C$_{3-6}$cycloalkyl,
(34) —(CH$_2$)$_p$C$_{2-5}$cycloheteroalkyl,
(35) aryl,
(36) heteroaryl,
(37) aryl-C$_{1-10}$alkyl-, and
(38) heteroaryl-C$_{1-10}$alkyl-,
wherein each CH, CH$_2$, alkyl, alkenyl, cycloalkyl, cycloheteroalkyl, aryl and heteroaryl is unsubstituted or substituted with one to five substituents selected from: —C$_{1-6}$alkyl, halogen, —O—C$_{1-6}$alkyl and —CF$_3$;
R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$ cycloheteroalkyl,
(7) C$_{2-5}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^f$,
or R$^c$ and R$^d$ together with the atom(s) to which they are attached form a C$_{2-10}$cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$;
each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) C$_{3-6}$ cycloalkyl-C$_{1-10}$alkyl-,
(6) —C$_{2-5}$cycloheteroalkyl,
(7) C$_{2-5}$cycloheteroalkyl-C$_{1-10}$alkyl-,
(8) aryl,
(9) aryl-C$_{1-10}$alkyl-,
(10) heteroaryl, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents selected from R$^h$;
each R$^f$ is selected from the group consisting of:
(1) halogen,
(2) C$_{1-10}$alkyl,
(3) —C$_{0-6}$alkyl-OH,
(4) —O—C$_{1-6}$alkyl,
(5) oxo,
(6) —S(O)$_m$—C$_{1-4}$alkyl,
(7) —CN,
(8) —CF$_3$,
(9) —OCHF$_2$, and
(10) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
each R$^g$ is selected from the group consisting of:
(1) hydrogen,
(2) —C(O)R$^e$, and
(3) —C$_{1-10}$alkyl,
wherein alkyl is unsubstituted or substituted with one to five halogens;
each R$^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and —S(O)$_2$C$_{1-6}$alkyl;
R$^i$ is selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each R$^j$ is selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,

(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

R$^k$ is selected from the group consisting of:
(1) hydrogen,
(2) —C$_{1-6}$ alkyl,
(3) —C$_{1-6}$alkyl-SO$_2$C$_{1-6}$alkyl,
(4) —CF$_3$, and
(5) —CHF$_2$,
wherein each alkyl is unsubstituted or substituted with one to three substituents independently selected from: —OH, —OC$_{1-6}$alkyl, halogen, cyano, and —S(O)$_2$C$_{1-6}$alkyl;

each R$^L$ is independently selected from the group consisting of:
(1) —CO$_2$C$_{1-6}$alkyl,
(2) —C$_{1-10}$alkyl,
(3) —C$_{2-10}$ alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with 1-4 substituents selected from C$_{1-6}$alkyl, halogen, and —OC$_{1-6}$alkyl;

each R$^m$ is independently selected from the group consisting of:
(1) —C$_{1-10}$alkyl,
(2) —C$_{2-10}$ alkenyl,
(3) —C$_{3-6}$ cycloalkyl,
(4) C$_{3-6}$ cycloalkyl-C$_{1-10}$alkyl-,
(5) —C$_{2-5}$cycloheteroalkyl,
(6) C$_{2-5}$cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;

each n is independently selected from: 0, 1 or 2;
each m is independently selected from: 0, 1 or 2;
each p is independently selected from: 0, 1, 2, 3, 4, 5 or 6; and
each r is independently selected from: 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, "a" is a single bond.

In another embodiment of the present invention, "a" is a single bond and R$^6$ is present.

In another embodiment of the present invention, "a" is a single bond, R$^6$ is present, and Y is selected from the group consisting of: oxygen, sulfur, —CR$^g$R$^g$, C═O, —C(R$^g$) OC$_{1-6}$alkyl, —CF$_2$, and —NR$^c$. In another embodiment of the present invention, "a" is a single bond, R$^6$ is present, and Y is —CR$^g$R$^g$. In a class of this embodiment, "a" is a single bond, R$^6$ is present, and Y is CH$_2$. In another class of this embodiment, "a" is a single bond, R$^6$ is hydrogen, and Y is CH$_2$.

In another embodiment of the present invention, "a" is a double bond and R$^6$ is absent.

In another embodiment of the present invention, "a" is a double bond, R$^6$ is absent and Y is selected from the group consisting of: C—R$^g$, —C—OC$_{1-6}$alkyl, CF and N. In a class of this embodiment, Y is selected from the group consisting of: —C—R$^g$. In a subclass of this class, Y is —CH.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: CR$^1$, N and N-oxide. In a class of this embodiment, U is selected from the group consisting of: CR$^1$ and N. In another class of this embodiment, U is CR$^1$. In another class of this embodiment, U is N or N-oxide. In another class of this embodiment, U is N. In another class of this embodiment, U is N-oxide.

In another embodiment of the present invention, V is selected from the group consisting of: CR$^2$, N and N-oxide. In a class of this embodiment, V is selected from the group consisting of: CR$^2$ and N. In another class of this embodiment, V is CR$^2$. In another class of this embodiment, V is N or N-oxide. In another class of this embodiment, V is N. In another class of this embodiment, V is N-oxide.

In another embodiment of the present invention, W is selected from the group consisting of: CH, N and N-oxide, provided that no more than two of T, U, V and W are selected from N and N-oxide, further provided that if both T and W are N or N-oxide, then R$^3$ is absent, and further provided that both U and V are not N or N-oxide. In a class of this embodiment, W is selected from the group consisting of: CH and N, provided that no more than two of T, U, V and W are selected from N and N-oxide, further provided that if both T and W are N or N-oxide, then R$^3$ is absent, and further provided that both U and V are not N or N-oxide. In another class of this embodiment, W is CH, provided that no more than two of T, U, V and W are selected from N and N-oxide, further provided that if both T and W are N or N-oxide, then R$^3$ is absent, and further provided that both U and V are not N or N-oxide. In another class of this embodiment, W is N or N-oxide, provided that no more than two of T, U, V and W are selected from N and N-oxide, further provided that if both T and W are N or N-oxide, then R$^3$ is absent, and further provided that both U and V are not N or N-oxide. In another class of this embodiment, W is N, provided that no more than two of T, U, V and W are selected from N and N-oxide, further provided that if both T and W are N or N-oxide, then R$^3$ is absent, and further provided that both U and V are not N or N-oxide. In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T is CH, U is CR$^1$, V is CR$^2$, and W is CH. In a class of this embodiment, T is CH, U is CR$^1$, V is CH, and W is CH. In another class of this embodiment, T is CH, U is CH, V is CR$^2$, and W is CH.

In another embodiment of the present invention, T is N or N-oxide, U is CR$^1$, V is CR$^2$, and W is CH. In a class of this embodiment, T is N, U is CR$^1$, V is CR$^2$, and W is CH In another embodiment of the present invention, T is CH, U is N or N-oxide, and V is CR$^2$, and W is CH. In a class of this embodiment, T is CH, U is N, V is CR$^2$, and W is CH. In another embodiment of the present invention, T is CH, U is CR$^1$, V is N or N-oxide, and W is CH. In a class of this embodiment, T is CH, U is CR$^1$, and V is N or N-oxide, and W is CH. In another embodiment of the present invention, T is CH, U is CR$^1$, V is CR$^2$, and W is CH, N or N-oxide. In another embodiment of the present invention, T is CH, U is CR$^1$, V is CR$^2$, and W is N or N-oxide. In a class of this embodiment, T is CH, U is CR$^1$, V is CR$^2$, and W is N.

In another embodiment of the present invention, T is N or N-oxide, U is N or N-oxide, V is CR$^2$, and W is CH. In a class of this embodiment, T is N, U is N, V is CR$^2$, and W is CH. In another embodiment of the present invention, T is N or N-oxide, U is CR$^1$, V is N or N-oxide, and W is CH. In a class of this embodiment, T is N, U is CR$^1$, V is N, and W is CH. In another embodiment of the present invention, T is N or N-oxide, U is CR$^1$, V is CR$^2$, and W is N or N-oxide. In a class of this embodiment, T is N, U is CR$^1$, V is CR$^2$, and W is N. In another embodiment of the present invention, T is N or N-oxide, U is CR$^1$, V is CR$^2$, and W is N or N-oxide; and R$^3$ is absent. In a class of this embodiment, T is N, U is CR$^1$, V is CR$^2$, and W is N; and R$^3$ is absent. In another embodiment of the present invention, T is CH, U is N or N-oxide, V is CR$^2$, and W is N or N-oxide. In a class of this embodiment, T is CH, U is N, V is CR$^2$, and W is N. In another embodiment of the present invention, T is CH, U is CR$^1$, V is N or N-oxide, and W is N or N-oxide. In a class of this embodiment, T is CH, U is CR$^1$, V is N, and W is N. In another embodiment of the present invention, T is CH; U is CR$^1$; V is CR$^2$; and W is CH, N or N-oxide.

In another embodiment of the present invention, Y is selected from the group consisting of: oxygen and sulfur. In another embodiment of the present invention, Y is selected from the group consisting of: —CR$^g$R$^g$, C═O, —C(R$^g$)OC$_{1-6}$alkyl, —CF$_2$, and —NR$^c$. In another embodiment of the present invention, Y is selected from the group consisting of: —CR$^g$R$^g$, C═O, —CF$_2$, and —NR$^c$. In another embodiment of the present invention, Y is —CR$^g$R$^g$. In a class of this embodiment, Y is —CH$_2$. In another embodiment of the present invention, Y is selected from the group consisting of: —C—R$^g$, —C—OC$_{1-6}$alkyl, CF and N. In another embodiment of the present invention, Y is selected from the group consisting of: —C—R$^g$, CF and N.

In another embodiment of the present invention, A is selected from the group consisting of: aryl and heteroaryl, wherein each aryl and heteroaryl is unsubstituted or substituted with one to five substituents selected from R$^a$. In a class of this embodiment, A is selected from the group consisting of: aryl and heteroaryl, wherein each aryl and heteroaryl is unsubstituted or substituted with one to three substituents selected from R$^a$. In another class of this embodiment, A is selected from the group consisting of: phenyl and pyridine, wherein each phenyl and pyridine is unsubstituted or substituted with one to three substituents selected from R$^a$.

In another class of this embodiment, A is selected from the group consisting of: phenyl, pyrazine, and pyridine, wherein each phenyl, pyrazine, and pyridine is unsubstituted or substituted with one to five substituents selected from R$^a$. In another class of this embodiment, A is selected from the group consisting of: phenyl, pyrazine, and pyridine. In another class of this embodiment, A is selected from the group consisting of: phenyl and pyridine, wherein each phenyl and pyridine is unsubstituted or substituted with one to five substituents selected from R$^a$. In another class of this embodiment, A is selected from the group consisting of: phenyl and pyridine, wherein each phenyl and pyridine is unsubstituted or substituted with one to three substituents selected from R$^a$. In another class of this embodiment, A is selected from the group consisting of: phenyl and pyridine.

In another embodiment of the present invention, A is aryl, wherein each aryl is unsubstituted or substituted with one to five substituents selected from R$^a$. In a class of this embodiment, A is aryl, wherein each aryl is unsubstituted or substituted with one to three substituents selected from R$^a$. In another class of this embodiment, A is phenyl, wherein each phenyl is unsubstituted or substituted with one to three substituents selected from R$^a$.

In another embodiment of the present invention, A is heteroaryl, wherein heteroaryl is unsubstituted or substituted with one to five substituents selected from R$^a$. In a class of this embodiment, A is heteroaryl, wherein heteroaryl is unsubstituted or substituted with one to three substituents selected from R$^a$. In another class of this embodiment, A is pyridine, wherein each pyridine is unsubstituted or substituted with one to three substituents selected from R$^a$.

In another embodiment of the present invention, B is selected from the group consisting of: hydrogen, aryl, aryl-O—, aryl-C$_{1-10}$ alkyl-O—, C$_{3-6}$cycloalkenyl and heteroaryl, wherein B is unsubstituted or substituted with one to five substituents selected from R$^b$. In a class of this embodiment, B is selected from the group consisting of: hydrogen, phenyl, phenyl-O—, phenyl-CH$_2$—O—, cyclopentenyl, pyridine, isoxazole and indazole, wherein B is unsubstituted or substituted with one to five substituents selected from R$^b$.

In another embodiment of the present invention, B is selected from the group consisting of: aryl, aryl-O—, aryl-C$_{1-10}$ alkyl-O—, C$_{3-6}$cycloalkenyl and heteroaryl, wherein B is unsubstituted or substituted with one to five substituents selected from R$^b$. In a class of this embodiment, B is selected from the group consisting of: phenyl, phenyl-O—, phenyl-CH$_2$—O—, cyclopentenyl, pyridine, isoxazole and indazole, wherein B is unsubstituted or substituted with one to five substituents selected from R$^b$.

In another embodiment of the present invention, B is selected from the group consisting of: aryl, and heteroaryl, wherein each aryl and heteroaryl is unsubstituted or substituted with one to five substituents selected from R$^b$. In a class of this embodiment, B is selected from the group consisting of: phenyl and pyridine, wherein each phenyl and pyridine is unsubstituted or substituted with one to five substituents selected from R$^b$. In another embodiment of the present invention, B is aryl, wherein each aryl is unsubstituted or substituted with one to five substituents selected from R$^b$. In a class of this embodiment, B is phenyl, wherein each phenyl is unsubstituted or substituted with one to five substituents selected from R$^b$. In another embodiment of the present invention, B is heteroaryl, wherein heteroaryl is unsubstituted or substituted with one to five substituents selected from R$^b$. In a class of this embodiment, B is pyridine, wherein each pyridine is unsubstituted or substituted with one to five substituents selected from R$^b$.

In another embodiment of the present invention, B is selected from the group consisting of: phenyl, pyridine and pyrazole, wherein each phenyl, pyridine and pyrazole is unsubstituted or substituted with one to five substituents selected from $R^b$.

In another embodiment of the present invention, B is selected from the group consisting of: pyridine and pyrazole, wherein each pyridine and pyrazole is unsubstituted or substituted with one to five substituents selected from $R^b$. In a class of this embodiment, B is pyrazole, wherein pyrazole is unsubstituted or substituted with one to five substituents selected from $R^b$.

In another embodiment of the present invention, $R^1$ and $R^2$ are each independently selected from: a bond, hydrogen, —$OR^k$, and —$C_{1-6}$alkyl, wherein alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ and $R^2$ are each independently selected from: hydrogen, —$OR^k$ and —$C_{1-6}$alkyl, wherein alkyl is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: a bond, hydrogen, and —$C_{1-6}$alkyl, wherein alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ and $R^2$ are each independently selected from: hydrogen and —$C_{1-6}$alkyl, wherein alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ and $R^2$ are each independently selected from: a bond, hydrogen and —$C_{1-6}$alkyl, wherein alkyl is unsubstituted or substituted with one to three substituents selected from $R^L$, and wherein one of $R^1$ and $R^2$ is substituted with $R^7$. In another class of this embodiment, $R^1$ and $R^2$ are each independently selected from: bond, hydrogen and ethyl, wherein ethyl is unsubstituted or substituted with one to three substituents selected from $R^L$, and wherein one of $R^1$ and $R^2$ is substituted with $R^7$.

In another embodiment, $R^1$ and $R^2$ are each independently selected from: hydrogen, and —$C_{1-6}$alkyl, wherein each alkyl is substituted with one to three substituents selected from $R^L$, and wherein one of $R^1$ and $R^2$ is substituted with one substituent selected from $R^7$. In another embodiment, $R^1$ and $R^2$ are each independently selected from: hydrogen, and $C_2$alkyl, wherein each alkyl is substituted with one to three substituents selected from $R^L$, and wherein one of $R^1$ and $R^2$ is substituted with one substituent selected from $R^7$.

In another embodiment of the present invention, $R^1$ and $R^2$ are each independently selected from: hydrogen and —$C_{1-6}$alkyl, wherein alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ and $R^2$ are each independently selected from: hydrogen and —$C_{1-6}$alkyl, wherein alkyl is unsubstituted or substituted with one to three substituents selected from $R^L$, and wherein one of $R^1$ and $R^2$ is substituted with $R^7$. In another class of this embodiment, $R^1$ and $R^2$ are each independently selected from: hydrogen, and —$C_{1-6}$alkyl, wherein one of $R^1$ and $R^2$ is —$C_{1-6}$alkyl substituted with $R^7$, and wherein alkyl is unsubstituted or substituted with one to three substituents independently selected from $R^L$. In another class of this embodiment, $R^1$ and $R^2$ are each independently selected from: hydrogen and ethyl, wherein ethyl is unsubstituted or substituted with one to three substituents selected from $R^L$, and wherein one of $R^1$ and $R^2$ is substituted with $R^7$. In another class of this embodiment, $R^1$ and $R^2$ are each independently selected from: hydrogen and ethyl, wherein ethyl is unsubstituted or substituted with one to three substituents selected from $R^L$, and wherein one of $R^1$ and $R^2$ is ethyl substituted with $R^7$.

In another embodiment of the present invention, $R^1$ is —CH(cyclopropyl)-CH(CH$_3$)—CO$_2$H. In another embodiment of the present invention, $R^1$ is —CH(cyclopropyl)-CH(CH$_3$)—CO$_2$H, and $R^2$ is hydrogen. In another embodiment of the present invention, $R^2$ is —CH(cyclopropyl)-CH(CH$_3$)—CO$_2$H. In another embodiment of the present invention, $R^2$ is —CH(cyclopropyl)-CH(CH$_3$)—CO$_2$H, and $R^1$ is hydrogen.

In another embodiment of the present invention, $R^1$ is —CH(cyclobutyl)-CH(CH$_3$)—CO$_2$H. In another embodiment of the present invention, $R^1$ is —CH(cyclobutyl)-CH(CH$_3$)—CO$_2$H, and $R^2$ is hydrogen. In another embodiment of the present invention, $R^2$ is —CH(cyclobutyl)-CH(CH$_3$)—CO$_2$H. In another embodiment of the present invention, $R^2$ is —CH(cyclobutyl)-CH(CH$_3$)—CO$_2$H, and R is hydrogen.

In another embodiment, $R^1$ is independently selected from: a bond, hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is unsubstituted or substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is independently selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein R is unsubstituted or substituted with $R^7$, or $R^1$ and $R^2$ together with the atom(s) to which they are attached form a $C_{3-6}$cycloalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is independently selected from: a bond, hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is unsubstituted or substituted with $R^7$. In another class of this embodiment, $R^1$ is independently selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is unsubstituted or substituted with $R^7$.

In another embodiment of the present invention, $R^1$ is independently selected from: a bond, hydrogen, —$OR^k$ and —$C_{1-6}$alkyl, wherein alkyl is unsubstituted or substituted with one to three substituents selected from $R^L$, and wherein $R^1$ is unsubstituted or substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is independently selected from: hydrogen, —$OR^k$ and —$C_{1-6}$alkyl, wherein alkyl is unsubstituted or substituted with one to three substituents selected from $R^L$, and wherein $R^1$ is unsubstituted or substituted with $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is selected from: a bond, hydrogen, —$OR^k$ and —$C_{1-6}$alkyl, wherein alkyl is unsubstituted or substituted with one to three substituents selected from $R^L$, and wherein $R^1$ is unsubstituted or substituted with $R^7$. In another class of this embodiment, $R^1$ is selected from: hydrogen, —$OR^k$ and —$C_{1-6}$alkyl, wherein alkyl is unsubstituted or substituted with one to three substituents selected from $R^L$, and wherein $R^1$ is unsubstituted or substituted with $R^7$.

In another embodiment of the present invention, $R^1$ is selected from: a bond, hydrogen and —$C_{1-6}$alkyl, wherein alkyl is unsubstituted or substituted with one to three substituents selected from $R^L$, and wherein $R^1$ is substituted with a $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is selected from: a bond, hydrogen, and —$C_{1-6}$alkyl, wherein alkyl is unsubstituted or substituted with one to three substituents selected from $R^L$, and wherein $R^1$ is unsubstituted or substituted with $R^7$.

In another embodiment of the present invention, R is selected from: hydrogen and —$C_{1-6}$alkyl, wherein alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is selected from: hydrogen and —$C_{1-6}$alkyl-, wherein alkyl is unsubstituted or substituted with one to three substituents selected from $R^L$, and wherein $R^1$ is substituted with $R^7$. In another class of this embodiment, $R^1$ is selected from: hydrogen and ethyl, wherein ethyl is unsubstituted or substituted with one to three substituents selected from $R^L$, and wherein $R^1$ is substituted with $R^7$, or $R^1$ and $R^2$ together with the atom(s) to which they are attached form a $C_{3-4}$cycloalkyl ring or a $C_{2-4}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is selected from: hydrogen and ethyl, wherein ethyl is unsubstituted or substituted with one to three substituents selected from $R^L$, and wherein $R^1$ is substituted with $R^7$.

In another embodiment of the present invention, $R^1$ is selected from: —$C_{1-6}$alkyl, wherein alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^1$ is selected from: —$C_{1-6}$alkyl-, wherein alkyl is unsubstituted or substituted with one to three substituents selected from $R^L$, and wherein R is substituted with $R^7$. In another class of this embodiment, $R^1$ is ethyl, wherein ethyl is unsubstituted or substituted with one to three substituents selected from $R^L$, and wherein R is substituted with $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^1$ is ethyl-, wherein ethyl is unsubstituted or substituted with one to three substituents selected from $R^L$, and wherein R is substituted with $R^7$.

In another embodiment, $R^1$ is —$C_{1-6}$alkyl, wherein alkyl is substituted with one to three substituents selected from $R^L$, and wherein alkyl is substituted with one substituent selected from $R^7$. In another embodiment, $R^1$ is —$C_2$alkyl, wherein alkyl is substituted with one to three substituents selected from $R^L$, and wherein alkyl is substituted with one substituent selected from $R^7$.

In another embodiment of the present invention, R is hydrogen.

In another embodiment, $R^1$ is independently selected from: a bond, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein R is substituted with $R^7$; and $R^2$ is hydrogen.

In another embodiment of the present invention, R is selected from: a bond, —$OR^k$ and —$C_{1-6}$alkyl, wherein alkyl is unsubstituted or substituted with one to three substituents selected from $R^L$, and wherein $R^1$ is substituted with $R^7$; and $R^2$ is hydrogen. In a class of this embodiment, $R^1$ is selected from: —OH, —$OC_{1-6}$alkyl, and —$C_{1-6}$alkyl-, wherein each alkyl is unsubstituted or substituted with one to three substituents selected from $R^L$, and wherein $R^1$ is substituted with $R^7$; and $R^2$ is hydrogen.

In another embodiment of the present invention, $R^1$ is —$C_{1-6}$alkyl, wherein alkyl is unsubstituted or substituted with one to three substituents selected from $R^L$, and wherein R is substituted with $R^7$; and $R^2$ is hydrogen. In a class of this embodiment, $R^1$ is ethyl, wherein ethyl is unsubstituted or substituted with one to three substituents selected from $R^L$, and wherein R is substituted with $R^7$; and $R^2$ is hydrogen.

In another embodiment, $R^2$ is independently selected from: a bond, hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^2$ is independently selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring, wherein each $R^1$ and $R^2$ is unsubstituted or substituted with one to three substituents selected from $R^L$, and wherein one of $R^1$ and $R^2$ is substituted with $R^7$.

In another class of this embodiment, $R^2$ is independently selected from: a bond, hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$. In another class of this embodiment, $R^2$ is independently selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$.

In another embodiment of the present invention, $R^2$ is independently selected from: a bond, hydrogen, —$OR^k$ and —$C_{1-6}$alkyl, wherein alkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another class of this embodiment, $R^2$ is selected from: a bond, hydrogen, —$OR^k$ and —$C_{1-6}$alkyl, wherein alkyl is unsubstituted or substituted with one to three substituents selected from $R^L$, and wherein $R^2$ is substituted with $R^7$. In another class of this embodiment, $R^2$ is selected from: hydrogen, —$OR^k$ and —$C_{1-6}$alkyl, wherein alkyl is unsubstituted or substituted with one to three substituents selected from $R^L$, and wherein $R^2$ is substituted with $R^7$.

In another embodiment of the present invention, $R^2$ is selected from: a bond, hydrogen, and —$C_{1-6}$alkyl, wherein alkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In a class of this embodiment, $R^2$ is selected from: a bond, hydrogen, and —$C_{1-6}$alkyl, wherein alkyl is unsubstituted or substituted with one to three substituents selected from $R^L$, and wherein $R^2$ is substituted with $R^7$.

In another embodiment of the present invention, $R^2$ is selected from: hydrogen and —$C_{1-6}$alkyl, wherein alkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^2$ is selected from: hydrogen and —$C_{1-6}$alkyl-, wherein alkyl is unsubstituted or substituted with one to three substituents selected from $R^L$, and wherein $R^2$ is substituted with $R^7$. In another class of this embodiment, $R^2$ is selected from: hydrogen and ethyl, wherein ethyl is unsubstituted or substituted with one to three substituents selected from $R^L$, and wherein $R^2$ is substituted with $R^7$, or $R^1$ and $R^2$ together with the atom(s) to which they are attached form a $C_{3-4}$cycloalkyl ring or a $C_{2-4}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^2$ is selected from: hydrogen and ethyl, wherein ethyl is unsubstituted or substituted with one to three substituents selected from $R^L$, and wherein $R^2$ is substituted with $R^7$.

In another embodiment of the present invention, $R^2$ is selected from: —$C_{1-6}$alkyl, wherein alkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another class of this embodiment, $R^2$ is —$C_{1-6}$alkyl-, wherein alkyl is unsubstituted or substituted with one to three substituents selected from $R^L$, and wherein $R^2$ is substituted with $R^7$. In another class of this embodiment, $R^2$ is ethyl, wherein ethyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with $R^7$. In another class of this embodiment, $R^2$ is ethyl, wherein ethyl is unsubstituted or substituted with one to three substituents selected from $R^L$, and wherein $R^2$ is substituted with $R^7$.

In another embodiment, $R^2$ is —$C_{1-6}$alkyl, wherein alkyl is substituted with one to three substituents selected from $R^L$, and wherein alkyl is substituted with one substituent selected from $R^7$. In another embodiment, $R^2$ is —$C_2$alkyl, wherein alkyl is substituted with one to three substituents selected from $R^L$, and wherein alkyl is substituted with one substituent selected from $R^7$.

In another embodiment of the present invention, $R^2$ is hydrogen.

In another embodiment, $R^2$ is independently selected from: a bond, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$; and $R^1$ is hydrogen.

In another embodiment of the present invention, $R^2$ is selected from: a bond, —$OR^k$ and —$C_{1-6}$alkyl, wherein alkyl is unsubstituted or substituted with one to three substituents selected from $R^L$, and wherein $R^2$ is substituted with $R^7$; and $R^1$ is hydrogen. In a class of this embodiment, $R^2$ is selected from: —OH, —$OC_{1-6}$alkyl, and —$C_{1-6}$alkyl-, wherein alkyl is unsubstituted or substituted with one to three substituents selected from $R^L$, and wherein $R^2$ is substituted with $R^7$; and $R^1$ is hydrogen.

In another embodiment of the present invention, $R^2$ is —$C_{1-6}$alkyl, wherein alkyl is unsubstituted or substituted with one to three substituents selected from $R^L$, and wherein $R^2$ is substituted with $R^7$; and $R^1$ is hydrogen. In a class of this embodiment, $R^2$ is ethyl, wherein ethyl is unsubstituted or substituted with one to three substituents selected from $R^L$, and wherein $R^2$ is substituted with $R^7$; and $R^1$ is hydrogen.

In one class of the embodiments of the present invention, at least one of $R^1$ and $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-. wherein each alkyl, cycloalkyl and cycloheteroalkyl is unsubstituted or substituted with one to three substituents independently selected from $R^L$, and wherein one alkyl, cycloalkyl or cycloheteroalkyl is substituted with $R^7$. In another class of the embodiments of the present invention, one of $R^1$ and $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein one alkyl, cycloalkyl or cycloheteroalkyl is substituted with $R^7$. In another class of the embodiments of the present invention, at least one of $R^1$ and $R^2$ is —$C_{1-6}$alkyl, wherein alkyl is unsubstituted or substituted with one to three substituents independently selected from $R^L$, and wherein one alkyl is substituted with $R^7$. In another class of the embodiments of the present invention, one of $R^1$ and $R^2$ is —$C_{1-6}$alkyl, wherein alkyl is unsubstituted or substituted with one to three substituents independently selected from $R^L$, and wherein alkyl is substituted with $R^7$. In another class of the embodiments of the present invention, one of $R^1$ and $R^2$ is —$C_{1-6}$alkyl, wherein alkyl is substituted with one or two substituents independently selected from $R^L$, and wherein alkyl is substituted with $R^7$. In another class of the embodiments of the present invention, at least one of $R^1$ and $R^2$ is ethyl, wherein ethyl is unsubstituted or substituted with one to three substituents independently selected from $R^L$, and wherein one ethyl is substituted with $R^7$. In another class of the embodiments of the present invention, one of $R^1$ and $R^2$ is ethyl, wherein ethyl is unsubstituted or substituted with one to three substituents independently selected from $R^L$, and wherein ethyl is substituted with $R^7$. In another class of the embodiments of the present invention, one of $R^1$ and $R^2$ is ethyl, wherein ethyl is substituted with one or two substituents independently selected from $R^L$, and wherein ethyl is substituted with $R^7$.

In another embodiment, $R^3$ is absent or when present is selected from the group consisting of: hydrogen, halogen, —$OR^e$, —CN, —$C_{1-6}$alkyl, —$C_{3-6}$cycloalkyl, and $C_{3-6}$cycloalkyl-$C_{1-3}$alkyl-, wherein each alkyl and cycloalkyl is unsubstituted or substituted with one to three substituents selected from $R^i$. In another embodiment of the present invention, when present, $R^3$ is selected from the group consisting of: hydrogen, halogen, —$OR^e$, —CN and —$C_{1-6}$alkyl, wherein alkyl is unsubstituted or substituted with one to three substituents selected from $R^i$. In another embodiment of the present invention, when present, $R^3$ is selected from the group consisting of: hydrogen, halogen and —$C_{1-6}$alkyl, wherein alkyl is unsubstituted or substituted with one to three substituents selected from $R^i$. In a class of this embodiment, when present, $R^3$ is selected from the group consisting of: hydrogen and —$C_{1-6}$alkyl, wherein alkyl is unsubstituted or substituted with one to three substituents selected from $R^i$. In another class of this embodiment, when present, $R^3$ is —$C_{1-6}$alkyl, wherein alkyl is unsubstituted or substituted with one to three substituents selected from $R^i$. In another class of this embodiment, when present $R^3$ is hydrogen.

In another embodiment of the present invention, $R^3$ is absent or when present is selected from the group consisting of: hydrogen and halogen. In a class of this embodiment, $R^3$ is present and is selected from the group consisting of: hydrogen and halogen. In another class of this embodiment, $R^3$ is selected from the group consisting of: hydrogen and halogen. In another class of this embodiment, $R^3$ present and is selected from the group consisting of: hydrogen, and F. In another class of this embodiment, $R^3$ is selected from the group consisting of: hydrogen, and F.

In another embodiment of the present invention, $R^4$ is selected from the group consisting of: hydrogen, halogen, $OR^e$, $C_{1-6}$alkyl, $C_{1-6}$alkyl-O—, $C_{3-6}$cycloalkyl, $C_{3-6}$cycloalkyl-O—, $C_{3-6}$cycloalkyl-$C_{1-10}$alkyl-, $C_{3-6}$cycloalkyl-$C_{1-10}$alkyl-O—, $C_{2-5}$cycloheteroalkyl, $C_{2-5}$cycloheteroalkyl-O—, $C_{2-5}$cycloheteroalkyl-$C_{1-10}$alkyl-, $C_{2-5}$cycloheteroalkyl-$C_{1-10}$alkyl-O—, aryl, aryl-O—, aryl-$C_{1-10}$alkyl-, heteroaryl, heteroaryl-O—, and heteroaryl-$C_{1-10}$alkyl-, wherein each alkyl, cycloalkyl, cycloheteroalkyl, aryl and heteroaryl is unsubstituted or substituted with one to three substituents selected from $R^j$, provided that when $R^4$ is: —$OR^e$, $C_{1-6}$alkyl-O—, $C_{3-6}$cycloalkyl-O—, $C_{3-6}$cycloalkyl-$C_{1-10}$alkyl-O—, $C_{2-5}$cycloheteroalkyl-O—, $C_{2-5}$cycloheteroalkyl-$C_{1-10}$alkyl-O—, aryl-O—, or heteroaryl-O—; then Y is selected from the group consisting of: —$CR^gR^g$, C=O, and —$CF_2$. In a class of this embodiment, $R^4$ is selected from the group consisting of: hydrogen, halogen, $OR^c$, $C_{1-6}$alkyl, $C_{1-6}$alkyl-O—, $C_{3-6}$cycloalkyl, $C_{3-6}$cycloalkyl-O—, $C_{3-6}$cycloalkyl-$C_{1-10}$alkyl-, $C_{3-6}$cycloalkyl-$C_{1-10}$alkyl-O—, $C_{2-5}$cycloheteroalkyl, $C_{2-5}$cycloheteroalkyl-O—, $C_{2-5}$cycloheteroalkyl-$C_{1-10}$alkyl-, $C_{2-5}$cycloheteroalkyl-$C_{1-10}$alkyl-O—, aryl, aryl-O—, aryl-$C_{1-10}$alkyl-, heteroaryl, heteroaryl-O—, and heteroaryl-$C_{1-10}$alkyl-, wherein each alkyl, cycloalkyl, cycloheteroalkyl, aryl and heteroaryl is unsubstituted or substituted with one to three substituents selected from $R^j$, provided that when $R^4$ is: —$OR^e$, $C_{1-6}$alkyl-O—, $C_{3-6}$cycloalkyl-O—, $C_{3-6}$cycloalkyl-$C_{1-10}$alkyl-O—, $C_{2-5}$cycloheteroalkyl-O—, $C_{2-5}$cycloheteroalkyl-$C_{1-10}$alkyl-O—, aryl-O—, or heteroaryl-O—; then Y is selected from the group consisting of: —$CH_2$, C=O, and —$CF_2$. In another class of this embodiment of the present invention, $R^4$ is selected from the group consisting of: hydrogen, halogen, $OR^c$, $C_{1-6}$alkyl, $C_{1-6}$alkyl-O—, $C_{3-6}$cycloalkyl, $C_{3-6}$cycloalkyl-O—, $C_{3-6}$cycloalkyl-$C_{1-10}$alkyl-, $C_{3-6}$cycloalkyl-$C_{1-10}$alkyl-O—, $C_{2-5}$cycloheteroalkyl, $C_{2-5}$cycloheteroalkyl-O—, $C_{2-5}$cycloheteroalkyl-$C_{1-10}$alkyl-, $C_{2-5}$cycloheteroalkyl-$C_{1-10}$alkyl-O—, aryl, aryl-O—, aryl-$C_{1-10}$alkyl-, heteroaryl, heteroaryl-O—, and heteroaryl-$C_{1-10}$alkyl-, wherein each alkyl, cycloalkyl, cycloheteroalkyl, aryl and heteroaryl is unsubstituted or substituted with one to three substituents selected from $R^j$, provided that when $R^4$ is: —$OR^e$, —$C_{1-6}$alkyl-O—, $C_{3-6}$cycloalkyl-O—, $C_{3-6}$cycloalkyl-$C_{1-10}$alkyl-O—, $C_{2-5}$cycloheteroalkyl-O—, $C_{2-5}$cycloheteroalkyl-$C_{1-10}$alkyl-O—, aryl-O—, or heteroaryl-O—; then Y is —$CR^gR^g$. In a subclass of this class, Y is —$CH_2$.

In another embodiment of the present invention, $R^4$ is selected from the group consisting of: hydrogen, halogen, $OR^c$, $C_{1-6}$alkyl, and $C_{1-6}$alkyl-O—, wherein each alkyl is unsubstituted or substituted with one to three substituents selected from $R^j$, provided that when $R^4$ is: $OR^e$ or —$C_{1-6}$alkyl-O—, then Y is —$CR^gR^g$. In another class of this embodiment, $R^4$ is selected from the group consisting of: hydrogen, halogen, $OR^e$, $C_{1-6}$alkyl, and $C_{1-6}$alkyl-O—, wherein each alkyl is unsubstituted or substituted with one to three substituents selected from $R^j$, provided that when $R^4$ is: $OR^e$ or —$C_{1-6}$alkyl-O—, then Y is —$CH_2$. In another embodiment of the present invention, $R^4$ is selected from the group consisting of: hydrogen, halogen and $C_{1-6}$alkyl, wherein alkyl is unsubstituted or substituted with one to three substituents selected from $R^j$. In another embodiment of the present invention, $R^4$ is selected from the group consisting of: hydrogen and $C_{1-6}$alkyl, wherein alkyl is unsubstituted or substituted with one to three substituents selected from $R^j$. In another embodiment of the present invention, $R^4$ is —$C_{1-6}$alkyl, wherein alkyl is unsubstituted or substituted with one to three substituents selected from $R^j$. In another embodiment of the present invention, $R^4$ is hydrogen.

In another embodiment of the present invention, $R^5$ is selected from the group consisting of: hydrogen, —$C_{1-6}$alkyl and —$C_{3-6}$cycloalkyl, wherein each alkyl and cycloalkyl is unsubstituted or substituted with one to three substituents selected from $R^j$. In another embodiment of the present invention, $R^5$ is selected from the group consisting of: hydrogen and —$C_{1-6}$alkyl, wherein alkyl is unsubstituted or substituted with one to three substituents selected from $R^j$. In another embodiment of the present invention, $R^5$ is —$C_{1-6}$alkyl, wherein alkyl is unsubstituted or substituted with one to three substituents selected from $R^j$. In another embodiment of the present invention, $R^5$ is hydrogen.

In another embodiment of the present invention, $R^6$ is absent, or when present $R^6$ is selected from the group consisting of: hydrogen, —$C_{1-6}$alkyl, and —$C_{3-6}$cycloalkyl, wherein each alkyl and cycloalkyl is unsubstituted or substituted with one to three substituents selected from $R^j$. In another embodiment of the present invention, $R^6$ is absent, or when present $R^6$ is selected from the group consisting of: hydrogen and —$C_{1-6}$alkyl, wherein alkyl is unsubstituted or substituted with one to three substituents selected from $R^j$. In a class of this embodiment, $R^6$ is absent, or when present $R^6$ is —$C_{1-6}$alkyl, wherein alkyl is unsubstituted or substituted with one to three substituents selected from $R^j$. In another class of this embodiment, $R^6$ is absent, or when present $R^6$ is hydrogen. In another class of this embodiment, $R^6$ is hydrogen.

In another embodiment of the present invention, $R^7$ is —$CO_2R^8$. In a class of this embodiment, $R^7$ is —$CO_2H$.

In another embodiment of the present invention, $R^8$ is selected from the group consisting of: hydrogen, —$C_{1-6}$alkyl and —$C_{3-6}$cycloalkyl, wherein each alkyl and cycloalkyl is unsubstituted or substituted with one to three substituents selected from $R^j$. In a class of this embodiment, $R^8$ is selected from the group consisting of: hydrogen and —$C_{1-6}$alkyl, wherein alkyl is unsubstituted or substituted with one to three substituents selected from $R^j$. In another class of this embodiment, $R^8$ is —$C_{1-6}$alkyl, wherein alkyl is unsubstituted or substituted with one to three substituents selected from $R^j$. In another class of this embodiment, $R^8$ is hydrogen.

In another embodiment of the present invention, $R^9$ is selected from the group consisting of: —$C_{1-6}$alkyl-$NR^cS(O)_nR^e$, —$C_{1-6}$alkyl-$S(O)_nR^e$, —$C_{1-6}$alkyl-$S(O)_nNR^cR^d$, —$C_{1-6}$alkyl-$NR^cR^d$, —$C_{1-6}$alkyl-$C(O)NR^cR^d$, —$C_{1-6}$alkyl-$NR^cC(O)R^e$, —$C_{1-6}$alkyl-$NR^cC(O)OR^e$, —$C_{1-6}$alkyl-$NR^cC(O)NR^cR^d$, —$C_{1-6}$alkyl-heteroaryl, and —$C_{1-6}$alkyl-$C_{2-10}$cycloheteroalkyl, wherein each alkyl, cycloheteroalkyl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In another embodiment of the present invention, $R^9$ is selected from the group consisting of: —$C_{1-6}$alkyl-$NR^cS(O)_nR^e$, —$C_{1-6}$alkyl-$S(O)_nR^e$, —$C_{1-6}$alkyl-$S(O)_nNR^cR^d$, —$C_{1-6}$alkyl-$NR^cR^d$, —$C_{1-6}$alkyl-$C(O)NR^cR^d$, —$C_{1-6}$alkyl-$NR^cC(O)R^e$, —$C_{1-6}$alkyl-$NR^cC(O)OR^e$, —$C_{1-6}$alkyl-$NR^cC(O)NR^cR^d$, —$C_{1-6}$alkyl-heteroaryl, and —$C_{1-6}$alkyl-$C_{2-10}$cycloheteroalkyl, wherein each alkyl, cycloheteroalkyl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In another embodiment of the present invention, $R^9$ is selected from the group consisting of: —$C_{1-6}$alkyl-$NR^cR^d$, and —$C_{1-6}$alkyl-$C_{2-10}$ cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In a class of this embodiment, $R^9$ is selected from the group consisting of: —$C_{1-6}$alkyl-$NR^cR^d$, and —$C_{1-6}$alkyl-$C_{2-10}$ cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$.

In another embodiment of the present invention, $R^9$ is selected from the group consisting of: —$C_{1-6}$alkyl-$NR^cR^d$ and —$C_{1-6}$alkyl-$C_{2-10}$ cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$C_{1-6}$alkyl-O—$C_{1-6}$alkyl, —$S(O)_2$—$C_{1-4}$alkyl, —CN, —$OCHF_2$, —$OCF_3$, —$CF_3$, —$C_{0-6}$alkyl-$NR^cR^d$, and —$C(O)NH_2$. In another embodiment of the present invention, $R^9$ is selected from the group consisting of: —$C_{1-6}$alkyl-$NR^cR^d$, and —$C_{1-6}$alkyl-$C_{2-10}$cycloheteroalkyl, wherein each alkyl and cycloheteroalkyl is unsubstituted or substituted with one to five substituents independently selected from: —$CH_3$, —$CH_2CH_3$, F, OH, —$OCH_3$, —$CH_2OCH_3$, —$SO_2CH_3$, —CN, —$OCHF_2$, —$OCF_3$, —$CF_3$, —$C_{0-6}$alkyl-$NR^cR^d$, and —$C(O)NH_2$.

In another embodiment of the present invention, $R^9$ is selected from the group consisting of: —$CH_2NH_2$, —$CH_2NH(CH_3)$, —$CH_2NH(CH(CH_3)_2)$, —$CH_2NH(C(CH_3)_3$, —$CH_2NH(CH_2CF_3)$, —$CH(CH_3)N(CH_3)_2$, —$CH_2N(CH_3)_2$, —$CH_2N(CH_2CH_3)_2$, —$CH(CH_3)N(CH_2CH_3)_2$, —$CH(CH_3)N(CH_3)(CH_2CH_3)$, —$CH_2N(CH_3)(CH_2CH_3)$, —$CH_2N(CH_3)(CH_2CF_3)$, —$CH_2N(CH(CH_3)_2)_2$, —$CH_2N(CH_3)(CH(CH_3)_2)$, —$CH_2N(CH_2CH_3)(CH(CH_3)_2)$, —$CH(CH_3)N(CH_2CH_3)(CH(CH_3)_2)$, —$CH_2N(CH(CH_3)_2)(C(CH_3)_3)$, —$CH_2N(CH_3)(C(CH_3)_3)$, —$CH_2N(CH_2CH_3)(C(CH_3)_3)$, —$CH_2N(CH_3)(cyclopropyl)$, —$CH_2N(CH_3)(tetrahydrofuran)$, —$CH_2N(cyclopropyl)_2$, —$CH_2N(cyclopropyl)(oxetane)$, —$CH_2$-azetidine, —$CH_2$-pyrrolidine, —$CH(CH_3)$-pyrrolidine, —$(CH_2)_2$-pyrrolidine, —$CH(OCH_3)CH_2$-pyrrolidine, —$CH(CH_2OCH_3)$-pyrrolidine, —$CH_2$-piperidine, —$CH_2$-piperazine, —$CH_2$-morpholine, —$CH_2$-(4-azaspiro[2.5]octane), —$CH_2$-(3-azabicyclo[3.1.0]hexane), —$CH_2$-(3-methoxy-8-azabicyclo[3.2.1]octane), —$CH_2$-(8-azabicyclo[3.2.1]octane), —$CH_2$-(hexahydro-2H-furo[3,2-b]pyrrole), —$CH_2$-(5,6,7,8-tetrahydroimidazo[1,5-a]pyrazine), —$CH_2$-(1-oxa-7-azaspiro[4.4]nonane), —$CH_2$-(4-oxa-7-azaspiro[2.5]octane), —$CH_2$-(8-oxa-5-azaspiro[3.5]nonane), —$CH_2$-(2-oxa-5-azabicyclo[2.2.1]heptane), —$CH_2$-(2-oxa-6-azaspiro[3.4]octane), —$CH_2$-(3-oxa-8-azabicyclo[3.2.1]octane), —$CH_2$-((1s,4s)-7-azabicyclo[2.2.1]heptane), —$CH_2$-(2-oxa-5-azaspiro[3.4]octane), —$CH_2$-(5-azaspiro[3.4]octane), —$CH_2$-(2-oxa-5-azaspiro[3.4]octane), —$CH_2$-((1R,4S)-2-azabicyclo[2.2.1]heptane), —$CH_2$-(7-azabicyclo[2.2.1]heptane), —$CH_2$-(2-azabicyclo[3.1.0]hexane), —$CH_2$-(5-azaspiro[2.5]octane), —$CH_2$-(6-azaspiro[2.5]octane), —$CH_2$-(5-azaspiro[3.5]nonane), and —$CH_2$-(5-azaspiro[2.4]heptane), wherein each —$CH_2$, alkyl and cycloheteroalkyl is unsubstituted or substituted with one to five substituents independently selected from: —$C_{1-6}$alkyl, halogen, OH, —O—$C_{1-6}$alkyl, —$C_{1-6}$alkyl-O—$C_{1-6}$alkyl, —$S(O)_2$—$C_{1-4}$alkyl, —CN, —$OCHF_2$, —$OCF_3$, —$CF_3$, —$C_{0-6}$alkyl-$NR^cR^d$, and —$C(O)NH_2$.

In another embodiment of the present invention, $R^9$ is selected from the group consisting of: —$CH_2NH_2$, —$CH_2NH(CH_3)$, —$CH_2NH(CH(CH_3)_2)$, —$CH_2NH(C(CH_3)_3$, —$CH_2NH(CH_2CF_3)$, —$CH(CH_3)N(CH_3)_2$, —$CH_2N(CH_3)_2$, —$CH_2N(CH_2CH_3)_2$, —$CH(CH_3)N(CH_2CH_3)_2$, —$CH(CH_3)N(CH_3)(CH_2CH_3)$, —$CH_2N(CH_3)(CH_2CH_3)$, —$CH_2N(CH_3)(CH_2CF_3)$, —$CH_2N(CH(CH_3)_2)_2$, —$CH_2N(CH_3)(CH(CH_3)_2)$, —$CH_2N(CH_2CH_3)(CH(CH_3)_2)$, —$CH(CH_3)N(CH_2CH_3)(CH(CH_3)_2)$, —$CH_2N(CH(CH_3)_2)(C(CH_3)_3)$, —$CH_2N(CH_3)(C(CH_3)_3)$, —$CH_2N(CH_2CH_3)(C(CH_3)_3)$, —$CH_2N(CH_3)(cyclopropyl)$, —$CH_2N(CH_3)(tetrahydrofuran)$, —$CH_2N(cyclopropyl)_2$, —$CH_2N(cyclopropyl)(oxetane)$, —$CH_2$-azetidine, —$CH_2$-pyrrolidine, —$CH(CH_3)$-pyrrolidine, —$(CH_2)_2$-pyrrolidine, —$CH(OCH_3)CH_2$-pyrrolidine, —$CH(CH_2OCH_3)$-pyrrolidine, —$CH_2$-piperidine, —$CH_2$-piperazine, —$CH_2$-morpholine, —$CH_2$-(4-azaspiro[2.5]octane), —$CH_2$-(3-azabicyclo[3.1.0]hexane), —$CH_2$-(3-methoxy-8-azabicyclo[3.2.1]octane), —$CH_2$-(8-azabicyclo[3.2.1]octane), —$CH_2$-(hexahydro-2H-furo[3,2-b]pyrrole), —$CH_2$-(5,6,7,8-tetrahydroimidazo[1,5-a]pyrazine), —$CH_2$-(1-oxa-7-azaspiro[4.4]nonane), —$CH_2$-(4-oxa-7-azaspiro[2.5]octane), —$CH_2$-(8-oxa-5-azaspiro[3.5]nonane), —$CH_2$-(2-oxa-5-azabicyclo[2.2.1]heptane), —$CH_2$-(2-oxa-6-azaspiro[3.4]octane), —$CH_2$-(3-oxa-8-azabicyclo[3.2.1]octane), —$CH_2$-((1s,4s)-7-azabicyclo[2.2.1]heptane), —$CH_2$-(2-oxa-5-azaspiro[3.4]octane), —$CH_2$-(5-azaspiro[3.4]octane), —$CH_2$-(2-oxa-5-azaspiro[3.4]octane), —$CH_2$-((1R,4S)-2-azabicyclo[2.2.1]heptane), —$CH_2$-(7-azabicyclo[2.2.1]heptane), —$CH_2$-(2-azabicyclo[3.1.0]hexane), —$CH_2$-(5-azaspiro[2.5]octane), —$CH_2$-(6-azaspiro[2.5]octane), —$CH_2$-(5-azaspiro[3.5]nonane), and —$CH_2$-(5-azaspiro[2.4]heptane), wherein each alkyl and cycloheteroalkyl is unsubstituted or substituted with one to five substituents independently selected from: —$CH_3$, —$CH_2CH_3$, F, OH, —$OCH_3$, —$CH_2OCH_3$, —$SO_2CH_3$, —CN, —$OCHF_2$, —$OCF_3$, —$CF_3$, —$C_{0-6}$alkyl-$NR^cR^d$, and —$C(O)NH_2$.

In another embodiment of the present invention, $R^9$ is selected from the group consisting of: —$CH_2NH(CH(CH_3)_2)$, —$CH_2N(CH_2CH_3)_2$, —$CHN(CH_2CH_3)_2$, —$CH_2N(CH_3)(CH_2CH_3)$, —$CH_2N(CH(CH_3)_2)_2$, —$CH_2N(CH_3)(CH(CH_3)_2)$, —$CH_2N(CH_3)(C(CH_3)_3)$, —$CH_2$-pyrrolidine, —$CH_2$-piperidine, —$CH_2$-(4-azaspiro[2.5]octane), and —$CH_2$-(3-azabicyclo[3.1.0]hexane), wherein each —$CH_2$, alkyl, and cycloheteroalkyl is unsubstituted or substituted with one to five substituents independently selected from: —$C_{1-6}$alkyl, and —$CH_3$.

In another embodiment of the present invention, $R^9$ is selected from the group consisting of: —$CH_2NH(CH(CH_3)_2)$, —$CH_2N(CH_2CH_3)_2$, —$CH(CH_3)N(CH_2CH_3)_2$, —$CH_2N(CH_3)(CH_2CH_3)$, —$CH_2N(CH(CH_3)_2)_2$, —$CH_2N(CH_2CH_3)(CH(CH_3)_2)$, —$CH_2N(CH_3)(C(CH_3)_3)$, —$CH_2$-pyrrolidine, —$CH_2$-piperidine, —$CH_2$-(4-azaspiro[2.5]octane), and —$CH_2$-(3-azabicyclo[3.1.0]hexane), wherein each —$CH_2$ is unsubstituted or substituted with one to five substituents independently selected from: —$C_{1-6}$alkyl, and —$CH_3$.

In another embodiment of the present invention, $R^9$ is selected from the group consisting of: —$C_{1-6}$alkyl-$NR^cR^d$, and —$C_{1-6}$alkyl-$C_{2-5}$cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In a class of this embodiment, $R^9$ is selected from the group consisting of: —$C_{1-6}$alkyl-$NR^cR^d$, and —$C_{1-6}$alkyl-$C_{2-5}$cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$.

In another embodiment of the present invention, $R^9$ is selected from the group consisting of: —$CH_2$—$NH_2$, —$CH_2$—$NH(CH_3)$, —$CH_2$—$N(CH_3)_2$, —$CH_2$-azetidine, $CH_2$-pyrrolidine, and $CH_2$-morpholine, wherein each —$CH_2$ is unsubstituted or substituted with one to two substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$, and wherein cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In another embodiment of the present invention, $R^9$ is selected from the group consisting of: —$CH_2$—$NH_2$, —$CH_2$—$NH(CH_3)$, —$CH_2$—$N(CH_3)_2$, —$CH_2$-azetidine, $CH_2$-pyrrolidine, and $CH_2$-morpholine, wherein —$CH_2$ is unsubstituted or substituted with one to two substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$, and wherein cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In another embodiment of the present invention, $R^9$ is —$C_{1-6}$alkyl-$NR^cR^d$, wherein alkyl is unsubstituted or substituted with one to four substituents selected from —$C_{1-6}$alkyl, halogen, —$C_{0-6}$alkyl-OH, —O—$C_{1-6}$alkyl and —$CF_3$. In a class of this embodiment, $R^9$ is —$C_{1-6}$alkyl-$NR^cR^d$, wherein alkyl is unsubstituted or substituted with one to four substituents selected from —$C_{1-6}$alkyl. In another embodiment of the present invention, $R^9$ is selected from the group consisting of: —$CH_2$—$NH_2$, —$CH_2$—$NH(CH_3)$, and —$CH_2$—$N(CH_3)_2$, wherein each $CH_2$ is unsubstituted or substituted with one to four substituents selected from —$C_{1-6}$alkyl, halogen, —$C_{0-6}$alkyl-OH, —O—$C_{1-6}$alkyl and —$CF_3$. In a class of this embodiment, $R^9$ is selected from the group consisting of: —$CH_2$—$NH_2$, —$CH_2$—$NH(CH_3)$, and —$CH_2$—$N(CH_3)_2$, wherein each $CH_2$ is unsubstituted or substituted with one to four substituents selected from —$C_{1-6}$alkyl.

In another embodiment of the present invention, $R^9$ is —$C_{1-6}$alkyl-$C_{2-5}$cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In a class of this embodiment, $R^9$ is —$C_{1-6}$alkyl-$C_{2-5}$cycloheteroalkyl, wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In another embodiment of the present invention, $R^9$ is selected from the group consisting of: —$CH_2$-azetidine, $CH_2$-pyrrolidine, and $CH_2$-morpholine, wherein $CH_2$ is unsubstituted or substituted with one to two substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$, and wherein cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$. In a class of this embodiment, $R^9$ is selected from the group consisting of: —$CH_2$-azetidine, $CH_2$-pyrrolidine, and $CH_2$-morpholine, wherein $CH_2$ is unsubstituted or substituted with one to two substituents independently selected from: —$C_{1-6}$alkyl, OH, and —$S(O)_2$—$C_{1-4}$alkyl, and wherein cycloheteroalkyl is unsubstituted or substituted with one to five substituents independently selected from: —$C_{1-6}$alkyl, OH, and —$S(O)_2$—$C_{1-4}$alkyl. In another class of this embodiment, $R^9$ is selected from the group consisting of: —$CH_2$-azetidine, $CH_2$-pyrrolidine, and $CH_2$-morpholine, wherein $CH_2$ is unsubstituted or substituted with one to two substituents independently selected from: —$C_{1-6}$alkyl, OH, and —$S(O)_2$—$C_{1-4}$alkyl, and wherein cycloheteroalkyl is unsubstituted or substituted with one to four substituents independently selected from: —$C_{1-6}$alkyl, OH, and —$S(O)_2$—$C_{1-4}$alkyl.

In another embodiment of the present invention, $R^a$ is selected from the group consisting of: —$C_{1-6}$alkyl, halogen, —$OR^e$, —$C(O)R^e$, —$OC(O)R^e$, —$CO_2R^e$, —CN, —$CF_3$, —$OCF_3$, and —$OCHF_2$, wherein each alkyl is unsubstituted or substituted with one to four substituents selected from —$C_{1-6}$alkyl, halogen, —$C_{0-6}$alkyl-OH, —O—$C_{1-6}$alkyl and —$CF_3$. In another embodiment of the present invention, $R^a$ is selected from the group consisting of: —$C_{1-6}$alkyl, halogen, —$OR^e$, —CN, —$CF_3$, —$OCF_3$, and —$OCHF_2$, wherein each alkyl is unsubstituted or substituted with one to four substituents selected from —$C_{1-6}$alkyl, halogen, —$C_{1-6}$alkyl-OH, —O—$C_{1-6}$alkyl and —$CF_3$. In another embodiment of the present invention, $R^a$ is selected from the group consisting of: —$C_{1-6}$alkyl, and halogen, wherein alkyl is unsubstituted or substituted with one to four substituents selected from —$C_{1-6}$alkyl, halogen, —$C_{0-6}$alkyl-OH, —O—$C_{1-6}$alkyl and —$CF_3$. In another embodiment of the present invention, $R^a$ is —$C_{1-6}$alkyl, wherein alkyl is unsubstituted or substituted with one to four substituents selected from —$C_{1-6}$alkyl, halogen, —$C_{0-6}$alkyl-OH, —O—$C_{1-6}$alkyl and —$CF_3$. In another embodiment of the present invention, $R^a$ is halogen. In a class of this embodiment, $R^a$ is F.

In another embodiment of the present invention, $R^b$ is independently selected from the group consisting of: —$C_{1-10}$alkyl, —$C_{2-10}$alkenyl, —$CF_3$, halogen, —CN, —OH, —$OC_{1-10}$alkyl, —$OC_{2-10}$alkenyl, —$O(CH_2)_pOC_{1-10}$alkyl, —$O(CH_2)_pNR^cS(O)_mR^e$, —$O(CH_2)_pS(O)_mR^e$, —$O(CH_2)_pS(O)_mNR^cR^d$, —$O(CH_2)_pNR^cR^d$, —$C(O)R^e$, —$OC(O)R^e$, —$CO_2R^e$, —$C(O)NR^cR^d$, —$NR^cC(O)R^e$, —$NR^cC(O)OR^e$, —$NR^cC(O)NR^cR^d$, —$OCF_3$, and —$OCHF_2$, wherein each CH, $CH_2$, alkyl and alkenyl is unsubstituted or substituted with one to four substituents selected from: —$C_{1-6}$alkyl, halogen, —O—$C_{1-6}$alkyl and —$CF_3$. In another embodiment of the present invention, $R^b$ is independently selected from the group consisting of: —$C_{1-10}$alkyl, —$C_{2-10}$alkenyl, —$CF_3$, halogen, —CN, —OH, —$OC_{1-10}$alkyl, —$OC_{2-10}$alkenyl, —$O(CH_2)_pOC_{1-10}$alkyl, —$O(CH_2)_pNR^cR^d$, —$C(O)R^e$, —$OC(O)R^e$, —$CO_2R^e$, —$OCF_3$, and —$OCHF_2$, wherein each CH, $CH_2$, alkyl and alkenyl is unsubstituted or substituted with one to four substituents selected from: —$C_{1-6}$alkyl, halogen, —O—$C_{1-6}$alkyl and —$CF_3$.

In another embodiment of the present invention, $R^b$ is independently selected from the group consisting of: —$C_{1-10}$alkyl, —$CF_3$, halogen, —CN, —OH, —$OC_{1-10}$alkyl, —$OCF_3$, and —$OCHF_2$, wherein each CH and alkyl is unsubstituted or substituted with one to four substituents selected from: —$C_{1-6}$alkyl, halogen, —O—$C_{1-6}$alkyl and —$CF_3$. In another embodiment of the present invention, $R^b$ is independently selected from the group consisting of: halogen, and —$OC_{1-10}$alkyl, wherein alkyl is unsubstituted or substituted with one to four substituents selected from: —$C_{1-6}$alkyl, halogen, —O—$C_{1-6}$alkyl and —$CF_3$. In a class of this embodiment, $R^b$ is independently selected from the group consisting of: F and —$OCH_3$.

In another embodiment of the present invention, $R^b$ is independently selected from the group consisting of: —$C_{1-10}$alkyl, halogen, —CN, —OH and —$OC_{1-10}$alkyl, wherein each alkyl is unsubstituted or substituted with one to five substituents selected from: —$C_{1-6}$alkyl, halogen, —O—$C_{1-6}$alkyl and —$CF_3$. In a class of this embodiment of the present invention, $R^b$ is independently selected from the group consisting of: —$CH_2CH_3$, F, Cl, —CN, —OH, —$OCH_3$ and —$OCH_2CH_3$.

In another embodiment of the present invention, $R^b$ is independently selected from the group consisting of: halogen, —CN, —OH, and —$OC_{1-10}$alkyl, wherein each alkyl is unsubstituted or substituted with one to five substituents selected from: —$C_{1-6}$alkyl, halogen, —O—$C_{1-6}$alkyl and —$CF_3$. In a class of embodiment of the present invention, $R^b$ is independently selected from the group consisting of: halogen, —CN, —OH, and —$OC_{1-10}$alkyl. In another class of this embodiment of the present invention, $R^b$ is independently selected from the group consisting of: F, Cl, —CN, —OH, —$OCH_3$ and —$OCH_2CH_3$. In another class of this embodiment of the present invention, $R^b$ is independently selected from the group consisting of: F, —CN, —OH and —$OCH_3$.

In another embodiment of the present invention, $R^c$ and $R^d$ are each independently selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are each independently selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^c$ and $R^d$ are each independently selected from the group consisting of: hydrogen and $C_{1-10}$alkyl, wherein each alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are each independently selected from the group consisting of: hydrogen and $C_{1-10}$alkyl, wherein each alkyl is unsubstituted or substituted with one to three substituents independently selected from $R^f$. In another class of this embodiment, $R^c$ and $R^d$ are each independently selected from the group consisting of: hydrogen and $C_{1-10}$alkyl.

In another embodiment of the present invention, $R^c$ and $R^d$ are each —$C_{1-10}$alkyl, wherein alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are —$C_{1-10}$alkyl, wherein alkyl is unsubstituted or substituted with one to three substituents independently selected from $R^f$. In another class of this embodiment, $R^c$ and $R^d$ are —$C_{1-10}$alkyl. In another embodiment of the present invention, $R^c$ and $R^d$ are hydrogen.

In another embodiment of the present invention, $R^c$ and $R^d$ are each independently selected from the group consisting of: hydrogen, $C_{1-10}$alkyl, $C_{3-6}$cycloalkyl and $C_{2-5}$cycloheteroalkyl, wherein each alkyl, cycloalkyl and cycloheteroalkyl is unsubstituted or substituted with one to three substituents independently selected from $R^f$. In a class of this embodiment, $R^c$ and $R^d$ are each independently selected from the group consisting of: hydrogen, —$CH_3$, —$CH_2CH_3$, —$CH(CH_3)_2$, —$C(CH_3)_3$, cyclopropyl, tetrahydrofuran and oxetane, wherein each alkyl, cycloalkyl, and cycloheteroalkyl is unsubstituted or substituted with one to three substituents independently selected from $R^f$. In another class of this embodiment, $R^c$ and $R^d$ are each independently selected from the group consisting of: hydrogen, —$CH_3$, —$CH_2CH_3$, —$CH(CH_3)_2$, —$C(CH_3)_3$, cyclopropyl, tetrahydrofuran and oxetane.

In another embodiment of the present invention, $R^c$ and $R^d$ are each independently selected from the group consisting of: hydrogen and $C_{1-10}$alkyl, wherein each alkyl is unsubstituted or substituted with one to three substituents independently selected from $R^f$. In a class of this embodiment of the present invention, $R^c$ and $R^d$ are each independently selected from the group consisting of: hydrogen and $C_{1-10}$alkyl, wherein each alkyl is unsubstituted or substituted with one to three substituents independently selected from $R^f$. In another class of this embodiment of the present invention, $R^c$ and $R^d$ are each independently selected from the group consisting of: hydrogen, —$CH_3$, —$CH_2CH_3$, —$CH(CH_3)_2$, and —$C(CH_3)_3$.

In another embodiment of the present invention, $R^c$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl- $C_{1-10}$alkyl-, aryl, heteroaryl, aryl-$C_{1-10}$alkyl-, and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^c$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^c$ is selected from the group consisting of: hydrogen and $C_{1-10}$alkyl, wherein alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is selected from the group consisting of: hydrogen and $C_{1-10}$alkyl, wherein alkyl is unsubstituted or substituted with one to three substituents independently selected from $R^f$. In another class of this embodiment, $R^c$ is selected from the group consisting of: hydrogen and $C_{1-10}$alkyl.

In another embodiment of the present invention, $R^c$ is —$C_{1-10}$alkyl, wherein alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is —$C_{1-10}$alkyl, wherein alkyl is unsubstituted or substituted with one to three substituents independently selected from $R^f$. In another class of this embodiment, $R^c$ is —$C_{1-10}$alkyl. In another embodiment of the present invention, $R^c$ is hydrogen.

In another embodiment of the present invention, $R^c$ is selected from the group consisting of: hydrogen, $C_{1-10}$alkyl, $C_{3-6}$cycloalkyl and $C_{2-5}$cycloheteroalkyl, wherein each alkyl, cycloalkyl and cycloheteroalkyl is unsubstituted or substituted with one to three substituents independently selected from $R^f$. In a class of this embodiment, $R^c$ is selected from the group consisting of: hydrogen, —$CH_3$, —$CH_2CH_3$, —$CH(CH_3)_2$, —$C(CH_3)_3$, cyclopropyl, tetrahydrofuran and oxetane, wherein each alkyl, cycloalkyl, and cycloheteroalkyl is unsubstituted or substituted with one to three substituents independently selected from $R^f$. In another class of this embodiment, $R^c$ is selected from the group consisting of: hydrogen, —$CH_3$, —$CH_2CH_3$, —$CH(CH_3)_2$, —$C(CH_3)_3$, cyclopropyl, tetrahydrofuran and oxetane.

In another embodiment of the present invention, $R^c$ is selected from the group consisting of: hydrogen and $C_{1-10}$alkyl, wherein each alkyl is unsubstituted or substituted with one to three substituents independently selected from $R^f$. In a class of this embodiment of the present invention, $R^c$ is selected from the group consisting of: hydrogen and $C_{1-10}$alkyl, wherein each alkyl is unsubstituted or substituted with one to three substituents independently selected from $R^f$. In another class of this embodiment of the present invention, $R^c$ is selected from the group consisting of: hydrogen, —$CH_3$, —$CH_2CH_3$, —$CH(CH_3)_2$, and —$C(CH_3)_3$.

In another embodiment of the present invention, $R^d$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In another embodiment of the present invention, $R^d$ is independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$. In another embodiment of the present invention, $R^d$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^d$ is selected from the group consisting of: hydrogen and $C_{1-10}$alkyl, wherein alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is selected from the group consisting of: hydrogen and $C_{1-10}$alkyl, wherein alkyl is unsubstituted or substituted with one to three substituents independently selected from $R^f$. In another class of this embodiment, $R^d$ is selected from the group consisting of: hydrogen and $C_{1-10}$alkyl.

In another class of this embodiment, $R^d$ is —$C_{1-10}$alkyl, wherein alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is —$C_{1-10}$alkyl, wherein alkyl is unsubstituted or substituted with one to three substituents independently selected from $R^f$. In another class of this embodiment, $R^d$ is —$C_{1-10}$alkyl. In another embodiment of the present invention, $R^d$ is hydrogen.

In another embodiment of the present invention, $R^d$ is selected from the group consisting of: hydrogen, $C_{1-10}$alkyl, $C_{3-6}$cycloalkyl and $C_{2-5}$cycloheteroalkyl, wherein each alkyl, cycloalkyl and cycloheteroalkyl is unsubstituted or substituted with one to three substituents independently selected from $R^f$. In a class of this embodiment, $R^d$ is selected from the group consisting of: hydrogen, —$CH_3$, —$CH_2CH_3$, —$CH(CH_3)_2$, —$C(CH_3)_3$, cyclopropyl, tetrahydrofuran and oxetane, wherein each alkyl, cycloalkyl, and cycloheteroalkyl is unsubstituted or substituted with one to three substituents independently selected from $R^f$. In another class of this embodiment, $R^d$ is selected from the group consisting of: hydrogen, —$CH_3$, —$CH_2CH_3$, —$CH(CH_3)_2$, —$C(CH_3)_3$, cyclopropyl, tetrahydrofuran and oxetane.

In another embodiment of the present invention, $R^d$ is selected from the group consisting of: hydrogen and $C_{1-10}$alkyl, wherein each alkyl is unsubstituted or substituted with one to three substituents independently selected from $R^f$. In a class of this embodiment of the present invention, $R^d$ is selected from the group consisting of: hydrogen and $C_{1-10}$alkyl, wherein each alkyl is unsubstituted or substituted with one to three substituents independently selected from $R^f$. In another class of this embodiment of the present invention, $R^d$ is selected from the group consisting of: hydrogen, —$CH_3$, —$CH_2CH_3$, —$CH(CH_3)_2$, and —$C(CH_3)_3$.

In another embodiment of the present invention, each $R^e$ is independently selected from the group consisting of: hydrogen, —$C_{1-10}$alkyl, —$C_{2-10}$alkenyl, aryl, aryl-$C_{1-10}$alkyl-, heteroaryl and heteroaryl-$C_{1-10}$alkyl-, wherein each alkyl, alkenyl, aryl and heteroaryl is unsubstituted or substituted with one to three substituents selected from $R^h$. In another embodiment of the present invention, each $R^e$ is independently selected from the group consisting of: hydrogen, and —$C_{1-10}$alkyl, wherein alkyl is unsubstituted or substituted with one to three substituents selected from $R^h$. In another embodiment of the present invention, each $R^e$ is —$C_{1-10}$alkyl-, wherein each alkyl is unsubstituted or substituted with one to three substituents selected from $R^h$. In another embodiment of the present invention, each $R^e$ is hydrogen.

In another embodiment of the present invention, each $R^f$ is selected from the group consisting of: halogen, —$C_{1-10}$alkyl, —$C_{0-6}$alkyl-OH, —O—$C_{1-6}$alkyl, oxo, —$S(O)_m$—$C_{1-4}$alkyl, —CN, —$CF_3$, —$OCHF_2$, and —$OCF_3$, wherein each alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is selected from the group consisting of: halogen, —$C_{1-10}$alkyl, —$C_{0-6}$alkyl-OH, and —$S(O)_m$—$C_{1-4}$alkyl, wherein each alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is selected from the group consisting of: —$C_{0-6}$alkyl-OH, and —$S(O)_m$—$C_{1-4}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^f$ is selected from the group consisting of: —OH, and —$S(O)_2CH_3$. In another embodiment of the present invention, $R^f$ is —$C_{0-6}$alkyl-OH, wherein alkyl is unsubstituted or substituted with one to three substituents independently selected from: —OH, halogen, $C_{1-6}$alkyl, cyano and $S(O)_2C_{1-6}$alkyl. In a class of this embodiment, $R^f$ is —OH. In another embodiment of the present invention, $R^f$ is —$S(O)_m$—$C_{1-4}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, $R^f$ is —$S(O)_2CH_3$.

In another embodiment of the present invention, each $R^f$ is selected from the group consisting of: $C_{1-10}$alkyl, —$CF_3$, —$C_{0-6}$alkyl-OH, and —$S(O)_m$—$C_{1-4}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^f$ is selected from the group consisting of: —$CH_3$, —$CF_3$, —OH, and —$S(O)_2CH_3$.

In another embodiment, each $R^f$ is selected from the group consisting of: $C_{1-10}$alkyl and —$CF_3$, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^f$ is selected from the group consisting of: —$CH_3$, and —$CF_3$.

In another embodiment of the present invention, each $R^g$ is selected from the group consisting of: hydrogen and —$C_{1-10}$alkyl, wherein alkyl is unsubstituted or substituted with one to five halogens. In another embodiment of the present invention, each $R^g$ is —$C_{1-10}$alkyl, wherein alkyl is unsubstituted or substituted with one to five halogens. In another embodiment of the present invention, $R^g$ is hydrogen.

In another embodiment of the present invention, each $R^h$ is selected from the group consisting of: halogen, $C_{1-10}$alkyl, —OH, —O—$C_{1-4}$alkyl, —CN, —$CF_3$, —$OCHF_2$ and —$OCF_3$, wherein each alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is selected from the group consisting of: halogen and $C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In a class of this embodiment, $R^h$ is —$C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another class of this embodiment, each $R^h$ is halogen.

In another embodiment of the present invention, each $R^i$ is selected from the group consisting of: —$C_{1-6}$alkyl, —OR$^e$, —NR$^c$S(O)$_m$R$^e$, halogen, —S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)R$^e$, —NR$^c$C(O)NR$^c$R$^d$, —CF$_3$, —OCF$_3$ and —OCHF$_2$. In another embodiment of the present invention, each R$^i$ is selected from the group consisting of: —C$_{1-6}$alkyl, —OR$^e$, —NR$^c$S(O)$_m$R$^e$, halogen, —NR$^c$R$^d$, —C(O)R$^e$, —OC(O)R$^e$, —CO$_2$R$^e$, —CN, —CF$_3$, —OCF$_3$ and —OCHF$_2$. In another embodiment of the present invention, each R$^i$ is selected from the group consisting of: —C$_{1-6}$alkyl, —OR$^e$, and halogen. In another embodiment of the present invention, each R$^i$ is selected from the group consisting of: —C$_{1-6}$alkyl and halogen. In another embodiment of the present invention, R$^i$ is —C$_{1-6}$alkyl.

In another embodiment of the present invention, each R$^j$ is selected from the group consisting of: —C$_{1-6}$alkyl, —OR$^e$, —NR$^c$S(O)$_m$R$^e$, halogen, —S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$ and —OCHF$_2$. In another embodiment of the present invention, each R$^j$ is selected from the group consisting of: —C$_{1-6}$alkyl, —OR$^e$, halogen, —NR$^c$R$^d$, —C(O)R$^e$, —OC(O)R$^e$, —CO$_2$R$^e$, —CN, —CF$_3$, —OCF$_3$, and —OCHF$_2$. In another embodiment of the present invention, each R$^j$ is selected from the group consisting of: —C$_{1-6}$alkyl, —OR$^e$, and halogen. In another embodiment of the present invention, each R$^j$ is selected from the group consisting of: —C$_{1-6}$alkyl and halogen. In another embodiment of the present invention, R$^j$ is —C$_{1-6}$alkyl.

In another embodiment of the present invention, R$^k$ is selected from the group consisting of: hydrogen, —C$_{1-6}$alkyl, —CF$_3$ and —CHF$_2$, wherein each alkyl is unsubstituted or substituted with one to three substituents independently selected from: —OH, —OC$_{1-6}$alkyl, halogen, cyano, and —S(O)$_2$C$_{1-6}$alkyl. In another embodiment of the present invention, R$^k$ is selected from the group consisting of: hydrogen and —C$_{1-6}$ alkyl, wherein alkyl is unsubstituted or substituted with one to three substituents independently selected from: —OH, —OC$_{1-6}$alkyl, halogen, cyano, and —S(O)$_2$C$_{1-6}$alkyl. In another embodiment of the present invention, R$^k$ is —C$_{1-6}$ alkyl, wherein alkyl is unsubstituted or substituted with one to three substituents independently selected from: —OH, —OC$_{1-6}$alkyl, halogen, cyano, and —S(O)$_2$C$_{1-6}$alkyl. In another embodiment of the present invention, R$^k$ is hydrogen.

In another embodiment of the present invention, each R$^L$ is independently selected from the group consisting of: —CO$_2$C$_{1-6}$alkyl, —C$_{1-10}$alkyl, —C$_{2-10}$ alkenyl, —C$_{2-10}$ alkynyl and —C$_{3-6}$cycloalkyl, wherein each alkyl, alkenyl, alkynyl, and cycloalkyl is unsubstituted or substituted with 1-4 substituents selected from C$_{1-6}$alkyl, halogen, and —OC$_{1-6}$alkyl. In another embodiment of the present invention, each R$^L$ is independently selected from the group consisting of: —C$_{1-10}$alkyl, and —C$_{3-6}$cycloalkyl, wherein each alkyl and cycloalkyl is unsubstituted or substituted with 1-4 substituents selected from C$_{1-6}$alkyl, halogen, and —OC$_{1-6}$alkyl. In a class of this embodiment, each R$^L$ is independently selected from the group consisting of: —CH$_3$, and cyclopropyl, wherein —CH$_3$ and cyclopropyl is unsubstituted or substituted with 1-4 substituents selected from C$_{1-6}$alkyl, halogen, and —OC$_{1-6}$alkyl. In another class of this embodiment, each R$^L$ is independently selected from the group consisting of: —CH$_3$, and cyclopropyl. In another embodiment of the present invention, R$^L$ is —C$_{1-10}$alkyl, wherein alkyl is unsubstituted or substituted with one to four substituents selected from C$_{1-6}$alkyl, halogen, and —OC$_{1-6}$alkyl. In a class of this embodiment, R$^L$ is —CH$_3$, wherein —CH$_3$ is unsubstituted or substituted with one to three substituents selected from C$_{1-6}$alkyl, halogen, and —OC$_{1-6}$alkyl. In another class of this embodiment, R$^L$ is —CH$_3$. In another embodiment of the present invention, R$^L$ is —C$_{3-6}$cycloalkyl, wherein cycloalkyl is unsubstituted or substituted with one to four substituents selected from C$_{1-6}$alkyl, halogen, and —OC$_{1-6}$alkyl. In a class of this embodiment, R$^L$ is cyclopropyl, wherein cyclopropyl is unsubstituted or substituted with one to four substituents selected from C$_{1-6}$alkyl, halogen, and —OC$_{1-6}$alkyl. In another class of this embodiment, R$^L$ is cyclopropyl.

In another embodiment of the present invention, each R$^L$ is independently selected from the group consisting of: —CH$_3$, cyclopropyl, and cyclobutyl, wherein each alkyl and cycloalkyl is unsubstituted or substituted with 1-4 substituents selected from C$_{1-6}$alkyl, halogen, and —OC$_{1-6}$alkyl. In another embodiment of the present invention, each R$^L$ is independently selected from the group consisting of: —CH$_3$, cyclopropyl, and cyclobutyl. In a class of this embodiment of the present invention, each R$^L$ is cyclobutyl.

In another embodiment of the present invention, each R$^m$ is independently selected from the group consisting of: —C$_{1-10}$alkyl, —C$_{2-10}$ alkenyl, —C$_{3-6}$ cycloalkyl, —C$_{2-5}$cycloheteroalkyl, aryl and heteroaryl. In another embodiment of the present invention, each R$^m$ is independently selected from the group consisting of: —C$_{1-10}$alkyl and —C$_{2-10}$ alkenyl. In another embodiment of the present invention, each R$^m$ is —C$_{1-10}$alkyl.

In another embodiment of the present invention, n is 0, 1 or 2. In a class of this embodiment, n is 0 or 1. In another class of this embodiment, n is 1 or 2. In another class of this embodiment, n is 0. In another class of this embodiment, n is 1. In another class of this embodiment, n is 2.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, each p is independently selected from: 0, 1, 2, 3, 4, 5 or 6. In another embodiment of the present invention, p is 0, 1, 2, 3 or 4. In a class of this embodiment, p is 0, 1, 2 or 3. In a class of this embodiment, p is 0, 1 or 2. In another embodiment of the present invention, p is 1, 2, 3 or 4. In a class of this embodiment, p is 1, 2 or 3. In another class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6.

In another embodiment of the present invention, each r is independently selected from: 0, 1, 2 or 3. In a class of this embodiment, r is 0, 1 or 2. In another class of this embodiment, r is 1, 2 or 3. In a class of this embodiment, r is 1 or 2. In another class of this embodiment, r is 0 or 1. In another class of this embodiment, r is 0 or 2. In another class of this embodiment, r is 0 or 1. In another class of this embodiment, r is 1 or 3. In another class of this embodiment, r is 2 or 3. In another class of this embodiment, r is 0 or 2. In another class of this embodiment, r is 0. In another class of this embodiment, r is 1. In another class of this embodiment, r is 2. In another class of this embodiment, r is 3.

In another embodiment of the present invention, the invention relates to compounds of structural formula Ia:

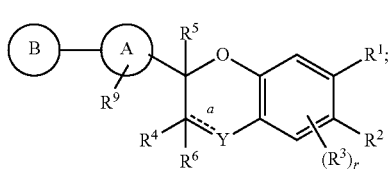

Ia or a pharmaceutically acceptable salt thereof.

In another embodiment of the present invention, the invention relates to compounds of structural formula Ib:

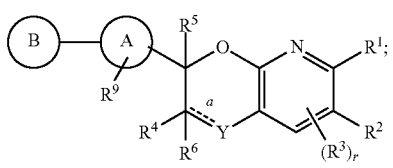

Ib or a pharmaceutically acceptable salt thereof.

In another embodiment of the present invention, the invention relates to compounds of structural formula Ic:

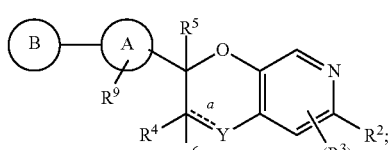

Ic or a pharmaceutically acceptable salt thereof.

In another embodiment of the present invention, the invention relates to compounds of structural formula Id:

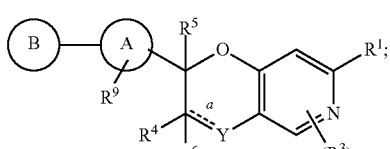

Id or a pharmaceutically acceptable salt thereof.

In another embodiment of the present invention, the invention relates to compounds of structural formula Ie:

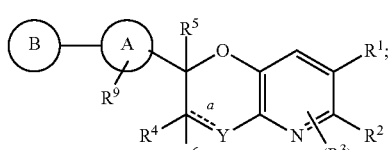

Ie or a pharmaceutically acceptable salt thereof.

In another embodiment of the present invention, the invention relates to compounds of structural formula If:

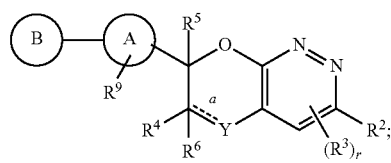

If or a pharmaceutically acceptable salt thereof.

In another embodiment of the present invention, the invention relates to compounds of structural formula Ig:

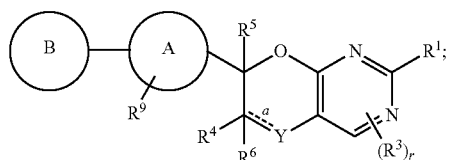

Ig or a pharmaceutically acceptable salt thereof.

In another embodiment of the present invention, the invention relates to compounds of structural formula Ih:

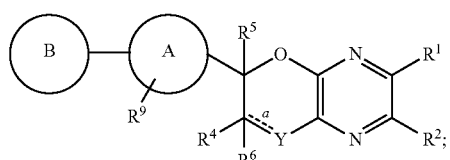

Ih or a pharmaceutically acceptable salt thereof.

In another embodiment of the present invention, the invention relates to compounds of structural formula Ii:

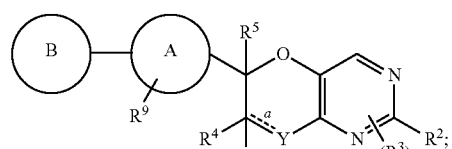

Ii or a pharmaceutically acceptable salt thereof.

In another embodiment of the present invention, the invention relates to compounds of structural formula Ij:

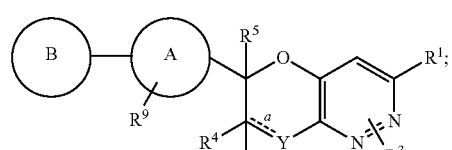

Ij or a pharmaceutically acceptable salt thereof.

In another embodiment of the present invention, the invention relates to compounds of structural formula Ik:

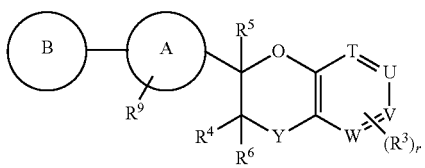

or a pharmaceutically acceptable salt thereof.

In another embodiment of the present invention, the invention relates to compounds of structural formula Il:

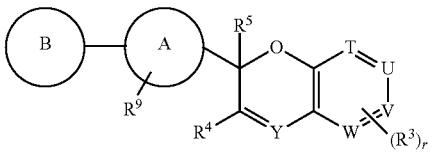

or a pharmaceutically acceptable salt thereof.

In another embodiment of the present invention, the invention relates to compounds of structural formula Im:

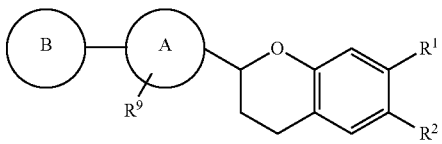

or a pharmaceutically acceptable salt thereof.

In another embodiment of the present invention, the invention relates to compounds of structural formula In:

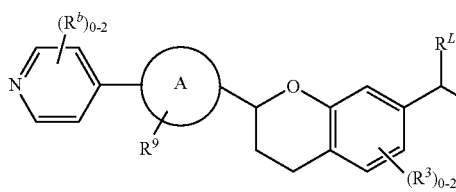

or a pharmaceutically acceptable salt thereof.

In another embodiment of the present invention, the invention relates to compounds of structural formula Io:

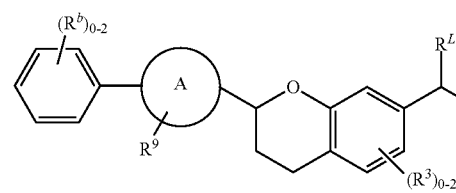

or a pharmaceutically acceptable salt thereof.

The compound of structural formula I includes the compounds of structural formulas Ia, Ib, Ic, Id, Ie, If, Ig, Ih, Ii, Ij, Ik, Il, Im, In and Io, and pharmaceutically acceptable salts, hydrates and solvates thereof.

Another embodiment of the present invention relates to compounds of structural Formula Ik:

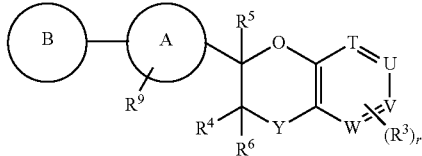

wherein
T is CH;
U is $CR^1$;
V is $CR^2$;
W is CH;
Y is selected from the group consisting of: —$CR^gR^g$;
A is selected from the group consisting of: aryl and heteroaryl, wherein each aryl and heteroaryl is unsubstituted or substituted with one to five substituents selected from $R^a$;
B is selected from the group consisting of:
  (1) aryl, and
  (2) heteroaryl,
wherein each aryl and heteroaryl is unsubstituted or substituted with one to five substituents selected from $R^b$;
$R^1$ and $R^2$ are each independently selected from:
  (1) hydrogen, and
  (2) —$C_{1-6}$alkyl,
wherein one of $R^1$ and $R^2$ is —$C_{1-6}$alkyl substituted with $R^7$, and wherein alkyl is unsubstituted or substituted with one to three substituents independently selected from $R^L$;
$R^3$ is hydrogen;
$R^4$ is hydrogen;
$R^5$ is hydrogen;
$R^6$ is hydrogen;
$R^7$ is —$CO_2R^8$;
$R^8$ is hydrogen;
$R^9$ is selected from the group consisting of:
  (1) —$C_{1-6}$alkyl-$NR^cR^d$, and
  (2) —$C_{1-6}$alkyl-$C_{2-5}$cycloheteroalkyl,
wherein alkyl is unsubstituted or substituted with one to four substituents selected from —$C_{1-6}$alkyl, halogen, —$C_{0-6}$alkyl-OH, —O—$C_{1-6}$alkyl and —$CF_3$, and wherein cycloheteroalkyl is unsubstituted or substituted with one to three substituents selected from $R^f$;
r is 0, 1, 2 or 3; and
$R^a$, $R^b$, $R^c$, $R^d$, $R^e$, $R^f$, $R^g$, $R^h$, $R^i$, $R^j$, $R^k$, $R^L$, $R^m$, n, m, and p are as defined above;
or a pharmaceutically acceptable salt thereof.

Another embodiment of the present invention relates to compounds of structural Formula Ik:

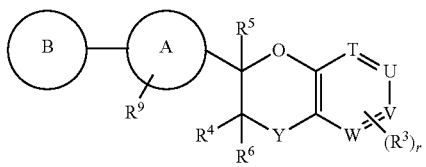

wherein
T is CH;
U is CR$^1$;
V is CH;
W is CH;
Y is —CH$_2$;
A is selected from the group consisting of: phenyl and pyridine, wherein each phenyl and pyridine is unsubstituted or substituted with one to three substituents selected from R$^a$;
B is selected from the group consisting of:
  (1) phenyl, and
  (2) pyridine,
wherein phenyl and pyridine is unsubstituted or substituted with one to five substituents selected from R$^b$;
R$^1$ is —C$_{1-6}$alkyl, wherein alkyl is unsubstituted or substituted with one to three substituents selected from R$^L$, and wherein R$^1$ is substituted with R$^7$;
R$^2$ is hydrogen;
R$^3$ is hydrogen;
R$^4$ is hydrogen;
R$^5$ is hydrogen;
R$^6$ is hydrogen;
R$^7$ is —CO$_2$R$^8$;
R$^8$ is hydrogen;
R$^9$ is selected from the group consisting of:
  (1) —CH$_2$—NH$_2$,
  (2) —CH$_2$—NH(CH$_3$),
  (3) —CH$_2$—N(CH$_3$)$_2$,
  (4) —CH$_2$-azetidine,
  (5) —CH$_2$-pyrrolidine, and
  (6) —CH$_2$-morpholine,
wherein —CH$_2$ is unsubstituted or substituted with one to two substituents selected from: —C$_{1-6}$alkyl, halogen, OH, —O—C$_{1-6}$alkyl, —S(O)$_2$—C$_{1-4}$alkyl, —CN, —OCHF$_2$, —OCF$_3$, —CF$_3$, and —C$_{0-6}$alkyl-NR$^c$R$^d$, and wherein cycloheteroalkyl is unsubstituted or substituted with one to four substituents selected from: —C$_{1-6}$alkyl, halogen, OH, —O—C$_{1-6}$alkyl, —S(O)$_2$—C$_{1-4}$alkyl, —CN, —OCHF$_2$, —OCF$_3$, —CF$_3$, and —C$_{0-6}$alkyl-NR$^c$R$^d$; and
r is 0, 1 or 2; and
R$^a$, R$^b$, R$^c$, R$^d$, R$^e$, R$^f$, R$^g$, R$^h$, R$^i$, R$^j$, R$^k$, R$^L$, R$^m$, n, m, and p are as defined above;
or a pharmaceutically acceptable salt thereof.

Another embodiment of the present invention relates to compounds of structural Formula Ik:

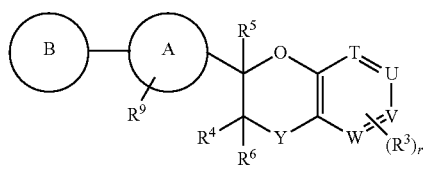

Ik wherein
T is CH;
U is CR$^1$;
V is CR$^2$;
W is CH;
Y is —CR$^g$R$^g$;
A is selected from the group consisting of:
  (1) aryl, and
  (2) heteroaryl,
wherein each aryl and heteroaryl is unsubstituted or substituted with one to five substituents selected from R$^a$;
B is selected from the group consisting of:
  (1) aryl, and
  (2) heteroaryl,
wherein each aryl and heteroaryl is unsubstituted or substituted with one to five substituents selected from R$^b$;
R$^1$ and R$^2$ are each independently selected from:
  (1) hydrogen, and
  (2) —C$_{1-6}$alkyl,
wherein each alkyl is substituted with one to three substituents selected from R$^L$, and wherein one of R$^1$ and R$^2$ is substituted with R$^7$;
R$^3$ is selected from the group consisting of:
  (1) hydrogen, and
  (2) halogen;
R$^4$ is hydrogen;
R$^5$ is hydrogen;
R$^6$ is hydrogen;
R$^7$ is —CO$_2$R$^8$;
R$^8$ is hydrogen;
R$^9$ is selected from the group consisting of:
  (1) —C$_{1-6}$alkyl-NR$^c$R$^d$, and
  (2) —C$_{1-6}$alkyl-C$_{2-10}$cycloheteroalkyl,
wherein each alkyl and cycloheteroalkyl is unsubstituted or substituted with one to five substituents independently selected from: —C$_{1-6}$alkyl, halogen, OH, —O—C$_{1-6}$alkyl, —C$_{1-6}$alkyl-O—C$_{1-6}$alkyl, —S(O)$_2$—C$_{1-4}$alkyl, —CN, —OCHF$_2$, —OCF$_3$, —CF$_3$, —C$_{0-6}$alkyl-NR$^c$R$^d$, and —C(O)NH$_2$;
R$^g$ is hydrogen; and
r is 0, 1, 2 or 3;
or a pharmaceutically acceptable salt thereof.

Another embodiment of the present invention relates to compounds of structural Formula Ik:

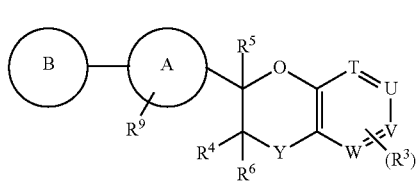

Ik wherein
T is CH;
U is CR$^1$;
V is CH;
W is CH;
Y is —CH$_2$;
A is selected from the group consisting of:
  (1) phenyl, and
  (2) pyridine,
wherein each phenyl and pyridine is unsubstituted or substituted with one to three substituents selected from R$^a$;
B is heteroaryl, wherein heteroaryl is unsubstituted or substituted with one to five substituents selected from R$^b$;
R$^1$ is —C$_{1-6}$alkyl, wherein alkyl is substituted with one to three substituents selected from R$^L$, and wherein alkyl is substituted with one substituent selected from R$^7$;
R$^3$ is hydrogen;
R$^4$ is hydrogen;
R$^5$ is hydrogen;
R$^6$ is hydrogen;
R$^7$ is —CO$_2$R$^8$;
R$^8$ is hydrogen;

$R^9$ is selected from the group consisting of:
(1) —CH$_2$NH(CH(CH$_3$)$_2$),
(2) —CH$_2$N(CH$_2$CH$_3$)$_2$,
(3) —CH$_2$N(CH$_2$CH$_3$)$_2$,
(4) —CH$_2$N(CH$_3$)(CH$_2$CH$_3$),
(5) —CH$_2$N(CH(CH$_3$)$_2$)$_2$,
(6) —CH$_2$N(CH$_2$CH$_3$)(CH(CH$_3$)$_2$),
(7) —CH$_2$N(CH$_3$)(C(CH$_3$)$_3$),
(8) —CH$_2$-pyrrolidine,
(9) —CH$_2$-piperidine,
(10) —CH$_2$-(4-azaspiro[2.5]octane), and
(11) —CH$_2$-(3-azabicyclo[3.1.0]hexane),
wherein each —CH$_2$, alkyl, and cycloheteroalkyl is unsubstituted or substituted with one to five substituents independently selected from: —C$_{1-6}$alkyl, and —CH$_3$;
r is 0 or 1;
or a pharmaceutically acceptable salt thereof.

Illustrative, but non-limiting, examples of the compounds of the present invention that are useful as agonists of G-protein-coupled receptor 40 (GPR40) are the following compounds:

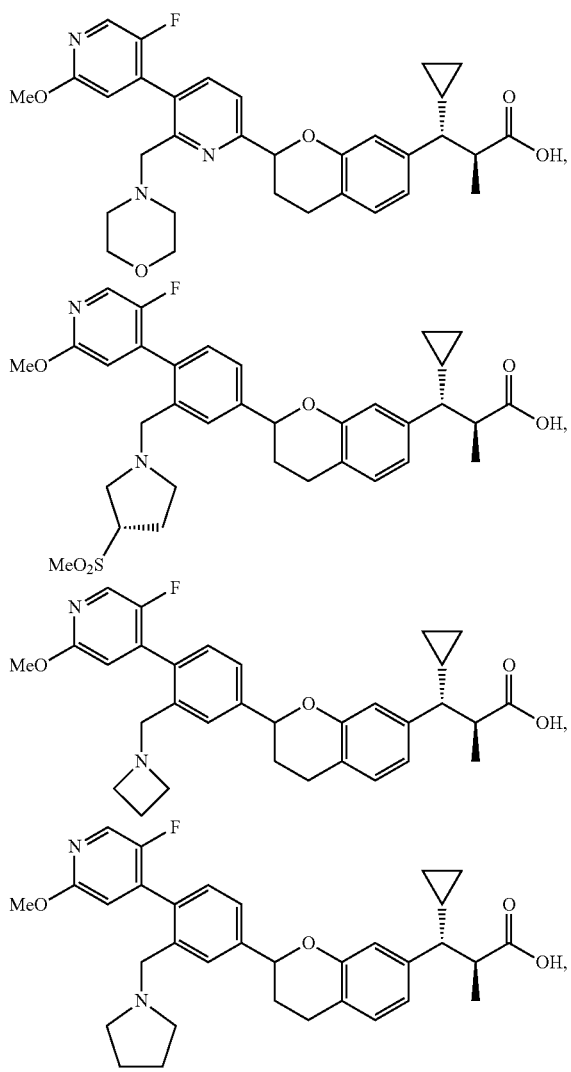

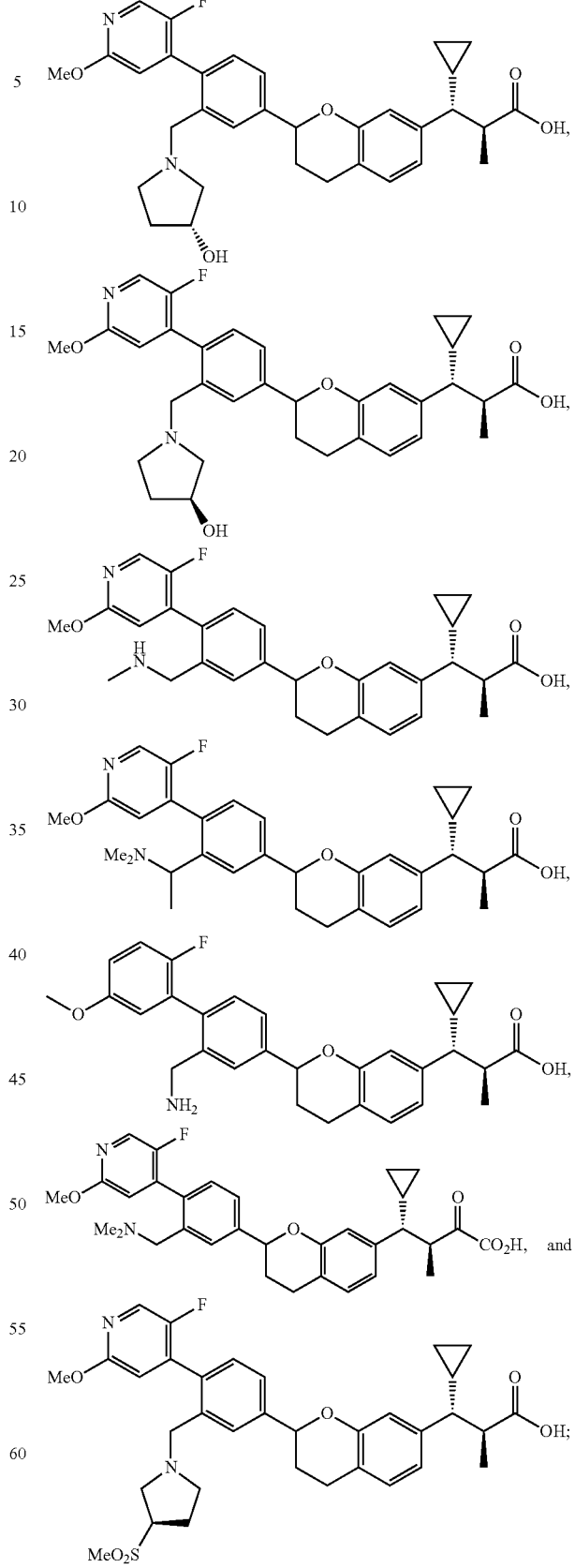

and pharmaceutically acceptable salts thereof.

Also illustrative, but non-limiting, examples of the compounds of the present invention that are useful as agonists of G-protein-coupled receptor 40 (GPR40) are the following compounds:
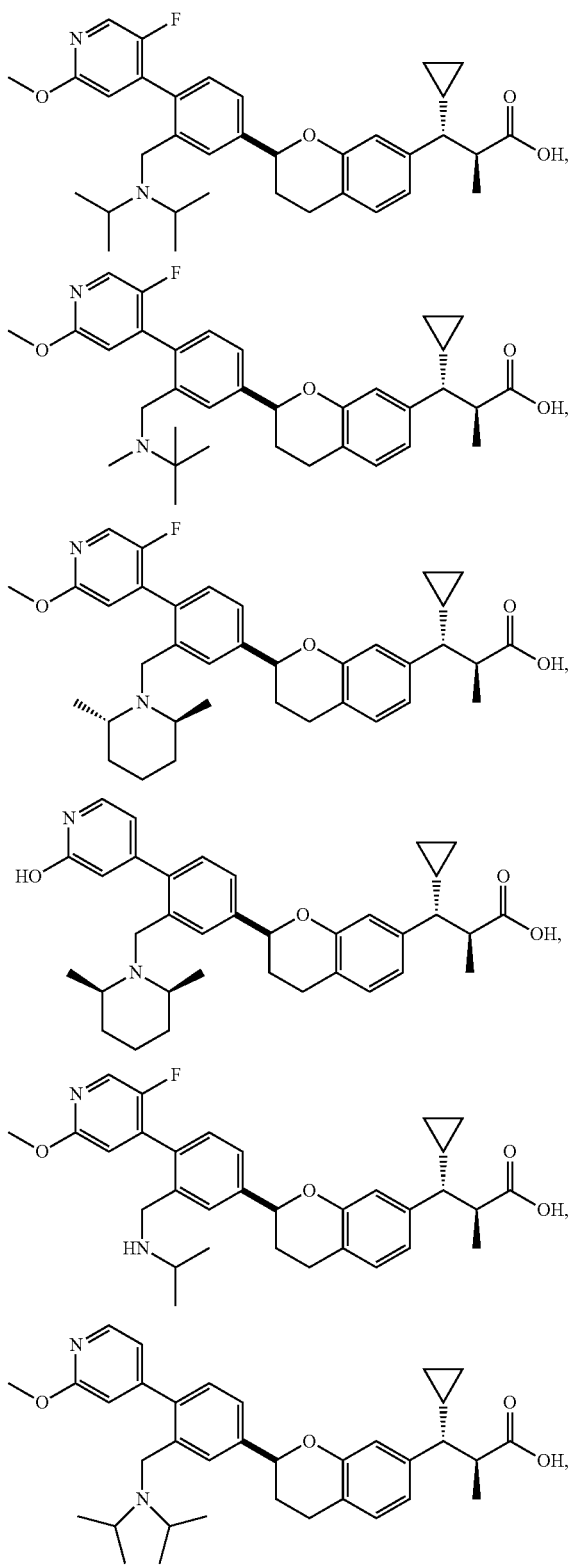
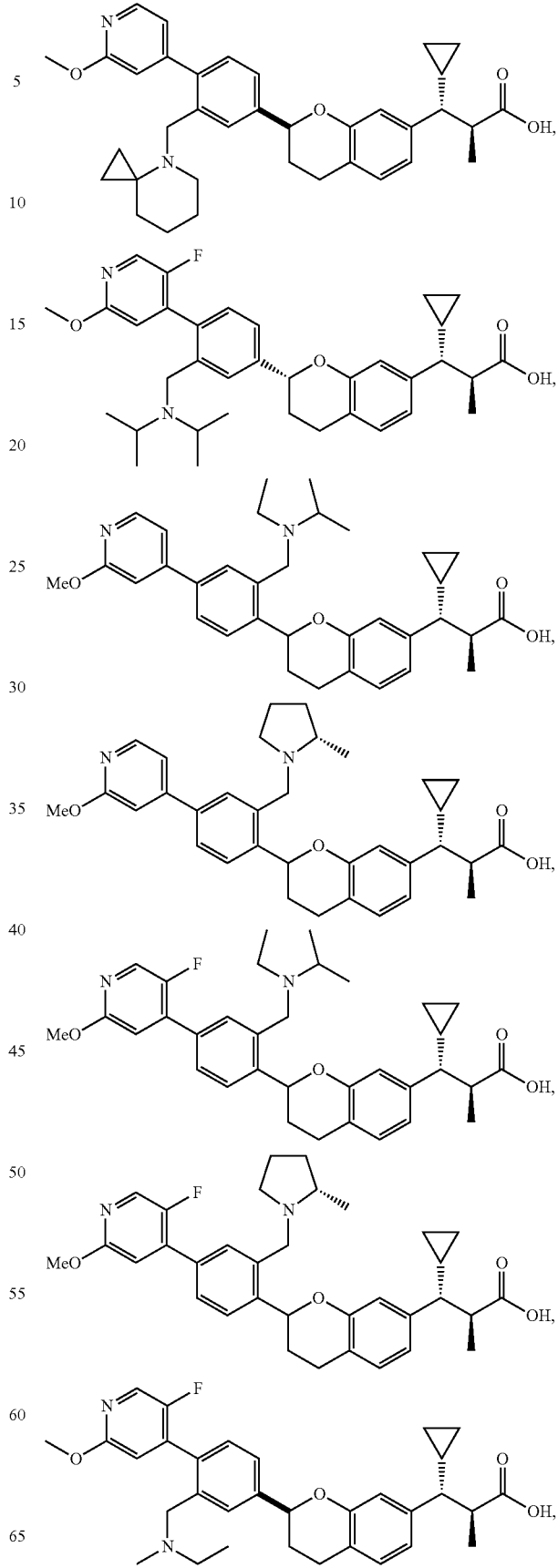

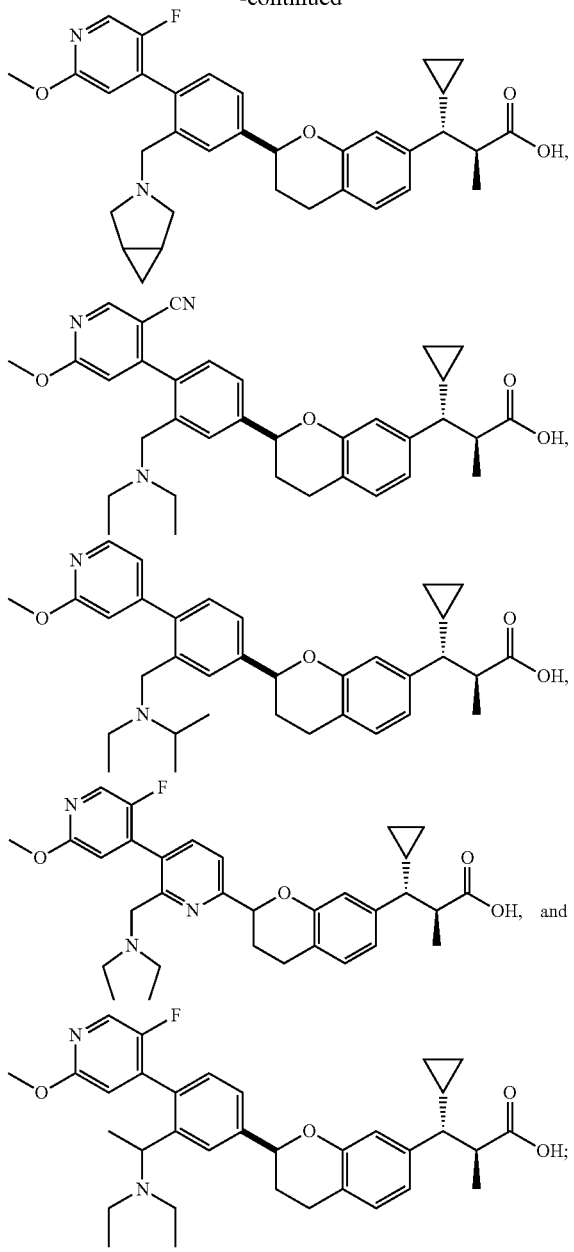

and pharmaceutically acceptable salts thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, may also be linear or branched, or combinations thereof, unless the carbon chain is defined otherwise. The term —C$_2$alkyl is ethyl. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl. In another embodiment of the present invention, alkyl is ethyl. In another embodiment of the present invention, alkyl is selected from methyl, ethyl, isopropyl, and tert-butyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is 2-methyl-1-propenyl.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like. In one embodiment, alkynyl is —C$_2$alkyne-CH$_3$.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclopropane, cyclobutane and cyclohexane. In another embodiment of the present invention, cycloalkyl is selected from: cyclopropane. In another embodiment of the present invention, cycloalkyl is selected from cyclopropyl and cyclobutyl.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like. In one embodiment of the present invention, cycloalkenyl is cyclopentenyl.

"Cycloheteroalkyl" means a saturated monocyclic, bicyclic or bridged carbocyclic ring or ring system containing at least one ring heteroatom selected from N, NH, S (including SO and SO$_2$) and O. The cycloheteroalkyl ring may be substituted on the ring carbons and/or the ring nitrogen(s). Cycloheteroalkyl bicyclic carbocyclic ring or ring system include spirocyclic rings. In one embodiment of the present invention, "cycloheteroalkyl" means a saturated monocyclic, bicyclic or bridged carbocyclic ring or ring system containing 2 to 10 carbon atoms and at least one ring heteroatom selected from N, NH, S (including SO and SO$_2$) and O. In another embodiment of the present invention, "cycloheteroalkyl" means a saturated monocyclic, bicyclic or bridged carbocyclic ring or ring system containing 2 to 10 carbon atoms and at least one ring heteroatom selected from N, NH, and O. Examples of cycloheteroalkyl include but are not limited to: tetrahydrofuran, pyrrolidine, tetrahydrothiophene, azetidine, piperazine, piperidine, morpholine, oxetane and tetrahydropyran. In one embodiment of the present invention, cycloheteroalkyl is selected from: azetidine, pyrrolidine and morpholine. In another embodiment of the present invention, cycloheteroalkyl is selected from: tetrahydrofuran and oxetane. In another embodiment of the present invention, cycloheteroalkyl is selected from: azetidine, pyrrolidine, piperidine, piperazine, and morpholine. In another embodiment of the present invention, cycloheteroalkyl is selected from: azetidine, pyrrolidine, piperidine, piperazine, morpholine, 4-azaspiro[2.5]octane, 3-azabicyclo[3.1.0]hexane, 3-methoxy-8-azabicyclo[3.2.1]octane, 8-azabicyclo[3.2.1]octane, hexahydro-2H-furo[3,2-b]pyrrole, 5,6,7,8-tetrahydroimidazo[1,5-a]pyrazine, 1-oxa-7-azaspiro[4.4]nonane, 4-oxa-7-azaspiro[2.5]octane, 8-oxa-5-azaspiro[3.5]nonane, 2-oxa-5-azabicyclo[2.2.1]heptane, 2-oxa-6-azaspiro[3.4]octane), 3-oxa-8-azabicyclo[3.2.1]octane, (1s,4s)-7-azabicyclo[2.2.1]heptane, 2-oxa-5-azaspiro[3.4]octane, 5-azaspiro[3.4]octane, 2-oxa-5-azaspiro[3.4]octane, (1R,4S)-2-azabicyclo[2.2.1]heptane, 7-azabicyclo[2.2.1]heptane, 2-azabicyclo[3.1.0]hexane, 5-azaspiro[2.5]octane, 6-azaspiro[2.5]octane, 5-azaspiro[3.5]nonane, and 5-azaspiro[2.4]heptane.

"Cycloheteroalkenyl" means a nonaromatic monocyclic, bicyclic or bridged carbocyclic ring or ring system containing at least one double bond and containing at least one heteroatom selected from N, NH, S (including SO and $SO_2$) and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl. In another embodiment of the present invention, aryl-O— is phenyl-O—. In another embodiment of the present invention, aryl-$C_{1-10}$alkyl-O— is phenyl-$CH_2$—O—.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzopyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is selected from: pyridine, isoxazole, pyrimidine, thiazole, benzimidazole, benzthiazole, benzoxazole, and benzisoxazole. In another embodiment of the present invention, heteroaryl is selected from: pyridine, isoxazole and benzopyrazole. In another embodiment of the present invention, heteroaryl is pyridine or thiazole. In another embodiment of the present invention, heteroaryl is pyridine. In another embodiment of the present invention heteroaryl is selected from: pyrazine and pyridine. In another embodiment of the present invention heteroaryl is selected from: pyridine, and pyrazole.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.
"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

For example, —$NR^cC(O)R^e$ is equivalent to —$N(R^c)C(O)R^e$.

Unless expressly depicted or described otherwise, substituents depicted in a structural formula with a "floating" bond, such as but not limited to $R^3$, is permitted on any available carbon atom in the ring to which the substituent is attached. In one embodiment of the present invention, $R^3$ may be substituted on any CH in the ring to which $R^3$ is attached.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies.

Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide, trifluoroacetate, and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) hyperglycemia; (3) insulin resistance; (4) Metabolic Syndrome; (5) obesity; (6) hypercholesterolemia; (7) hypertriglyceridemia (elevated levels of triglyceride-rich-lipoproteins); (8) mixed or diabetic dyslipidemia; (9) low HDL cholesterol; (10) high LDL cholesterol; (11) hyperapo-B liproteinemia; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammalian subject or patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of a GPR40 agonist in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dyslipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequalae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver, cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to a human or other mammal in need of treatment.

The term "patient" should be understood to mean a human or other mammal in need of treatment.

The administration of the compound of structural formula I in order to practice the present methods of therapy is carried out by administering a therapeutically effective amount of the compound of structural formula I to the mammal (human or other mammal) in need of such treatment or prophylaxis. The need for a prophylactic administration according to the methods of the present invention is determined via the use of well known risk factors. The therapeutically effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with a therapeutically effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which may be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may preferably be provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention may be indicated, generally satisfactory results could be obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

The compounds of this invention may be used in pharmaceutical compositions comprising (a) the compound(s) or a pharmaceutically acceptable salt thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy

The compounds of the present invention may be useful in methods for the prevention or treatment of the aforementioned diseases, disorders and conditions in combination with other therapeutic agents.

The compounds of the present invention may be useful in combination with one or more other drugs in the treatment, prevention, suppression or amelioration of diseases or conditions for which compounds of formula I or the other drugs may have utility, where the combination of the drugs together are safer, more effective or more therapeutically effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to: (1) dipeptidyl peptidase-IV (DPP-4) inhibitors (e.g., sitagliptin, omarigliptin, trelagliptin, teneligliptin, bisegliptin, anagliptin, vildagliptin, saxagliptin, alogliptin, melogliptin, linagliptin, gosogliptin, evogliptin, and gemigliptin), (2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine, insulin lispro and inhalable formulations of each); (4) leptin and leptin derivatives and agonists; (5) amylin and amylin analogs (e.g., pramlintide); (6) sulfonylurea and non-sulfonylurea insulin secretagogues (e.g., tolbutamide, glyburide, glipizide, glimepiride, mitiglinide, meglitinides, nateglinide and repaglinide); (7) α-glucosidase inhibitors (e.g., acarbose, voglibose and miglitol); (8) glucagon receptor antagonists (e.g., MK-3577, MK-0893, LY-2409021 and KT6-971); (9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); (10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevelam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe); (11)

HDL-raising drugs, (e.g., niacin and nicotinic acid receptor agonists, and extended-release versions thereof; (12) antiobesity compounds; (13) agents intended for use in inflammatory conditions, such as aspirin, non-steroidal anti-inflammatory drugs or NSAIDs, glucocorticoids, and selective cyclooxygenase-2 or COX-2 inhibitors; (14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan, medoxomil, valsartan, telmisartan, and eprosartan), renin inhibitors (e.g., aliskiren), beta blockers, and calcium channel blockers; (15) glucokinase activators (GKAs) (e.g., AZD6370); (16) inhibitors of 11β-hydroxysteroid dehydrogenase type 1, (e.g., such as those disclosed in U.S. Pat. No. 6,730,690, and LY-2523199); (17) CETP inhibitors (e.g., anacetrapib, evacetrapib, torcetrapib, and AT-03); (18) inhibitors of fructose 1,6-bisphosphatase, (e.g., MB-07803, and such as those disclosed in U.S. Pat. Nos. 6,054,587; 6,110,903; 6,284,748; 6,399,782; and 6,489,476); (19) inhibitors of acetyl CoA carboxylase-1 or 2 (ACC1 or ACC2); (20) AMP-activated Protein Kinase (AMPK) activators (e.g., MB-11055); (21) other agonists of the G-protein-coupled receptors: (i) GPR-109, (ii) GPR-119 (e.g., MBX2982 and PSN821), (iii) GPR-40 (e.g., fasiglifam, JTT-851, TAK-875, and P-11187, and (iv) GPR-120 (e.g., KDT-501); (22) SSTR3 antagonists (e.g., pasireotide, and such as those disclosed in WO 2009/011836); (23) neuromedin U receptor agonists (e.g., such as those disclosed in WO 2009/042053, including, but not limited to, neuromedin S (NMS)); (24) SCD inhibitors; (25) GPR-105 antagonists (e.g., such as those disclosed in WO 2009/000087); (26) SGLT inhibitors (e.g., LIK-066, ASP1941, SGLT-3, ertugliflozin, empagliflozin, dapagliflozin, canagliflozin, BI-10773, PF-04971729, remogliflozin, luseogliflozin, tofogliflozin, ipragliflozin, and LX-4211); (27) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (28) inhibitors of fatty acid synthase; (29) inhibitors of acyl coenzyme A:monoacylglycerol acyltransferase 1 and 2 (MGAT-1 and MGAT-2); (30) agonists of the TGR5 receptor (also known as GPBAR1, BG37, GPCR19, GPR131, and M-BAR) (eg., sodium taurocholate); (31) ileal bile acid transporter inhibitors (eg., elobixibat); (32) PACAP, PACAP mimetics, and PACAP receptor 3 agonists; (33) PPAR agonists; (34) protein tyrosine phosphatase-1B (PTP-1B) inhibitors; (35) IL-1b antibodies and inhibitors, (e.g., gevokizumab, canakinumab, danazol, AC-201, and BLX-1002); and (36) bromocriptine mesylate and rapid-release formulations thereof.

Of particular interest are dipeptidyl peptidase-IV (DPP-4) inhibitors that may be useful in combination with compounds of the present invention. Such inhibitors include, without limitation, sitagliptin (disclosed in U.S. Pat. No. 6,699,871), omarigliptin, trelagliptin, teneligliptin, bisegliptin, anagliptin, LC15-0444, vildagliptin, saxagliptin, alogliptin, melogliptin, linagliptin, gosogliptin, evogliptin, gemigliptin, and pharmaceutically acceptable salts thereof, and fixed-dose combinations of these compounds with metformin hydrochloride, pioglitazone, rosiglitazone, simvastatin, atorvastatin, or a sulfonylurea.

Other GPR-40 agonists that may be useful in combination with compounds of the formulas described herein include, but are not limited to: (1) 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide; (2) 5-(4-((3-(2,6-dimethyl-4-(3-(methylsulfonyl)propoxy)phenyl) phenyl)-methoxy)-phenyl)isothiazole-3-ol 1-oxide; and (3) 5-(4-((3-(2-methyl-6-(3-hydroxypropoxy)-pyridine-3-yl)-2-methylphenyl)methoxy)-phenyl)isothiazole-3-ol 1-oxide; and (4) 5-[4-[[3-[4-(3-aminopropoxy)-2,6-dimethylphenyl]phenyl]-methoxy]phenyl]isothiazole-3-ol 1-oxide, and pharmaceutically acceptable salts thereof.

Antiobesity compounds that may be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); $β_3$ adrenergic receptor agonists; CB-1 receptor inverse agonists and antagonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that may be useful in combination with a compound of the present invention, see S. Chaki et al., "Recent advances in feeding suppressing agents: potential therapeutic strategy for the treatment of obesity," Expert Opin. Ther. Patents, 11: 1677-1692 (2001); D. Spanswick and K. Lee, "Emerging antiobesity drugs," Expert Opin. Emerging Drugs, 8: 217-237 (2003); J. A. Fernandez-Lopez, et al., "Pharmacological Approaches for the Treatment of Obesity," Drugs, 62: 915-944 (2002); and K. M. Gadde, et al., "Combination pharmaceutical therapies for obesity," Exp. Opin. Pharmacother., 10: 921-925 (2009).

Glucagon receptor antagonists that may be useful in combination with the compounds of formula I include, but are not limited to: (1) N-[4-((1S)-1-{3-(3,5-dichlorophenyl)-5-[6-(trifluoromethoxy)-2-naphthyl]-1H-pyrazol-1-yl)} ethyl)benzoyl]-3-alanine; (2) N-[4-((1R)-1-{3-(3,5-dichlorophenyl)-5-[6-(trifluoromethoxy)-2-naphthyl]-1H-pyrazol-1-yl)}ethyl)benzoyl]-β-alanine; (3) N-(4-{1-[3-(2,5-dichlorophenyl)-5-(6-methoxy-2-naphthyl)-1H-pyrazol-1-yl] ethyl}benzoyl)-β-alanine; (4) N-(4-{(1S)-1-[3-(3,5-dichlorophenyl)-5-(6-methoxy-2-naphthyl)-1H-pyrazol-1-yl]ethyl}benzoyl)-β-alanine; (5) N-(4-{(1S)-1-[(R)-(4-chlorophenyl)(7-fluoro-5-methyl-1H-indol-3-yl)methyl] butyl}benzoyl)-β-alanine; and (6) N-(4-{(1S)-1-[(4-chlorophenyl)(6-chloro-8-methylquinolin-4-yl)methyl] butyl}benzoyl)-β-alanine; and pharmaceutically acceptable salts thereof.

Another embodiment of the present invention relates to a pharmaceutical composition comprising one or more of the following agents: (a) a compound of structural formula I; (b) one or more compounds selected from the group consisting of: (1) dipeptidyl peptidase-IV (DPP-4) inhibitors (e.g., sitagliptin, omarigliptin, trelagliptin, teneligliptin, biseglipitin, anagliptin, vildagliptin, saxagliptin, alogliptin, melogliptin, linagliptin, gosogliptin, evogliptin, and gemigliptin); (2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®); (iii) protein tyrosine phosphatase-1B (PTP-1B) inhibitors, such as ISI-113715, and TTP814; (3) sulfonylurea and non-sulfonylurea insulin secretagogues, (e.g., tolbutamide, glyburide, glipizide, glimepiride, mitiglinide, and meglitinides, such as nateglinide and repaglinide); (4) α-glucosidase inhibitors (e.g., acarbose, voglibose and miglitol); (5) glucagon receptor antagonists; (6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe); (7) HDL-raising drugs, such as niacin or a salt thereof and extended-release versions thereof; and nicotinic acid receptor agonists; (8) antiobesity compounds; (9) agents intended for use in inflammatory conditions, such as aspirin, non-steroidal anti-inflammatory drugs (NSAIDs), glucocorticoids, and selective cyclooxygenase-2 (COX-2) inhibitors; (10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers); (11) glucokinase activators (GKAs) (e.g., AZD6370, GKM-001, TMG-123, HMS-5552, DS-7309, PF-04937319, TTP-399, ZYGK-1); (12) inhibitors of 11β-hydroxysteroid dehydrogenase type 1 (e.g., such as those disclosed in U.S. Pat. No. 6,730,690; WO 03/104207; and WO 04/058741); (13) inhibitors of cholesteryl ester transfer protein (CETP), (e.g., torcetrapib, evacetrapib, anacetrapib, and AT-03); (14) inhibitors of fructose 1,6-bisphosphatase (e.g., MB-07803, and such as those disclosed in U.S. Pat. Nos. 6,054,587; 6,110,903; 6,284,748; 6,399,782; and 6,489,476); (15) inhibitors of acetyl CoA carboxylase-1 or 2 (ACC1 or ACC2); (16) AMP-activated Protein Kinase (AMPK) activators (e.g., MB-11055); (17) agonists of the G-protein-coupled receptors: (i) GPR-109, (ii) GPR-119 (e.g., MBX2982, and PSN821), (iii) GPR-40 (e.g., fasiglifam, JTT-851, P-11187, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)-methoxy)phenyl)-isothiazole-3-ol 1-oxide, 5-(4-((3-(2-methyl-6-(3-hydroxypropoxy)pyridine-3-yl)-2-methyl-phenyl)methoxy)phenyl)-isothiazole-3-ol 1-oxide, and 5-[4-[[3-[4-(3-aminopropoxy)-2,6-dimethylphenyl]phenyl]-methoxy]phenyl]isothiazole-3-ol 1-oxide), and (iv) GPR-120 (e.g., KDT-501); (18) SSTR3 antagonists (e.g., pasireotide, and such as those disclosed in WO 2009/011836); (19) neuromedin U receptor agonists (e.g., such as those disclosed in WO2009/042053, including, but not limited to, neuromedin S (NMS)); (20) inhibitors of stearoyl-coenzyme A delta-9 desaturase (SCD); (21) GPR-105 antagonists (e.g., such as those disclosed in WO 2009/000087); (22) inhibitors of glucose uptake, such as sodium-glucose transporter (SGLT) inhibitors and its various isoforms, such as SGLT-1; SGLT-2 (e.g., LIK-066, ertugliflozin, ASP1941, luseogliflozin, BI110773, tofogliflozin, LX4211, canagliflozin, dapagliflozin and remogliflozin; and SGLT-3); (23) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (24) inhibitors of fatty acid synthase; (25) inhibitors of acyl coenzyme A:monoacylglycerol acyltransferase 1 and 2 (MGAT-1 and MGAT-2); (26) agonists of the TGR5 receptor (also known as GPBAR1, BG37, GPCR19, GPR131, and M-BAR) (eg., sodium taurocholate); (28) bromocriptine mesylate and rapid-release formulations thereof, and (29) IL-1b antibodies and inhibitors (e.g., gevokizumab, canakinumab, danazol, AC-201, and BLX-1002); and (c) a pharmaceutically acceptable carrier.

Specific compounds that may be useful in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupropion, phentermine, losartan, losartan with hydrochlorothiazide, olmesartan, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention may also provide a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

For the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an effective amount of a compound of the present invention and an amount of another pharmaceutical agent effective to threat that disorder, such that together they give effective relief.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" or "a therapeutically effective dose" means the amount the compound of structural formula I that will elicit the biological or medical response of a tissue, system, animal, mammal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes, but is not limited to, humans, and companion animals such as dogs and cats.

The weight ratio of the compound of the Formula I to the second active ingredient may be varied and will depend upon the effective dose of each ingredient. Generally, a therapeutically effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI). All temperatures are degrees Celsius unless otherwise noted.

List of Abbreviations

Ac is acetyl; ACN or AcCN is acetonitrile; AcO is acetoxy; AcOH or HOAc is acetic acid; Ac$_2$O is acetic anhydride; Alk is alkyl; anh. is anhydrous; aq or aq. is aqueous; Ar is aryl; atm is atmosphere; Boc is tert-butoxycarbonyl; Bn-O is phenyl-CH$_2$—O or benzyloxy; Br is broad; n-BuLi is n-butyl lithium; t-BuOK is potassium tert-butoxide; ° C. is degrees celsius; Cataxium precatalyst or Cataxium Pd precat or precatalyst is cataCXium A Pd G3 (Aldrich); Cbz is benzyloxycarbonyl; CH$_2$Cl$_2$ is dichloromethane; conc or conc. is concentrated; CV is column volumes; D is deuterium; DCM is dichloromethane; DCE is 1,2-dichloroethane; DEA is diethyl amine; DIAD is diisopropyl azodicarboxylate; DIBAL or DIBAL-H is diisobutylaluminium hydride; DIPEA is N,N-diisopropylethylamine; DIPA is diisopropyl amine; DMA is dimethylacetamide; DMAP is 4-dimethylaminopyridine; DME is dimethyl ether; DMF is N,N-dimethylformamide; DMS is dimethyl sulfide; DMSO is dimethylsulfoxide; E or eq. is equivalent; EA or EtOAc is ethyl acetate; ESI is electrospray ionization; Et is ethyl; EtO is ethoxy; Et$_2$O is diethyl ether; EtMgBr is ethyl magnesium bromide; EtOH is ethanol; g is gram(s); h or hr or hrs is hour(s); hex is hexanes; HPLC is high pressure liquid chromatography; HOAc or AcOH is acetic acid; kg is kilogram(s); IPA is isopropanol; KOAc is potassium acetate; KOtBu is potassium tert-butoxide; L is liter, LAH is lithium aluminum hydride; M is molar; LC/MS or LC-MS is liquid chromatography-mass spectroscopy; LDA is lithium diisopropyl amide; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); Me is methyl; MeO is methoxy; MeOH is methyl alcohol or methanol; MPa is megapascal; MPLC is medium pressure liquid chromatography; MS is mass spectroscopy; MsCl or Ms-Cl is methane sulfonyl chloride; MeCN is acetonitrile; MeI is methyl iodide; MsCl is methane sulfonyl chloride; MTBE is methyl tert-butyl ether; N is normal; Na(OAc)$_3$BH is sodium triacetoxyborohydride; NaHMDS is sodium hexamethyl disilazide; NH$_4$OAc is ammonium acetate; NBS is N-bromo succinamide; NEt$_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; PE is petroleum ether, PG is protecting group; i-PrOH is isopropanol; Pd(OAc)$_2$ is palladium acetate; Pd(dppf)Cl$_2$ is [1,1'-Bis(diphenylphosphino)ferrocene]dichloropalladium(II); Pd(dppf)Cl$_2$ dichloromethane adduct is [1,1'-Bis(diphenylphosphino)ferrocene]dichloro-palladium(II) complex with dichloromethane; Pd(PPh$_3$)$_4$ is tetrakis or tetrakis(triphenyl-phosphine) palladium(0); PPh$_3$ is triphenylphosphine; precat is precatalyst; prep is preparative; prep. TLC or prep-TLC, or prep TCL is preparative thin layer chromatography; rt or r.t. or RT is room temperature; Ru-Josiphos is generated using (Me-allyl)$_2$Ru(COD) (Aldrich) and Josiphos SL-J502-2 (Aldrich); R$_f$ is retention factor; sat or sat. is saturated; SEM is trimethylsilyl ethoxy methyl, SEMCl is trimethylsilyl ethoxy methyl chloride; SFC is supercritical fluid chromatography; S-Phos is 2-dicyclohexylphosphino-2',6'-dimethoxy-biphenyl; S-Phos(Pd) is chloro(2-dicyclohexyl-phosphino-2',6'-dimethoxy-1,1'-biphenyl)[2-(2-aminoethylphenyl)]palladium(II) [CAS-No. 1028206-58-7]; S-Phos precatalyst is S-Phos Pd G2 precatalyst—Aldrich; S-Phos second generation precatalyst is Chloro(2-dicyclohexyl-phosphino-2',6'-dimethoxy-1,1'-biphenyl)[2-(2'-amino-1,1'-biphenyl)]palladium-(II), SPhos-Pd-G2) [CAS-No. 1375325-64-6]; TBAF is tetrabutylammonium fluoride; TBDMSCl is tert-butyldimethylsilyl chloride; TBSCl is tert-butyl dimethylsilyl chloride; tert-butyl Xphos palladacycle Gen 1 is (2-Dicyclohexylphosphino-2',4',6'-triisopropyl-1,1'-biphenyl)[2-(2-aminoethyl)phenyl)]palladium(II) chloride; TEA is triethyl amine; Tf is trifluoromethane sulfonyl; Tf$_2$O is trifluoromethanesulfonic anhydride; THF is tetrahydrofuran; TFA is trifluoroacetic acid; TLC is thin-layer chromatography; Tos and Ts is p-toluene sulfonyl; TosCl and TsCl is p-toluene sulfonyl chloride; pTSA, pTsOH and TsOH is p-toluenesulfonic acid, Ts$_2$O is tosic anhydride or p-toluene sulfonic anhydride, and $2^{nd}$ generation Xphos precatalyst is chloro(2-dicyclohexylphosphino-2',4',6'-triisopropyl-1,1'-biphenyl)[2-(2'-amino-1,1'-biphenyl)]palladium(II).

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided to illustrate the invention and are not to be construed as limiting the invention in any manner. The scope of the invention is defined by the appended claims.

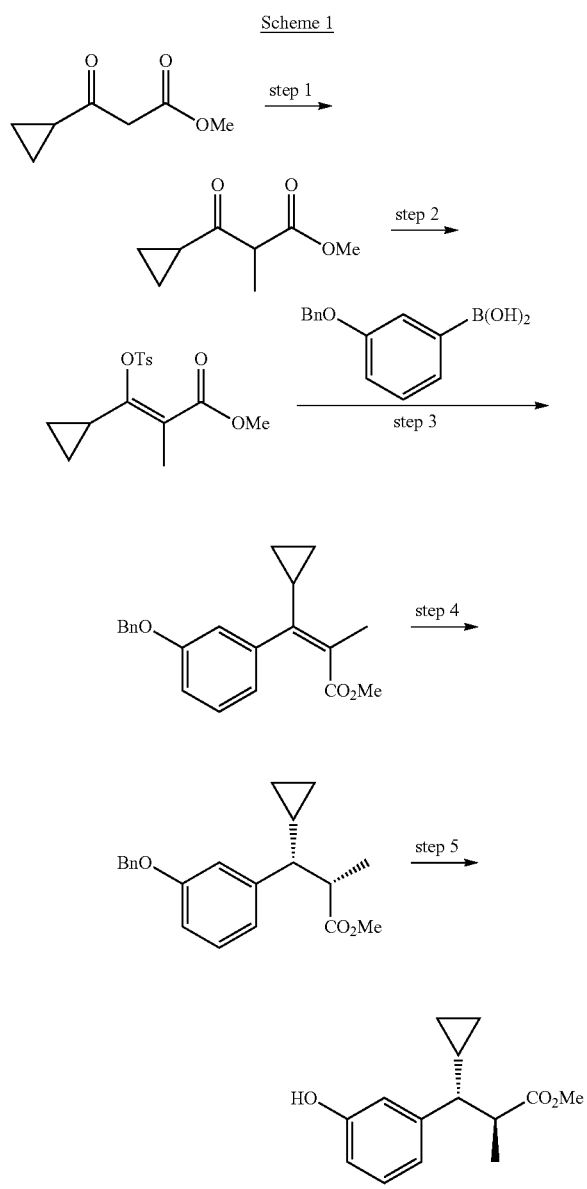

Step 1: MeI, K₂CO₃, THF; Step 2: NaHMDS, Ts₂O, MTBE; Step 3: Cataxium-Pd precat, K₃PO₄, MeCN; Step 4: Ru-Josiphos, BF₄H—Et₂O, H₂ gas, MeOH; Step 5: Pd/C, H₂ gas, MeOH Scheme 1 provides a route to Intermediate 1. The cyclopropyl β-ketoester was methylated and then trapped at the vinyl tosylate. Suzuki cross-coupling with m-benzyloxy phenylboronic acid delivered the "Z" enoate. Asymmetric reduction of the double bond was followed by debenzylation under hydrogen pressure.

Intermediate 1

(2R,3R)-Methyl 3-cyclopropyl-3-(3-hydroxyphenyl)-2-methylpropanoate

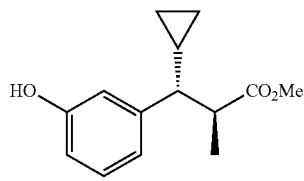 [SMILES: COC(=O)[C@@H](C)[C@H](c1cccc(O)c1)C1CC1]

Step 1: methyl 3-cyclopropyl-2-methyl-3-oxopropanoate

A slurry of NaH (0.563 g, 60% in mineral oil) in THF (20 mL) was cooled to 10° C., then methyl 3-cyclopropyl-3-oxopropanoate (2 g) was added in portions at rt over 30 minutes. Then MeI (0.88 mL) was added over 5 minutes at rt and the reaction was stirred at rt overnight. The reaction was then reverse quenched into a half saturated sodium bicarbonate solution (100 mL) and EtOAc (100 mL). The aqueous layer was separated and extracted once with 50 mL EtOAc. The combined organic layers were washed with water and brine, and concentrated to give the title compound, which was used in the next step without further purification.

Step 2: (Z)-methyl 3-cyclopropyl-2-methyl-3-(tosyloxy)acrylate

To a solution of methyl 3-cyclopropyl-2-methyl-3-oxopropanoate (5 g) in MTBE (50 mL) was added a 1M solution of NaHMDS in hexane (41 mL) keeping the internal temperature between 18-23° C. The reaction was stirred at rt for 30 min. Then tosic anhydride (10 g) was slurried in MTBE (200 mL), followed by the addition of the reaction mixture to the tosic anhydride slurry, while keeping the internal temperature between 19° C. and 24° C. After stirring 30 min, additional tosic anhydride (3.3 g, 0.3 eq) was added, and the reaction was stirred for 1 h. Then water (500 mL) and EtOAc (400 mL) were added to the reaction mixture. The aqueous layer was separated and extracted once with EtOAc. (100 mL) The combined organic layers were washed with water (200 mL) and brine (100 mL), and then concentrated to give the crude product, which was recrystallized from with MTBE/heptanes (1:1, 50 mL) to give the title compound.

Step 3: (Z)-methyl 3-(3-(benzyloxy)phenyl)-3-cyclopropyl-2-methylacrylate (Z)-methyl 3-cyclopropyl-2-methyl-3-(tosyloxy)acrylate (1.03 g) was dissolved in MeCN (10 mL), then aqueous potassium phosphate (1 M, 10 mL) was added, followed by (3-(benzyloxy)phenyl)boronic acid (1 g). The resulting slurry was degassed with a nitrogen stream for 30 min, then cataCXium A Pd G3 precatalyst (100 mg, Aldrich #761435) was added and the reaction was heated to 35° C. for 14 h. The slurry was then filtered through Celite™, and the Celite™ was washed with EtOAc (20 mL). Then EtOAc (40 mL) and water (50 mL) were added to the filtrate. The aqueous layer was separated, and extracted once with EtOAc (20 mL). The combined organic layers were washed with water (50 mL) and brine (20 mL), then concentrated to give a crude oil, which was purified via ISCO™ silica column (40 g, diluted with 0-30% Hexanes/EtOAc) to give the title product.

Step 4: (2S,3R)-methyl 3-(3-(benzyloxy)phenyl)-3-cyclopropyl-2-methylpropanoate

Bis(2-methylallyl)(1,5-cyclooctadiene)Ruthenium (II) (1.0 g) and Josiphos (1.86 g) were added to DCM (12 mL) and agitated for 20 min at rt. Then tetrafluoroboric acid-diethyl ether complex (1.0 g) was added slowly and stirred for 20 min at rt. Then the reaction mixture was diluted with DCM (100 mL) and added to a catalyst bomb with a MeOH rinse. (Z)-methyl 3-(3-(benzyloxy)phenyl)-3-cyclopropyl-2-methylacrylate (2.57 g, 7.97 mmol) was added to the catalyst bomb with MeOH (200 mL) and agitated to dissolve, The catalyst bomb was pressurized to 500 psi with hydrogen, then heated to 80° C. and shaken for 20 h. Then the reaction was cooled, filtered through Celite™ and washed with MeOH. The filtrate was concentrated to give the crude product.

Step 5: (2S,3R)-methyl 3-cyclopropyl-3-(3-hydroxyphenyl)-2-methylpropanoate

To a solution of (2S,3S)-methyl 3-(3-(benzyloxy)phenyl)-3-cyclopropyl-2-methylpropanoate (4.81 g, 13 mmol) and methanol (67 ml) in a 25 ml glass shaker vessel, was added 8% Pd-2% Pt/C—(1.5 g, 35 wt % loading, 50 w/w, Johnson Matthey lot #F27N23). Then the shaker vessel was evacuated and purged with nitrogen three times, and charged with 50 psig of hydrogen gas. The reaction was heated to 25° C. for 6 h, then filtered through Celite™, which was rinsed with MeOH (50 mL). The filtrate was concentrated to give the title compound.

Intermediate 2

(2S,3R)-methyl 3-(4-(acetoxymethyl)-3-hydroxyphenyl)-3-cyclopropyl-2-methylpropanoate

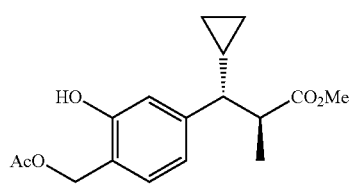 [SMILES: COC(=O)[C@@H](C)[C@H](c1ccc(COC(C)=O)c(O)c1)C1CC1]

Step 1: (2S,3R)-methyl 3-cyclopropyl-3-(4-formyl-3-hydroxyphenyl)-2-methylpropanoate To an acetonitrile (285 ml) solution of (2S,3R)-methyl 3-cyclopropyl-3-(3-hydroxyphenyl)-2-methylpropanoate (Intermediate 1, 2.00 g, 8.54 mmol), magnesium chloride (1.22 g, 12.8 mmol), and paraformaldehyde (1.28 g, 42.7 mmol) was added TEA (4.46 ml, 32.0 mmol). The resulting slurry was heated to reflux with an attached condenser. After 3 h, the homogenous yellow solution was cooled to rt and poured into 5% HCl (200 mL). The mixture was then extracted with ethyl acetate (2×250 mL). The combined organic layers were dried (MgSO$_4$) and concentrated. The resulting residue was purified by HPLC (ISCO™ 120 g, 0 to 50% EA/Hex) to give the title compound. $^1$H NMR (500 MHz, CDCl$_3$) δ 11.05 (s, 1H), 9.89 (s, 1H), 7.50 (s, 1H), 6.80 (m, 2H), 3.78 (s, 3H), 2.82 (m, 1H), 2.00 (t, 1H), 1.02 (m, 1H), 0.98 (s, 3H), 0.60 (m, 1H), 0.34 (m, 1H), 0.25 (m, 1H), 0.01 (m, 1H).

Step 2: Methyl 3-(4-hydroxy-3-(hydroxymethyl)phenyl)hex-4-ynoate

To a cooled (0° C.) ethanol (24 mL) solution of methyl (2S,3R)-methyl 3-cyclopropyl-3-(4-formyl-3-hydroxyphenyl)-2-methylpropanoate (1.5 g, 5.72 mmol) was added NaBH$_4$ (0.216 g, 5.72 mmol) in a single portion. After 30 minutes, the reaction was quenched by the dropwise addition of 1N HCl (20 mL) at 0° C. The reaction mixture was then poured into saturated ammonium chloride (50 mL) and extracted with EtOAc (2×50 mL). The combined organic layers were dried (MgSO$_4$) and concentrated. The resulting residue was purified by HPLC (ISCO™ 80 gram, 0 to 80% EtOAc/Hex) to give the title compound. $^1$H NMR (500 MHz, CDCl$_3$) δ 7.00 (d, 1H), 6.74 (s, 1H), 6.65 (d, 1H), 4.88 (s, 2H), 3.75 (s, 3H), 2.80 (m, 1H), 1.80 (t, 1H), 1.05 (m, 1H), 0.95 (d, 3H), 0.57 (m, 1H), 0.35 (m, 1H), 0.25 (m, 1H), 0.01 (m, 1H).

Step 3: (2S,3R)-methyl 3-(4-(acetoxymethyl)-3-hydroxyphenyl)-3-cyclopropyl-2-methylpropanoate Pyridine (4.0 ml, 49.5 mmol) was added dropwise to a stirred, cooled (0° C.) mixture of (2S,3R)-methyl 3-cyclopropyl-3-(3-hydroxy-4-(hydroxymethyl)phenyl)-2-methylpropanoate (10.94 g, 41.4 mmol) in CH$_2$Cl$_2$ (200 ml) at 0° C. Then a solution of acetyl chloride (2.94 ml, 41.4 mmol) in CH$_2$Cl$_2$ (7 mL) was added dropwise to the reaction mixture, and the reaction was stirred at 0° C. for 10 min. The reaction was then partitioned between DCM and saturated NH$_4$Cl. The layers were separated and the organic layer was washed with brine, dried over MgSO$_4$, filtered and concentrated in vacuo. The resulting residue was purified via MPLC (ISCO™ 220 g; product eluted at 28% EtOAc/hexane) with gradient elution 0-100% EtOAc/hexane to give the title compound. $^1$H NMR (500 MHz, CHCl$_3$-d): 0.01 (m, 1H), 0.23 (dq, 1H), 0.35-0.29 (m, 1H), 0.57-0.52 (m, 1H), 0.93 (d, 3H), 1.02 (m, 1H), 1.87 (t, 1H), 2.12 (s, 3H), 2.82-2.76 (m, 1H), 3.72 (s, 3H), 5.09 (s, 2H), 6.70 (d, 1H), 6.76 (s, 1H), 7.18 (d, 1H), 7.91 (s, 1H).

Intermediate 3

2-hydroxy-5-vinylbenzaldehyde

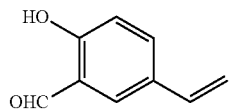

Step 1: 4-bromo-2-formylphenyl acetate

To a DCM solution of 5-bromo-2-hydroxybenzaldehyde (15 g, 74.6 mmol) and Ac$_2$O (7.04 ml, 74.6 mmol) was added pyridine (6.04 ml, 74.6 mmol). After 1 h, the reaction was poured into water (250 mL). The organic phase was separated, dried (Na$_2$SO$_4$) and concentrated. The residue was purified by HPLC (ISCO™ 220 gram, 0 to 50% EtOAc/Hex) to give the title compound. (m/z): 245.17 (M+H)⁺.

Step 2: 2-formyl-4-vinylphenyl acetate

To a nitrogen-sparged dioxane (50 mL) solution of 4-bromo-2-formylphenyl acetate (5.2 g, 21.39 mmol), was added vinyltri-n-butyltin (7.54 ml, 25.7 mmol), and tetrakis(triphenyl-phosphine)palladium(0) (0.742 g, 0.642 mmol). The reaction mixture was heated and stirred on a heating block for 16 h. Then the reaction was cooled to room temp and poured into NH₄Cl (100 mL, saturated). The mixture was extracted with EtOAc (2×100 mL). The combined organic layers were dried (MgSO₄) and concentrated. The resulting residue was purified by HPLC (ISCO™ 120 gram, 0 to 40% EtOAc/Hex) to give the title compound. (m/z): 191.25 (M+H)⁺.

Step 3: 2-hydroxy-5-vinylbenzaldehyde

To a MeOH (20 mL) solution of 2-formyl-4-vinylphenyl acetate (2.8 g, 14.72 mmol) was added K₂CO₃ (4.07 g, 29.4 mmol). The reaction mixture was stirred vigorously. After 16 h, the reaction mixture was treated with excess aqueous HCl (1 N, 50 mL) and stirred. After 1 h, the reaction mixture was poured into brine and extracted with DCM (2×50 mL). The combined organic layers were dried (Na₂SO₄) and concentrated. The resulting residue was purified by HPLC (ISCO™ 120 gram, 0 to 40% EtOAc/Hex) to give the title compound. ¹H NMR (500 MHz, CDCl₃) δ 11.01 (s, 1H), 9.91 (s, 1H), 7.62 (d, 1H), 7.59 (s, 1H), 7.00 (d, 1H), 6.70 (dd, 1H), 5.64 (d, 1H), 5.22 (d, 1H).

Intermediate 4

(2S,3R)-methyl 3-cyclopropyl-3-(2-(4-(5-fluoro-2-methoxypyridin-4-yl)-3-formylphenyl)chroman-7-yl)-2-methylpropanoate

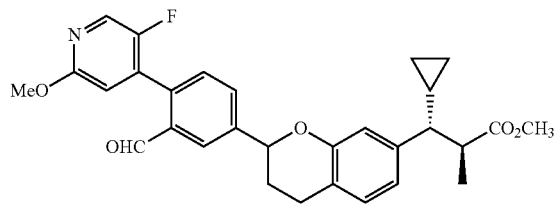 [SMILES: COC(=O)[C@@H](C)[C@H](c1ccc2c(c1)OC(c1ccc(-c3cc(OC)ncc3F)c(C=O)c1)CC2)C1CC1]

Step 1: (2S,3R)-methyl 3-cyclopropyl-3-(2-(3-formyl-4-hydroxyphenyl)chroman-7-yl)-2-methylpropanoate To a xylenes (1 mL) solution of (2S,3R)-methyl 3-(4-(acetoxymethyl)-3-hydroxyphenyl)-3-cyclopropyl-2-methylpropanoate (3 g, 9.79 mmol) was added 2-hydroxy-5-vinylbenzaldehyde (2.176 g, 14.69 mmol). The mixture was degassed and then heated to 170° C. in a sealed vial. After 45 minutes, the reaction mixture was cooled to room temp. The reaction mixture was loaded directly onto an ISCO™ cartridge and purified by HPLC (ISCO 40 gram, 0 to 50% EtOAc/Hex) to give the title compound. (m/z): 395.22 (M+H)⁺.

Step 2: (2S,3R)-methyl 3-cyclopropyl-3-(2-(3-formyl-4-(tosyloxy)phenyl)chroman-7-yl)-2-methylpropanoate To a DCM (35 mL) solution of (2S,3R)-methyl 3-cyclopropyl-3-(2-(3-formyl-4-hydroxyphenyl)chroman-7-yl)-2-methylpropanoate (2.8 g, 7.10 mmol) and TEA (1.484 ml, 10.65 mmol) was added p-toluenesulfonyl chloride (1.624 g, 8.52 mmol). After 1 h, the reaction was poured into water (25 mL) and extracted with DCM (2×25 mL). The combined organic layers were dried (NaSO₄) and concentrated. The resulting residue was purified by HPLC (ISCO 40 gram, 0 to 50% EtOAc/Hex) to give the title compound. (m/z): 549.27 (M+H)⁺.

Step 3: (2S,3R)-methyl 3-cyclopropyl-3-(2-(4-(5-fluoro-2-methoxypyridin-4-yl)-3-formylphenyl)chroman-7-yl)-2-methylpropanoate To a nitrogen-sparged THF (5 mL) solution of (2S,3R)-methyl 3-cyclopropyl-3-(2-(3-formyl-4-(tosyloxy)phenyl)chroman-7-yl)-2-methyl-propanoate (0.7180 g, 1.309 mmol), (5-fluoro-2-methoxypyridin-4-yl)boronic acid (0.336 g, 1.963 mmol), and SPhos 2ⁿᵈ generation precatalyst (0.047 g, 0.065 mmol) was added a N₂-sparged aqueous solution of potassium phosphate tribasic (1.309 ml, 3.93 mmol). The reaction mixture was evacuated and filled with N₂, then heated on a heating block at 80° C. for 1 h. The reaction mixture was partitioned between EtOAc (25 mL) and saturated NH₄Cl (25 mL). The aqueous layer was separated and extracted with EtOAc (25 mL). The combined organic layers were washed with brine, dried over MgSO₄, and concentrated in vacuo. The resulting residue was purified via MPLC (ISCO™ 24 g; product elutes at 20% EtOAc/hexane) with gradient elution 0-40% EtOAc/hexane to give the title compound. LC/MS (m/z): 504.4 (M+H)⁺.

Intermediates 4a and 4b

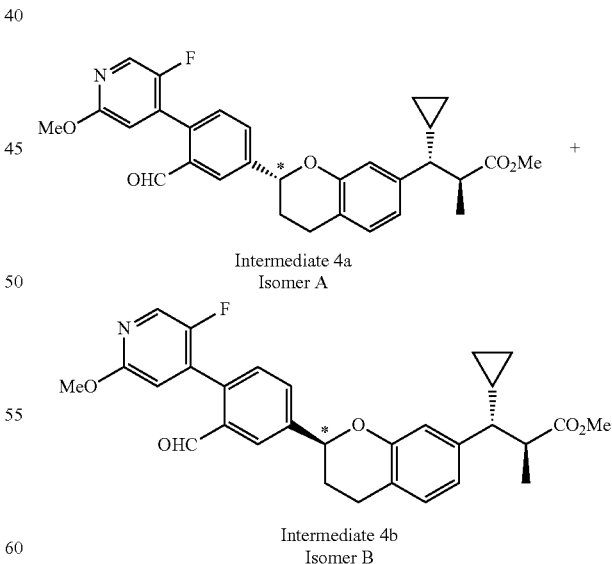

Intermediate 4a
Isomer A

Intermediate 4b
Isomer B

Methyl (2S,3R)-3-cyclopropyl-3-(2-(4-(5-fluoro-2-methoxypyridin-4-yl)-3-formylphenyl)-chroman-7-yl)-2-methylpropanoate (Intermediate 4) as a mixture of diastereomers at the carbon alpha to the chroman oxygen* was resolved using chiral SFC (AS-H column (20×250 mm; 50%

MeOH/CO₂) to give Intermediate 4a (Isomer A, retention time=2.4 min); and Intermediate 4b (Isomer B, retention time=3.4 min). The absolute configuration of Intermediate 4a (Isomer A) was assigned to be (RRS) using Vibrational Circular Dichroism (VCD) spectroscopy with confidence. Analysis was done comparing experimental data to the calculated VCD and IR spectra of the (RRS and SRS) configuration. The experimental VCD spectrum Intermediate 4a matched well with the calculated (RRS) spectrum over the region from 1000-1800 cm-1, resulting in an assignment of RRS). The absolute configuration of Intermediate 4b was assigned to be (SRS) using Vibrational Circular Dichroism (VCD) spectroscopy with confidence. Analysis was done comparing experimental data to the calculated VCD and IR spectra of the (RRS and SRS) configuration. The experimental VCD spectrum of Intermediate 4b matched well with the mirror image of the calculated (SRS) spectrum over the region from 1000-1800 cm-1, resulting in an assignment of (SRS).

Intermediate 5

(2S,3R)-Methyl 3-cyclopropyl-3-(3-hydroxy-4-iodophenyl)-2-methylpropanoate

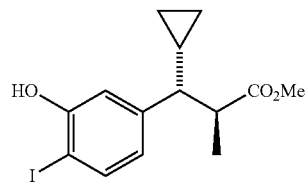 [SMILES: COC(=O)[C@@H](C)[C@H](c1ccc(I)c(O)c1)C1CC1]

To a solution of (2S,3R)-methyl 3-cyclopropyl-3-(3-hydroxyphenyl)-2-methylpropanoate (Intermediate 1, 1.47 g, 6.27 mmol) in DCM (50 ml) was added NIS (1.69 g, 7.53 mmol). The reaction was stirred at ambient temperature for 2 h, then diluted with DCM and aqueous saturated sodium thiosulfate solution. The layers were separated, and the combined organic layers were washed with brine, dried over MgSO₄, filtered, and concentrated in vacuo. The resulting residue was purified by silica gel column chromatography (ISCO system, RediSep 80 g column) using a gradient of 0-50% EtOAc/Hexanes as eluent to provide the title compound. LC/MS: m/z=361.17 [M+1].

Intermediate 6

(2S,3R) Methyl-3-cyclopropyl-3-(2-fluoro-hydroxyphenyl)-2-methylpropanoate

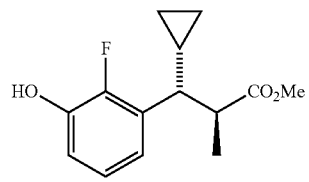 [SMILES: COC(=O)[C@@H](C)[C@H](c1cccc(O)c1F)C1CC1]

Step 1:

1,4-Dioxane (2400 ml) and water (240 ml) was added to a large reaction flask followed by degassing with nitrogen for 30 minutes. (Z)-Methyl 3-cyclopropyl-2-methyl-3-(tosyloxy)acrylate (240 g, 766 mmol), (2-fluoro-3-hydroxyphenyl)boronic acid (131 g, 843 mmol), Cs₂CO₃ (275 g, 843 mmol) and dichloro[1,1'-bis(diphenylphosphino)ferrocene]-palladium (II) dichloromethane adduct (25.03 g, 30.7 mmol) were added. The mixture was stirred at 80° C. for 3 h, then diluted with ethyl acetate (2 L) and water (1 L). The organic layer was separated and back extracted with ethyl acetate. The combined organic layers were washed with 10% NaCl solution (1 L×2) and dried over MgSO₄ (300 g), and concentrated. The resulting he crude residue was purified by column chromatography (0-50% EtOAc in hexanes) to afford methyl (Z)-3-cyclopropyl-3-(2-fluoro-3-hydroxyphenyl)-2-methylacrylate.

Step 2:

A 100 ml flask was charged with MeOH (16 ml) and (Z)-methyl 3-cyclopropyl-3-(2-fluoro-3-hydroxyphenyl)-2-methylacrylate (3 g, 11.87 mmol). The resulting solution was degassed with nitrogen. In another 100 ml flask was charged with MeOH (8 mL) that had been purged with nitrogen for 30 minutes. Bis(2-methylallyl)(1,5-cyclooctadiene)ruthenium (0.038 g, 0.119 mmol) and (S)-1-[(RP)-2-(di-tert-butylphosphino)ferrocenyl]ethyldiphenyl-phosphine (0.068 g, 0.125 mmol) were added to the second flask, followed by the addition of tetrafluoroboric acid-diethyl ether complex (0.038 g, 0.237 mmol). The solutions from both flasks were transferred to a 50 ml high pressure vessel. The vessel was charged to 3-4 MPa H₂ and heated to 80 to 90° C. The mixture was stirred for 18 hours, then cooled, filtered and concentrated to afford methyl (2S,3R) methyl-3-cyclopropyl-3-(2-fluoro-3-hydroxyphenyl)-2-methylpropanoate.

Intermediate 7

(2S,3R)-Methyl 3-cyclopropyl-3-(2-fluoro-3-hydroxy-4-iodophenyl)-2-methylpropanoate

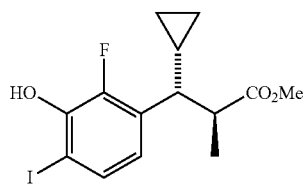 [SMILES: COC(=O)[C@@H](C)[C@H](c1ccc(I)c(O)c1F)C1CC1]

To a solution of (2S,3R)-Methyl 3-cyclopropyl-3-(2-fluoro-3-hydroxyphenyl)-2-methylpropanoate (Intermediate 6, 152 mg, 0.603 mmol) in DCM (4 mL) was added NIS (136 mg, 0.603 mmol) slowly in several small portions. The reaction was stirred at ambient temperature overnight, then diluted with DCM and aqueous saturated sodium thiosulfate solution. The organic layer was separated, washed with brine, dried over MgSO₄, filtered, and concentrated in vacuo. The resulting residue was purified by silica gel column chromatography (ISCO system, RediSep 40 g column) using a gradient of 0-25% EtOAc/Hexanes as eluent to give the title compound. LC/MS: m/z=379.16 [M+1].

Intermediate 8

(2S,3R) Methyl-3-cyclobutyl-3-(3-hydroxyphenyl)-2-methylpropanoate

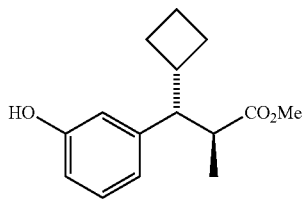 [SMILES: COC(=O)[C@@H](C)[C@H](c1cccc(O)c1)C1CCC1]

(2S,3R) Methyl-3-cyclobutyl-3-(3-hydroxyphenyl)-2-methylpropanoate was made in a similar fashion as described for Intermediate 1 ((2R,3R)-Methyl 3-cyclopropyl-3-(3-hydroxyphenyl)-2-methylpropanoate) using the appropriate reagents.

Intermediate 9

(2S,3R)-Methyl-3-cyclobutyl-3-(3-hydroxy-4-iodophenyl)-2-methylpropanoate

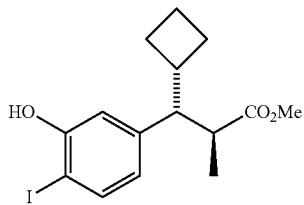 [SMILES: COC(=O)[C@@H](C)[C@H](c1ccc(I)c(O)c1)C1CCC1]

(2S,3R)-Methyl 3-cyclobutyl-3-(3-hydroxyphenyl)-2-methylpropanoate (Intermediate 8, 2.9 g, 11.68 mmol) was dissolved in CH$_2$Cl$_2$ (200 ml), and the mixture was cooled to 0° C., then N-Iodosuccinimide (2.63 g, 11.68 mmol) was added portionwise. The mixture was stirred at 25° C. for 5 h, then diluted with DCM and washed with 10% Na$_2$S$_2$O$_3$. The organic layer was dried over MgSO$_4$ and concentrated. The resulting crude material was purified by flash column (80 g ISCO, 0~30% EtOAc in hexane) to afford the title compound.

Example 1

(2S,3R)-3-cyclopropyl-3-(2-(3-((dimethylamino)methyl)-4-(5-fluoro-2-methoxypyridin-4-yl)phenyl)chroman-7-yl)-2-methylpropanoic acid

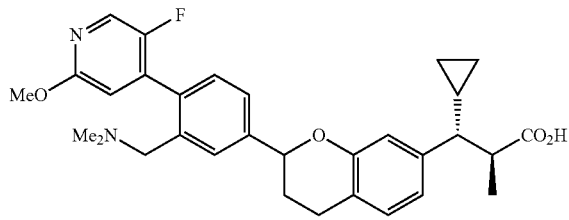 [SMILES: COc1cc(-c2ccc(C3CCc4ccc([C@H](C5CC5)[C@H](C)C(=O)O)cc4O3)cc2CN(C)C)c(F)cn1]

Step 1: (2S,3R)-methyl 3-cyclopropyl-3-(2-(3-((dimethylamino)methyl)-4-(5-fluoro-2-methoxypyridin-4-yl)phenyl)chroman-7-yl)-2-methylpropanoate To a solution of (2S,3R)-methyl 3-cyclopropyl-3-(2-(4-(5-fluoro-2-methoxypyridin-4-yl)-3-formylphenyl)chroman-7-yl)-2-methylpropanoate (0.5369 g, 1.066 mmol) in MeOH (5 mL, anhydrous)/CH$_2$Cl$_2$ (0.5 ml) at 0° C. was added a 2M solution of dimethylamine in MeOH (0.613 ml, 1.226 mmol), followed by titanium (IV) isopropoxide (0.625 ml, 2.132 mmol) at 0° C. under N$_2$. Then the reaction was warmed to ambient temperature. After 40 minutes, the reaction was added dropwise to a mixture of sodium borohydride (0.358 g, 9.46 mmol) in MeOH (5 mL, anhydrous) at room temperature. The reaction mixture was stirred for 35 min., then quenched at 0° C. with water and partitioned between EtOAc and brine. The aqueous layer was separated and extracted with EtOAc. The combined organic layers were dried over MgSO$_4$, and concentrated in vacuo. The resulting residue was purified by via MPLC (ISCO™ 12 g; product elutes at 34% EtOAc/hexane) with gradient elution 0-60% EtOAc/hexane to give the title compound. LC/MS (m/z): 533.42 (M+H)$^+$.

Step 2: (2S,3R)-3-cyclopropyl-3-(2-(3-((dimethylamino)methyl)-4-(5-fluoro-2-methoxypyridin-4-yl)phenyl)chroman-7-yl)-2-methylpropanoic acid To a solution of (2S,3R)-methyl 3-cyclopropyl-3-(2-(3-((dimethylamino)methyl)-4-(5-fluoro-2-methoxypyridin-4-yl)phenyl)chroman-7-yl)-2-methylpropanoate (0.3747 g, 0.703 mmol) in THF (6 ml)/MeOH (6 ml) was added 1 M aqueous LiOH (6 mL, 6.00 mmol) at ambient temperature. The resulting mixture was heated to 60° C. After 19 h, the reaction was concentrated in vacuo. The resulting residue was suspended in EtOAc, then 1 N HCl (8 mL) was added and the mixture was partitioned between EtOAc and saturated NH$_4$Cl. The organic layer was separated, washed with brine, dried over MgSO$_4$, and concentrated in vacuo. The resulting residue was purified via MPLC (ISCO™ 24 g; product elutes at 100% (3:1 EtOAc/EtOH)) with gradient elution 0-100% EtOAc/hexane followed by 3:1 EtOAc/EtOH) to give the title compound. LC/MS (m/z): 519.38 (M+H)$^+$.

Step 3: Sodium (2S,3R)-3-cyclopropyl-3-(2-(3-((dimethylamino)methyl)-4-(5-fluoro-2-methoxypyridin-4-yl)phenyl)chroman-7-yl-2-methylpropanoate SFC Separation The mixture of diastereomers was resolved on a OZ™ column (20×250 mm; 30% (MeOH+0.2% NH$_4$OH)/CO$_2$ to give 2 fractions: Fraction A: Retention time=4.9 min, and Fraction B: Retention time=5.7 min.

Step 4: Conversion to Sodium Salt

To a solution of (2S,3R)-3-cyclopropyl-3-(2-(3-((dimethylamino)methyl)-4-(5-fluoro-2-methoxypyridin-4-yl)phenyl)chroman-7-yl)-2-methylpropanoic acid (Fraction A, 0.147 g, 0.274 mmol) in acetonitrile (2 ml)/water (1 ml) was added 1 M aqueous sodium hydroxide (0.307 ml, 0.307 mmol) at ambient temperature. The resulting solution was sonicated for 2 minutes, and then lyophilized for 19 h to give the title compound. LC/MS (m/z): 519.67 (M+H)$^+$.

TABLE 1

Examples 2-12 were prepared in a similar manner to Example 1 starting from the appropriate starting materials.

| Example No. | Structure | Stereoisomers/ Chiral Conditions | LCMS (M + H)+ |
|---|---|---|---|
| 1a | 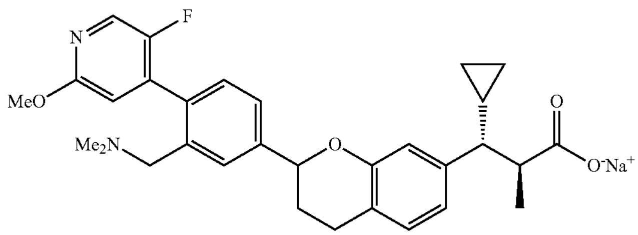 | Isomer A OZ column 30% MeOH (+0.2% NH₄OH)/CO₂ | 519.7 |
| 1b | 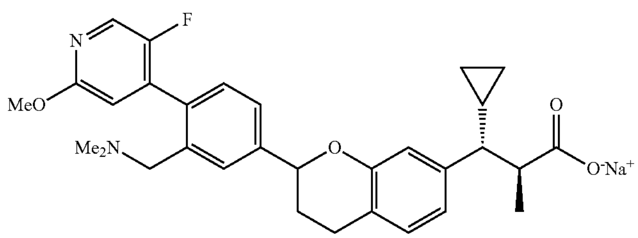 | Isomer B OZ column 30% MeOH (+0.2% NH₄OH)/CO₂ | 519.7 |
| 2 | 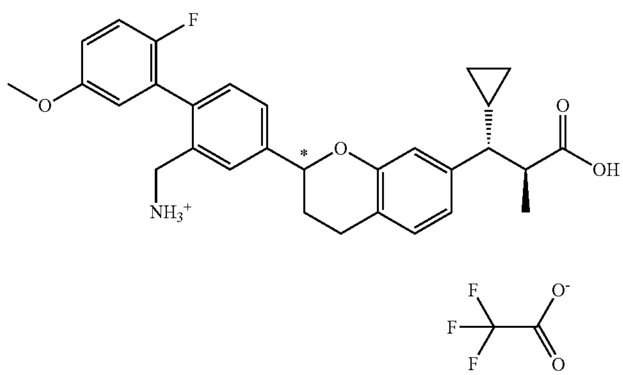 [SMILES: COc1ccc(F)c(-c2ccc(C3CCc4ccc([C@H](C5CC5)[C@H](C)C(=O)O)cc4O3)cc2C[NH3+])c1 ; O=C([O-])C(F)(F)F] | Mixture of 2 diastereomers at * | 490.6 |
| 3 | 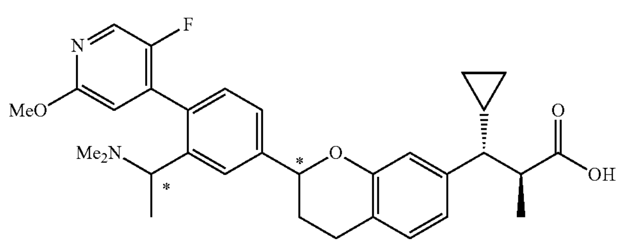 [SMILES: COc1cc(-c2ccc(C3CCc4ccc([C@H](C5CC5)[C@H](C)C(=O)O)cc4O3)cc2C(C)N(C)C)c(F)cn1] | Mixture of 4 diastereomers at * | 533.6 |
| 4 | 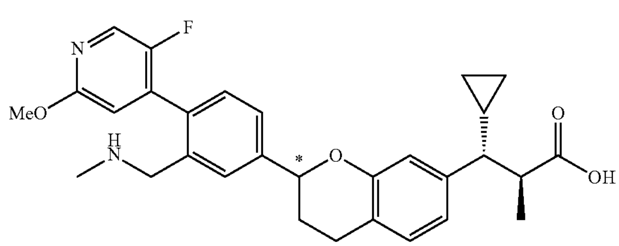 [SMILES: CNCc1cc(C2CCc3ccc([C@H](C4CC4)[C@H](C)C(=O)O)cc3O2)ccc1-c1cc(OC)ncc1F] | Mixture of 2 diastereomers at * | 505.5 |

TABLE 1-continued

Examples 2-12 were prepared in a similar manner to Example 1 starting from the appropriate starting materials.

| Example No. | Structure | Stereoisomers/ Chiral Conditions | LCMS (M + H)+ |
|---|---|---|---|
| 5 | 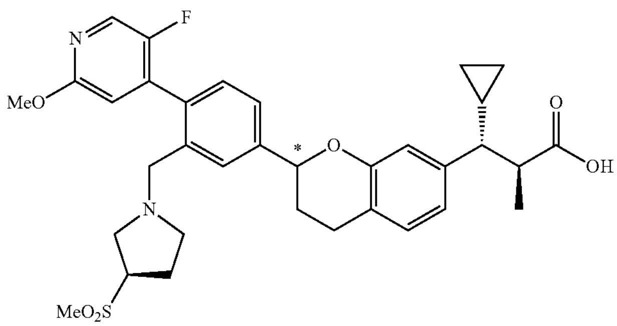 [SMILES: COc1cc(-c2ccc(C3CCc4ccc([C@H](C5CC5)[C@H](C)C(=O)O)cc4O3)cc2CN2CC[C@@H](S(C)(=O)=O)C2)c(F)cn1] | Mixtureo of 2 diastereomers at * | 623.9 |
| 6 | 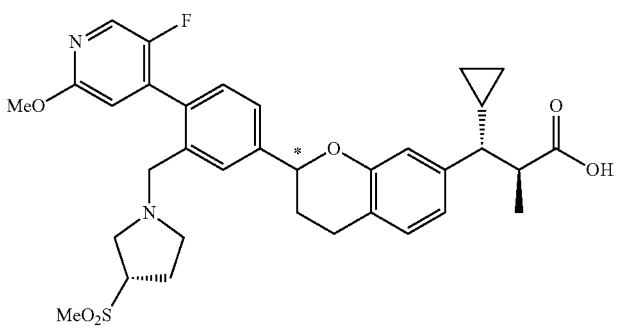 [SMILES: COc1cc(-c2ccc(C3CCc4ccc([C@H](C5CC5)[C@H](C)C(=O)O)cc4O3)cc2CN2CC[C@H](S(C)(=O)=O)C2)c(F)cn1] | Mixture of 2 diastereomers at * | 623.9 |
| 7 | 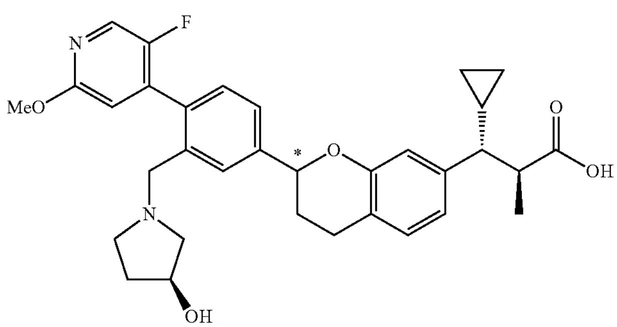 [SMILES: COc1cc(-c2ccc(C3CCc4ccc([C@H](C5CC5)[C@H](C)C(=O)O)cc4O3)cc2CN2CC[C@H](O)C2)c(F)cn1] | Mixture of 2 diastereomers at * | 561.8 |
| 8 | 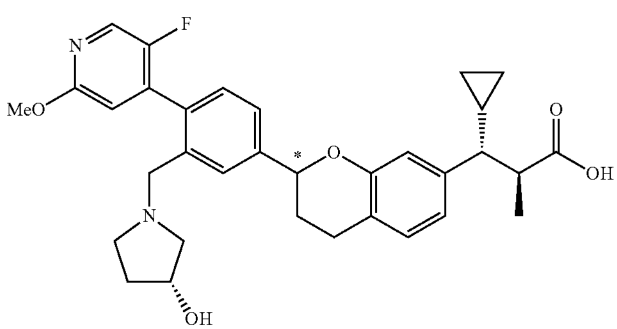 [SMILES: COc1cc(-c2ccc(C3CCc4ccc([C@H](C5CC5)[C@H](C)C(=O)O)cc4O3)cc2CN2CC[C@@H](O)C2)c(F)cn1] | Mixture of 2 diastereomers at * | 561.8 |

TABLE 1-continued

Examples 2-12 were prepared in a similar manner to Example 1 starting from the appropriate starting materials.

| Example No. | Structure | Stereoisomers/ Chiral Conditions | LCMS (M + H)+ |
|---|---|---|---|
| 9 | 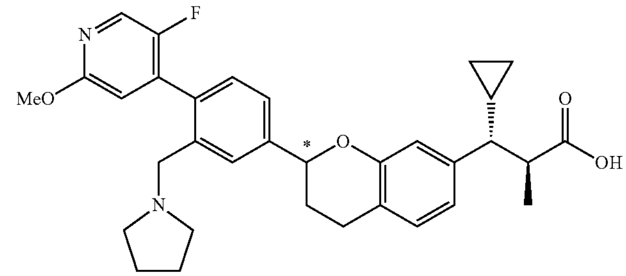 [SMILES: COc1cc(-c2ccc(C3CCc4ccc([C@H](C5CC5)[C@H](C)C(=O)O)cc4O3)cc2CN2CCCC2)c(F)cn1] | Mixture of 2 diastereomers at * | 545.6 |
| 9a | 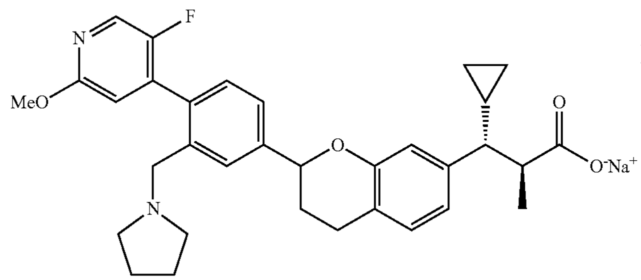 | Isomer A AD-H Column 45% IPA (0.1% DIPA)/CO$_2$ | 545.6 |
| 9b | 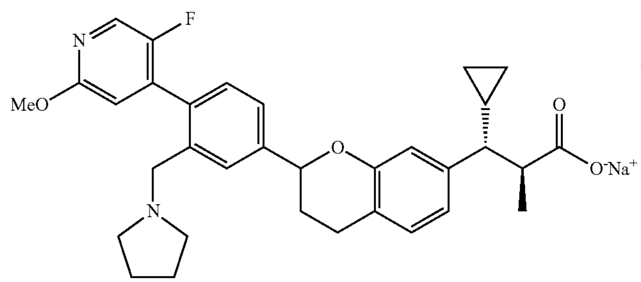 | Isomer B AD-H Column 45% IPA (0.1% DIPA)/CO$_2$ | 545.6 |
| 10 | 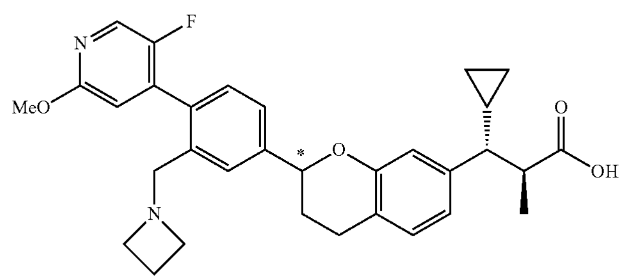 [SMILES: COc1cc(-c2ccc(C3CCc4ccc([C@H](C5CC5)[C@H](C)C(=O)O)cc4O3)cc2CN2CCC2)c(F)cn1] | Mixture of 2 diastereomers at * | 531.5 |
| 11a | 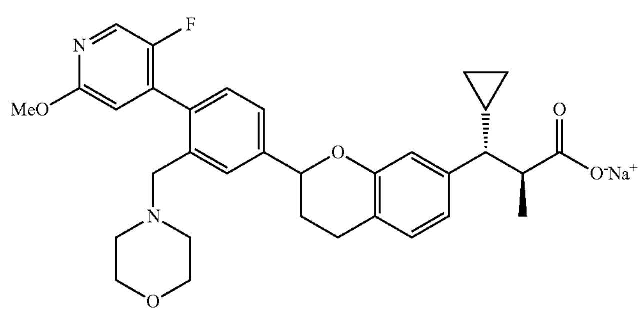 | Isomer A AS-H Column 30% MeOH (0.2% DEA)/CO$_2$ | 561.6 |

TABLE 1-continued

Examples 2-12 were prepared in a similar manner to Example 1 starting from the appropriate starting materials.

| Example No. | Structure | Stereoisomers/ Chiral Conditions | LCMS (M + H)+ |
|---|---|---|---|
| 11b | 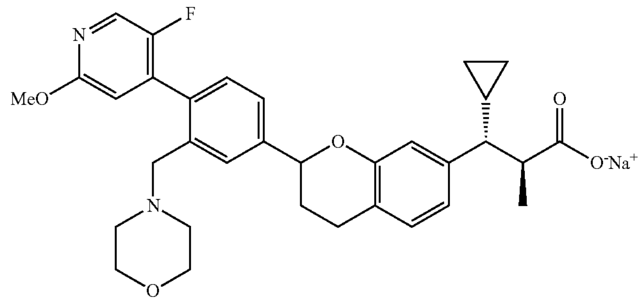 | Isomer B AS-H Column 30% MeOH (0.2% DEA)/CO₂ | 561.6 |
| 12 | 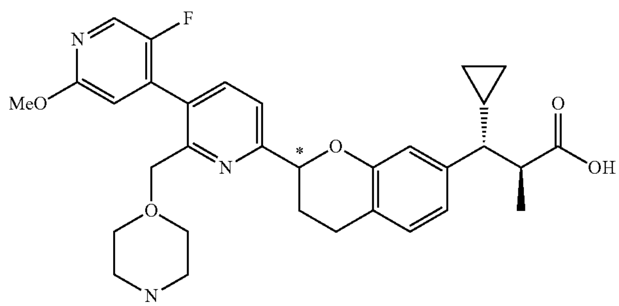 | Mixture of 2 diastereomers at * | 562.5 |

Example 13

(2S,3R)-3-cyclopropyl-3-(2-(4-(5-fluoro-2-methoxy-pyridin-4-yl)-3-(4-methylpiperazin-1-yl)methylphenyl)chroman-7-yl)-2-methylpropanoic acid

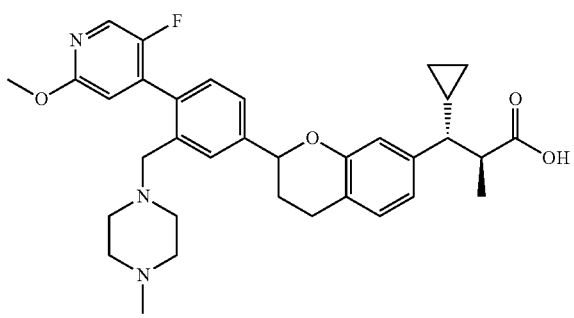 [SMILES: COc1cc(-c2ccc(C3CCc4ccc([C@H](C5CC5)[C@H](C)C(=O)O)cc4O3)cc2CN2CCN(C)CC2)c(F)cn1]

Step 1: Methyl (2S,3R)-3-cyclopropyl-3-(2-(4-(5-fluoro-2-methoxypyridin-4-yl)-3-((4-methylpiperazin-1-yl)methyl)phenyl)chroman-7-yl)-2-methylpropanoate Methyl (2S,3R)-3-cyclopropyl-3-(2-(4-(5-fluoro-2-methoxypyridin-4-yl)-3-formyl-phenyl)chroman-7-yl)-2-methylpropanoate (22 mg, 0.04 mmol), 1-methyl piperazine (5 mg, 0.054 mmol), Na(AcO)₃BH (14 mg, 0.067 mmol), and acetic acid (3 mg, 0.052 mmol) were dissolved in 1,2-dichloroethene (0.5 ml), and the resulting mixture was stirred at r.t. for 4.5 hours. The mixture was partitioned between EtOAc and saturated NaHCO₃. The organic layer was separated, washed with brine, dried (MgSO₄), filtered, and concentrated. The resulting residue was purified via gradient flash chromatography (0-100% EtOAc/hexanes over 8 minutes followed by 3/1 EtOAc in EtOH) to provide the title compound.

Step 2: (2S,3R)-3-cyclopropyl-3-(2-(4-(5-fluoro-2-methoxypyridin-4-yl-3-((4-methylpiperazin-1-yl)methyl)phenyl)chroman-7-yl)-2-methylpropanoic acid Methyl (2S,3R)-3-cyclopropyl-3-(2-(4-(5-fluoro-2-methoxypyridin-4-yl)-3-((4-methylpiperazin-1-yl)methyl)phenyl)chroman-7-yl)-2-methylpropanoate was hydrolyzed as described in Step 2 of Example 1 to give the title compound.

TABLE 2

Examples 14-32 were prepared in a similar manner to Example 13 starting from the appropriate starting materials. Where noted, the sodium salt of the acid was prepared according to the procedure outlined for Example 1. Chiral conditions for resolution of isomers were performed on the free acid.

| Example | Structure | Stereoisomers/ Chiral Conditions | Method | LC/MS (M + H)+ |
| --- | --- | --- | --- | --- |
| 13 | 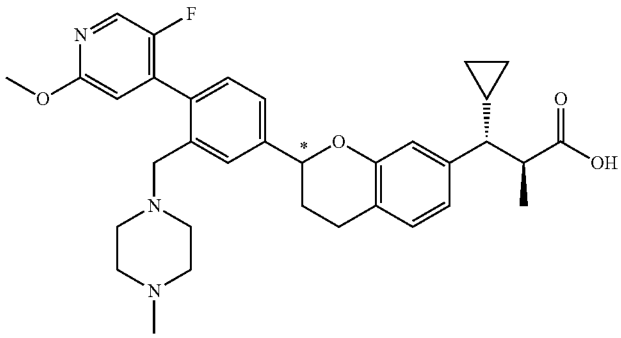 [SMILES: COc1cc(-c2ccc(C3CCc4ccc([C@H](C5CC5)[C@H](C)C(=O)O)cc4O3)cc2CN2CCN(C)CC2)c(F)cn1] | Mixture of 2 diastereomers at * | A | 574.6 |
| 14 | 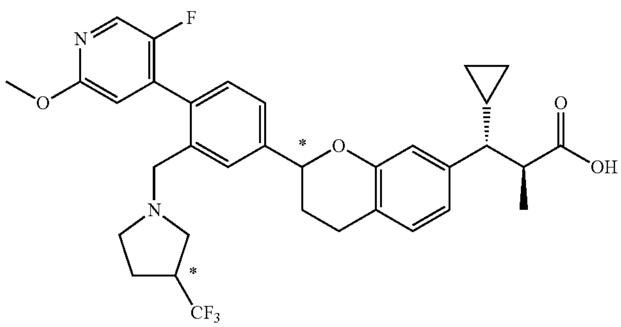 [SMILES: COc1cc(-c2ccc(C3CCc4ccc([C@H](C5CC5)[C@H](C)C(=O)O)cc4O3)cc2CN2CCC(C(F)(F)F)C2)c(F)cn1] | Mixtureo of four isomers at * | B | 613.6 |
| 15 | 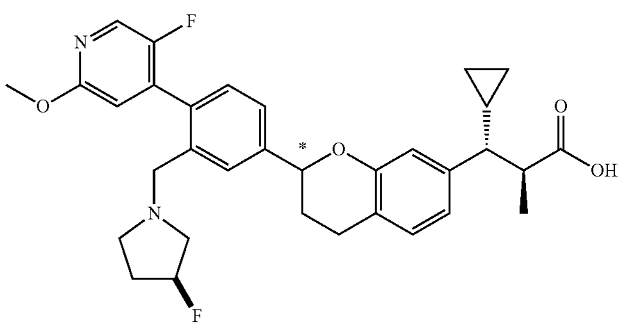 [SMILES: COc1cc(-c2ccc(C3CCc4ccc([C@H](C5CC5)[C@H](C)C(=O)O)cc4O3)cc2CN2CC[C@H](F)C2)c(F)cn1] | Mixture of 2 diastereomers at * | B | 563.6 |
| 16 | 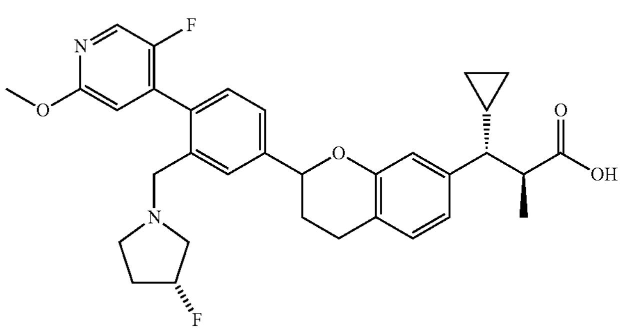 [SMILES: COc1cc(-c2ccc(C3CCc4ccc([C@H](C5CC5)[C@H](C)C(=O)O)cc4O3)cc2CN2CC[C@@H](F)C2)c(F)cn1] | Mixture of 2 diastereomers at * | B | 563.6 |

TABLE 2-continued

Examples 14-32 were prepared in a similar manner to Example 13 starting from the appropriate starting materials. Where noted, the sodium salt of the acid was prepared according to the procedure outlined for Example 1. Chiral conditions for resolution of isomers were performed on the free acid.

| Example | Structure | Stereoisomers/ Chiral Conditions | Method | LC/MS (M + H)+ |
|---|---|---|---|---|
| 17 | 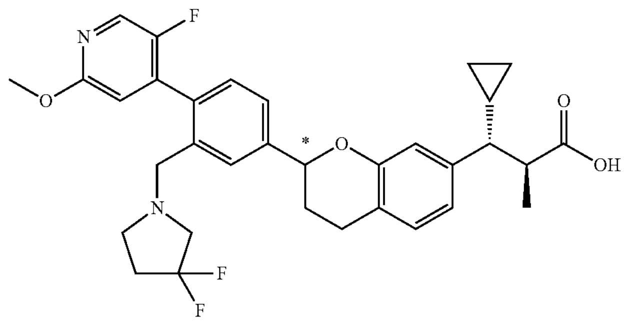 [SMILES: COc1cc(-c2ccc(C3CCc4ccc([C@H](C5CC5)[C@H](C)C(=O)O)cc4O3)cc2CN2CCC(F)(F)C2)c(F)cn1] | Mixture of 2 diastereomers at * | B | 581.8 |
| 18 | 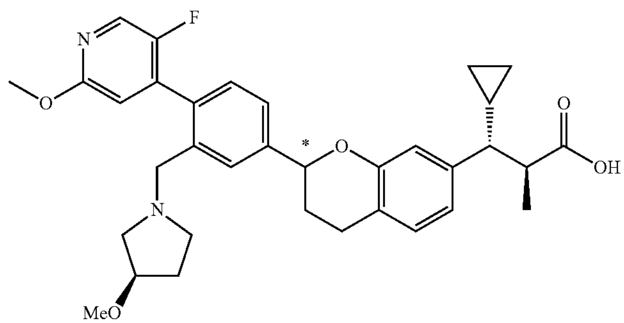 [SMILES: COc1cc(-c2ccc(C3CCc4ccc([C@H](C5CC5)[C@H](C)C(=O)O)cc4O3)cc2CN2CC[C@@H](OC)C2)c(F)cn1] | Mixture of 2 diastereomers at * | B | 575.8 |
| 19 | 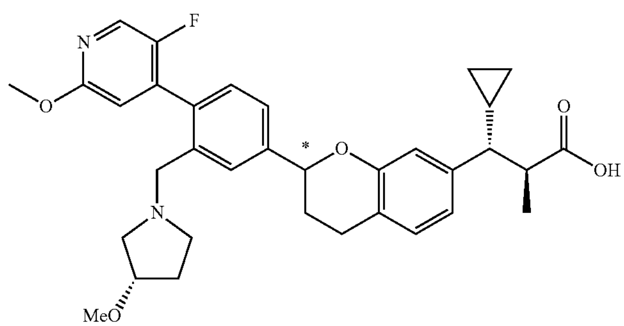 [SMILES: COc1cc(-c2ccc(C3CCc4ccc([C@H](C5CC5)[C@H](C)C(=O)O)cc4O3)cc2CN2CC[C@H](OC)C2)c(F)cn1] | Mixture of 2 diastereomers at * | B | 575.8 |
| 20 | 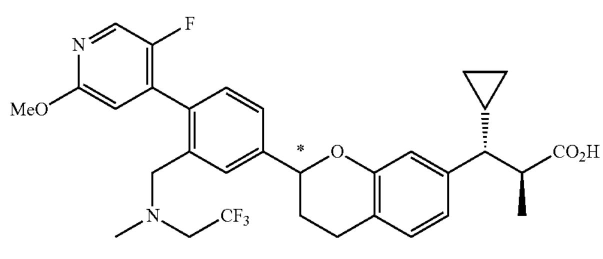 [SMILES: COc1cc(-c2ccc(C3CCc4ccc([C@H](C5CC5)[C@H](C)C(=O)O)cc4O3)cc2CN(C)CC(F)(F)F)c(F)cn1] | Mixture of 2 diastereomers at * | A | 587.8 |
| 21 | 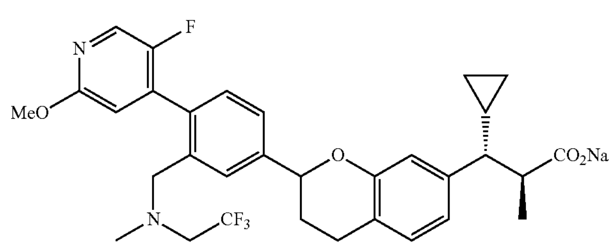 | Isomer A AD-H Column 30% IPA/CO$_2$ | A | 587.8 |

TABLE 2-continued

*Examples 14-32 were prepared in a similar manner to Example 13 starting from the appropriate starting materials. Where noted, the sodium salt of the acid was prepared according to the procedure outlined for Example 1. Chiral conditions for resolution of isomers were performed on the free acid.*

| Example | Structure | Stereoisomers/ Chiral Conditions | Method | LC/MS $(M + H)^+$ |
|---|---|---|---|---|
| 22 | 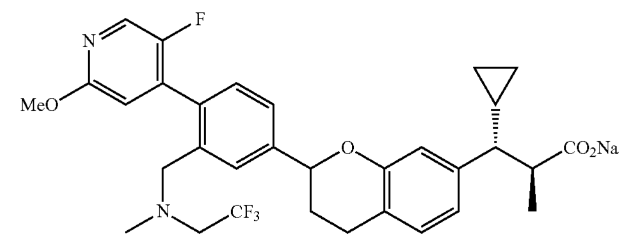 | Isomer B AD-H Column 30% IPA/$CO_2$ | A | 587.8 |
| 23 | 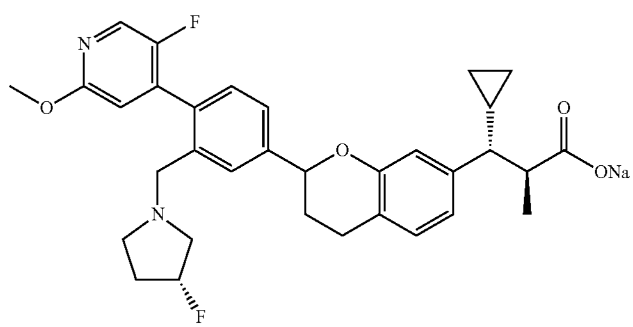 | Isomer A AD-H Column 35% IPA (0.1% DIPA)/ $CO_2$ | B | 563.6 |
| 24 | 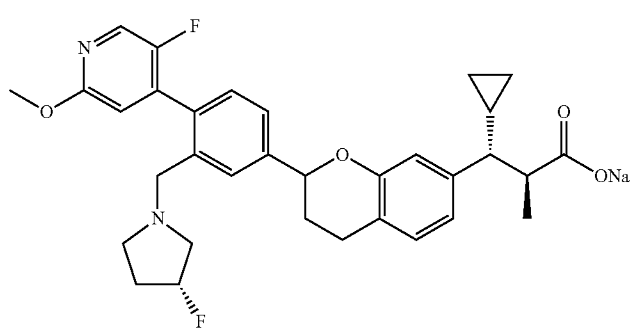 | Isomer B AD-H Column 35% IPA (0.1% DIPA)/ $CO_2$ | B | 563.6 |
| 25 | 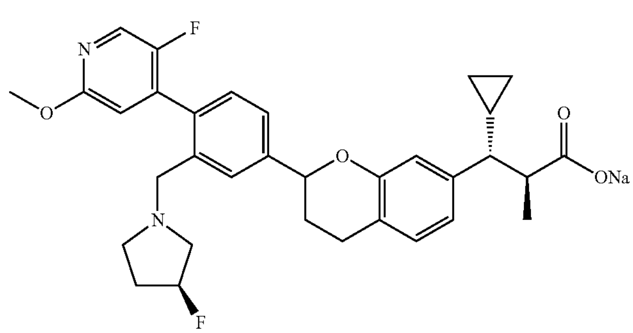 | Isomer A AD-H Column 35% IPA (0.1% DIPA)/ $CO_2$ | B | 563.6 |

TABLE 2-continued

Examples 14-32 were prepared in a similar manner to Example 13 starting from the appropriate starting materials. Where noted, the sodium salt of the acid was prepared according to the procedure outlined for Example 1. Chiral conditions for resolution of isomers were performed on the free acid.

| Example | Structure | Stereoisomers/ Chiral Conditions | Method | LC/MS $(M + H)^+$ |
|---|---|---|---|---|
| 26 | 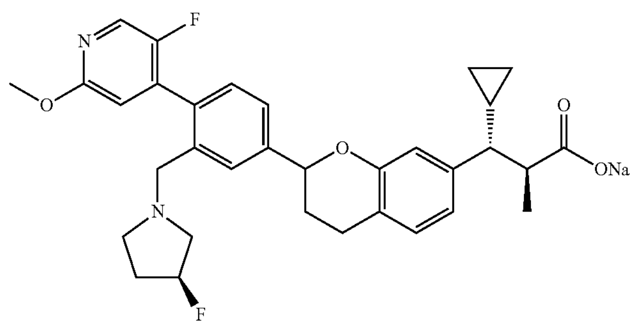 | Isomer B AD-H Column 35% IPA (0.1% DIPA)/ $CO_2$ | B | 563.6 |
| 27 | 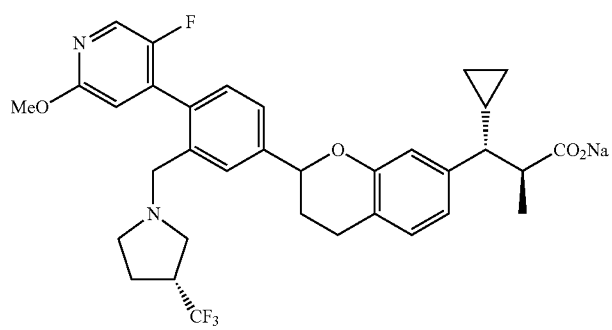 | Isomer A AD-H Column 30% IPA (0.1% DIPA)/ $CO_2$ | B | 613.9 |
| 28 | 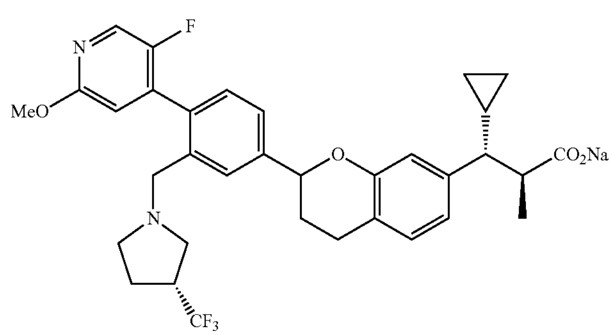 | Isomer B AD-H Column 30% IPA (0.1% DIPA)/ $CO_2$ | B | 613.9 |
| 29 | 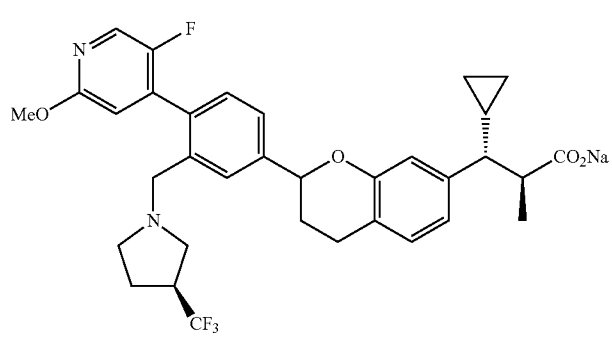 | Isomer A AD-H Column 30% IPA (0.2% DIPA)/ $CO_2$ | B | 613.7 |

TABLE 2-continued

Examples 14-32 were prepared in a similar manner to Example 13 starting from the appropriate starting materials. Where noted, the sodium salt of the acid was prepared according to the procedure outlined for Example 1. Chiral conditions for resolution of isomers were performed on the free acid.

| Example | Structure | Stereoisomers/Chiral Conditions | Method | LC/MS (M + H)+ |
|---|---|---|---|---|
| 30 | 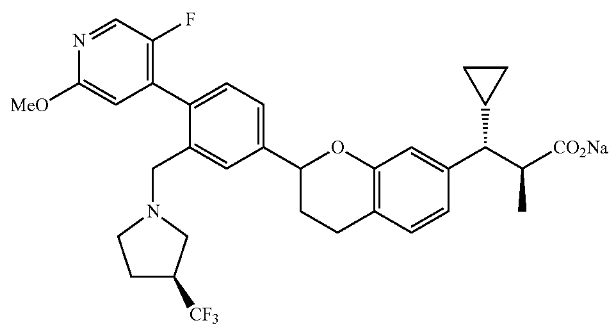 | Isomer A<br>AD-H Column<br>30% IPA<br>(0.2% DIPA)/<br>$CO_2$ | B | 613.7 |
| 31 | 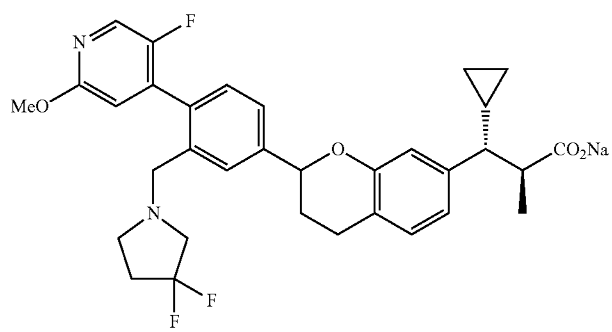 | Isomer A<br>AS-H Column<br>100% EtOH/<br>$CO_2$ | B | 581.8 |
| 32 | 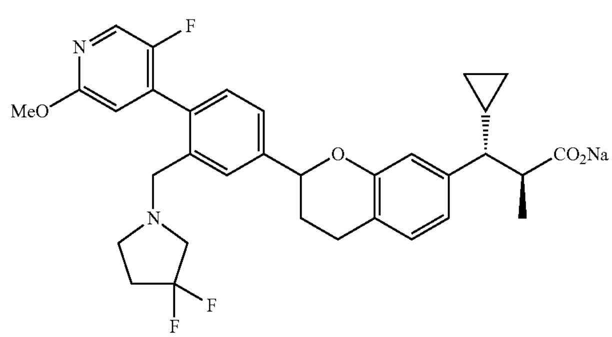 | Isomer A<br>AS-H Column<br>100% EtOH/<br>$CO_2$ | B | 581.8 |

Method A - Reductive amination as described in Step 1 of Example 13 using the free amine in the reductive amination;

Methos B - Triethylamine (1.2-1.4 eq.) was added to Step 1 of Example 13 using the HCl salt of the appropriate amine in the reductive amination.

Example 33

(2S,3R)-3-(2-(3-((4-(tert-butoxycarbonyl)piperazin-1-yl)methyl)-4-(5-fluoro-2-methoxypyridin-4-yl)phenyl)chroman-7-yl)-3-cyclopropyl-2-methylpropanoic acid

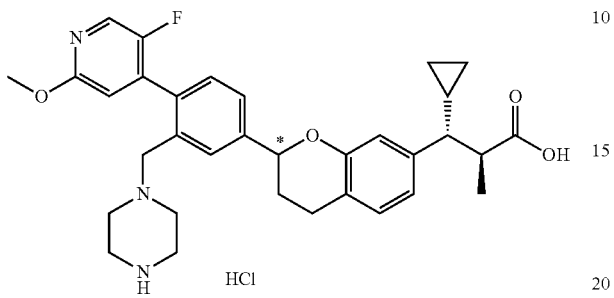

Step 1:
(2S,3R)-3-(2-(3-((4-(tert-butoxycarbonyl)piperazin-1-yl)methyl)-4-(5-fluoro-2-methoxypyridin-4-yl)phenyl)chroman-7-yl)-3-cyclopropyl-2-methylpropanoic acid was prepared in a similar manner to that described for Example 13 using the appropriate reagents.

Step 2:
(2S,3R)-3-(2-(3-((4-(tert-butoxycarbonyl)piperazin-1-yl)methyl)-4-(5-fluoro-2-methoxypyridin-4-yl)phenyl)chroman-7-yl)-3-cyclopropyl-2-methylpropanoic acid (28 mg, 0.043 mmol) was dissolved in HCl in dioxane (0.5 ml) and DCM (0.5 ml). A solid precipitated from the reaction mixture. The resulting solid was filtered, triturated with diethyl ether, and dried under vacuum to provide the HCl salt of (2S,3R)-3-(2-(3-((4-(tert-butoxycarbonyl)-piperazin-1-yl)methyl)-4-(5-fluoro-2-methoxypyridin-4-yl)phenyl)chroman-7-yl)-3-cyclopropyl-2-methylpropanoic acid as a mixture of 2 diastereomers at *. LC/MS: 560.6 (M+H)+.

Example 34

Sodium (2S,3R)-3-cyclopropyl-3-((S)-2-(4-(5-fluoro-2-methoxypyridin-4-yl)-3-((methylamino)methyl)phenyl)chroman-7-yl)-2-methylpropanoate

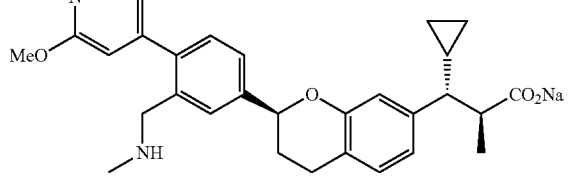

Intermediate 4b (Isomer B) was converted to the title compound using conditions similar to those described in Example 13. The sodium salt of Example 34 was prepared as described in Step 3 of Example 1. LC/MS (M+H)+=505.6.

General Procedure for Examples 35-73

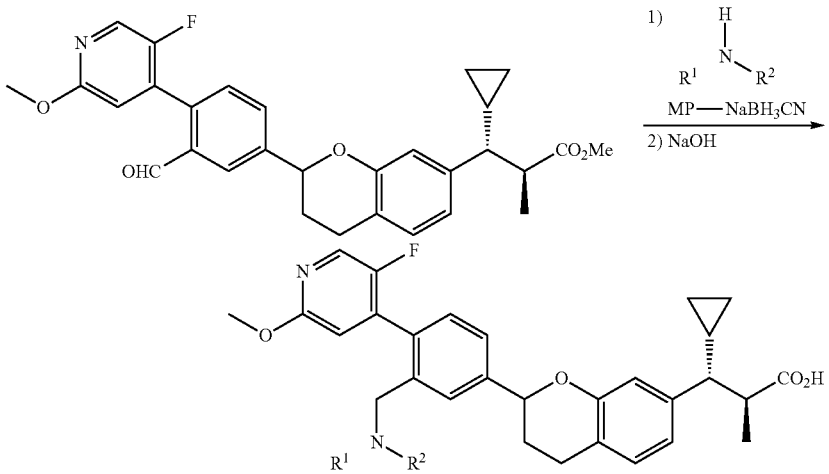

To a solution of (2S,3R)-methyl 3-cyclopropyl-3-(2-(4-(5-fluoro-2-methoxypyridin-4-yl)-3-formylphenyl)chroman-7-yl)-2-methylpropanoate in 1 ml MeOH/HOAc (10:1) was added the appropriate aldehyde and the reaction was stirred for 1 h. Then MP resin-cyanoborohydride (Biotage part #800405, 2.45 mmol/g, 100 mg) was added, and the mixture was stirred at rt for 4 h. The reaction was filtered and the solids were washed with 2×1 mL MeOH. The combined filtrates were dried and the resulting residue was re-dissolved in 1 mL THF/0.5 mL MeOH/0.5 mL 4N NaOH. The mixture was heated at 70° C. for 2 h, then 0.5 mL HOAc and 0.1 mL TFA were added. The resulting mixture was concentrated to give a residue, which was dissolved in 1.5 mL DMF/DMSO (1:1), filtered and purified via HPLC (reverse phase: acetonitrile/water gradient).

TABLE 3

Examples 35-73 were prepared according the above Scheme using the appropriate amine in the reductive amination step.

| Example | Structure | Stereoisomers/Chiral Conditions | LC/MS (M + H)+ |
|---|---|---|---|
| 35 | 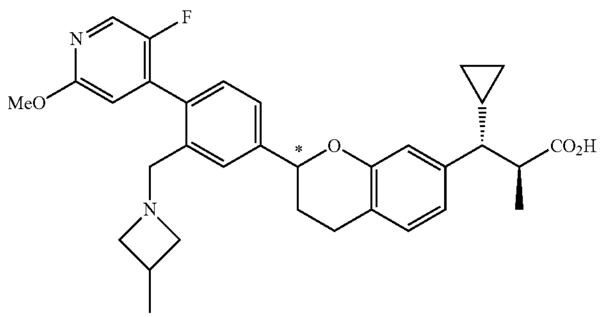 [SMILES: COc1cc(-c2ccc(C3CCc4ccc([C@H](C5CC5)[C@H](C)C(=O)O)cc4O3)cc2CN2CC(C)C2)c(F)cn1] | Mixture of 2 diastereomers at * | 545 |
| 36 | 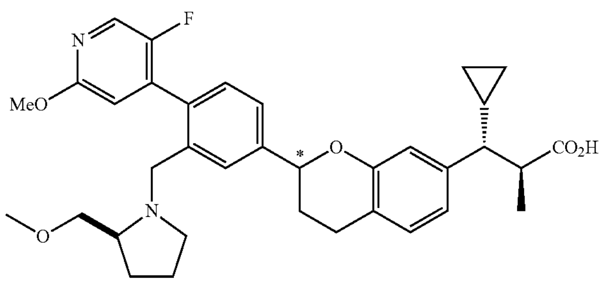 [SMILES: COC[C@@H]1CCCN1Cc1cc(C2CCc3ccc([C@H](C4CC4)[C@H](C)C(=O)O)cc3O2)ccc1-c1cc(OC)ncc1F] | Mixture of 2 diastereomers at * | 589 |
| 37 | 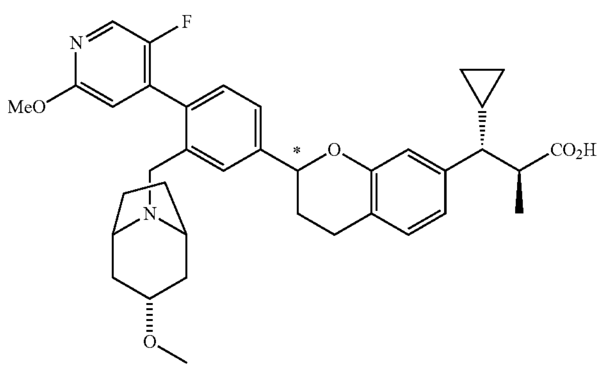 | Mixture of 2 diastereomers at * | 615 |
| 38 | 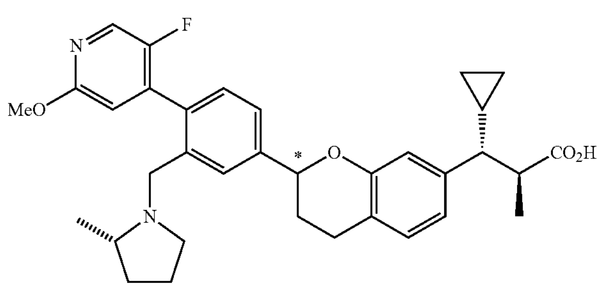 [SMILES: COc1cc(-c2ccc(C3CCc4ccc([C@H](C5CC5)[C@H](C)C(=O)O)cc4O3)cc2CN2CCC[C@@H]2C)c(F)cn1] | Mixture of 2 diastereomers at * | 559 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---|---|---|---|
| 39 | 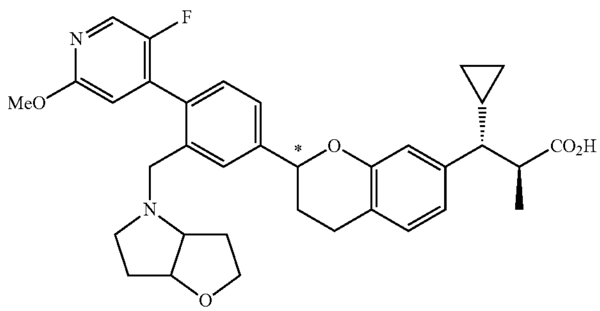 [SMILES: COc1cc(-c2ccc(C3CCc4ccc([C@H](C5CC5)[C@H](C)C(=O)O)cc4O3)cc2CN2CCC3OCCC32)c(F)cn1] | Mixture of 2 diastereomers at * | 587 |
| 40 | 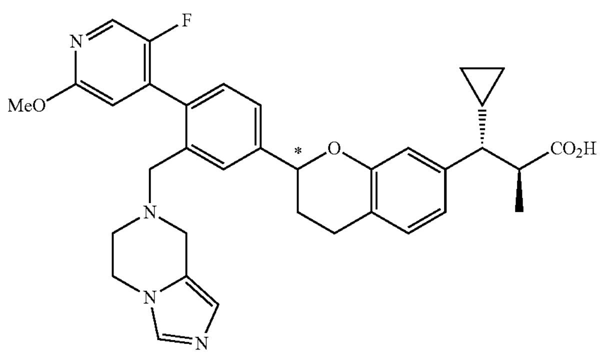 [SMILES: COc1cc(-c2ccc(C3CCc4ccc([C@H](C5CC5)[C@H](C)C(=O)O)cc4O3)cc2CN2CCn3cncc3C2)c(F)cn1] | Mixture of 2 diastereomers at * | 597 |
| 41 | 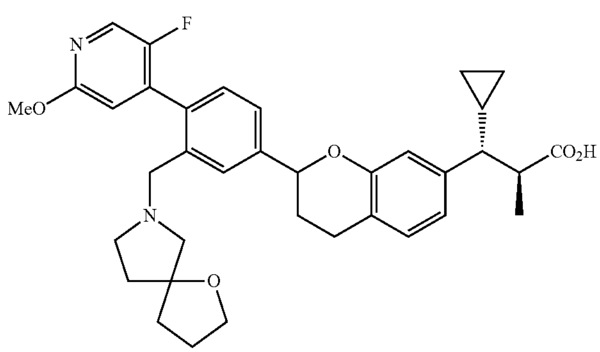 | Mixture of 2 diastereomers at * | 601 |
| 42 | 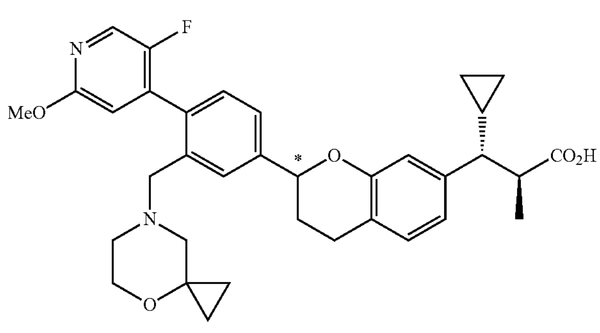 [SMILES: COc1cc(-c2ccc(C3CCc4ccc([C@H](C5CC5)[C@H](C)C(=O)O)cc4O3)cc2CN2CCOC3(CC3)C2)c(F)cn1] | Mixture of 2 diastereomers at * | 587 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---|---|---|---|
| 43 | 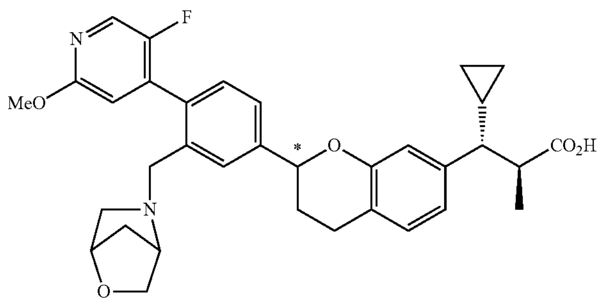 [SMILES: COc1cc(-c2ccc(C3CCc4ccc([C@H](C5CC5)[C@H](C)C(=O)O)cc4O3)cc2CN2CC3CC2CO3)c(F)cn1] | Mixture of 2 diastereomers at * | 573 |
| 44 | 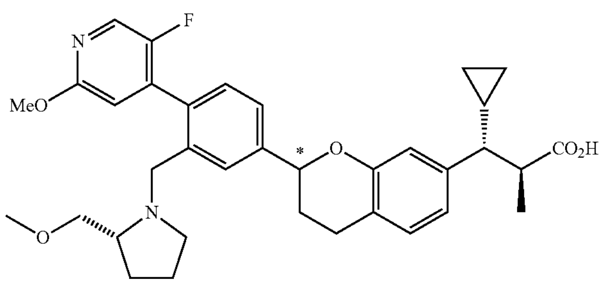 [SMILES: COC[C@H]1CCCN1Cc1cc(C2CCc3ccc([C@H](C4CC4)[C@H](C)C(=O)O)cc3O2)ccc1-c1cc(OC)ncc1F] | Mixture of 2 diastereomers at * | 589 |
| 45 | 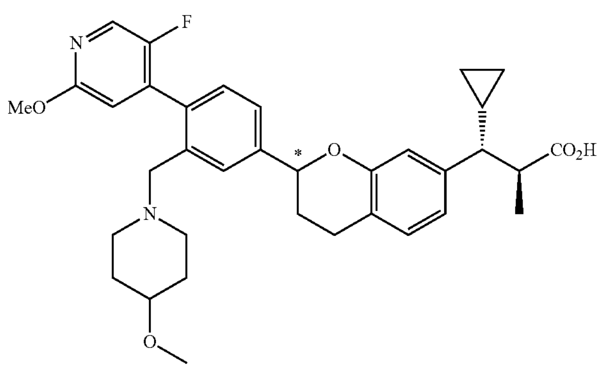 [SMILES: COc1cc(-c2ccc(C3CCc4ccc([C@H](C5CC5)[C@H](C)C(=O)O)cc4O3)cc2CN2CCC(OC)CC2)c(F)cn1] | Mixture of 2 diastereomers at * | 589 |
| 46 | 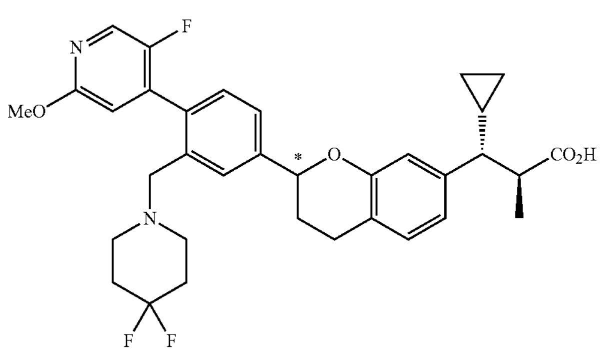 [SMILES: COc1cc(-c2ccc(C3CCc4ccc([C@H](C5CC5)[C@H](C)C(=O)O)cc4O3)cc2CN2CCC(F)(F)CC2)c(F)cn1] | Mixture of 2 diastereomers at * | 595 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---|---|---|---|
| 47 | 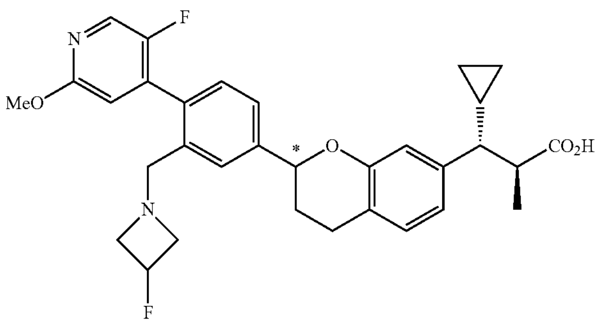 [SMILES: COc1cc(-c2ccc(C3CCc4ccc([C@H](C5CC5)[C@H](C)C(=O)O)cc4O3)cc2CN2CC(F)C2)c(F)cn1] | Mixture of 2 diastereomers at * | 549 |
| 48 | 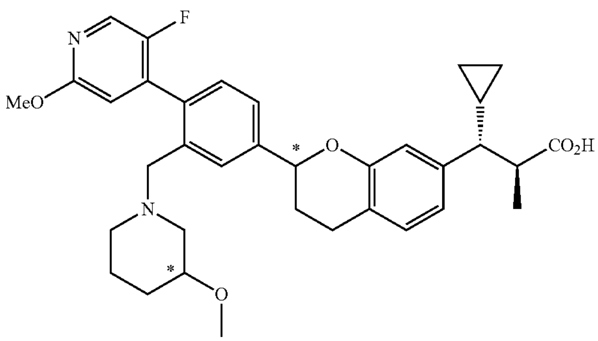 [SMILES: COc1cc(-c2ccc(C3CCc4ccc([C@H](C5CC5)[C@H](C)C(=O)O)cc4O3)cc2CN2CCCC(OC)C2)c(F)cn1] | Mixture of isomers at * | 589 |
| 49 | 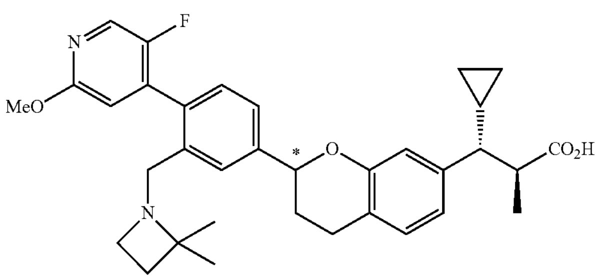 [SMILES: COc1cc(-c2ccc(C3CCc4ccc([C@H](C5CC5)[C@H](C)C(=O)O)cc4O3)cc2CN2CCC2(C)C)c(F)cn1] | Mixture of 2 diastereomers at * | 559 |
| 50 | 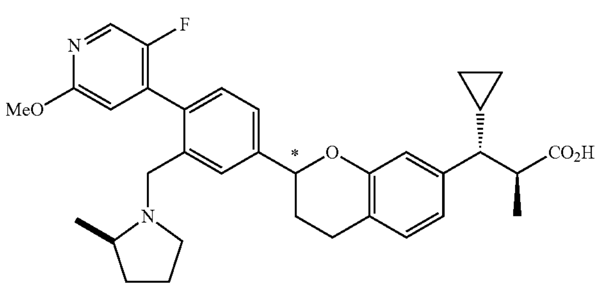 [SMILES: COc1cc(-c2ccc(C3CCc4ccc([C@H](C5CC5)[C@H](C)C(=O)O)cc4O3)cc2CN2CCC[C@H]2C)c(F)cn1] | Mixture of 2 diastereomers at * | 559 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---------|-----------|----------------------------------|----------------|
| 51 | 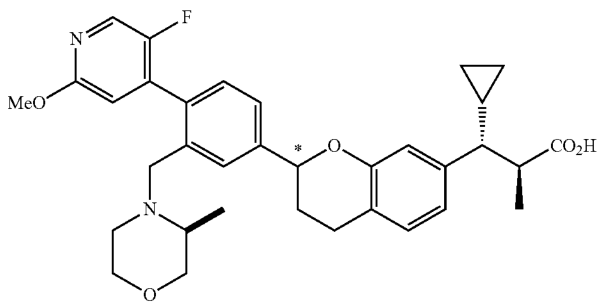 [SMILES: COc1cc(-c2ccc(C3CCc4ccc([C@H](C5CC5)[C@H](C)C(=O)O)cc4O3)cc2CN2CCOC[C@@H]2C)c(F)cn1] | Mixture of 2 diastereomers at * | 575 |
| 52 | 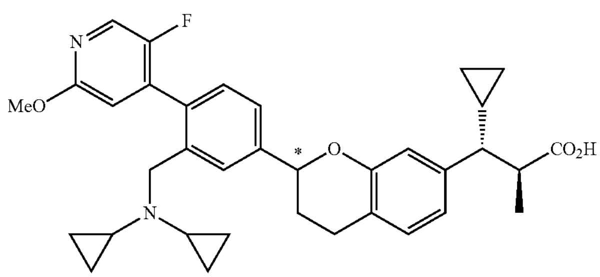 [SMILES: COc1cc(-c2ccc(C3CCc4ccc([C@H](C5CC5)[C@H](C)C(=O)O)cc4O3)cc2CN(C2CC2)C2CC2)c(F)cn1] | Mixture of 2 diastereomers at * | 571 |
| 53 | 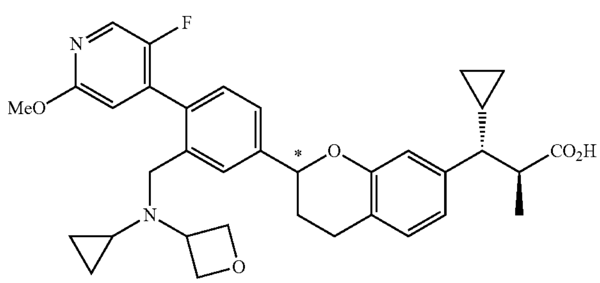 [SMILES: COc1cc(-c2ccc(C3CCc4ccc([C@H](C5CC5)[C@H](C)C(=O)O)cc4O3)cc2CN(C2CC2)C2COC2)c(F)cn1] | Mixture of 2 diastereomers at * | 587 |
| 54 | 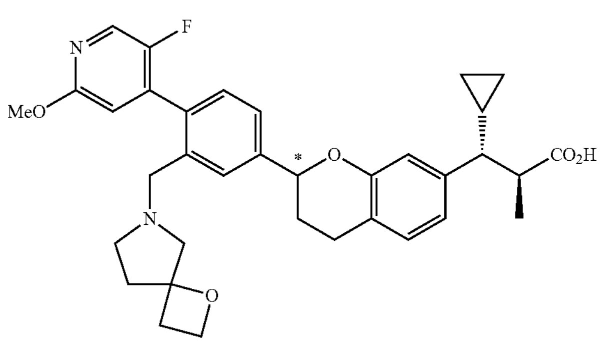 [SMILES: COc1cc(-c2ccc(C3CCc4ccc([C@H](C5CC5)[C@H](C)C(=O)O)cc4O3)cc2CN2CCC3(CCO3)C2)c(F)cn1] | Mixture of 2 diastereomers at * | 587 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---|---|---|---|
| 55 | 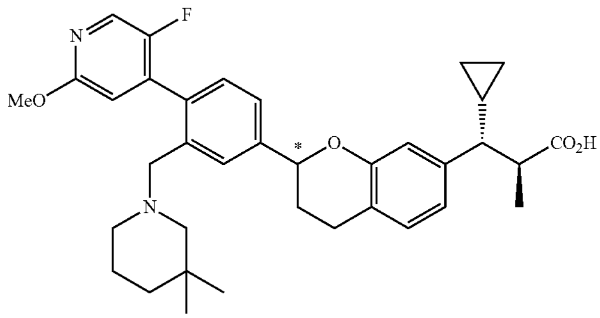 [SMILES: COc1cc(-c2ccc(C3CCc4ccc([C@H](C5CC5)[C@H](C)C(=O)O)cc4O3)cc2CN2CCCC(C)(C)C2)c(F)cn1] | Mixture of 2 diastereomers at * | 587 |
| 56 | 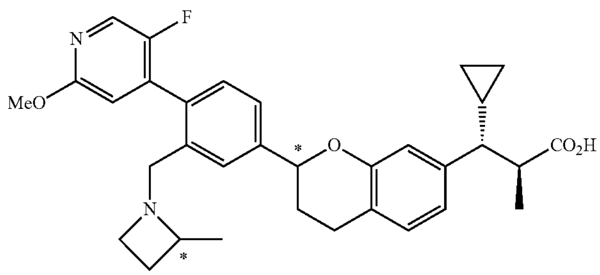 [SMILES: COc1cc(-c2ccc(C3CCc4ccc([C@H](C5CC5)[C@H](C)C(=O)O)cc4O3)cc2CN2CCC2C)c(F)cn1] | Mixture of isomer at * | 545 |
| 57 | 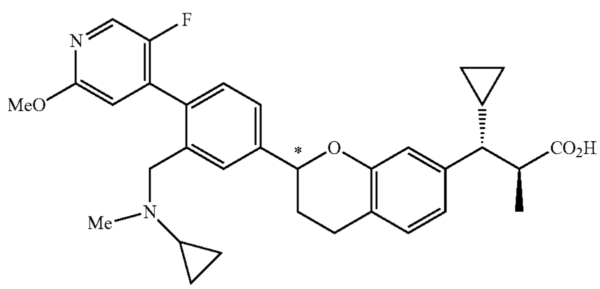 [SMILES: COc1cc(-c2ccc(C3CCc4ccc([C@H](C5CC5)[C@H](C)C(=O)O)cc4O3)cc2CN(C)C2CC2)c(F)cn1] | Mixture of 2 diastereomers at * | 545 |
| 58 | 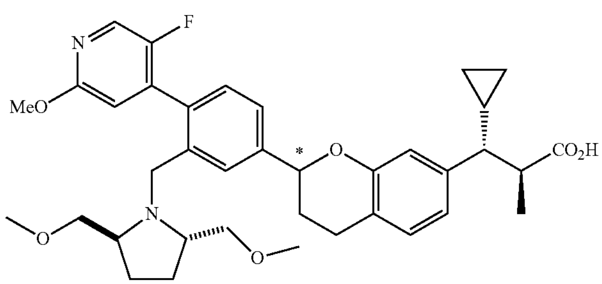 [SMILES: COC[C@@H]1CC[C@@H](COC)N1Cc1cc(C2CCc3ccc([C@H](C4CC4)[C@H](C)C(=O)O)cc3O2)ccc1-c1cc(OC)ncc1F] | Mixture of 2 diastereomers at * | 633 |
| 59 | 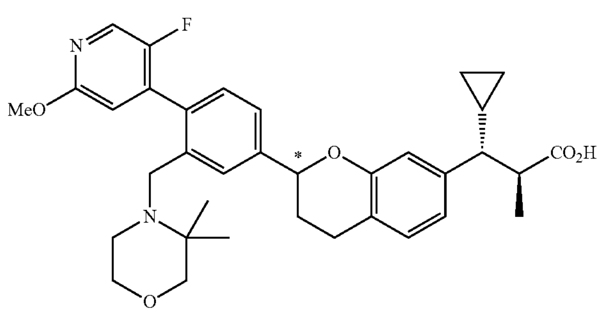 [SMILES: COc1cc(-c2ccc(C3CCc4ccc([C@H](C5CC5)[C@H](C)C(=O)O)cc4O3)cc2CN2CCOCC2(C)C)c(F)cn1] | Mixture of 2 diastereomers at * | 589 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---------|-----------|----------------------------------|----------------|
| 60 | 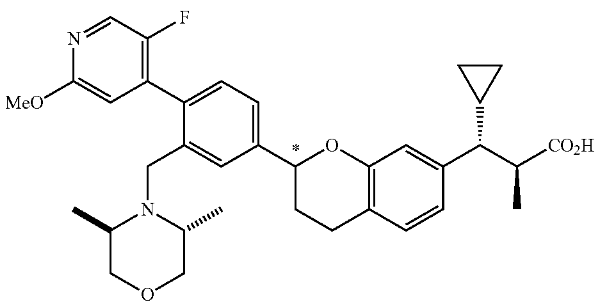 [SMILES: COc1cc(-c2ccc(C3CCc4ccc([C@H](C5CC5)[C@H](C)C(=O)O)cc4O3)cc2CN2[C@H](C)COC[C@H]2C)c(F)cn1] | Mixture of 2 diastereomers at * | 589 |
| 61 | 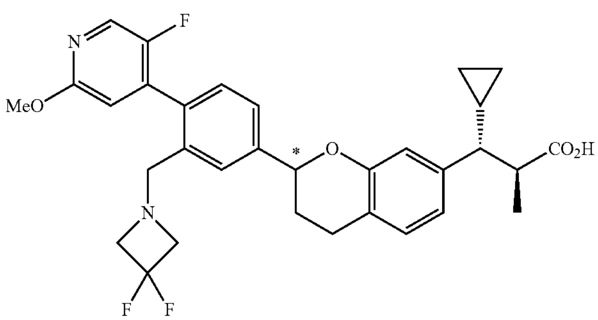 [SMILES: COc1cc(-c2ccc(C3CCc4ccc([C@H](C5CC5)[C@H](C)C(=O)O)cc4O3)cc2CN2CC(F)(F)C2)c(F)cn1] | Mixture of 2 diastereomers at * | 567 |
| 62 | 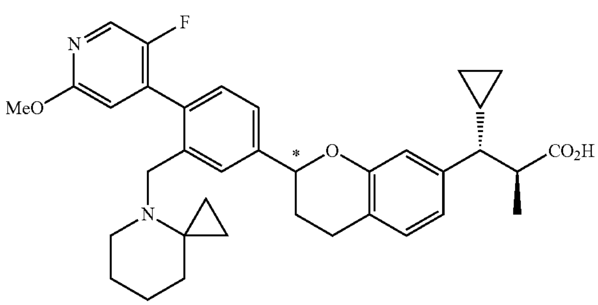 [SMILES: COc1cc(-c2ccc(C3CCc4ccc([C@H](C5CC5)[C@H](C)C(=O)O)cc4O3)cc2CN2CCCCC23CC3)c(F)cn1] | Mixture of 2 diastereomers at * | 585 |
| 63 | 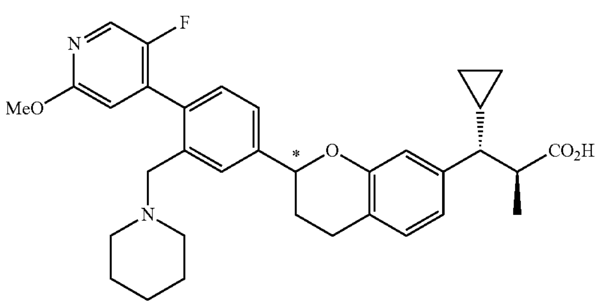 [SMILES: COc1cc(-c2ccc(C3CCc4ccc([C@H](C5CC5)[C@H](C)C(=O)O)cc4O3)cc2CN2CCCCC2)c(F)cn1] | Mixture of 2 diastereomers at * | 559 |
| 64 | 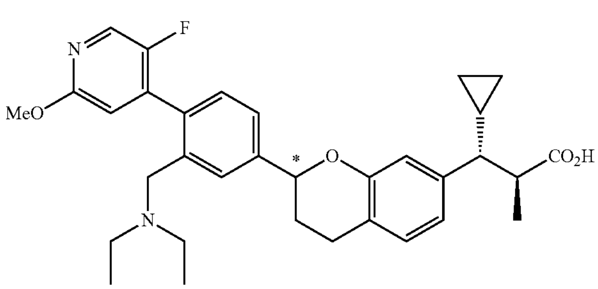 [SMILES: CCN(CC)Cc1cc(C2CCc3ccc([C@H](C4CC4)[C@H](C)C(=O)O)cc3O2)ccc1-c1cc(OC)ncc1F] | Mixture of 2 diastereomers at * | 547 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---|---|---|---|
| 65 | 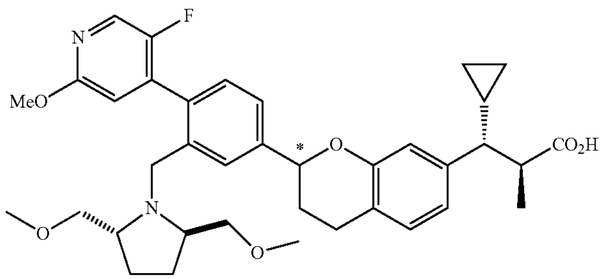 [SMILES: COC[C@H]1CC[C@H](COC)N1Cc1cc(C2CCc3ccc([C@H](C4CC4)[C@H](C)C(=O)O)cc3O2)ccc1-c1cc(OC)ncc1F] | Mixture of 2 diastereomers at * | 633 |
| 66 | 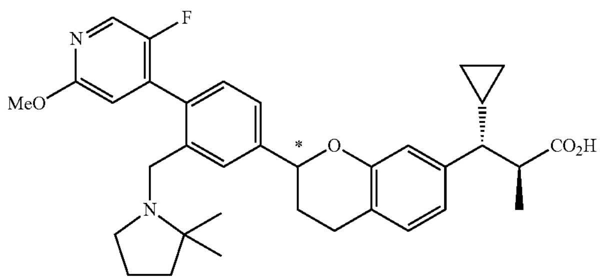 [SMILES: COc1cc(-c2ccc(C3CCc4ccc([C@H](C5CC5)[C@H](C)C(=O)O)cc4O3)cc2CN2CCCC2(C)C)c(F)cn1] | Mixture of 2 diastereomers at * | 573 |
| 67 | 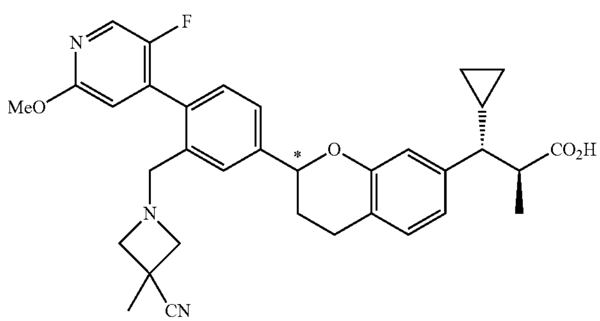 [SMILES: COc1cc(-c2ccc(C3CCc4ccc([C@H](C5CC5)[C@H](C)C(=O)O)cc4O3)cc2CN2CC(C)(C#N)C2)c(F)cn1] | Mixture of 2 diastereomers at * | 570 |
| 68 | 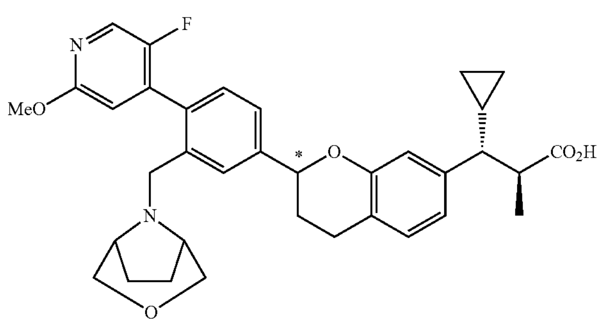 [SMILES: COc1cc(-c2ccc(C3CCc4ccc([C@H](C5CC5)[C@H](C)C(=O)O)cc4O3)cc2CN2C3CCC2COC3)c(F)cn1] | Mixture of 2 diastereomers at * | 587 |

TABLE 3-continued

Examples 35-73 were prepared according the above Scheme using the appropriate amine in the reductive amination step.

| Example | Structure | Stereoisomers/ Chiral Conditions | LC/MS (M + H)+ |
|---|---|---|---|
| 69 | 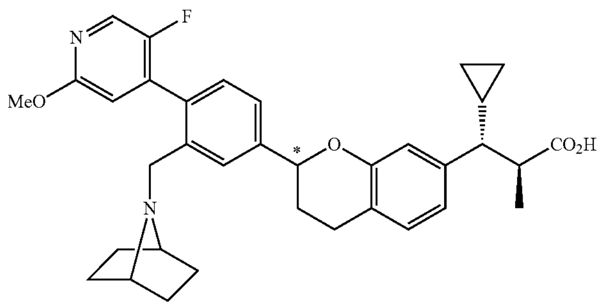 [SMILES: COc1cc(-c2ccc(C3CCc4ccc([C@H](C5CC5)[C@H](C)C(=O)O)cc4O3)cc2CN2C3CCC2CC3)c(F)cn1] | Mixture of 2 diastereomers at * | 571 |
| 70 | 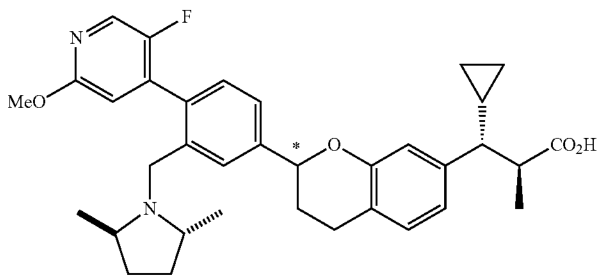 [SMILES: COc1cc(-c2ccc(C3CCc4ccc([C@H](C5CC5)[C@H](C)C(=O)O)cc4O3)cc2CN2[C@H](C)CC[C@H]2C)c(F)cn1] | Mixture of 2 diastereomers at * | 573 |
| 71 | 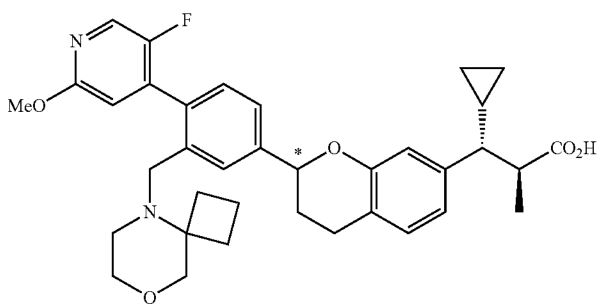 [SMILES: COc1cc(-c2ccc(C3CCc4ccc([C@H](C5CC5)[C@H](C)C(=O)O)cc4O3)cc2CN2CCOCC23CCC3)c(F)cn1] | Mixture of 2 diastereomers at * | 601 |
| 72 | 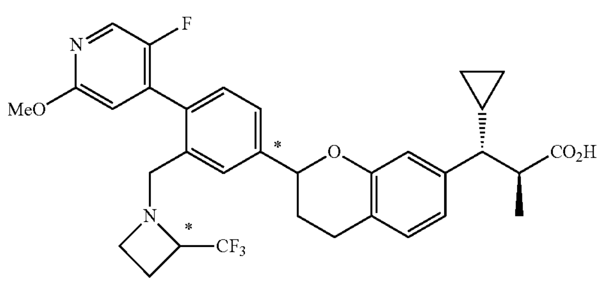 [SMILES: COc1cc(-c2ccc(C3CCc4ccc([C@H](C5CC5)[C@H](C)C(=O)O)cc4O3)cc2CN2CCC2C(F)(F)F)c(F)cn1] | Mixture of isomers at * | 599 |
| 73 | 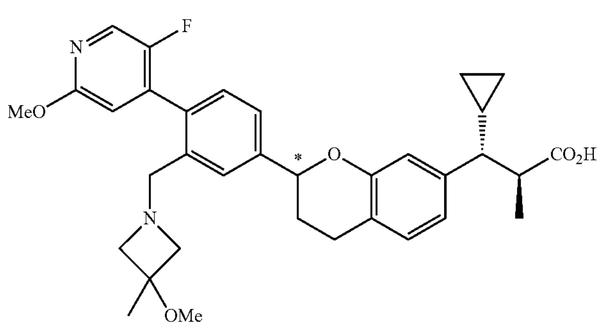 [SMILES: COc1cc(-c2ccc(C3CCc4ccc([C@H](C5CC5)[C@H](C)C(=O)O)cc4O3)cc2CN2CC(C)(OC)C2)c(F)cn1] | Mixture of 2 diastereomers at * | 575 |

Example 74

(2S,3R)-3-cyclopropyl-3-(2-(4-(2-ethoxy-5-fluoro-pyridin-4-yl)-3-(pyrrolidin-1-ylmethyl)phenyl)chroman-7-yl)-2-methylpropanoic acid

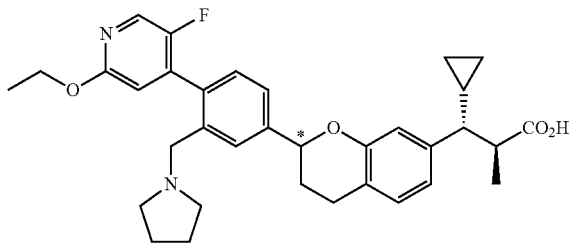 [SMILES: CCOc1cc(-c2ccc(C3CCc4ccc([C@H](C5CC5)[C@H](C)C(=O)O)cc4O3)cc2CN2CCCC2)c(F)cn1]

Step 1:

methyl (2S,3R)-3-cyclopropyl-3-(2-(3-formyl-4-(tosyloxy)phenyl)chroman-7-yl)-2-methylpropanoate (the product of Step 2 of Intermediate 4, 100 mg, 0.18 mmol) and 2$^{nd}$ generation SPhos precatalyst (13 mg, 0.018 mmol) were dissolved in nitrogen sparged THF (2 mL). Then boronic acid (67 mg, 0.36 mmol) and $K_3PO_4$ (0.55 mL of a 1 M aqueous solution) were added. The resulting mixture was heated at 80° C. for 2 hours, then diluted with EtOAc and filtered through a plug of Celite™. The filtrate was concentrated under reduced pressure, and the resulting residue was purified by gradient column chromatography (100/0 to 0/100 hexanes/EtOAc, $SiO_2$) to give (2S,3R)-methyl 3-cyclopropyl-3-(2-(4-(5-fluoro-2-ethoxypyridin-4-yl)-3-formylphenyl)chroman-7-yl)-2-methylpropanoate.

Step 2:

(2S,3R)-methyl 3-cyclopropyl-3-(2-(4-(5-fluoro-2-methoxypyridin-4-yl)-3-formylphenyl)chroman-7-yl)-2-methylpropanoate was converted to Example 74 (as a 1:1 mixture of 2 diastereomers at *) using conditions similar to those outlined above for Example 13. LC/MS (M+H)$^+$ 559.6.

TABLE 4

Examples 75-77 were prepared according to the procedure of Example 74 using the appropriate boronic acid and amine reagents in the reductive amination step. Where noted, the sodium salt of the acid was prepared according to the procedure of Example 1. Chiral conditions for resolution of isomers were performed on the free acid.

| Example | Structure | Stereoisomers/Chiral Conditions | LC/MS (M + H)$^+$ |
|---|---|---|---|
| 75 | 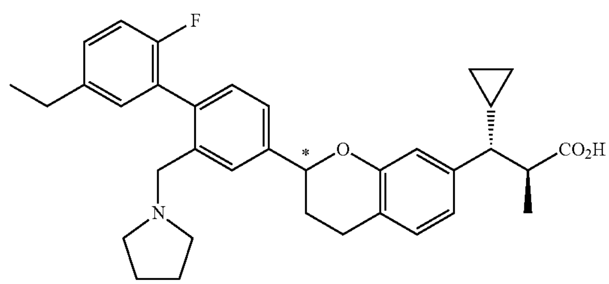 [SMILES: CCc1ccc(F)c(-c2ccc(C3CCc4ccc([C@H](C5CC5)[C@H](C)C(=O)O)cc4O3)cc2CN2CCCC2)c1] | Mixture of 2 diastereomers at * | 542.6 |
| 76 | 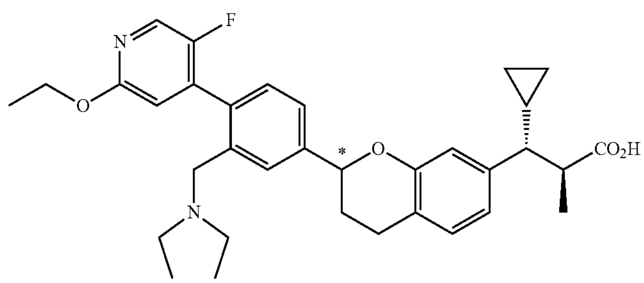 [SMILES: CCOc1cc(-c2ccc(C3CCc4ccc([C@H](C5CC5)[C@H](C)C(=O)O)cc4O3)cc2CN(CC)CC)c(F)cn1] | Mixture of 2 diastereomers at * | 561.6 |
| 77 | 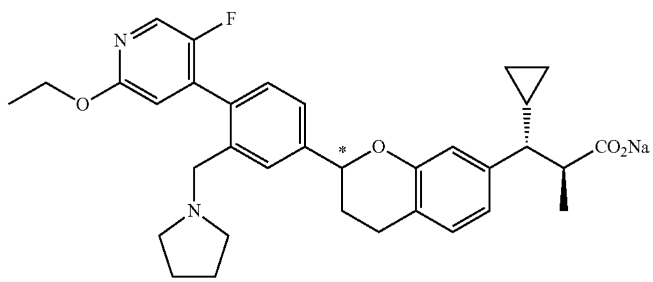 | Mixture of 2 diastereomers at * | 559.6 |

Example 78

(2S,3R)-3-(2-(4-(5-cyano-2-methoxypyridin-4-yl)-3-(pyrrolidin-1-ylmethyl)phenyl)chroman-7-yl)-3-cyclopropyl-2-methylpropanoic acid

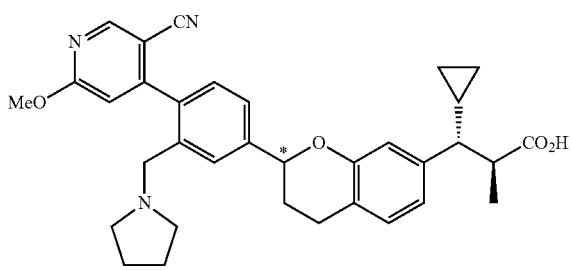 [SMILES: COc1cc(-c2ccc(C3CCc4ccc([C@H](C5CC5)[C@H](C)C(=O)O)cc4O3)cc2CN2CCCC2)c(C#N)cn1]

Step 1:
Methyl (2S,3R)-3-cyclopropyl-3-(2-(3-formyl-4-(tosyloxy)phenyl)chroman-7-yl)-2-methylpropanoate (the product of Step 2 of Intermediate 4, 500 mg, 0.91 mmol), $2^{nd}$ Generation Xphos precatalyst (36 mg, 0.046 mml), bis(pinacolato)diboron (231 mg, 0.91 mmol), and KOAc (268 mg, 2.73 mmol) were taken up in acetonitrile (5 mL). The slurry was sparged with nitrogen for 10 minutes and then heated to 85° C. for 16 h. The mixture was diluted with EtOAc and poured into saturated NaHCO₃ (aq.). The aqueous layer was extracted with EtOAc. The combined organic layers were dried (MgSO₄), filtered, and concentrated. The resulting residue was purified via gradient flash chromatography (0-50% EtOAc in hexanes, SiO₂) to provide methyl (2S,3R)-3-cyclopropyl-3-(2-(3-formyl-4-(4,4,5,5-tetramethyl-1,3,2-dioxaborolan-2-yl)phenyl)chroman-7-yl)-2-methylpropanoate.

Step 2:
Methyl (2S,3R)-3-cyclopropyl-3-(2-(3-formyl-4-(4,4,5,5-tetramethyl-1,3,2-dioxaborolan-2-yl)phenyl)chroman-7-yl)-2-methylpropanoate was converted into Example 78 (as a 1:1 mixture of 2 diasteromers at *) using conditions similar to those outlined for Example 74 using the appropriate reagents. LC/MS: 552.8 (M+H)⁺.

Example 79

Sodium (2S,3R)-3-cyclopropyl-3-((S)-2-(4-(4-methoxy-1H-pyrazol-3-yl)-3-(pyrrolidin-1-ylmethyl)phenyl)chroman-7-yl)-2-methylpropanoate

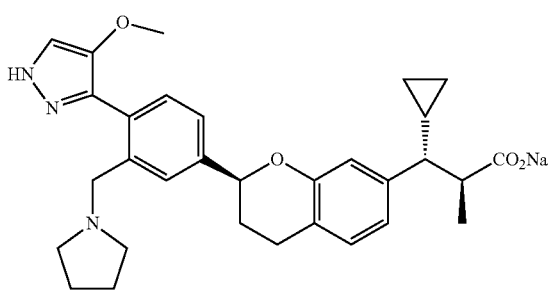

Step 1:
Methyl (2S,3R)-3-cyclopropyl-3-((2S)-2-(4-(4-methoxy-1-(tetrahydro-2H-pyran-2-yl)-1H-pyrazol-3-yl)-3-(pyrrolidin-1-ylmethyl)phenyl)chroman-7-yl)-2-methylpropanoate was prepared using conditions similar to those outlined for Example 74 starting from methyl (2S,3R)-3-cyclopropyl-3-(2-(3-formyl-4-(tosyloxy)phenyl)chroman-7-yl)-2-methylpropanoate (the product of Step 2 of Intermediate 4).

Step 2:
Methyl (2S,3R)-3-cyclopropyl-3-((2S)-2-(4-(4-methoxy-1-(tetrahydro-2H-pyran-2-yl)-1H-pyrazol-3-yl)-3-(pyrrolidin-1-ylmethyl)phenyl)chroman-7-yl)-2-methylpropanoate (15 mg, 0.024 mmol) was taken up in MeOH (0.5 ml) and HCl (0.049 ml of a 4M solution). The solution was stirred at 25° C. for 12 hours, then concentrated to afford methyl (2S,3R)-3-cyclopropyl-3-((S)-2-(4-(4-methoxy-1H-pyrazol-3-yl)-3-(pyrrolidin-1-ylmethyl)phenyl)chroman-7-yl)-2-methylpropanoate.

Step 3:
Methyl (2S,3R)-3-cyclopropyl-3-((S)-2-(4-(4-methoxy-1H-pyrazol-3-yl)-3-(pyrrolidin-1-ylmethyl)phenyl)chroman-7-yl)-2-methylpropanoate was converted into Example 79 using conditions outlined for Example 74. LC/MS: 516.5 (M+H)⁺. The sodium salt of Example 79 was prepared according to the procedure of Example 1.

Example 80

(2S,3R)-3-cyclopropyl-3-((R)-2-(3-((S)-1-(dimethylamino)ethyl)-4-(5-fluoro-2-methoxypyridin-4-yl)phenyl)chroman-7-yl)-2-methylpropanoic acid

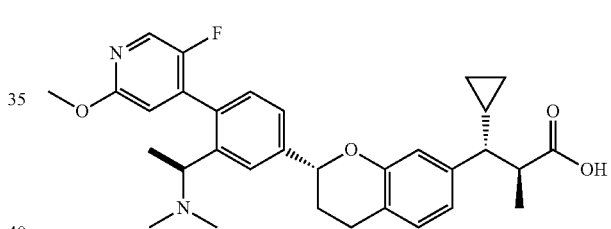

Step 1:
Methyl (2S,3R)-3-cyclopropyl-3-((R)-2-(4-(5-fluoro-2-methoxypyridin-4-yl)-3-formylphenyl)chroman-7-yl)-2-methylpropanoate (53 mg, 0.11 mmol, Intermediate 4a), (S)-(−)-2-methyl-2-propanesulfinamide (15 mg, 0.13 mmol) and Ti(OiPr)4 (0.068 ml, 0.23 mmol) were dissolved in THF (0.6 mL). The solution was stirred at 25° C. for 10 hours, then water was added, and the resulting precipitate was removed via filtration. The filtrate was washed with EtOAc. The combined layers were extracted with EtOAc. The organic layers were combined, dried (MgSO₄), filtered, and concentrated. The resulting residue was purified via gradient flash chromatography (0-60% EtOAc in hexanes, SiO₂) to provide methyl (2S,3R)-3-((R)-2-(3-((E)-(((S)-tert-butylsulfinyl)imino)methyl)-4-(5-fluoro-2-methoxypyridin-4-yl)phenyl)chroman-7-yl)-3-cyclopropyl-2-methylpropanoate.

Step 2:
The product of Step 1 (63 mg, 0.10 mmol) was taken up in DCM (1 ml). Methylmagnesium bromide (0.4 ml of a 1.4 M solution in 3/1 THF/toluene) was added. After stirring at 25° C. for 10 hours, the mixture was partitioned between saturated NH₄Cl/EtOAc. The aqueous layer was extracted with EtOAc. The combined organic layers were dried (MgSO₄), filtered, and concentrated. The resulting residue was purified via gradient flash chromatography (0-100% 3/1

EtOAc/EtOH in hexanes, SiO₂) to provide methyl (2S,3R)-3-((R)-2-(3-((S)-1-(((S)-tert-butylsulfinyl)amino)ethyl)-4-(5-fluoro-2-methoxypyridin-4-yl)phenyl)chroman-7-yl)-3-cyclopropyl-2-methylpropanoate.

Step 3:

The product of Step 2 (39 mg, 0.063 mmol) and HCl in dioxane (0.5 ml of a 4 M solution) were taken up in MeOH (0.05 ml). After stirring at 25° C. for 1 hour, the solution was concentrated to provide methyl (2S,3R)-3-((R)-2-(3-((S)-1-aminoethyl)-4-(5-fluoro-2-methoxypyridin-4-yl)phenyl)chroman-7-yl)-3-cyclopropyl-2-methylpropanoate hydrochloride, which was used directly in the next step.

Step 4:

The product of Step 3 (32 mg, 0.063 mmol), paraformaldehyde (17 mg, 0.56 mmol), and NaBH₄ (9.5 mg, 0.25 mmol) were taken up in 0.5 mL of trifluoroethanol. The mixture was stirred at 80° C. for 1 hour, then cooled and filtered. The filtrate was concentrated, and the resulting residue was purified via gradient flash chromatography (0-100% 3/1 EtOAc/EtOH in hexanes, SiO₂) to provide methyl (2S,3R)-3-cyclopropyl-3-((R)-2-(3-((S)-1-(dimethylamino)ethyl)-4-(5-fluoro-2-methoxypyridin-4-yl)phenyl)chroman-7-yl)-2-methylpropanoate.

Step 5:

Methyl (2S,3R)-3-cyclopropyl-3-((R)-2-(3-((S)-1-(dimethylamino)ethyl)-4-(5-fluoro-2-methoxypyridin-4-yl)phenyl)chroman-7-yl)-2-methylpropanoate was converted into Example 80 using hydrolysis conditions outlined in Step 2 of Example 1. LC/MS: 533.6 (M+H)⁺.

Example 81

(2S,3R)-3-cyclopropyl-3-((R)-2-(3-((R)-1-(dimethylamino)ethyl)-4-(5-fluoro-2-methoxypyridin-4-yl)phenyl)chroman-7-yl)-2-methylpropanoic acid

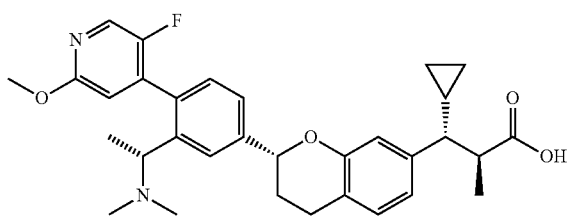 [SMILES: COc1cc(-c2ccc([C@H]3CCc4ccc([C@H](C5CC5)[C@H](C)C(=O)O)cc4O3)cc2[C@@H](C)N(C)C)c(F)cn1]

Example 81 was prepared using similar conditions outlined for Example 80 starting from Intermediate 4a and using (R)-2-methylpropane-2-sulfinamide in the first step. LC/MS: 533.6 (M+H)⁺.

Examples 82 and 83

(2S,3R)-3-cyclopropyl-3-((R)-2-(3-((S)-1-(dimethylamino)ethyl)-4-(5-fluoro-2-methoxypyridin-4-yl)phenyl)chroman-7-yl)-2-methylpropanoic acid and (2S,3R)-3-cyclopropyl-3-((R)-2-(3-((R)-1-(dimethylamino)ethyl)-4-(5-fluoro-2-methoxypyridin-4-yl)phenyl)chroman-7-yl)-2-methylpropanoic aid

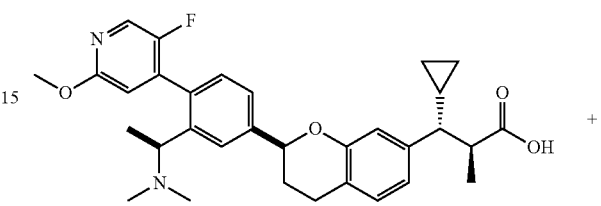

Example 82

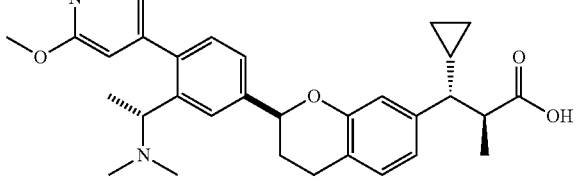

Example 83

Examples 82 and 83 were prepared in a similar fashion to the procedures outlined for Examples 80 and 81 using methyl (2S,3R)-3-cyclopropyl-3-((S)-2-(4-(5-fluoro-2-methoxypyridin-4-yl)-3-formylphenyl)chroman-7-yl)-2-methylpropanoate (Intermediate 4b) and the appropriate sulfinimide. Example 82: LC/MS: 533.6 (M+H)⁺. Example 83: LC/MS: 533.6 (M+H)⁺.

Example 84

Methyl (2S,3R)-3-cyclopropyl-3-(2-(4-(5-fluoro-2-methoxypyridin-4-yl)-3-(1-(pyrrolidin-1-yl)ethyl)phenyl)chroman-7-yl)-2-methylpropanoic acid

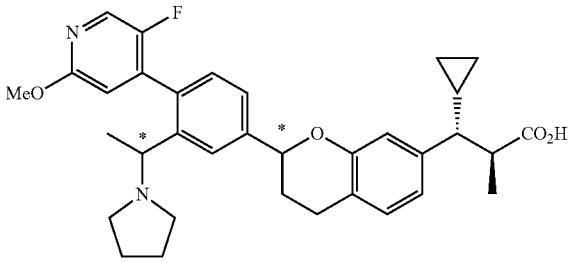

Step 1:

Methyl (2S,3R)-3-cyclopropyl-3-(2-(4-(5-fluoro-2-methoxypyridin-4-yl)-3-formylphenyl)chroman-7-yl)-2-methylpropanoate (129 mg, 0.25 mmol, Intermediate 4), pyrrolidine (24 mg, 0.33 mmol), benzotriazole (40 mg, 0.33 mmol), and molecular sieves were taken up in toluene (1.2 ml). The mixture was heated in a microwave reactor at 110°

C. for 5 hours. Then the mixture was filtered and concentrated. The resulting residue was purified via gradient flash chromatography (0-100% EtOAc in hexanes, SiO₂) to provide methyl (2S,3R)-3-(2-(3-((1H-benzo[d][1,2,3]triazol-1-yl)(pyrrolidin-1-yl)methyl)-4-(5-fluoro-2-methoxypyridin-4-yl)phenyl)chroman-7-yl)-3-cyclopropyl-2-methylpropanoate.

Step 2:

The product of Step 1 (65 mg, 0.098 mmol) was taken up in THF (1 mL). Methylmagnesium bromide (0.091 ml of a 1.4 M solution in THF/toluene (1/3)) was added to the solution. After 30 minutes, the solution was quenched with saturated NH₄Cl. The aqueous layer was extracted with EtOAc. The combined organic layers were dried (MgSO₄), filtered, and concentrated. The resulting residue was purified via HPLC (30×100 mm Waters Sunfire column; 5 micron; 30 mL/min.; 220 nM; 10% to 100% CH₃CN+0.05% TFA/water+0.05% TFA over 10 min) to provide methyl (2S,3R)-3-cyclopropyl-3-(2-(4-(5-fluoro-2-methoxypyridin-4-yl)-3-(1-(pyrrolidin-1-yl)ethyl)phenyl)chroman-7-yl)-2-methylpropanoate.

Step 3:

The product of Step 2 was converted to Example 84 using hydrolysis conditions outlined in Step 2 of Example 1 to provide Example 84 as a mixture of 4 isomers. LC/MS: 559.7 (M+H)⁺.

Example 85

(2S,3R)-3-cyclopropyl-3-(2-(2-((diethylamino)methyl)-5'-fluoro-2'-methoxy-[3,4'-bipyridin]-6-yl)chroman-7-yl)-2-methylpropanoic acid

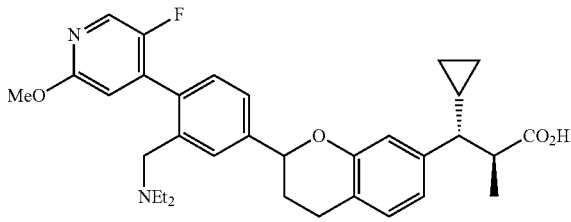

Step 1: 6-chloro-5'-fluoro-2'-methoxy-[3,4'-bipyridine]-4-carbaldehyde

To a THF solution of 5-bromo-2-chloroisonicotinaldehyde (2 g, 9.07 mmol), (5-fluoro-2-methoxypyridin-4-yl)boronic acid (1.551 g, 9.07 mmol) and 1,1'-bis(di-tert-butylphosphino)ferrocene palladium dichloride (0.296 g, 0.454 mmol) was added solid K₂CO₃ (5.02 g, 36.3 mmol). The resulting slurry was degassed and then stirred vigorously at room temperature. After 48 h, the reaction was poured into NH₄Cl (saturated, 100 mL) and extracted with EtOAc (2×100 mL). The combined organic layers were dried (MgSO₄) and concentrated. The resulting residue was purified by HPLC (ISCO 80 gram SiO2 cartridge, 0 to 50% EtOAc/Hex) to give the title compound. LC/MS (m/z): 267.2 (M+H)⁺.

Step 2: 6-chloro-4-(1,3-dioxolan-2-yl)-5'-fluoro-2'-methoxy-3,4'-bipyridine

To a toluene solution of 6-chloro-5'-fluoro-2'-methoxy-[3,4'-bipyridine]-2-carbaldehyde (445 mg, 1.669 mmol) and ethylene glycol (0.140 ml, 2.503 mmol) was added pTsOH (31.7 mg, 0.167 mmol). The mixture was then heated to 100 C on a heating block. After 16 h, the reaction was poured into NaHCO₃ (saturated, 25 mL) and extracted with EtOAc (2×25 mL). The combined organic layers were dried (MgSO₄) and concentrated. The resulting residue was purified by HPLC (ISCO 40 gram, 0 to 50% EtOAc/Hex) to give the title compound. LC/MS (m/z): 311.4 (M+H)⁺.

Step 3: (E)-4-(1,3-dioxolan-2-yl)-6-(2-ethoxyvinyl)-5'-fluoro-2'-methoxy-3,4'-bipyridine To a nitrogen-sparged THF (3 ml) solution of 6-chloro-4-(1,3-dioxolan-2-yl)-5'-fluoro-2'-methoxy-3,4'-bipyridine (180 mg, 0.579 mmol), (E)-2-(2-ethoxyvinyl)-4,4,5,5-tetramethyl-1,3,2-dioxaborolane (172 mg, 0.869 mmol) and Pd(PPh₃)₄ (66.9 mg, 0.058 mmol) was added Na₂CO₃ (184 mg, 1.738 mmol) and water (1 mL). The reaction was heated on a heating block. After 16 h, the mixture was poured into saturated NH₄Cl (25 mL) and extracted with EtOAc (2×25 mL). The combined organic layers were combined, dried (MgSO₄) and concentrated. The resulting residue was purified by HPLC (ISCO 40 gram, 0 to 50% EtOAc/Hexane gradient) to give the title compound. LC/MS (m/z): 347.5 (M+H)⁺.

Step 4: 4-(1,3-dioxolan-2-yl)-5'-fluoro-2'-methoxy-[3,4'-bipyridine]-6-carbaldehyde To a dioxane/water (1/1, 30 ml) solution of (E)-4-(1,3-dioxolan-2-yl)-6-(2-ethoxyvinyl)-5'-fluoro-2'-methoxy-3,4'-bipyridine (1.3 g, 3.75 mmol) was added osmium tetroxide (2.95 ml, 0.375 mmol, 4% solution in water). Then sodium periodate (2.408 g, 11.26 mmol) was added in a single portion. The resulting slurry was stirred vigorously. After 40 h, the reaction was poured into water (50 mL) and extracted with EtOAc (2×50 mL). The combined organic layers were dried (MgSO₄) and concentrated. The resulting residue was purified by HPLC (ISCO 40 gram SiO₂ cartridge, 0 to 50% EtOAc/Hexanes). LC/MS (m/z): 305.2 (M+H)⁺.

Step 5: 1-(4-(1,3-dioxolan-2-yl)-5'-fluoro-2'-methoxy-[3,4'-bipyridin]-6-yl)prop-2-en-1-ol To a cooled THF (20 ml) solution of 4-(1,3-dioxolan-2-yl)-5'-fluoro-2'-methoxy-[3,4'-bipyridine]-6-carbaldehyde (750 mg, 2.465 mmol) was added vinyl magnesium bromide (2.71 ml, 2.71 mmol). After 30 minutes, the reaction mixture was poured into NH₄Cl (saturated, 25 mL) and extracted with EtOAc (2×25 mL). The combined organic layers were dried (MgSO₄) and concentrated. The resulting residue was purified by HPLC (ISCO 40 gram SiO₂ cartridge, 0 to 100% EtOAc/Hexanes) to give the title compound. LC/MS (m/z): 333.4 (M+H)⁺.

Step 6: (2S,3R)-methyl 3-(4-(3-(4-(1,3-dioxolan-2-yl)-5'-fluoro-2'-methoxy-[3,4'-bipyridin]-6-yl)-3-oxopropyl)-3-hydroxyphenyl)-3-cyclopropyl-2-methylpropanoate To a nitrogen-sparged toluene solution of 1-(4-(1,3-dioxolan-2-yl)-5'-fluoro-2'-methoxy-[3,4'-bipyridin]-6-yl)prop-2-en-1-ol (628 mg, 1.889 mmol), (2S,3R)-methyl 3-cyclopropyl-3-(3-hydroxy-4-iodophenyl)-2-methylpropanoate (630 mg, 1.749 mmol), and t-buxphos palladacycle (60.1 mg, 0.087 mmol) was added N,N-dicyclohexylmethylamine (513 mg, 2.62 mmol). The mixture was degassed and backfilled with nitrogen three times, and then heated on a heating block 100° C. After 16 h, the reaction was cooled to rt and poured into NH₄Cl (saturated, 25 mL). The mixture was extracted with EtOAc (2×25 mL). The combined organic layers were dried (MgSO₄) and concentrated. The resulting residue was purified by HPLC (ISCO 40 gram SiO₂ cartridge, 0 to 100% EtOAc/Hexanes) to give the title compound. LC/MS (m/z): 565.5 (M+H)⁺.

Step 7: The Product of Step 6

To a cooled MeOH (10 ml) solution of (2S,3R)-methyl 3-(4-(3-(4-(1,3-dioxolan-2-yl)-5'-fluoro-2'-methoxy-[3,4'-bipyridin]-6-yl)-3-oxopropyl)-3-hydroxyphenyl)-3-cyclopropyl-2-methylpropanoate (30 mg, 0.053 mmol) was added NaBH₄ (4.02 mg, 0.106 mmol) in a single portion. After 1 h, the reaction mixture was poured into NH₄Cl (saturated, 25 mL) and extracted with EtOAc (2×25 ml). The combined organic layers were dried (MgSO₄) and concentrated. The resulting residue was purified by HPLC (ISCO 24 gram SiO₂ cartridge, 0 to 100% EtOAc/Hexanes) to give the title compound. LC/MS (m/z): 567.5 (M+H)⁺.

Step 8: (2S,3R)-methyl 3-(2-(4-(1,3-dioxolan-2-yl)-5'-fluoro-2'-methoxy-[3,4'-bipyridin]-6-yl)chroman-7-yl)-3-cyclopropyl-2-methylpropanoate To a cooled DCM (5 ml) solution of (2S,3R)-methyl 3-(4-(3-(4-(1,3-dioxolan-2-yl)-5'-fluoro-2'-methoxy-[3,4'-bipyridin]-6-yl)-3-hydroxypropyl)-3-hydroxyphenyl)-3-cyclopropyl-2-methylpropanoate (20 mg, 0.035 mmol) and triphenylphosphine (18.52 mg, 0.071 mmol) (polymer-bound) was added diisopropyl azodicarboxylate (0.014 ml, 0.071 mmol) dropwise. The reaction was allowed to warm to room temp overnight. After 16 h, the reaction was filtered and the filtrate was concentrated. The resulting residue was purified by HPLC (ISCO 24 gram SiO₂ cartridge, 0 to 50% EtOAc/Hexanes) to give the title compound. LC/MS (m/z): 549.5 (M+H)⁺.

Step 9: (2S,3R)-methyl 3-cyclopropyl-3-(2-(5'-fluoro-4-formyl-2'-methoxy-[3,4'-bipyridin]-6-yl)chroman-7-yl)-2-methylpropanoate To an acetone (10 ml) solution of (2S,3R)-methyl 3-(2-(4-(1,3-dioxolan-2-yl)-5'-fluoro-2'-methoxy-[3,4'-bipyridin]-6-yl)chroman-7-yl)-3-cyclopropyl-2-methylpropanoate (20 mg, 0.036 mmol) was added HCl (0.365 ml, 0.365 mmol). The reaction was heated to 50° C. on a heating block. After 3 days, the reaction was poured into NaHCO₃ (saturated, 10 mL) and extracted with EtOAc (2×10 mL). The combined organic layers were dried (MgSO₄) and concentrated. The resulting residue was purified by HPLC (ISCO 24 gram SiO₂ cartridge, 0 to 50% EtOAc/Hexanes) to give the title compound. LC/MS (m/z): 505.5 (M+H)⁺.

Step 10: (2S,3R)-methyl 3-cyclopropyl-3-(2-(4-((diethylamino)methyl)-5'-fluoro-2'-methoxy-[3,4'-bipyridin]-6-yl)chroman-7-yl)-2-methylpropanoate To a 1,2-dichloroethene (5 ml) solution of (2S,3R)-methyl 3-cyclopropyl-3-(2-(5'-fluoro-4-formyl-2'-methoxy-[3,4'-bipyridin]-6-yl)chroman-7-yl)-2-methylpropanoate (120 mg, 0.238 mmol), diethylamine (34.8 mg, 0.476 mmol), and DIPEA (0.125 ml, 0.714 mmol) was added sodium triacetoxyborohydride (101 mg, 0.476 mmol), followed by a single drop of acetic acid (6.81 μl, 0.119 mmol). The cloudy mixture was stirred at rt. After 16 h, the reaction was poured into NaHCO₃ (saturated, 25 mL) and extracted with DCM (2×25 mL). The combined organic layers were dried (Na₂SO₄) and concentrated. The resulting residue was purified by HPLC (ISCO 24 gram SiO₂ column, 0 to 100% EtOAc/Hexanes gradient) to give the title compound.

Step 11: (2S,3R)-3-cyclopropyl-3-(2-(4-((diethylamino)methyl)-5'-fluoro-2'-methoxy-[3,4'-bipyridin]-6-yl)chroman-7-yl)-2-methylpropanoic acid To a THF/MeOH/water (1/1/1, 5 ml) solution of the product of Step 10 (105 mg, 0.187 mmol) was added LiOH (44.8 mg, 1.869 mmol). The reaction was heated to 50° C. on a heating block. After 16 h, the reaction was poured into NH₄Cl (saturated, 25 mL) and extracted with EtOAc (2×25 mL). The combined organic layers were dried (MgSO₄) and concentrated. The resulting residue was purified by HPLC (ISCO 24 gram SiO₂ cartridge, 0 to 100% EtOAc/Hexanes gradient) to give the title compound. LC/MS (m/z): 548.6 (M+H)⁺.

Step 12: "R and S" sodium (2S,3R)-3-cyclopropyl-3-(2-(4-((diethylamino)methyl)-5'-fluoro-2'-methoxy-[3,4'-bipyridin]-6-yl)chroman-7-yl)-2-methylpropanoate

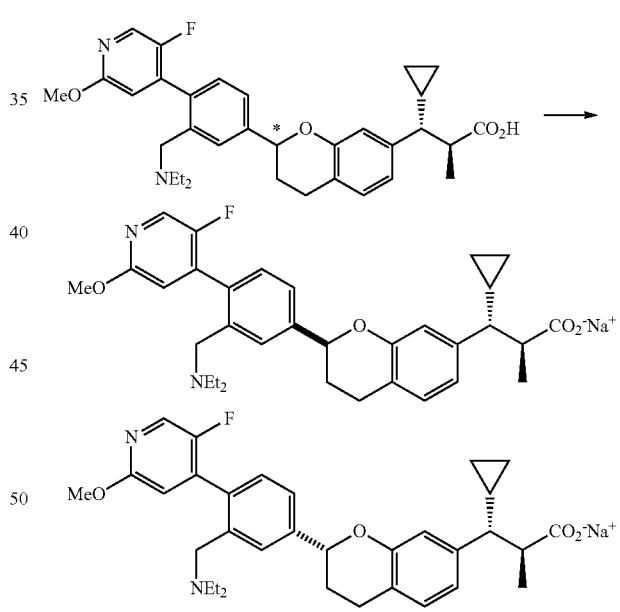

SFC Separation:

A mixture of diastereomers at the * carbon was separated via SFC separation (Whelk-O 1 column 30% MeOH (+0.1% DIPA)/CO₂) to give the individual diastereomers.

Sodium Salt Formation:

To a MeCN/water solution of each diastereomer from the SFC separation was added NaOH (1 eq, 0.10 M aqueous solution). The mixture was then frozen in a dry ice/acetone bath and lyophilized overnight to provide Examples 86 and 87.

TABLE 5

Examples 86-91 were prepared in a manner similar to Example 85 using the appropriate starting materials.

| Example | Structure | Stereoisomers/ Chiral Conditions | LC/MS (M + H)+ |
|---|---|---|---|
| 85 | 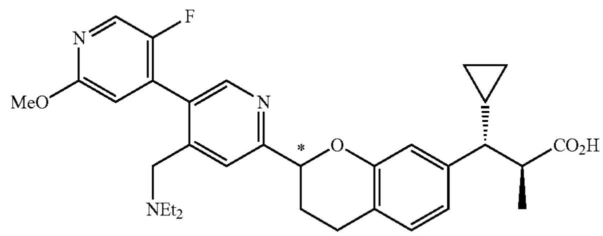 | 2 Diastereomers at * | 548.6 |
| 86 | 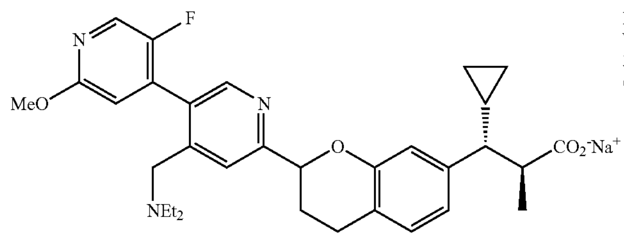 | Isomer A Whelk-O1 column 30% MeOH (+0.1% DIPA)/CO2 | 548.6 |
| 87 | 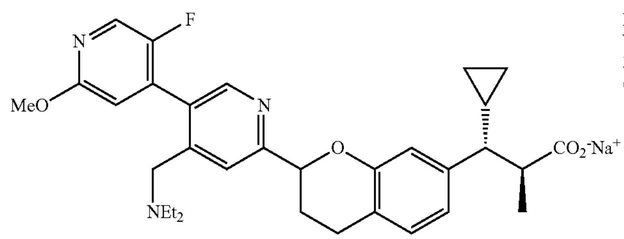 | Isomer B Whelk-O1 column 30% MeOH (+0.1% DIPA)/CO2 | 548.6 |
| 88 | 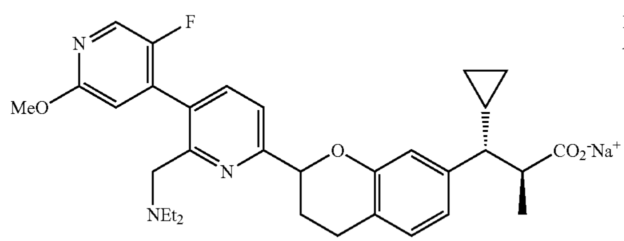 | Isomer A AD-H column 17% IPA/CO$_2$ | 548.6 |
| 89 | 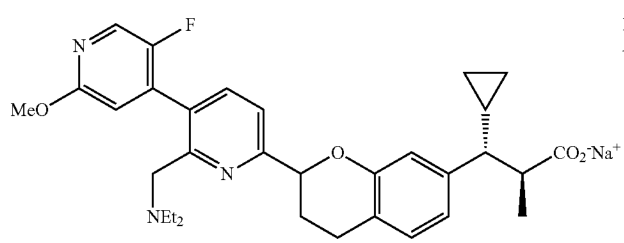 | Isomer B AD-H column 17% IPA/CO$_2$ | 548.6 |
| 90 | 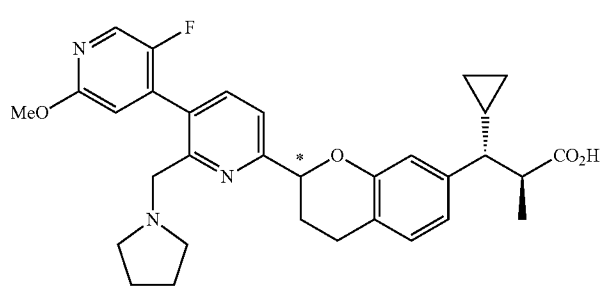 [SMILES: COc1cc(-c2ccc(C3CCc4ccc([C@H](C5CC5)[C@H](C)C(=O)O)cc4O3)nc2CN2CCCC2)c(F)cn1] | 2 Diastereomers at * | 546.5 |

TABLE 5-continued

Examples 86-91 were prepared in a manner similar to Example 85 using the appropriate starting materials.

| Example | Structure | Stereoisomers/<br>Chiral Conditions | LC/MS<br>(M + H)+ |
|---|---|---|---|
| 91 | 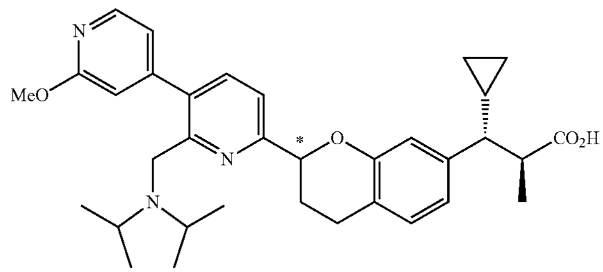 [SMILES: COc1cc(-c2ccc(C3CCc4ccc([C@H](C5CC5)[C@H](C)C(=O)O)cc4O3)nc2CN(C(C)C)C(C)C)ccn1] | 2 Diastereomers at * | 558.6 |

Example 92

(2S,3R)-3-cyclobutyl-3-(2-(4-(5-fluoro-2-methoxy-pyridin-4-yl)-3-(pyrrolidin-1-ylmethyl)phenyl)chroman-7-yl)-2-methylpropanoic acid

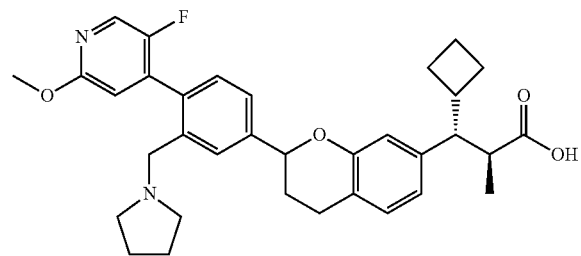 [SMILES: COc1cc(-c2ccc(C3CCc4ccc([C@H](C5CCC5)[C@H](C)C(=O)O)cc4O3)cc2CN2CCCC2)c(F)cn1]

Step 1: 4-((tert-butyldimethylsilyl)oxy)benzaldehyde tert-Butyldimethylsilyl chloride (14.8 g, 98.0 mmol) was added portionwise to a stirred, cooled 0° C. mixture of 4-hydroxy-benzaldehyde (9.97 g, 82.0 mmol) and imidazole (11.1 g, 163 mmol) in DMF (150 mL). The resulting mixture was stirred at 0° C. for 1 h, and then warmed to 25° C. for 12 h. The mixture was cooled, water (500 mL) was added and the mixture was extracted with ethyl acetate (150 mL×3). The combined organic layers were washed with water (100 mL×3), dried (Na$_2$SO$_4$), filtered and the filtrate was evaporated under reduced pressure. The resulting residue was purified by column chromatography on silica gel (eluting with petroleum ether/ethyl acetate (v/v)=100:1-20:1) to give the title compound. $^1$H NMR (400 MHz, CDCl$_3$): δ=11.89 (s, 1H), 7.80 (d, J=8.0 Hz, 2H), 7.96 (d, J=8.8 Hz, 2H), 1.00 (s, 9H), 0.25 (s, 6H).

Step 2: 1-(4-((tert-butyldimethylsilyl)oxy)phenyl)prop-2-en-1-ol

Vinylmagnesium bromide (89 mL, 89 mmol) was added dropwise over 20 minutes to a stirred, cooled 0° C. solution of 4-((tert-butyldimethylsilyl)oxy)benzaldehyde (10.5 g, 44.4 mmol) in THF (150 mL) under a nitrogen atmosphere. The resulting mixture was stirred at 0° C. for 1 h, then cooled. Aqueous ammonium chloride (saturated, 10 mL) was added to the mixture and the mixture was extracted with ethyl acetate (15 mL×2). The combined organic layers were washed with brine (saturated, 20 mL), dried (Na$_2$SO$_4$), filtered and the filtrate was evaporated under reduced pressure to give the title compound, which was used in the next step without further purification. MS (ESI) m/z: 247.1 [M−17]+

Step 3: (2S,3R)-methyl 3-cyclobutyl-3-(3-hydroxy-4-(3-(4-hydroxyphenyl-3-oxopropyl phenyl)-2-methylpropanoate To a mixture of lithium acetate (1.98 g, 30.0 mmol), 1-(4-((tert-butyldimethylsilyl)oxy)phenyl)prop-2-en-1-ol (4.96 g, 15.0 mmol), (2S,3R)-methyl 3-cyclobutyl-3-(3-hydroxy-4-iodophenyl)-2-methylpropanoate (3.74 g, 9.99 mmol), tetra-n-butylammonium chloride (2.78 g, 9.99 mmol) and lithium chloride (1.27 g, 30.0 mmol) in DMF (80 mL) were added PdOAc$_2$ (0.224 g, 0.999 mmol) under a N$_2$ atmosphere. The resulting mixture was heated to 80° C. for 2 hours. Then the reaction mixture was cooled to rt, poured into water (200 mL), and extracted with ethyl acetate (100 mL×3). The combined organic layers were washed with water (100 mL×3), brine (120 mL), dried (Na$_2$SO$_4$) and concentrated in vacuo to give the crude product, which was purified by flash silica gel chromatography (ISCO®; 120 g SepaFlash® Silica Flash Column, Eluent of 0~40% EA/PE gradient at 85 mL/min) to give the title compound. MS (ESI) m/z: 379.2[M−17]+

Step 4: (2S,3R)-methyl 3-cyclobutyl-3-(3-hydroxy-4-(3-hydroxy-3-(4-hydroxyphenyl)propyl phenyl-2-methylpropanoate Sodium borohydride (0.597 g, 15.8 mmol) was added to a stirred, cooled 0° C. mixture of (2S,3R)-methyl 3-cyclobutyl-3-(3-hydroxy-4-(3-(4-hydroxyphenyl)-3-oxopropyl)phenyl)-2-methylpropanoate (3.91 g, 7.89 mmol) in THF (80 mL). The resulting mixture was stirred at 0° C. for 1 h, then warmed to 25° C. for 12 h. Then the mixture was cooled, aqueous ammonium chloride (saturated, 30 mL) was added and the mixture was extracted with ethyl acetate (40 mL×3). The combined organic layers were washed with brine (saturated, 30 mL), dried (Na$_2$SO$_4$), filtered and the filtrate was evaporated under reduced pressure. The resulting residue was purified by flash silica gel chromatography (ISCO®; 80 g SepaFlash® Silica Flash Column, Eluent of 0~40% EA/PE gradient at 60 mL/min) to give the title compound. MS (ESI) m/z: 381.2 [M−17]⁺

Step 5: (2S,3R)-methyl 3-cyclobutyl-3-((RS)-2-(4-hydroxyphenyl)chroman-7-yl)-2-methylpropanoate DIAD (1.64 mL, 8.46 mmol) was added dropwise to a solution of (2S, 3R)-methyl 3-cyclobutyl-3-(3-hydroxy-4-(3-hydroxy-3-(4-hydroxyphenyl)propyl)phenyl)-2-methylpropanoate (2.81 g, 5.64 mmol) and triphenylphosphine (2.22 g, 8.46 mmol) in DCM (80 mL) cooled in an ice bath under a nitrogen atmosphere. The resulting mixture was stirred at 0° C. for 1 h, then warmed to 25° C. and stirred for another 12 h. Then the mixture was concentrated in vacuo to give a residue, which was purified by column chromatography on silica gel (eluting with PE/EA=30:1~6:1, v/v) to give the title compound. MS (ESI) m/z: 381.2 [M+H]⁺

Step 6: (2S, 3R)-methyl 3-cyclobutyl-3-((RS)-2-(3-formyl-4-hydroxyphenyl)chroman-7-yl)-2-methylpropanoate A mixture of (2S, 3R)-methyl 3-cyclobutyl-3-(2-(4-hydroxyphenyl)chroman-7-yl)-2-methyl-propanoate (4.71 g, 4.95 mmol), magnesium chloride (2.83 g, 29.7 mmol), Et₃N (9.66 mL, 69.3 mmol) and paraformaldehyde (2.97 g, 99 mmol) in MeCN (50 mL) was heated to reflux at 90° C. for 6 hours. Then the mixture was cooled, and 1N HCl (60 mL) was added. After stirring at rt for 30 min, the mixture was extracted with EtOAc (50 mL×2). The combined organic layers were washed with brine (saturated, 50 mL), dried (Na₂SO₄), filtered and the filtrate was evaporated under reduced pressure. The resulting residue was purified by flash silica gel chromatography (ISCO®; 80 g SepaFlash® Silica Flash Column, Eluent of 0~40% EA/PE gradient at 60 mL/min) to give the title compound.

Step 7: (2S, 3R)-methyl 3-cyclobutyl-3-((RS)-2-(3-formyl-4-(tosyloxy)phenyl)chroman-7-yl)-2-methylpropanoate To a solution of (2S, 3R)-methyl 3-cyclobutyl-3-(2-(3-formyl-4-hydroxyphenyl)chroman-7-yl)-2-methylpropanoate (1.23 g, 2.26 mmol) in DCM (35 mL) was added triethylamine (0.47 mL, 3.39 mmol) and tosyl chloride (0.517 g, 2.71 mmol). The reaction was stirred at 25° C. for 1 h, then quenched with water (25 mL), and extracted with DCM (10 mL) twice. The combined organic layers were dried over anhydrous Na₂SO₄ and filtered. The filtrate was concentrated in vacuo to give the crude product, which was purified by flash silica gel chromatography (ISCO®; 40 g SepaFlash® Silica Flash Column, Eluent of 0~20% EA/PE gradient at 40 mL/min) to give the title compound. MS (ESI) m/z: 563.2 [M+H]⁺

Step 8: (2S, 3R)-methyl 3-cyclobutyl-3-((RS)-2-(4-(5-fluoro-2-methoxypyridin-4-yl)-3-formylphenyl)chroman-7-yl)-2-methylpropanoate To a solution of (2S, 3R)-methyl 3-cyclobutyl-3-(2-(3-formyl-4-(tosyloxy)phenyl)chroman-7-yl)-2-methylpropanoate (1.18 g, 2.06 mmol) in 1,4-dioxane (24 mL) and water (6.0 mL) were added potassium phosate tribasic (1.31 g, 6.17 mmol), 2ⁿᵈ generation SPhos precatalyst (0.0740 g, 0.103 mmol) and (5-fluoro-2-methoxypyridin-4-yl)boronic acid (0.703 g, 4.11 mmol) under nitrogen. The reaction mixture was stirred at 80° C. for 2 h, and then cooled to room temperature. Water (10 mL) was added to the reaction mixture, and the aqueous phase was extracted with EtOAc (15 mL×3). The combined organic layers were washed with water (25 mL) and brine (25 mL), dried over anhydrous MgSO₄ and filtered. The filtrate was concentrated under reduced pressure. The resulting crude product was purified by flash silica gel chromatography (ISCO®; 40 g SepaFlash® Silica Flash Column, eluent of 0~20% EA/PE gradient at 40 mL/min) to give the title compound. MS (ESI) m/z: 518.3 [M+H]⁺

Step 9: (2S, 3R)-methyl 3-cyclobutyl-3-((RS)-2-(4-(5-fluoro-2-methoxypyridin-4-yl)-3-(pyrrolidin-1-ylmethyl)phenylchroman-7-yl)-2-methylpropanoate To a solution of (2S, 3R)-methyl 3-cyclobutyl-3-(2-(4-(5-fluoro-2-methoxypyridin-4-yl)-3-formylphenyl)chroman-7-yl)-2-methylpropanoate (500 mg, 0.966 mmol) and pyrrolidine (137 mg, 1.93 mmol) in MeOH (10 mL) was added titanium (IV) isopropoxide (549 mg, 1.93 mmol). The resulting mixture was stirred at 80° C. for 1 h, then cooled to 0° C. Sodium borohydride (439 mg, 11.6 mmol) was added to the mixture in one portion. The reaction was stirred at 25° C. for 30 min, then quenched by the slow addition of 1N HCl (10 mL). The mixture was extracted with EtOAc (20 mL×3). The combined organic layers were washed with sodium bicarbonate (5%, 15 mL×2), dried (Na₂SO₄), filtered and the filtrate was evaporated under reduced pressure to give the title compound, which was used to next step without further purification. MS (ESI) m/z: 573.3 [M+H]⁺

Step 10: (2S, 3R)-3-cyclobutyl-3-((RS)-2-(4-(5-fluoro-2-methoxypyridin-4-yl)-3-(pyrrolidin-1-ylmethyl)phenyl)chroman-7-yl)-2-methylpropanoic acid To a solution of the product of Step 9 (550 mg, 0.960 mmol) in a co-solvent of THF/MeOH/H₂O (8 mL/8 mL/8 mL) was added lithium hydroxide monohydrate (403 mg, 9.60 mmol). The reaction mixture was stirred at 50° C. for 16 hours, then acidified with aqueous HCl (1 M) to pH=5-6, and extracted with ethyl acetate (10 mL×3). The combined organic layers were concentrated in vacuo to give crude product, which was purified by preparative HPLC (on a GILSON 281 instrument fitted with a Waters XSELECT C18 150*30 mm*5 um using water and acetonitrile as the eluents; Mobile phase A: water (neutral), mobile phase B: acetonitrile. Gradient: 35-65% B, 0-10 min; 100% B, 10.5-12.5 min; 5% B, 13-15 min) to give the title compound. MS (ESI) m/z: 559.3 [M+H]⁺

Step 11: SFC Separation and Sodium Salt Formation

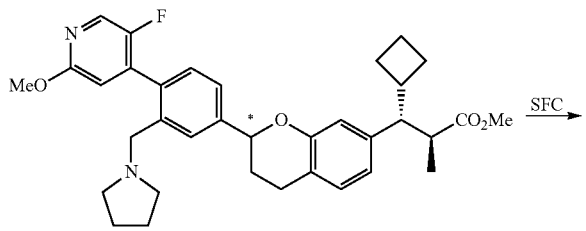

-continued

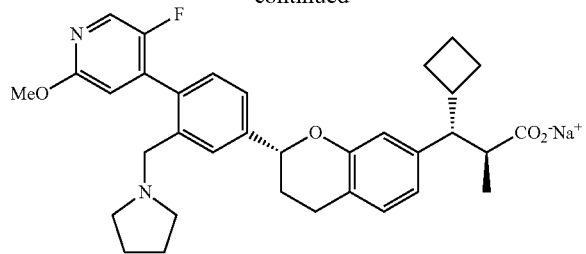

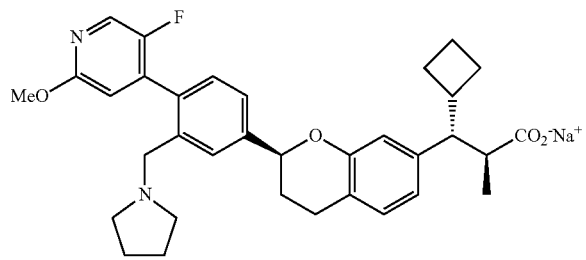

A mixture of 2 diastereomers at the * carbon was separated into individual diastereomers via SFC separation (Method: Column: Chiralpak AD-3 50*4.6 mm I.D., 3 um; Mobile phase: A: $CO_2$ B: iso-propanol (0.05% DEA) Gradient: hold 5% for 0.2 min, then from 5% to 40% of B in 1.4 min and hold 40% for 1.05 min, then 5% of B for 0.35 min; Flow rate: 4 mL/min; Column temp: 40° C.) to give the two individual diastereomers. To a separate solution of each diastereomer from the previous step in MeCN (1 mL) and water (1 mL) was added a solution of aqueous NaOH (1.0 eq, 0.5 M aqueous solution). The mixture was stirred for 1 h at rt, and then lyophilized to give the sodium salt of the starting diastereomer. MS (ESI) m/z: 559.3 [M+H]$^+$ $^1$H NMR (400 MHz, MeOD) δ=8.12 (s, 1H), 7.82 (s, 1H), 7.55 (t, J=6.4 Hz, 1H), 7.35 (d, J=8.0 Hz, 1H), 6.97 (t, J=7.6 Hz, 1H), 6.82 (d, J=4.0 Hz, 1H), 6.65 (s, 2H), 5.13 (s, 1H), 4.09-3.99 (m, 2H), 3.94 (s, 3H), 3.04-2.62 (m, 8H), 2.51-2.39 (m, 1H), 2.26 (br. s., 1H), 2.11 (m, 2H), 1.92-1.79 (m, 5H), 1.78-1.45 (m, 4H), 0.84-0.74 (m, 3H).

TABLE 6

Examples 93-103 were prepared in a similar manner to Example 92 using the appropriate intermediates and commercially available starting materials.

| Example | Structure | M.W. | Isomer | LC/MS (ESI) observed [M + 1]$^+$ |
|---|---|---|---|---|
| 92 | 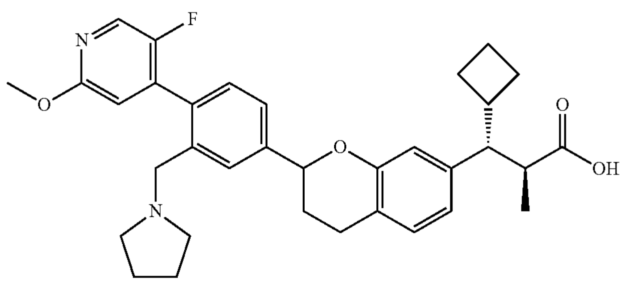 [SMILES: COc1cc(-c2ccc(C3CCc4ccc([C@H](C5CCC5)[C@H](C)C(=O)O)cc4O3)cc2CN2CCCC2)c(F)cn1] | 558.7 | Isomer A | 559.3 |
| 93 | 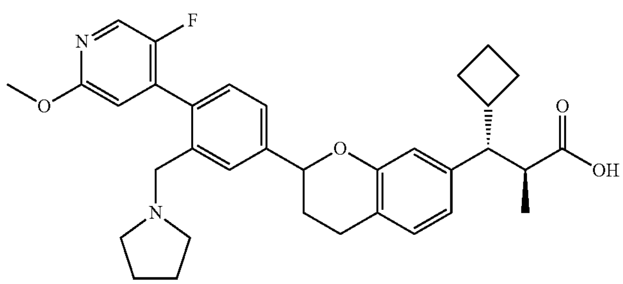 [SMILES: COc1cc(-c2ccc(C3CCc4ccc([C@H](C5CCC5)[C@H](C)C(=O)O)cc4O3)cc2CN2CCCC2)c(F)cn1] | 558.7 | Isomer B | 559.3 |
| 94 | 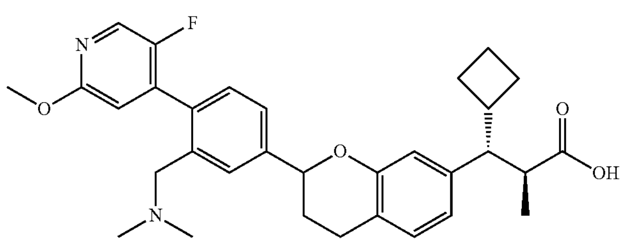 [SMILES: COc1cc(-c2ccc(C3CCc4ccc([C@H](C5CCC5)[C@H](C)C(=O)O)cc4O3)cc2CN(C)C)c(F)cn1] | 532.7 | Isomer A | 533.2 |

TABLE 6-continued

Examples 93-103 were prepared in a similar manner to Example 92 using the appropriate intermediates and commercially available starting materials.

| Example | Structure | M.W. | Isomer | LC/MS (ESI) observed [M + 1]⁺ |
|---------|-----------|------|--------|-------------------------------|
| 95 | 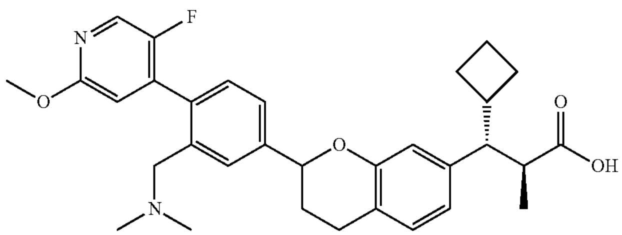 [SMILES: COc1cc(-c2ccc(C3CCc4ccc([C@H](C5CCC5)[C@H](C)C(=O)O)cc4O3)cc2CN(C)C)c(F)cn1] | 532.7 | Isomer B | 533.2 |
| 96 | 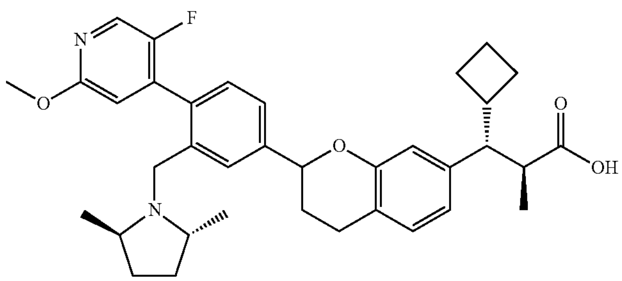 [SMILES: COc1cc(-c2ccc(C3CCc4ccc([C@H](C5CCC5)[C@H](C)C(=O)O)cc4O3)cc2CN2[C@H](C)CC[C@H]2C)c(F)cn1] | 586.74 | Isomer A | 587.1 |
| 97 | 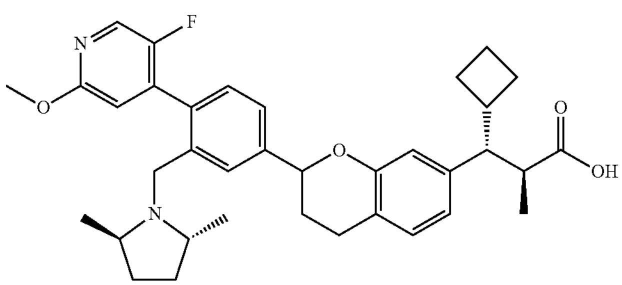 [SMILES: COc1cc(-c2ccc(C3CCc4ccc([C@H](C5CCC5)[C@H](C)C(=O)O)cc4O3)cc2CN2[C@H](C)CC[C@H]2C)c(F)cn1] | 586.7 | Isomer B | 587.1 |
| 98 | 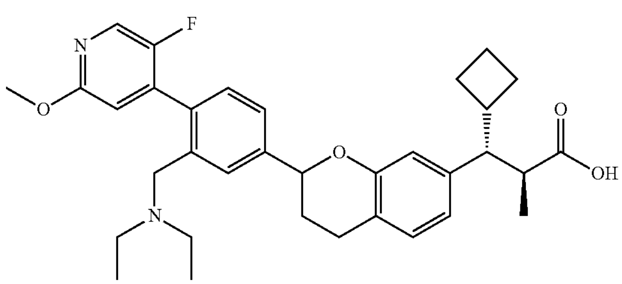 [SMILES: CCN(CC)Cc1cc(C2CCc3ccc([C@H](C4CCC4)[C@H](C)C(=O)O)cc3O2)ccc1-c1cc(OC)ncc1F] | 560.7 | Isomer A | 561.3 |
| 99 | 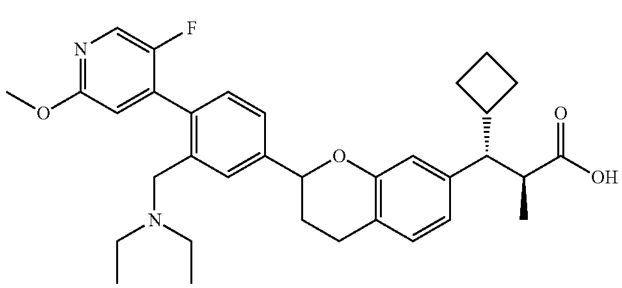 [SMILES: CCN(CC)Cc1cc(C2CCc3ccc([C@H](C4CCC4)[C@H](C)C(=O)O)cc3O2)ccc1-c1cc(OC)ncc1F] | 560.7 | Isomer B | 561.3 |

TABLE 6-continued

Examples 93-103 were prepared in a similar manner to Example 92 using the appropriate intermediates and commercially available starting materials.

| Example | Structure | M.W. | Isomer | LC/MS (ESI) observed [M + 1]+ |
|---------|-----------|------|--------|-------------------------------|
| 100 | 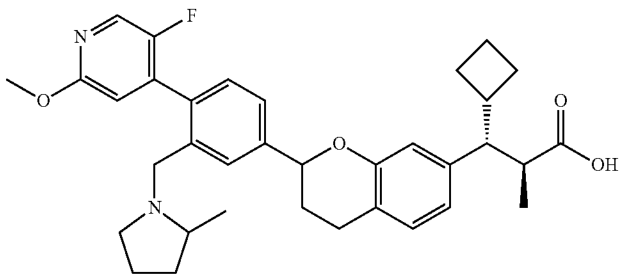 [SMILES: COc1cc(-c2ccc(C3CCc4ccc([C@H](C5CCC5)[C@H](C)C(=O)O)cc4O3)cc2CN2CCCC2C)c(F)cn1] | 572.7 | Isomer A | 573.2 |
| 101 | 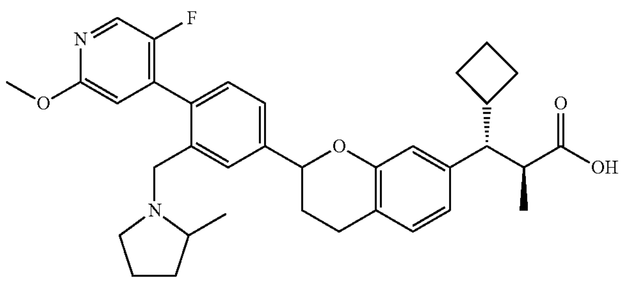 [SMILES: COc1cc(-c2ccc(C3CCc4ccc([C@H](C5CCC5)[C@H](C)C(=O)O)cc4O3)cc2CN2CCCC2C)c(F)cn1] | 572.7 | Isomer B | 573.2 |
| 102 | 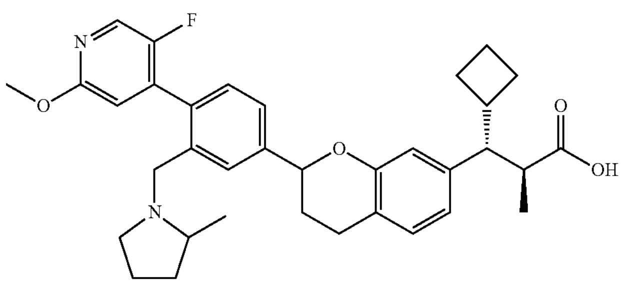 [SMILES: COc1cc(-c2ccc(C3CCc4ccc([C@H](C5CCC5)[C@H](C)C(=O)O)cc4O3)cc2CN2CCCC2C)c(F)cn1] | 572.7 | Isomer C | 573.2 |
| 103 | 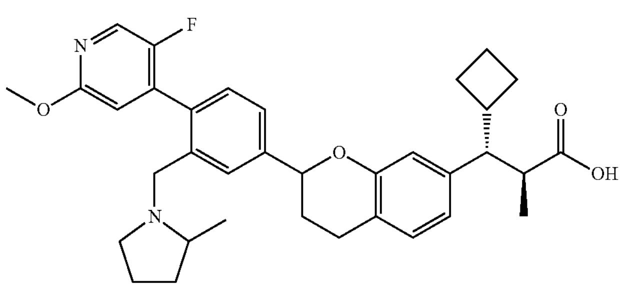 [SMILES: COc1cc(-c2ccc(C3CCc4ccc([C@H](C5CCC5)[C@H](C)C(=O)O)cc4O3)cc2CN2CCCC2C)c(F)cn1] | 572.7 | Isomer D | 573.2 |

Examples 104 and 105

(2S, 3R)-3-cyclobutyl-3-(2-(3-((2,2-dimethylpyrrolidin-1-yl)methyl)-4-(5-fluoro-2-methoxypyridin-4-yl)phenyl)chroman-7-yl)-2-methylpropanoic acid

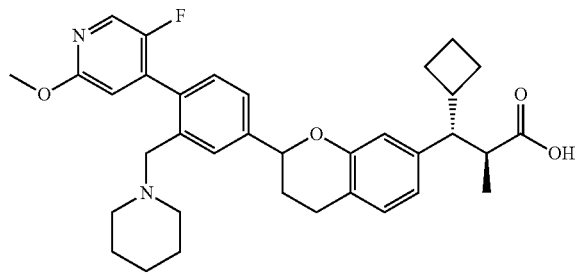 [SMILES: COc1cc(-c2ccc(C3CCc4ccc([C@H](C5CCC5)[C@H](C)C(=O)O)cc4O3)cc2CN2CCCCC2)c(F)cn1]

Step 1: (2S, 3R)-methyl 3-cyclobutyl-3-(2-(4-(5-fluoro-2-methoxypyridin-4-yl)-3-(hydroxymethyl)phenyl)chroman-7-yl)-2-methylpropanoate To a solution of (2S, 3R)-methyl-3-cyclobutyl-3-(2-(4-(5-fluoro-2-methoxypyridin-4-yl)-3-formylphenyl)chroman-7-yl)-2-methylpropanoate (1 g, 1.93 mmol) in MeOH (15 mL) was added NaBH$_4$ (0.146 g, 3.86 mmol) at 0° C. The reaction mixture was stirred at 0° C. for 1 hour, then poured into water (20 mL), and extracted with EtOAc (20 mL×3). The combined organic layers were washed with brine (saturated, 100 mL), dried (Na$_2$SO$_4$), filtered and the filtrate was evaporated under reduced pressure to give the title compound, which was used in the next step without purification. MS (ESI) m/z: 520.3[M+H]$^+$

Step 2: (2S, 3R)-methyl 3-cyclobutyl-3-(2-(4-(5-fluoro-2-methoxypyridin-4-yl)-3-(((methylsulfonyl)oxy)methyl)phenyl)chroman-7-yl)-2-methylpropanoate To a solution of the product of Step 1 (1.00 g, 1.93 mmol) and TEA (0.402 ml, 2.89 mmol) in DCM (15 mL) was added MsCl (0.180 ml, 2.31 mmol) at 0° C. The mixture was stirred at 0° C. for 1 hour, then poured into water (20 mL) and extracted with EtOAc (20 mL×3). The combined organic layers were washed with brine (saturated, 30 mL), dried (Na$_2$SO$_4$), filtered and the filtrate was evaporated under reduced pressure to give the title compound, which was used in the next step. MS (ESI) m/z: 598.3[M+H]$^+$

Step 3: (2S, 3R)-methyl 3-cyclobutyl-3-(2-(4-(5-fluoro-2-methoxypyridin-4-yl)-3-(piperidin-1-ylmethyl)phenyl)chroman-7-yl)-2-methylpropanoate To a mixture of the product of Step 2 (300 mg, 0.502 mmol) and piperidine (214 mg, 2.510 mmol) in MeCN (2.0 mL) were added K$_2$CO$_3$ (416 mg, 3.01 mmol) and sodium iodide (451 mg, 3.01 mmol). The resulting mixture was stirred at 50° C. for 6 h and then allowed to reach room temperature. The mixture was poured into water (10 mL) and extracted with EtOAc (15 mL×3). The combined organic layers were washed with brine (saturated, 10 mL), dried (Na$_2$SO$_4$), filtered and the filtrate was evaporated under reduced pressure to give the title compound, which was used in the next step without purification. MS (ESI) m/z: 587.4[M+H]$^+$

Step 4: (2S, 3R)-3-cyclobutyl-3-(2-(4-(5-fluoro-2-methoxypyridin-4-yl)-3-(piperidin-1-ylmethyl)phenyl)chroman-7-yl)-2-methylpropanoic acid To a solution of the product of Step 3 (400 mg, 0.682 mmol) in a co-solvent of water (4 mL), THF (4 mL) and MeOH (4 mL) was added LiOH (327 mg, 13.6 mmol). The reaction mixture was stirred at 50° C. for 64 hours, then poured into water (10 mL) and citric acid (500 mg) was added. The mixture was extracted with EtOAc (15 mL×3). The combined organic layers were washed with brine (10 mL×3), dried over Na$_2$SO$_4$, filtered and the filtrate was evaporated under reduced pressure to give the title compound. MS (ESI) m/z: 573.2[M+H]$^+$

Step 5: SFC Separation of (2S, 3R)-3-cyclobutyl-3-(2-(4-(5-fluoro-2-methoxypyridin-4-yl)-3-(piperidin-1-ylmethyl)phenyl)chroman-7-yl)-2-methylpropanoic acid

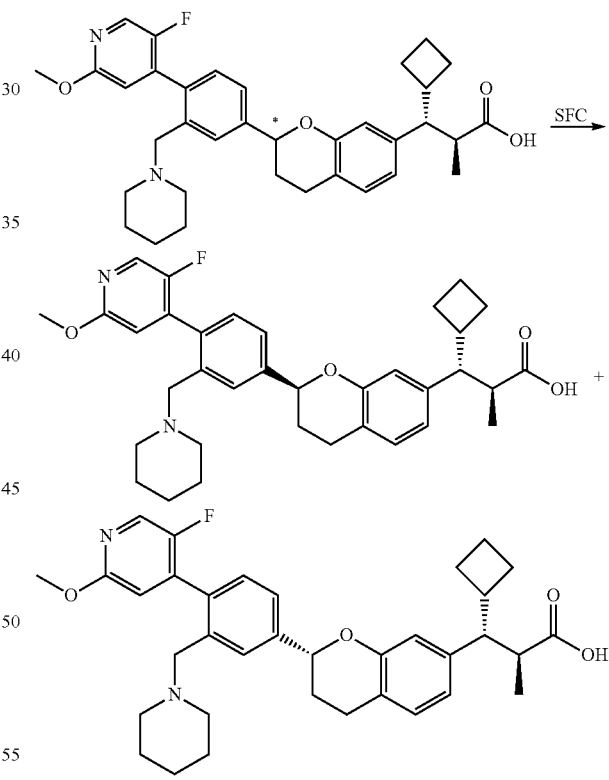

A mixture of 2 diastereomers at * of (2S, 3R)-3-cyclobutyl-3-(2-(4-(5-fluoro-2-methoxypyridin-4-yl)-3-(piperidin-1-ylmethyl)phenyl)chroman-7-yl)-2-methylpropanoic acid (440 mg, 0.768 mmol) was separated by SFC Instrument: SFC-B (12#-102); Method: Column: Chiralpak AD-3 50*4.6 mm I.D., 3 um; Mobile phase: A: CO$_2$ B: iso-propanol (0.05% DEA) Gradient: hold 5% for 0.2 min, then from 5% to 40% of B in 1.4 min and hold 40% for 1.05 min, then 5% of B for 0.35 min; Flow rate: 4 mL/min; Column temp: 40° C.) to give (2S, 3R)-3-cyclobutyl-3-((S)-

2-(4-(5-fluoro-2-methoxy pyridin-4-yl)-3-(piperidin-1-ylmethyl)phenyl)chroman-7-yl)-2-methylpropanoic acid (Isomer 1, faster eluting) and (2S, 3R)-3-cyclobutyl-3-((S)-2-(4-(5-fluoro-2-methoxypyridin-4-yl)-3-(piperidin-1-ylmethyl)phenyl)chroman-7-yl)-2-methylpropanoic acid (Isomer 2, slower eluting).

Step F: Sodium Salt of (2S, 3R)-3-cyclobutyl-3-(2-(4-(5-fluoro-2-methoxypyridin-4-yl)-3-(piperidin-1-ylmethyl)phenyl)chroman-7-yl)-2-methylpropanoic acid To a separate solution of each isomer separated by SFC in MeCN (1 mL) and water (1 mL) was added NaOH (1 eq, 0.5 M aqueous solution), and the mixtures was stirred for 1 h at rt. Then the reaction mixture was lyophilized by the lyophilizer to give the product as a sodium salt. EXAMPLE 104 (Isomer 1 faster eluting): $^1$H NMR (400 MHz, MEOD) δ=8.08 (s, 1H), 7.72 (s, 1H), 7.51 (d, J=8.0 Hz, 1H), 7.31 (d, J=7.6 Hz, 1H), 6.99 (d, J=7.6 Hz, 1H), 6.80 (d, J=4.8 Hz, 1H), 6.71-6.63 (m, 2H), 5.18 (d, J=8.0 Hz, 1H), 3.94 (s, 3H), 3.71 (s, 2H), 3.01-2.93 (m, 1H), 2.81-2.67 (m, 3H), 2.49 (s, 5H), 2.29 (d, J=14.1 Hz, 1H), 2.16-2.04 (m, 2H), 1.89-1.74 (m, 2H), 1.73-1.64 (m, 2H), 1.63-1.49 (m, 5H), 1.44 (s, 2H), 0.85 (d, J=6.8 Hz, 3H); MS (ESI) m/z: 573.2[M+H]$^+$; EXAMPLE 105 (Isomer 2 slower eluting): $^1$H NMR (400 MHz, MeOD) δ=8.08 (s, 1H), 7.72 (s, 1H), 7.52 (d, J=7.6 Hz, 1H), 7.31 (d, J=7.6 Hz, 1H), 7.00 (d, J=8.4 Hz, 1H), 6.80 (d, J=4.8 Hz, 1H), 6.67 (s, 2H), 5.14 (d, J=8.8 Hz, 1H), 3.94 (s, 3H), 3.67 (s, 2H), 3.03-2.95 (m, 1H), 2.80-2.68 (m, 3H), 2.58-2.38 (m, 5H), 2.28 (d, J=13.5 Hz, 1H), 2.15-2.03 (m, 2H), 1.87-1.72 (m, 2H), 1.64 (d, J=8.2 Hz, 2H), 1.53 (d, J=5.5 Hz, 5H), 1.44 (s, 2H), 0.87 (d, J=6.8 Hz, 3H); MS (ESI) m/z: 573.2[M+H]$^+$

TABLE 7

Examples 106-109 were prepared in a similar manner to Examples 104 and 105 using the appropriate intermediates and commercially available starting materials.

| Example | Structure | M.W. | Isomer | LC/MS (ESI) observed [M + 1]$^+$ |
|---|---|---|---|---|
| 106 | 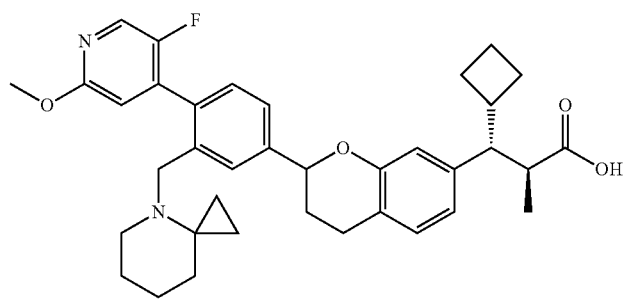 [SMILES: COc1cc(-c2ccc(C3CCc4ccc([C@H](C5CCC5)[C@H](C)C(=O)O)cc4O3)cc2CN2CCCCC23CC3)c(F)cn1] | 598.3 | Isomer A | 599.3 |
| 107 | 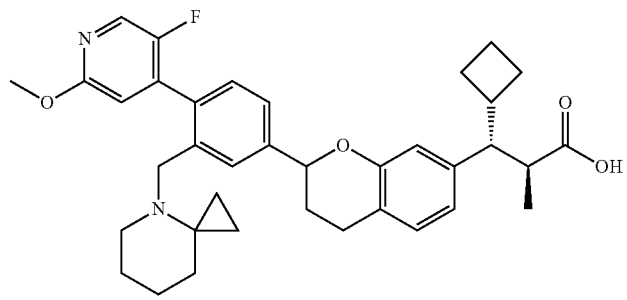 [SMILES: COc1cc(-c2ccc(C3CCc4ccc([C@H](C5CCC5)[C@H](C)C(=O)O)cc4O3)cc2CN2CCCCC23CC3)c(F)cn1] | 598.3 | Isomer B | 599.3 |
| 108 | 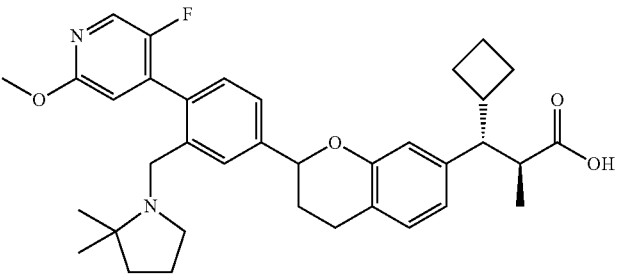 | 586.7 | Isomer A | 587.3 |

TABLE 7-continued

Examples 106-109 were prepared in a similar manner to Examples 104 and 105 using the appropriate intermediates and commercially available starting materials.

| Example | Structure | M.W. | Isomer | LC/MS (ESI) observed [M + 1]+ |
|---|---|---|---|---|
| 109 | 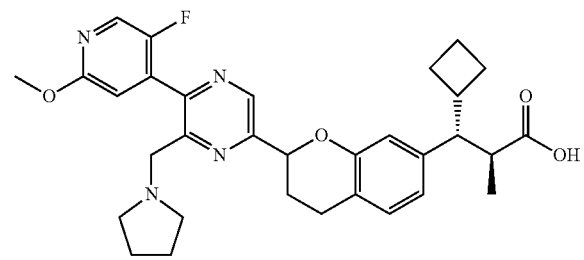 [SMILES: COc1cc(-c2ncc(C3CCc4ccc([C@H](C5CCC5)[C@H](C)C(=O)O)cc4O3)nc2CN2CCCC2)c(F)cn1] | 586.7 | Isomer B | 587.3 |

Example 110

(2S,3R)-3-cyclopropyl-3-(2-(5-(5-fluoro-2-methoxy-pyridin-4-yl)-6-(pyrrolidin-1-ylmethyl)pyrazin-2-yl)chroman-7-yl)-2-methylpropanoic acid

Step 1: methyl 5-(5-fluoro-2-methoxypyridin-4-yl)-6-methylpyrazine-2-carboxylate To a nitrogen-purged solution of methyl 5-chloro-6-methylpyrazine-2-carboxylate (15 g, 80 mmol), (5-fluoro-2-methoxypyridin-4-yl)boronic acid (16.49 g, 96 mmol), Pd (dppf) Cl₂ dichloromethane adduct (1.2 g, 1.469 mmol) and Pd(dppf)Cl₂ (4.6 g, 6.29 mmol) in THF (199 ml) and water (40.8 ml) was added potassium phosphate tribasic (51.2 g, 241 mmol) under a nitrogen atmosphere. A reflux condenser was attached and the mixture was vigorously refluxed with a 100° C. oil bath with stirring. After 105 min, the reaction was cooled to rt and partitioned between EtOAc (200 mL) and water (200 mL). The layers were separated and the aqueous layer was extracted with ethyl acetate (150 mL). The organic layers were combined, filtered through Celite™, washed with brine, dried over anhydrous MgSO₄, filtered and evaporated to afford a crude residue. The resulting residue was purified via column chromatography on silica gel (ISCO RediSep Gold 330 g silica gel column, gradient elution with 0% to 50% EtOAc in hexanes) to give the title compound.

Step 2: methyl 6-(2-(dimethylamino)vinyl)-5-(5-fluoro-2-methoxypyridin-4-yl)pyrazine-2-carboxylate A solution of methyl 5-(5-fluoro-2-methoxypyridin-4-yl)-6-methylpyrazine-2-carboxylate (3.94 g, 14.2 mmol) in DMF (59 mL) and DMF-DMA (59 mL) was heated under nitrogen at 130° C. overnight. The reaction was cooled to rt and partitioned between ethyl acetate (500 mL), hexanes (200 mL) and brine (500 mL). They layers were separated and the organic layer was washed twice more with brine (250 mL each). The organic layer was dried over anhydrous MgSO₄, filtered and evaporated until there was solid slurried in a minimal amount of solvent. The slurry was filtered and the solid was washed with a minimal amount of EtOAc, 1:1 hexanes:EtOAc, then hexanes. Air was pulled through the solid until it was dry to afford the title compound.

Step 3: methyl 5-(5-fluoro-2-methoxypyridin-4-yl)-6-formylpyrazine-2-carboxylate Sodium periodate (4.92 g, 23.02 mmol) was added to a stirred, room temperature mixture of methyl 6-(2-(dimethylamino)vinyl)-5-(5-fluoro-2-methoxypyridin-4-yl)pyrazine-2-carboxylate (2.55 g, 7.67 mmol) in THF (102 ml) and water (51.2 ml) and the mixture was stirred at rt for 4.5 h. To the reaction mixture was added 350 mL sat. aq. NaHCO₃ and 350 mL EtOAc. The resulting mixture was then stirred. The layers were separated and the aqueous layer was extracted with ethyl acetate (100 mL). The organic layers were combined, washed with brine, dried over anhydrous MgSO₄, filtered and evaporated to afford a crude residue. The resulting residue was purified via column chromatography on silica gel (ISCO RediSep Gold 80 g silica gel column, gradient elution with 0% to 100% EtOAc in hexanes) to give the title compound.

Step 4: methyl 6-(1,3-dioxolan-2-yl)-5-(5-fluoro-2-methoxypyridin-4-yl)pyrazine-2-carboxylate Ethylene glycol (0.402 ml, 7.21 mmol) and p-toluenesulfonic acid monohydrate (0.091 g, 0.481 mmol) were added to a stirred, room temperature mixture of methyl 5-(5-fluoro-2-methoxy-pyridin-4-yl)-6-formylpyrazine-2-carboxylate (1.4 g, 4.81 mmol) in benzene (48.1 ml). A Dean-Stark trap and reflux condenser were attached and the mixture was stirred at reflux for 18 h. The reaction was then cooled to rt, partitioned between benzene and saturated aqueous sodium bicarbonate and stirred for 1 h. The layers were separated. The organic layer was washed with brine, dried over anhydrous MgSO₄, filtered and evaporated to afford a crude residue. The resulting residue was purified via column chromatography on silica gel (ISCO RediSep Gold 80 g silica gel column, gradient elution with 0% to 70% EtOAc in hexanes) to give the title compound.

Step 5: (6-(1,3-dioxolan-2-yl)-5-(5-fluoro-2-methoxypyridin-4-yl)pyrazin-2-yl)methanol A 1M solution of DIBAL-H in THF (7.16 ml, 7.16 mmol) was added dropwise over 30 min to a stirred, 0° C. mixture of methyl 6-(1,3-dioxolan-2-yl)-5-(5-fluoro-2-methoxypyridin-4-yl)pyrazine-2-carboxylate (1.2 g, 3.58 mmol) in THF (71.6 ml). The resulting mixture was stirred at 0° C. for 2.5 h. A 1M solution of DIBAL-H in THF (1.5 mL, 1.5 mmol) was added and stirring was continued at 0° C. for 1.5 h. A 1M solution of DIBAL-H in THF (3 mL, 3 mmol) was added and stirring was continued at 0° C. for 1 h. A 1M solution of DIBAL-H in THF (3 mL, 3 mmol) was added and stirring was continued at 0° C. for 20 min. The reaction was slowly poured into a 0° C. saturated aqueous sodium potassium tartrate solution with stirring. The resulting mixture was stirred for 15 min. The layers were separated and the aqueous layer was extracted with ethyl acetate. The organic layers were combined, and partitioned with brine. A viscous emulsion formed, which was allowed to sit overnight. The layers were separated and the brine layer was extracted with EtOAc. The organic layers were combined, dried over anhydrous Na$_2$SO$_4$, filtered and evaporated to afford a crude residue. The resulting residue was purified via column chromatography on silica gel (ISCO RediSep Gold 40 g silica gel column, gradient elution with 0% to 100% EtOAc in hexanes then isocratic at 100% EtOAc) to give the title compound.

Step 6: 6-(1,3-dioxolan-2-yl)-5-(5-fluoro-2-methoxypyridin-4-yl)pyrazine-2-carbaldehyde Dess-Martin periodinane (1.677 g, 3.95 mmol) was added in a single portion to a solution of (6-(1,3-dioxolan-2-yl)-5-(5-fluoro-2-methoxypyridin-4-yl)pyrazin-2-yl)methanol (0.810 g, 2.64 mmol) in DCM (52.7 ml) at rt and the resulting mixture was stirred at rt for 2 h. The reaction was quenched with 1M aq. Na$_2$S$_2$O$_3$ (50 mL) and sat. aq. NaHCO$_3$ (50 mL), and the resulting mixture was stirred for 1 h. The layers were separated and the aqueous layer was extracted with dichloromethane. The organic layers were combined, washed with brine, dried over anhydrous Na$_2$SO$_4$, filtered and evaporated to afford a crude residue. The resulting residue was redissolved in DCM, and was purified via column chromatography on silica gel (ISCO RediSep Gold 40 g silica gel column, gradient elution with 0% to 100% EtOAc in hexanes) to give the title compound.

Step 7: 1-(6-(1,3-dioxolan-2-yl)-5-(5-fluoro-2-methoxypyridin-4-yl)pyrazin-2-yl)prop-2-en-1-ol Vinylmagnesium bromide (1 M in THF; 1.352 ml, 1.352 mmol) was added dropwise over 5 min. to a stirred, −40° C. (dry ice/MeCN bath) mixture of 6-(1,3-dioxolan-2-yl)-5-(5-fluoro-2-methoxypyridin-4-yl)pyrazine-2-carbaldehyde (0.344 g, 1.127 mmol) in THF (14.26 ml) and the mixture was stirred at −40° C. for 3 h. The reaction was quenched with 25 mL 20% aq. sodium citrate and partitioned with EtOAc. The layers were separated and the aqueous layer was extracted with ethyl acetate. The organic layers were combined, washed with brine, dried over anhydrous Na$_2$SO$_4$, filtered and evaporated to afford a crude residue. The resulting residue was purified via column chromatography on silica gel (ISCO RediSep Gold 40 g silica gel column, gradient elution with 0% to 100% EtOAc in hexanes) to give the title compound.

Step 8: (2S,3R)-methyl 3-(4-(3-(6-(1,3-dioxolan-2-yl)-5-(5-fluoro-2-methoxypyridin-4-yl)pyrazin-2-yl)-3-oxopropyl)-3-hydroxyphenyl)-3-cyclopropyl-2-methylpropanoate N,N-Dicyclohexylmethyl-amine (177 μl, 0.833 mmol) was added to a stirred, room temperature, nitrogen-purged mixture of (2S,3R)-methyl 3-cyclopropyl-3-(3-hydroxy-4-iodophenyl)-2-methylpropanoate (Intermediate 5, 150 mg, 0.416 mmol), 1-(6-(1,3-dioxolan-2-yl)-5-(5-fluoro-2-methoxypyridin-4-yl)pyrazin-2-yl)prop-2-en-1-ol (167 mg, 0.500 mmol) and chloro(2-di-t-butylphosphino-2',4',6'-tri-i-propyl-1,1'-biphenyl)[2-(2-aminoethyl)phenyl] palladium (II), min. 98% (t-butyl XPhos palladacycle Gen. 1] (42.9 mg, 0.062 mmol) in toluene (4.2 mL) and the mixture was stirred at 90° C. for 1.5 h. The reaction was then cooled to rt and evaporated to a minimal volume. A small amount of CH$_2$Cl$_2$ was added to the crude mixture to dissolve everything. The solution was loaded onto a hexanes-equilibrated 40 g silica gel column. The column was subjected to gradient elution with 0% to 100% EtOAc in hexanes) to give the title compound.

Step 9: (2S,3R)-methyl 3-(4-(3-(6-(1,3-dioxolan-2-yl)-5-(5-fluoro-2-methoxypyridin-4-yl)pyrazin-2-yl)-3-hydroxypropyl)-3-hydroxyphenyl)-3-cyclopropyl-2-methylpropanoate The product of Step 8 (189 mg, 0.334 mmol) was dissolved in EtOH (3.8 mL) and NaBH$_4$ (29 mg, 0.767 mmol) was added at 25° C. The mixture was stirred at 25° C. for 2 h. The reaction was then quenched with sat. aq. NH$_4$Cl and partioned with EtOAc. The layers were separated and the aqueous layer was extracted with ethyl acetate. The EtOAc phases were combined, washed with brine, dried over anhydrous MgSO$_4$, filtered and evaporated to afford a crude residue. The resulting residue was purified via column chromatography on silica gel (ISCO RediSep Gold 120 g silica gel column, gradient elution with 0% to 100% EtOAc in hexanes) to give the title compound.

Step 10: (2S,3R)-methyl 3-(2-(6-(1,3-dioxolan-2-yl)-5-(5-fluoro-2-methoxypyridin-4-yl)pyrazin-2-yl)chroman-7-yl)-3-cyclopropyl-2-methylpropanoate To a 0° C. solution of (2S,3R)-methyl 3-(4-(3-(6-(1,3-dioxolan-2-yl)-5-(5-fluoro-2-methoxypyridin-4-yl)pyrazin-2-yl)-3-hydroxypropyl)-3-hydroxyphenyl)-3-cyclopropyl-2-methylpropanoate (0.158 g, 0.278 mmol) in CH$_2$Cl$_2$ (2.78 ml) was added triphenylphosphine (0.102 g, 0.390 mmol). Diisopropylazodicarboxylate (0.076 ml, 0.390 mmol) was added dropwise. The mixture was stirred at 0° C. for 1.5 h. The reaction mixture was loaded onto a hexanes-equilibrated 24 g ISCO RediSep gold silica gel column. The column was subjected to gradient elution 0% to 100% EtOAc in hexanes to afford the title compound.

Step 11: (2S,3R)-methyl 3-cyclopropyl-3-(2-(5-(5-fluoro-2-methoxypyridin-4-yl)-6-formylpyrazin-2-yl)chroman-7-yl)-2-methylpropanoate 2M HCl (aq) (1.5 ml, 3.00 mmol) was added to a stirred, room temperature mixture of the product of Step 10 (124 mg, 0.226 mmol) in acetone (3 ml). The solution became cloudy, and acetone was added dropwise until reaction went clear again (~0.5 mL acetone was added). The reaction was capped with a pressure-release cap and heated in a heating block at 60° C. for 6.5 h. The heat was then turned off and the solution stirred overnight. The reaction was again heated to 60° C. and kept at that temperature for 8 h. The reaction was cooled to rt and partitioned between ethyl acetate and saturated aqueous sodium bicarbonate. The layers were separated and the aqueous layer was extracted with ethyl acetate. The organic layers were combined, washed with brine, dried over anhydrous $Na_2SO_4$, filtered and evaporated to afford a crude residue. The resulting residue was purified via column chromatography on silica gel (ISCO RediSep Gold 24 g silica gel column, gradient elution with 0% to 100% EtOAc in hexanes) to give the title compound.

Step 12: (2S,3R)-methyl 3-cyclopropyl-3-(2-(5-(5-fluoro-2-methoxypyridin-4-yl)-6-(pyrrolidin-1-ylmethyl)pyrazin-2-yl)chroman-7-yl)-2-methylpropanoate Sodium triacetoxyborohydride (72.3 mg, 0.341 mmol) was added to a stirred, room temperature mixture of (2S,3R)-methyl 3-cyclopropyl-3-(2-(5-(5-fluoro-2-methoxypyridin-4-yl)-6-formylpyrazin-2-yl)chroman-7-yl)-2-methylpropanoate (115 mg, 0.227 mmol), pyrrolidine (56.4 µl, 0.682 mmol) and HOAc (41.7 µl, 0.728 mmol) in DCE (2.3 mL) and the mixture was stirred at rt for 5.5 h. The reaction was partitioned between ethyl acetate and saturated aqueous sodium hydrogen carbonate, and stirred for 30 min. The layers were separated and the aqueous layer was extracted with EtOAc. The organic layers were combined, washed with brine, dried over anhydrous $Na_2SO_4$, filtered and evaporated to afford a crude residue. The resulting residue was purified via column chromatography on silica gel (ISCO RediSep Gold 24 g silica gel column, gradient elution with 0% to 20% MeOH in methylene chloride) to give the title compound.

Step 13: (2S,3R)-3-cyclopropyl-3-(2-(5-(5-fluoro-2-methoxypyridin-4-yl)-6-(pyrrolidin-1-ylmethyl)pyrazin-2-yl)chroman-7-yl)-2-methylpropanoic acid (Example 100)

2 M LiOH (aq.) (0.250 ml, 0.500 mmol) was added to a stirred, room temperature mixture of the product of Step 12 (21 mg, 0.037 mmol) in THF (0.5 ml) and MeOH (0.125 ml) and the mixture was stirred at 55° C. for 19 h. The reaction was cooled to rt. To the reaction mixture, was added 0.2 mL 2N aq. HCl (pH changed to ~pH 4). The reaction mixture was concentrated. The resulting residue was dissolved in DMSO and purified via reversed-phase C18 column chromatography (ISCO RediSep C18 column 4.3 g, gradient elution with 0% to 100% MeCN in water w/0.1% HCOOH) to give the desired product with impurities present. The material was dissolved in DMSO (1.3 mL) and subjected to reversed-phase HPLC (Waters XBridge C18, Sum, 19×100 mm, 25 ml/min, 12 minute run time, gradient elution from 10% to 45% MeCN in water adjusted to pH 10 with ammonium hydroxide). The product containing fraction was frozen with a dry ice/isopropanol bath and lyophilized for 3 days to afford the title compound. LC/MS (m/z): 547.1 $(M+H)^+$.

Examples 110A and 110B (2S,3R)-3-cyclopropyl-3-(2-(5-(5-fluoro-2-methoxypyridin-4-yl)-6-(pyrrolidin-1-ylmethyl)pyrazin-2-yl)chroman-7-yl)-2-methylpropanoic acid (Isomer 1, faster eluting) and (2S,3R)-3-cyclopropyl-3-(2-(5-(5-fluoro-2-methoxypyridin-4-yl)-6-(pyrrolidin-1-ylmethyl)pyrazin-2-yl)chroman-7-yl)-2-methylpropanoic acid (Isomer 2, slower eluting)

Chiral SFC separation of 45 mg of (2S,3R)-3-cyclopropyl-3-(2-(5-(5-fluoro-2-methoxypyridin-4-yl)-6-(pyrrolidin-1-ylmethyl)pyrazin-2-yl)chroman-7-yl)-2-methylpropanoic (Example 100) via Chiralpak AD-H column (isocratic elution 45% EtOH with 0.1% DIPA in $CO_2$, 50 ml/min, 120 bar; 40° C., 0.5 mL injection volume) afforded a faster eluting peak and a slower eluting peak. The material isolated from concentration of the faster eluting peak fractions was subjected to column chromatography on silica gel (ISCO RediSep Gold 4 g silica gel column, gradient elution with 0% to 50% MeOH in methylene chloride) to give (2S,3R)-3-cyclopropyl-3-((S)-2-(5-(5-fluoro-2-methoxypyridin-4-yl)-6-(pyrrolidin-1-ylmethyl)pyrazin-2-yl)chroman-7-yl)-2-methylpropanoic acid (Isomer 1, Example 100a) 547.4 $(M+H)^+$. The material isolated from concentration of the slower eluting peak fractions was dissolved in $CH_2Cl_2$ and partitioned with saturated aqueous ammonium chloride. The organic layer was dried over anhydrous sodium sulfate, filtered and evaporated to afford a crude residue which was purified via column chromatography on silica gel (ISCO RediSep Gold 4 g silica gel column, gradient elution with 0% to 50% MeOH in methylene chloride) to give (2S,3R)-3-cyclopropyl-3-((R)-2-(5-(5-fluoro-2-methoxypyridin-4-yl)-6-(pyrrolidin-1-ylmethyl)pyrazin-2-yl)chroman-7-yl)-2-methylpropanoic acid (Isomer 2, Example 100b) 547.4 $(M+H)^+$.

Example 111

(2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoic acid

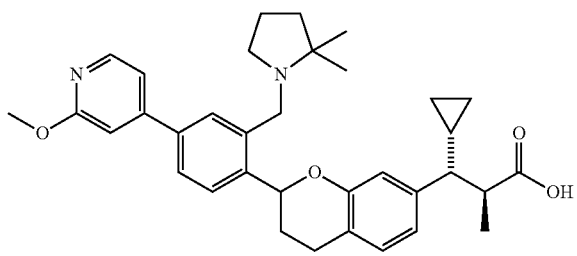 [SMILES: COc1cc(-c2ccc(C3CCc4ccc([C@H](C5CC5)[C@H](C)C(=O)O)cc4O3)c(CN3CCCC3(C)C)c2)ccn1]

Step 1: 4-chloro-2-((2,2-dimethylpyrrolidin-1-yl)methyl)benzaldehyde

To a solution of 2-(bromomethyl)-4-chlorobenzaldehyde (1.8 g, 7.71 mmol, Biogen Organics) and potassium carbonate (3.20 g, 23.13 mmol) in DMF (25.7 ml) was added 2,2-dimethylpyrrolidine, HCl (1.359 g, 10.02 mmol) at rt. The resulting solution was stirred at rt for 15 h. Then the reaction mixture was filtered, concentrated, purified directly by reverse phase C-18 (100 g silica gel; eluting with $H_2O$ w/0.1% formic acid and $CH_3CN$ to give the title compound. LC/MS: 252.1 $(M+H)^+$.

Step 2: 1-(4-chloro-2-((2,2-dimethylpyrrolidin-1-yl)methyl)phenyl)prop-2-en-1-ol 4-chloro-2-((2,2-dimethylpyrrolidin-1-yl)methyl)benzaldehyde was (1500 mg, 5.96 mmol) dissolved in THF (60 ml) and cooled in an acetone/dry ice bath, then vinylmagnesium bromide (11.9 ml, 11.92 mmol) was added dropwise. The mixture is allowed to warm rt over 2 h. After 24 h, the mixture is quenched with 20% NH₄Cl (aqueous) and diluted with EtOAc. The aqueous layer was extracted with EtOAc. The combined organic layers were washed with brine, dried over MgSO4, and filtered. After concentration, the mixture purified via silica gel (40 g column using a 0-100% 3:1 EtOAc-EtOH/Hexane gradient to give the title compound. LC/MS: 280.2 (M+H)⁺.

Step 3: Methyl (2S,3R)-3-(4-(3-(4-chloro-2-((2,2-dimethylpyrrolidin-1-yl)methyl)phenyl)-3-oxopropyl)-3-hydroxyphenyl-3-cyclopropyl-2-methylpropanoate The product of Step 2 (1.243 g, 4.44 mmol), (2S,3R)-methyl 3-cyclopropyl-3-(3-hydroxy-4-iodophenyl)-2-methylpropanoate (1 g, 2.78 mmol, Intermediate 5) were dissolved in toluene (27.8 mL). The mixture was degassed and flushed with N₂ for 5 minutes, then N,N-dicyclohexylmethylamine (0.892 ml, 4.16 mmol) was added. The reaction mixture was degassed, flushed with N₂, and heated to 90° C. under N₂ for 6 h. Then the reaction mixture was cooled in an ice bath. The resulting solid was filtered, and washed with EtOAc. The filtrate was concentrated to give a residue, which was purified via SiO₂ gel chromatography (40 g column using a gradient of 0-100% Hexane/EtOAc) to give the title compound. LC/MS: 512.4 (M+H)⁺.

Step 4: Methyl (2S,3R)-3-(4-(3-(4-chloro-2-((2,2-dimethylpyrrolidin-1-yl)methyl)-phenyl)-3-hydroxypropyl)-3-hydroxyphenyl)-3-cyclopropyl-2-methylpropanoate The product of Step 3 (1.5 g, 2.93 mmol) was suspended in MeOH (29.3 ml)) in a 200 ml RB flask in an ice bath. Then sodium borohydride (0.554 g, 14.65 mmol) was added slowly. The reaction was stirred at rt for 3 h, then quenched with water (2 mL) and concentrated. NH₄Cl solution (10 ml) was added to the resulting residue and the mixture was extracted with EtOAc (3×). The combined organic layers were washed with brine (3×), dried over MgSO₄, filtered, and concentrated. The resulting residue was purified by gradient silica gel chromatography (40 g silica gel column, gradient: 0-100% EtOAc/Hexane) to give the title compound.

Step 5: Methyl (2S,3R)-3-(2-(4-chloro-2-((2,2-dimethylpyrrolidin-1-yl)methyl)phenyl)-chroman-7-yl)-3-cyclopropyl-2-methylpropanoate To a solution of methyl (2S,3R)-3-(4-(3-(4-chloro-2-((2,2-dimethylpyrrolidin-1-yl)methyl)-phenyl)-3-hydroxypropyl)-3-hydroxyphenyl)-3-cyclopropyl-2-methylpropanoate in DCM (1.65 equivalents+04 μl) was added triphenylphosphine (607 mg, 2.315 mmol). The reaction was cooled to 0° C., and DIAD (450 μl, 2.315 mmol) was added at 0° C. After 3 h the reaction mixture was concentrated to reduce the volume, and purified via gradient silica gel chromatography (40 g silica gel column, gradient: 0-100%; EtOAc/Hexane) to afford (2S,3R)-methyl 3-(2-(4-chloro-2-((2,2-dimethylpyrrolidin-1-yl)methyl)phenyl)chroman-7-yl)-3-cyclopropyl-2-methylpropanoate.

Step 6: Methyl (2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoate To a solution of (2S,3R)-methyl 3-(2-(4-chloro-2-((2,2-dimethylpyrrolidin-1-yl)methyl)phenyl)chroman-7-yl)-3-cyclopropyl-2-methylpropanoate (120 mg, 0.242 mmol) and (2-methoxypyridin-4-yl)boronic acid (74.0 mg, 0.484 mmol) in THF (3 mL) at rt was added chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst (2ⁿᵈ generation Xphos precatalyst, 19.03 mg, 0.024 mmol). The reaction mixture was degassed and purged with N₂, then potassium phosphate 1N (0.726 mL, 0.726 mmol) was added. The mixture was degassed and purged with N₂ again, then warmed to 80° C. and stirred for 3 h. Then the reaction mixture was diluted with EtOAc, filtered through a Celite™ plug and concentrated in vacuo. The resulting residue was purified by column chromatography over silica gel (24 g, eluting with Hexanes/EtOAc (100:0 to 0:100)) to give (2S,3R)-methyl 3-cyclopropyl-3-(2-(2-((2,2-dimethylpyrrolidin-1-yl)methyl)-4-(2-methoxypyridin-4-yl)phenyl)chroman-7-yl)-2-methylpropanoate.

Step 7: (2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoic acid To a solution of (2S,3R)-methyl 3-cyclopropyl-3-(2-(2-((2,2-dimethylpyrrolidin-1-yl)methyl)-4-(2-methoxypyridin-4-yl)phenyl)chroman-7-yl)-2-methylpropanoate (118 mg, 0.207 mmol) in THF/MeOH (2 mL/2 mL) at rt, was added lithium hydroxide (2075 μl, 2.075 mmol). The reaction mixture was stirred for 60 h at 55° C., then concentrated. The resulting residue was re-dissolved in DMSO:CH₃CN:H₂O (2:1:1), and then acidified with formic acid (10 eq). The resulting mixture was directly purified by reverse phase C-18 chromatography (eluting with H₂O w/0.1% formic acid and CH₃CN) to give (2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoic acid.

Examples 111a and 111b

Sodium (2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoate

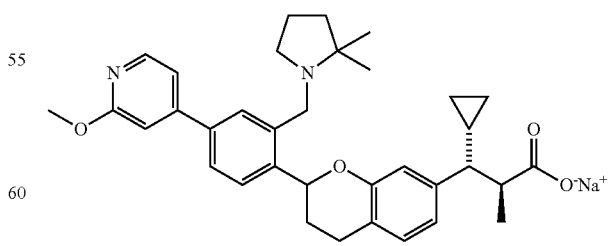

Example 111a [Isomer 1]
Example 111b [Isomer 2]

Step 1: SFC Separation of (2S,3R)-3-cyclopropyl-3-(2-(2-(((2,2-dimethylpyrrolidin-1-yl)methyl)-4-(2-methoxypyridin-4-yl)phenyl)chroman-7-yl)-2-methylpropanoic acid Isomer 1 and Isomer 2 (2S,3R)-3-cyclopropyl-3-(2-(2-(((2,2-dimethylpyrrolidin-1-yl)methyl)-4-(2-methoxypyridin-4-yl)phenyl)chroman-7-yl)-2-methylpropanoic acid (98 mg, 0.177 mmol) were separated by SFC chiral separation and re-purified using the following reverse phase conditions: Isomer 1: peak 1 (D1 from chiral separation) was re-purified by Reverse Phase C-18 eluting with H₂O w/0.1% formic acid and CH₃CN. Isomer 2, peak 2 (D2 from chiral separation) was re-purified by Reverse Phase C-18 eluting with H₂O w/0.1% formic acid and CH₃CN.

Step 2: Sodium (2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoate Isomer 1 was dissolved in acetonitrile/water (2 mL/2 mL) and 0.1 N NaOH (1 eq) was added. The reaction mixture was mixed and lyophilized to give sodium (2S,3R)-3-cyclopropyl-3-(2-(2-(((2,2-dimethylpyrrolidin-1-yl)methyl)-4-(2-methoxypyridin-4-yl)phenyl)chroman-7-yl)-2-methylpropanoate (Example 111a). Isomer 2 was dissolved in acetonitrile/water (2 mL/2 mL) and 0.1N NaOH (1 eq) was added. The reaction mixture was, mixed and lyophilized to give sodium (2S,3R)-3-cyclopropyl-3-(2-(2-((2,2-dimethylpyrrolidin-1-yl)methyl)-4-(2-methoxypyridin-4-yl)phenyl)chroman-7-yl)-2-methylpropanoate (Example 111b).

TABLE 8

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)⁺ |
|---|---|---|---|
| 111 | 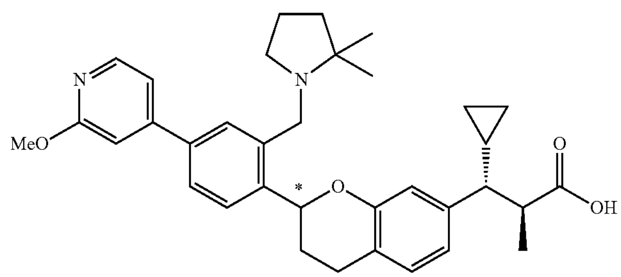 [SMILES: COc1cc(-c2ccc(C3CCc4ccc([C@H](C5CC5)[C@H](C)C(=O)O)cc4O3)c(CN3CCCC3(C)C)c2)ccn1] | Mixture of 2 diastereomers at * | 555.4 |
| 111a | 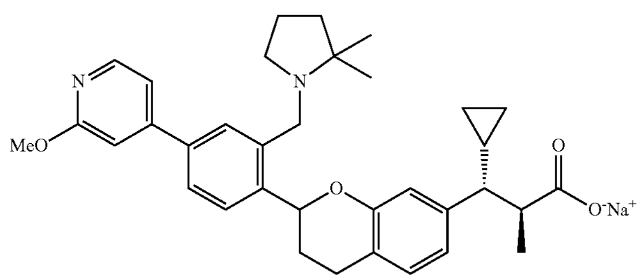 | Isomer 1 (Peak 1) Chiralpak AD-H Methanol with 0.25% Isopropylamine/ CO₂ | 555.5 |
| 111b | 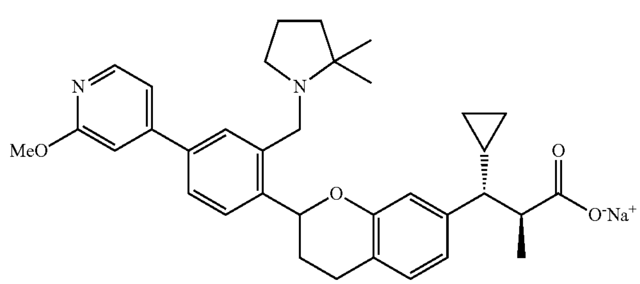 | Isomer 2 (Peak 2) Chiralpak AD-H Methanol with 0.25% Isopropylamine/ CO₂ | 555.5 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 112 | 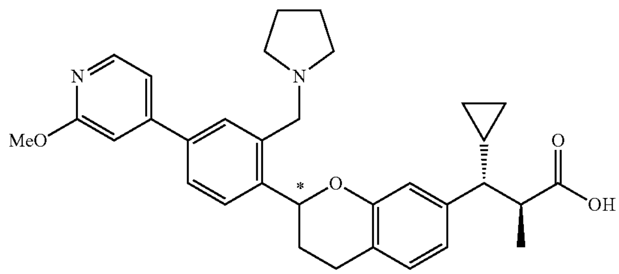 | Mixture of 2 diastereomers at * | 527.5 |
| 112a | 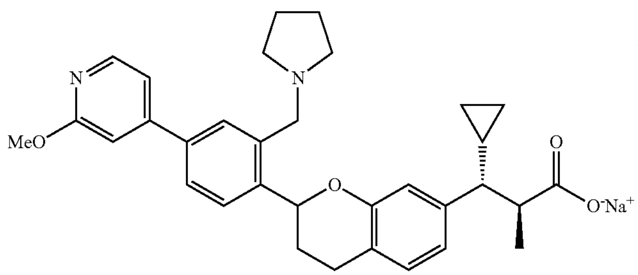 | Isomer 1 (Peak 1) AD-H ethanol with 0.1% DIPA/ $CO_2$ | 527.5 |
| 112b | 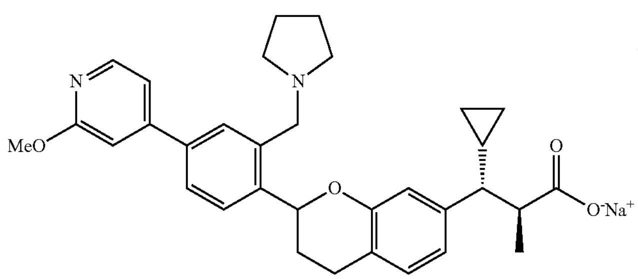 | Isomer 2 (Peak 2) AD-H ethanol with 0.1% DIPA/ $CO_2$ | 527.5 |
| 113 | 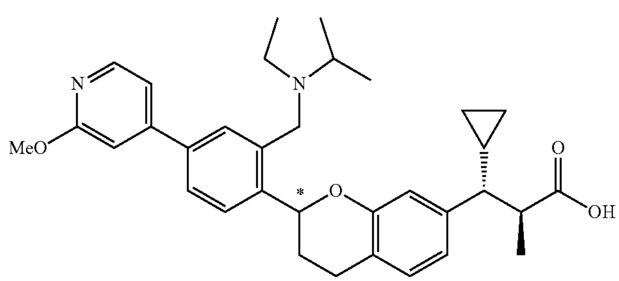 [SMILES: CCN(Cc1cc(-c2ccnc(OC)c2)ccc1C1CCc2ccc([C@H](C3CC3)[C@H](C)C(=O)O)cc2O1)C(C)C] | Mixture of 2 diastereomers at * | 543.4 |
| 113a | 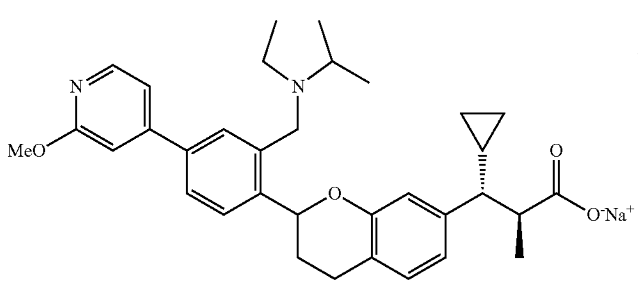 | Isomer 1 (Peak 1) AD-H 25% ethanol/$CO_2$ | 543.4 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 113b | 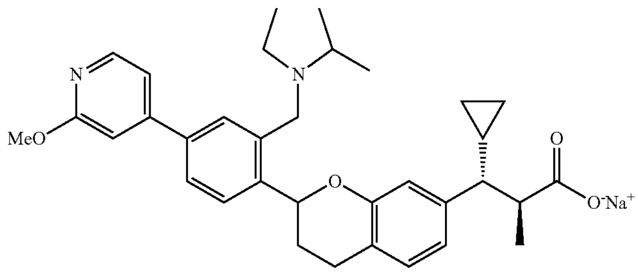 | Isomer 2 (Peak 2) AD-H 25% ethanol/$CO_2$ | 543.4 |
| 114 | 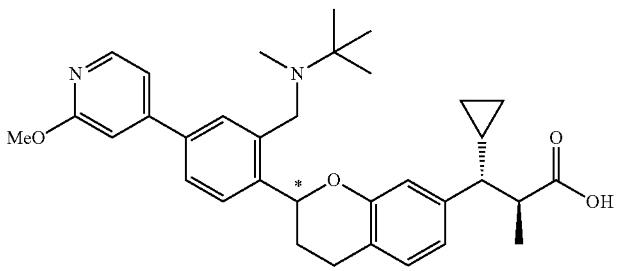 | Mixture of 2 diastereomers at * | 543.4 |
| 114a | 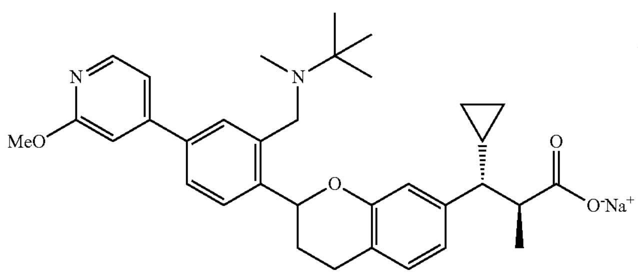 | Isomer 1 (Peak 1) AD-H 50% ethanol + DIPA/$CO_2$ | 543.4 |
| 114b | 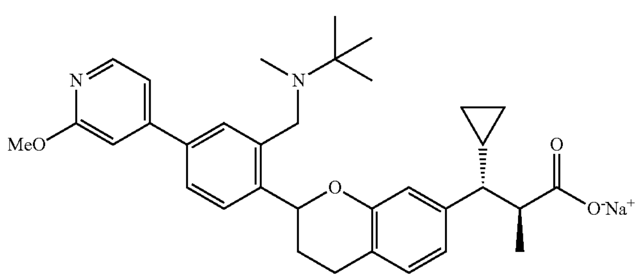 | Isomer 2 (Peak 2) AD-H 50% ethanol + DIPA/$CO_2$ | 543.5 |
| 115 | 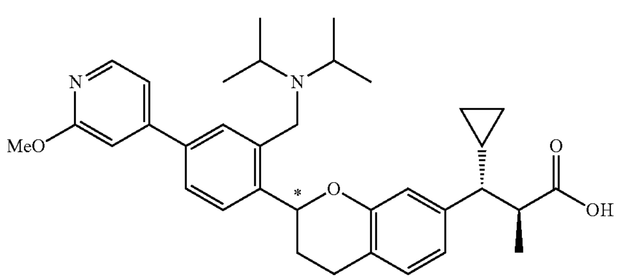 [SMILES: COc1cc(-c2ccc(C3CCc4ccc([C@H](C5CC5)[C@H](C)C(=O)O)cc4O3)c(CN(C(C)C)C(C)C)c2)ccn1] | Mixture of 2 diastereomers at * | 557.5 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 115a | 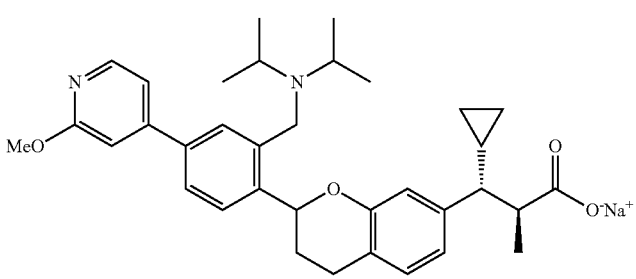 | Isomer 1 (Peak 1) AD-H 25% ethanol + DIPA/CO$_2$ | 557.5 |
| 115b | 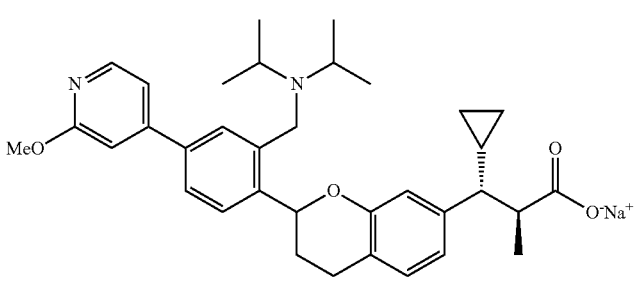 | Isomer 2 (Peak 2) AD-H 25% ethanol + DIPA/CO$_2$ | 557.5 |
| 116 | 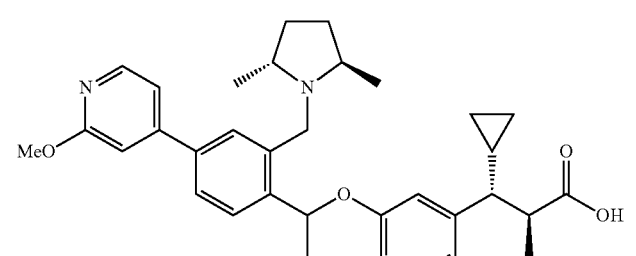 | Mixture of 4 diastereomers at * and pyrrolidine | 555.5 |
| 116a | 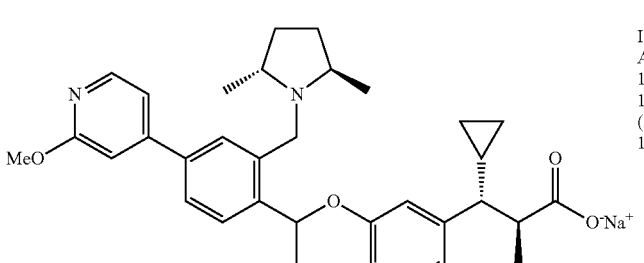 | Isomer 1 (Peak 1) AD-H (2 × 25 + 2 × 15 cm) 15% isopropanol (0.1% DEA)/CO$_2$, 100 bar | 555.5 |
| 116b | 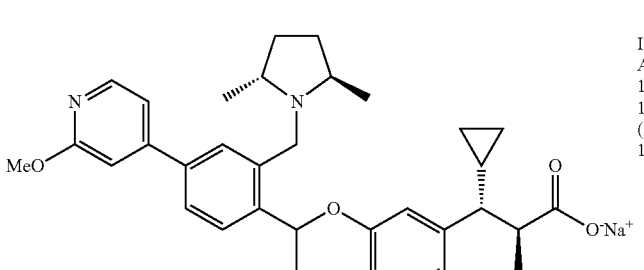 | Isomer 2 (Peak 2) AD-H (2 × 25 + 2 × 15 cm) 15% isopropanol (0.1% DEA)/CO$_2$, 100 bar | 555.5 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/Chiral Conditions | LC/MS (M + H)+ |
|---|---|---|---|
| 116c | 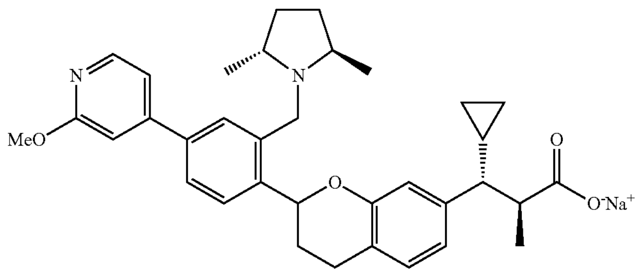 | Isomer 3 (Peak 3) AD-H (2 × 25 + 2 × 15 cm) 30% isopropanol (0.1% DEA)/CO$_2$, 100 bar | 555.5 |
| 116d | 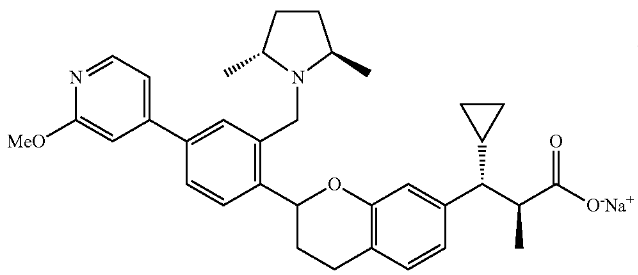 | Isomer 4 (Peak 4) AD-H (2 × 25 + 2 × 15 cm) 30% isopropanol (0.1% DEA)/CO$_2$, 100 bar | 555.5 |
| 117 | 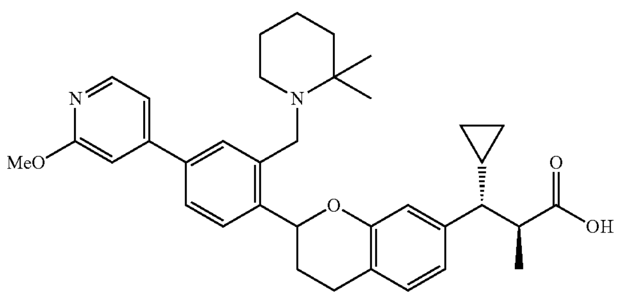 [SMILES: COc1cc(-c2ccc(C3CCc4ccc([C@H](C5CC5)[C@H](C)C(=O)O)cc4O3)c(CN3CCCCC3(C)C)c2)ccn1] | Mixture of 2 diastereomers at * | 569.5 |
| 117a | 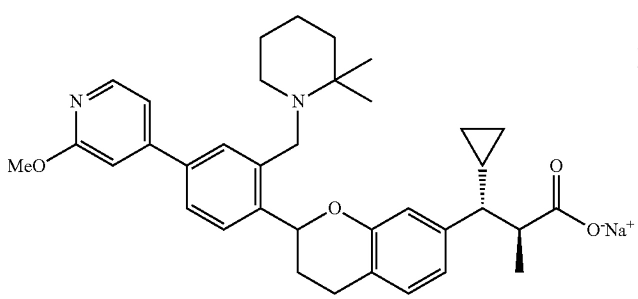 | Isomer 1 (Peak 1) AD-H, 21 × 250 mm, 40% IPA + DIPA/CO$_2$ | 569.5 |
| 117b | 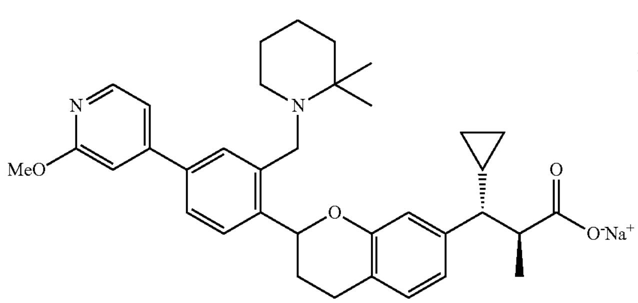 | Isomer 2 (Peak 2) AD-H, 21 × 250 mm, 40% IPA + DIPA/CO$_2$ | 569.5 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 118a | 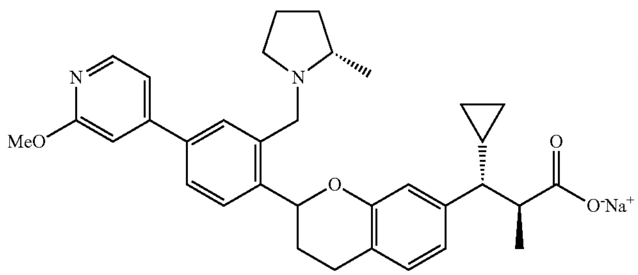 | Isomer 1 Separation by normal phase silica column (EtOAc/Hexane) | 541.4 |
| 118b | 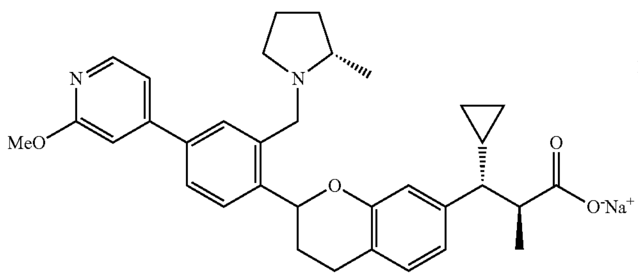 | Isomer 2 Separation by normal phase silica column (EtOAc/Hexane) | 541.4 |
| 119a | 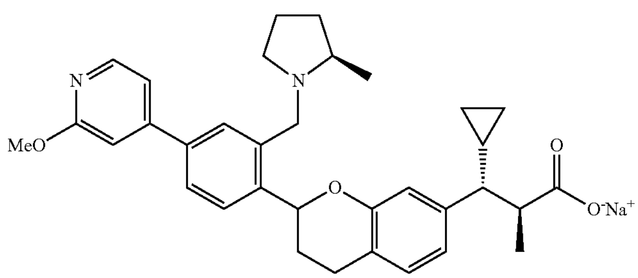 | Isomer 1 Separation by normal phase silica column (EtOAc/Hexane) | 541.4 |
| 119b | 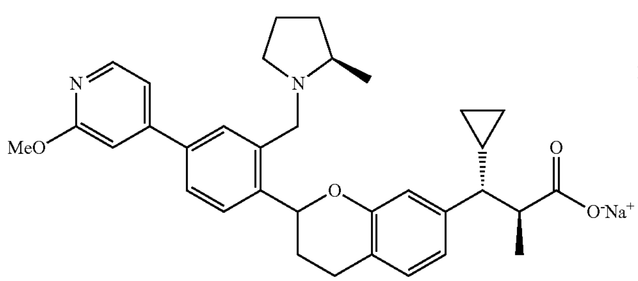 | Isomer 2 Separation by normal phase silica column (EtOAc/Hexane) | 541.4 |
| 120 | 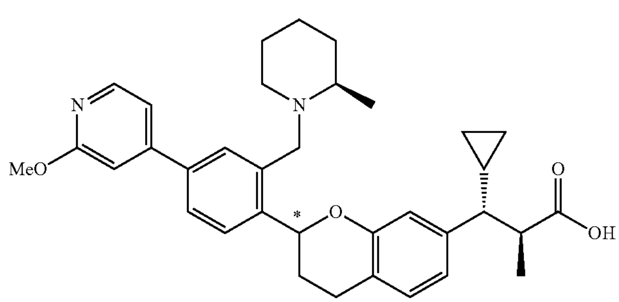 [SMILES: COc1cc(-c2ccc(C3CCc4ccc([C@H](C5CC5)[C@H](C)C(=O)O)cc4O3)c(CN3CCCC[C@H]3C)c2)ccn1] | Mixture of 2 diastereomers at * | 555.5 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 120a | 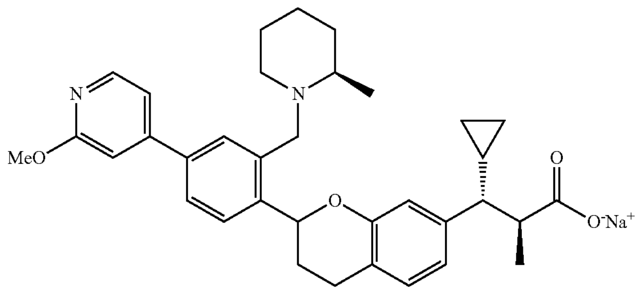 | Isomer 1 (Peak 1) AD-H, 21 × 250 mm, 35% ethanol + DIPA/ CO$_2$ | 555.5 |
| 120b | 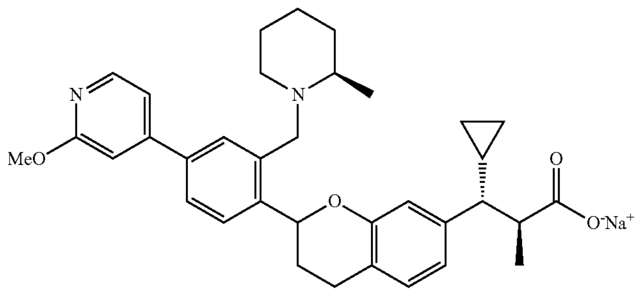 | Isomer 2 (Peak 2) AD-H, 21 × 250 mm, 35% ethanol + DIPA/ CO$_2$ | 555.5 |
| 121 | 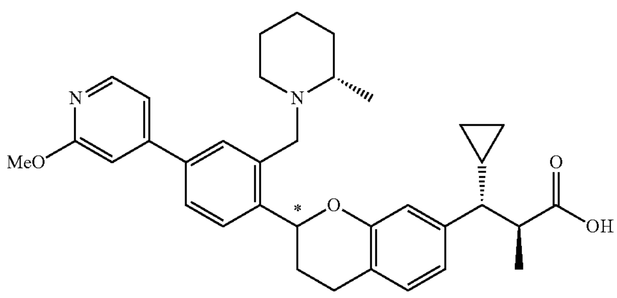 [SMILES: COc1cc(-c2ccc(C3CCc4ccc([C@H](C5CC5)[C@H](C)C(=O)O)cc4O3)c(CN3CCCC[C@@H]3C)c2)ccn1] | Mixture of 2 diastereomers at * | 555.5 |
| 122 | 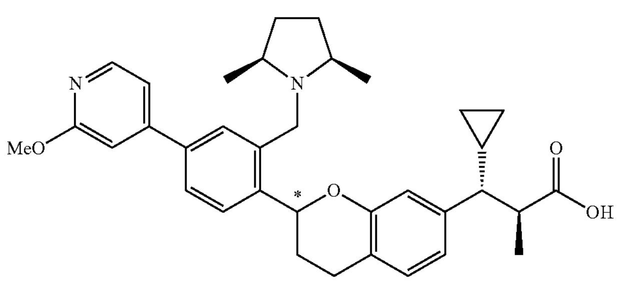 [SMILES: COc1cc(-c2ccc(C3CCc4ccc([C@H](C5CC5)[C@H](C)C(=O)O)cc4O3)c(CN3[C@H](C)CC[C@@H]3C)c2)ccn1] | Mixture of 2 diastereomers at * | 555.5 |
| 122a | 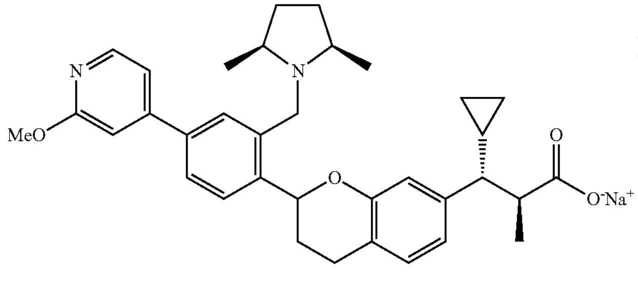 | Isomer 1 (Peak 1) AD-H, 21 × 250 mm, 40% EtOH + DIPA/ CO$_2$ | 555.5 |

TABLE 8-continued

Examples 112-122 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 122b | 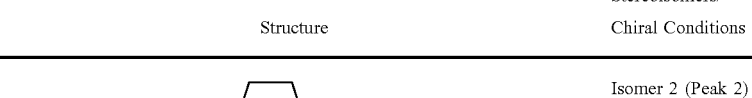 | Isomer 2 (Peak 2) AD-H, 21 × 250 mm, 40% EtOH + DIPA/ CO$_2$ | 555.5 |

TABLE 9

Examples 123-133 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 123a | 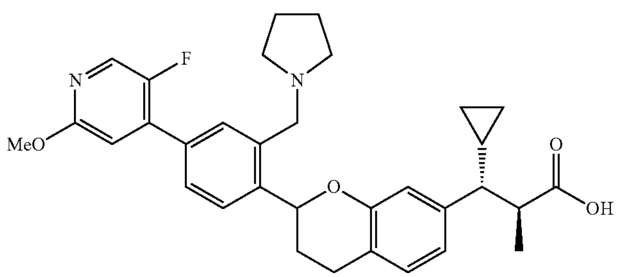 [SMILES: COc1cc(-c2ccc(C3CCc4ccc([C@H](C5CC5)[C@H](C)C(=O)O)cc4O3)c(CN3CCCC3)c2)c(F)cn1] | Isomer 1 (Peak 1) OZ, 4.6 × 250 mm, 30% methanol + DEA/ CO$_2$ | 545.4 |
| 123b | 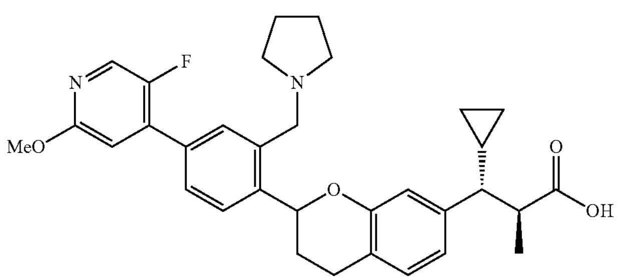 [SMILES: COc1cc(-c2ccc(C3CCc4ccc([C@H](C5CC5)[C@H](C)C(=O)O)cc4O3)c(CN3CCCC3)c2)c(F)cn1] | Isomer 2 (Peak 2) OZ, 4.6 × 250 mm, 30% methanol + DEA/ CO$_2$ | 545.3 |
| 124 | 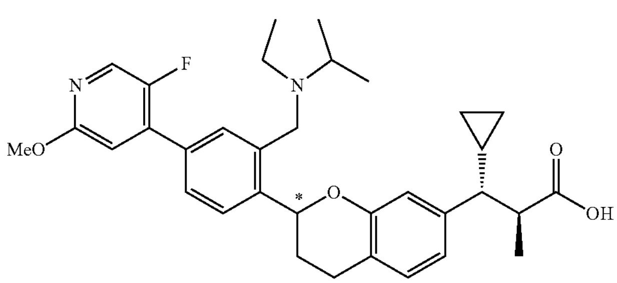 [SMILES: CCN(Cc1cc(-c2cc(OC)ncc2F)ccc1C1CCc2ccc([C@H](C3CC3)[C@H](C)C(=O)O)cc2O1)C(C)C] | Mixture of 2 diastereomers at * | 561.4 |

TABLE 9-continued

Examples 123-133 were prepared in a similar manner to Example 111 starting from the appropriate starting materials. Chiral conditions for resolution of isomers were performed on the free acid.

| Example | Structure | Stereoisomers/ Chiral Conditions | LC/MS $(M + H)^+$ |
|---|---|---|---|
| 124a | 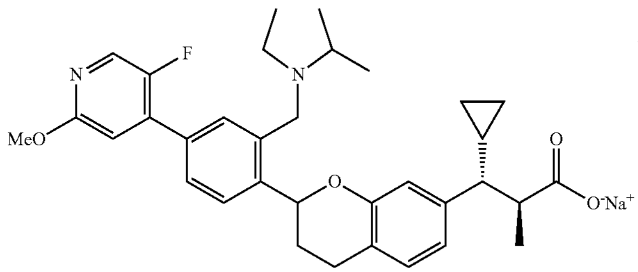 | Isomer 1 (Peak 1) AD-H 20% isopropanol (0.1% DEA)/CO$_2$, 100 bar | 561.5 |
| 124b | 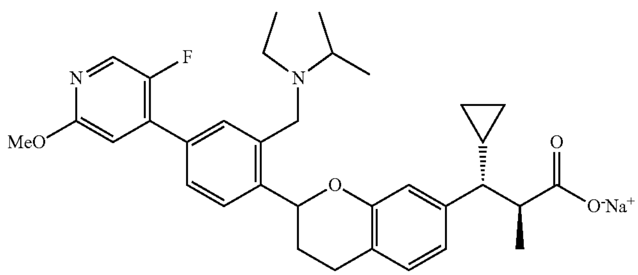 | Isomer 2 (Peak 2) AD-H 20% isopropanol (0.1% DEA)/CO$_2$, 100 bar | 561.5 |
| 125 | 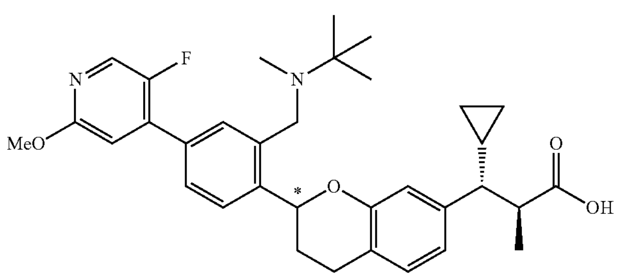 [SMILES: COc1cc(-c2ccc(C3CCc4ccc([C@H](C5CC5)[C@H](C)C(=O)O)cc4O3)c(CN(C)C(C)(C)C)c2)c(F)cn1] | Mixture of 2 diastereomers at * | 561.5 |
| 125a | 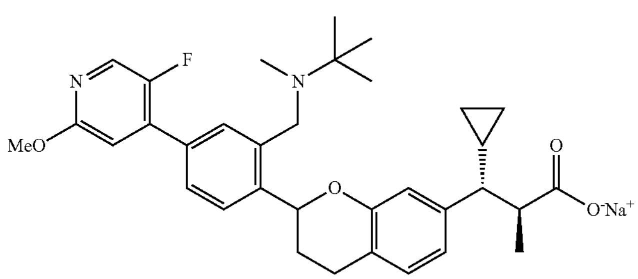 | Isomer 1 (Peak 1) 2 × OJ-H, 21 × 250 mm, 25% MeOH + DIPA/ CO$_2$ | 561.5 |
| 125b | 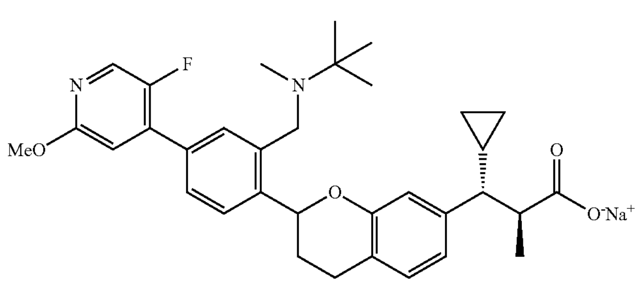 | Isomer 2 (Peak 2) 2 × OJ-H, 21 × 250 mm, 25% MeOH + DIPA/ CO$_2$ | 561.4 |

TABLE 9-continued

Examples 123-133 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
| --- | --- | --- | --- |
| 126 | 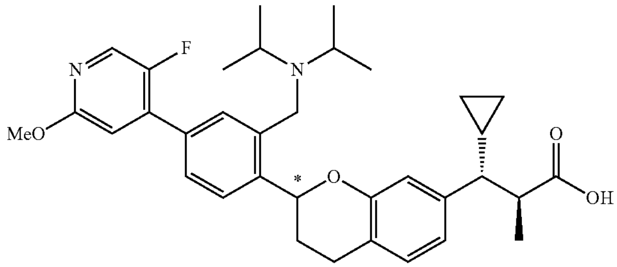 [SMILES: COc1cc(-c2ccc(C3CCc4ccc([C@H](C5CC5)[C@H](C)C(=O)O)cc4O3)c(CN(C(C)C)C(C)C)c2)c(F)cn1] | Mixture of 2 diastereomers at * | 575.5 |
| 126a | 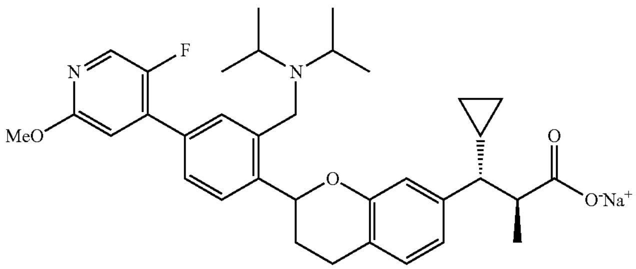 | Isomer 1 (Peak 1) 2 × AS-H, 21 × 250 mm, 30% EtOH + DIPA/ $CO_2$ | 575.5 |
| 126b | 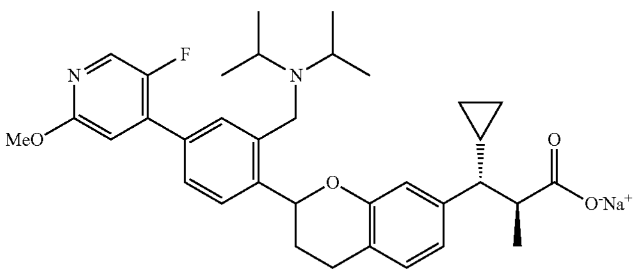 | Isomer 2 (Peak 2) 2 × AS-H, 21 × 250 mm, 30% EtOH + DIPA/ $CO_2$ | 575.5 |
| 127 | 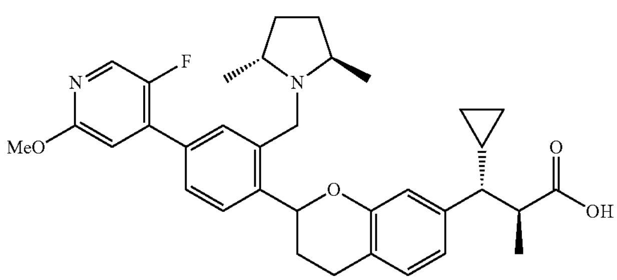 [SMILES: COc1cc(-c2ccc(C3CCc4ccc([C@H](C5CC5)[C@H](C)C(=O)O)cc4O3)c(CN3[C@H](C)CC[C@H]3C)c2)c(F)cn1] | Mixture of 4 diastereomers at * and pyrrolidine | 573.5 |
| 128 | 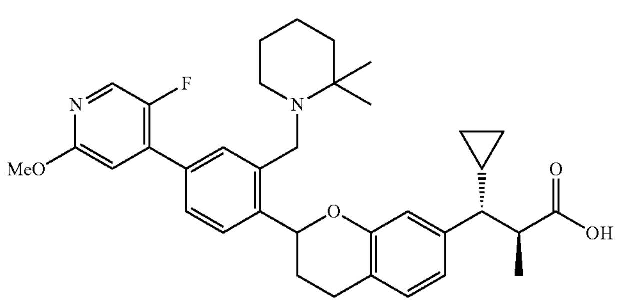 [SMILES: COc1cc(-c2ccc(C3CCc4ccc([C@H](C5CC5)[C@H](C)C(=O)O)cc4O3)c(CN3CCCCC3(C)C)c2)c(F)cn1] | Mixture of 2 diastereomers at * | 587.5 |

TABLE 9-continued

Examples 123-133 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
| --- | --- | --- | --- |
| 128a | 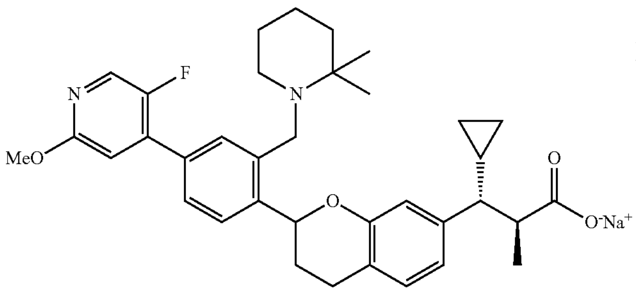 | Isomer 1 (Peak 1) AD-H, 21 × 250 mm, 40% EtOH + DIPA/ CO$_2$ | 587.5 |
| 128b | 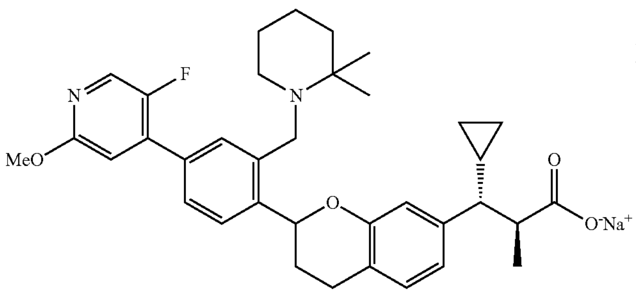 | Isomer 2 (Peak 2) AD-H, 21 × 250 mm, 40% EtOH + DIPA/ CO$_2$ | 587.5 |
| 129a | 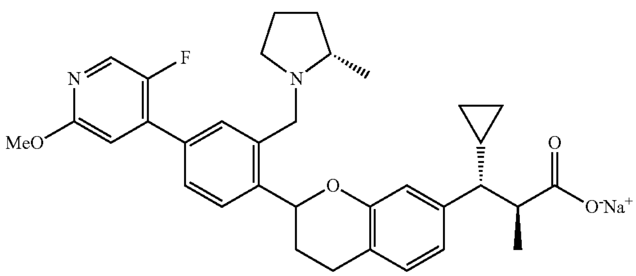 | Isomer 1 Separation by normal phase silica column (EtOAc/Hexane) | 559.5 |
| 129b | 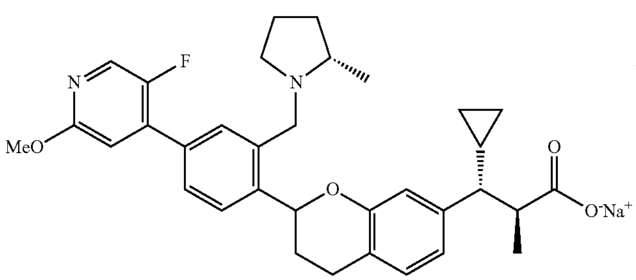 | Isomer 2 Separation by normal phase silica column (EtOAc/Hexane) | 559.4 |
| 130a | 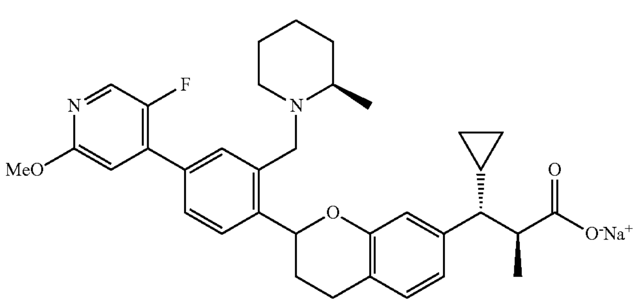 | Isomer 1 Separation by normal phase silica column (EtOAc/Hexane) | 573.5 |

TABLE 9-continued

Examples 123-133 were prepared in a similar manner to Example 111 starting from the appropriate starting materials. Chiral conditions for resolution of isomers were performed on the free acid.

| Example | Structure | Stereoisomers/ Chiral Conditions | LC/MS (M + H)+ |
|---|---|---|---|
| 130b | 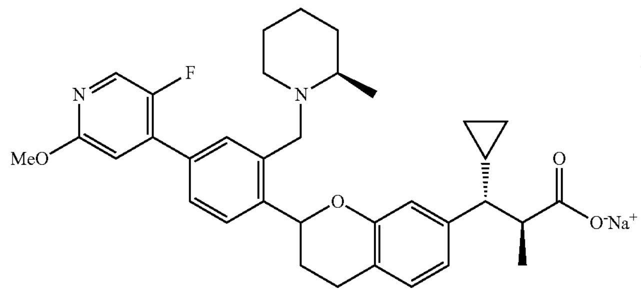 | Isomer 2 Separation by normal phase silica column (EtOAc/Hexane) | 573.5 |
| 131 | 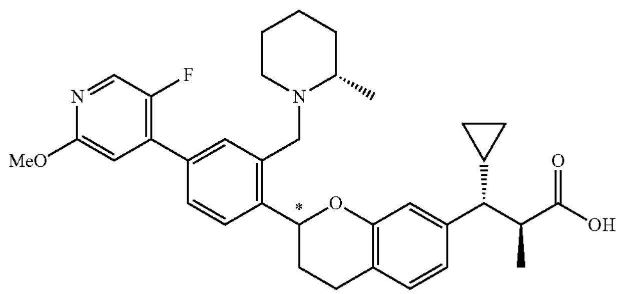 [SMILES: COc1cc(-c2ccc(C3CCc4ccc([C@H](C5CC5)[C@H](C)C(=O)O)cc4O3)c(CN3CCCC[C@@H]3C)c2)c(F)cn1] | Mixture of 2 diastereomers at * | 573.5 |
| 132 | 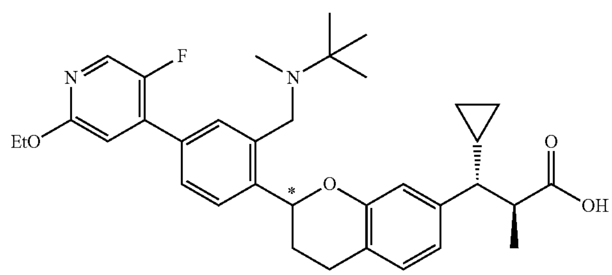 [SMILES: CCOc1cc(-c2ccc(C3CCc4ccc([C@H](C5CC5)[C@H](C)C(=O)O)cc4O3)c(CN(C)C(C)(C)C)c2)c(F)cn1] | Mixture of 2 diastereomers at * | 575.5 |
| 132a | 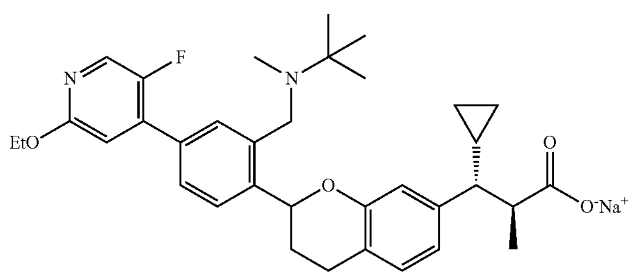 | Isomer 1 (Peak 1) OJ-H, 21 × 250 mm, 20% MeOH + DIPA/ $CO_2$ | 575.5 |
| 132b | 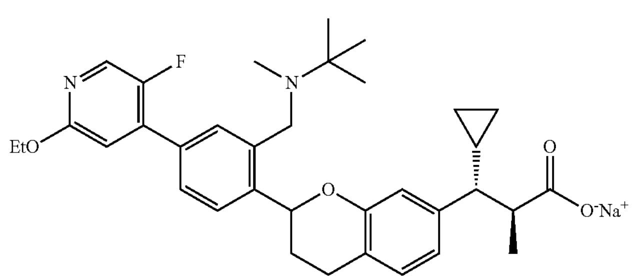 | Isomer 2 (Peak 2) OJ-H, 21 × 250 mm, 20% MeOH + DIPA/ $CO_2$ | 575.5 |

TABLE 9-continued

Examples 123-133 were prepared in a similar manner to Example 111 starting from the appropriate starting materials. Chiral conditions for resolution of isomers were performed on the free acid.

| Example | Structure | Stereoisomers/Chiral Conditions | LC/MS (M + H)+ |
|---|---|---|---|
| 133 | 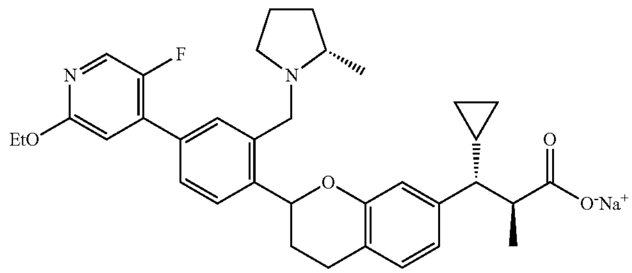 | Isomer 1 Separation by normal phase silica column (EtOAc/Hexane) | 573.5 |

Example 134

(2S, 3R)-3-cyclopropyl-3-((S)-2-(4-(5-fluoro-2-methoxypyridin-4-yl)-3-(((S)-2-(methoxymethyl)pyrrolidin-1-yl)methyl)phenyl)chroman-7-yl)-2-methylpropanoic acid

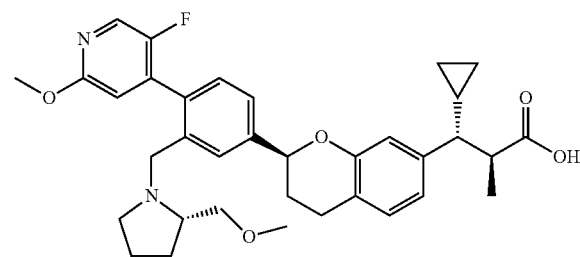 [SMILES: COC[C@@H]1CCCN1Cc1cc([C@@H]2CCc3ccc([C@H](C4CC4)[C@H](C)C(=O)O)cc3O2)ccc1-c1cc(OC)ncc1F]

Step 1: 4-bromo-2-formylphenyl acetate

To a solution of 5-bromo-2-hydroxybenzaldehyde (40.0 g, 199 mmol) in DCM (400 mL) was added dropwise Et$_3$N (41.6 mL, 298 mmol) at 0° C. Then a solution of acetic anhydride (44.7 g, 438 mmol) in DCM (150 mL) was added dropwise to the mixture at 0° C. over 30 min. The reaction was stirred at 0° C. for 30 min then quenched with water (500 mL) at 0° C. The organic layer was washed with 1N HCl (200 mL), water (200 mL), brine (200 mL), dried over anhydrous MgSO$_4$ and filtered. The filtrate was concentrated under reduced pressure to give the title compound, which was used directly in the next step without further purification.

Step 2: 2-formyl-4-vinylphenyl acetate

To a mixture of 4-bromo-2-formylphenyl acetate (20.0 g, 82.0 mmol) in dioxane (200 mL) was added Pd(Ph$_3$P)$_4$ (3.80 g, 3.29 mmol) under N$_2$. Then tributyl(vinyl)tin (57.4 g, 181 mmol) was added to the reaction in one portion. The mixture was stirred at 100° C. for 12 h. Then the reaction mixture was poured into KF solution (10%, 500 mL) and was extracted with EtOAc (200 mL×3). The combined organic layers were washed with saturated sodium chloride solution (350 mL), dried over Na$_2$SO$_4$ and filtered. The filtrate was concentrated in vacuo. The resulting residue was purified by silica gel chromatography (eluted with PE/EtOAc (1:0~30:1, v/v)) to give the title compound.

Step 3: (2S, 3R)-methyl 3-cyclopropyl-3-((RS)-2-(3-formyl-4-hydroxyphenyl)chroman-7-yl)-2-methylpropanoate A mixture of 2-formyl-4-vinylphenyl acetate (6.48 g, 34.1 mmol) and (2S, 3R)-methyl 3-cyclopropyl-3-(3-hydroxy-4-(hydroxymethyl)phenyl)-2-methylpropanoate (6.00 g, 22.7 mmol) under a N$_2$ atmosphere was heated to 175° C. with a heating block. After 65 min, the reaction was cooled to rt. The resulting residue was dissolved in EtOAc (500 mL). The resulting mixture was purified via silica gel chromatography (eluted with PE/EtOAc (50:1~10:1, v/v)) to give the title compound.

Step 4: (2S, 3R)-methyl 3-cyclopropyl-3-((RS)-2-(3-formyl-4-(tosyloxy)phenyl)chroman-7-yl)-2-methylpropanoate To a solution of (2S, 3R)-methyl 3-cyclopropyl-3-((RS)-2-(3-formyl-4-hydroxyphenyl)chroman-7-yl)-2-methylpropanoate (3.40 g, 8.62 mmol) in DCM (350 mL) was added TEA (1.80 mL, 12.9 mmol) and TsCl (1.97 g, 10.3 mmol). The reaction was stirred at 25° C. for 2 h, then quenched with water (250 mL). The mixture was extracted with DCM (200 mL) twice, and the combined organic layers were dried over anhydrous Na$_2$SO$_4$ and filtered. The filtrate was concentrated in vacuo to give the crude product. The crude product was purified by silica gel chromatography (eluted with PE/EtOAc (30:1~10:1, v/v)) to give the title compound.

Step 5: (2S, 3R)-methyl 3-cyclopropyl-3-((RS)-2-(4-(5-fluoro-2-methoxypyridin-4-yl)-3-formylphenyl)chroman-7-yl)-2-methylpropanoate To a solution of (2S, 3R)-methyl 3-cyclopropyl-3-((RS)-2-(3-formyl-4-(tosyloxy)phenyl)chroman-7-yl)-2-methylpropanoate (4.10 g, 7.47 mmol) in THF (60 mL) and water (12 mL) were added potassium phosphate tribasic (4.76 g, 22.4 mmol), 2nd generation SPhos precatalyst (0.269 g, 0.374 mmol) and (5-fluoro-2-methoxypyridin-4-yl)boronic acid (2.55 g, 14.9 mmol) under nitrogen. The reaction mixture was stirred at 80° C. for 4 h, and then was cooled to room temperature. Water (100 mL) was added to the mixture, and the mixture was extracted with EtOAc (50 mL×3). The combined organic layers were washed with water (100 mL) and brine (100 mL), dried over anhydrous MgSO$_4$ and filtered. The filtrate was concentrated under reduced pressure. The resulting residue was purified by silica gel chromatography (eluted with PE/EtOAc (30:1~10:1, v/v)) to give the title compound.

Step 6: (2S, 3R)-methyl 3-cyclopropyl-3-((R)-2-(4-(5-fluoro-2-methoxypyridin-4-yl)-3-formylphenyl)chroman-7-yl)-2-methylpropanoate, and (2S, 3R)-methyl and 3-cyclopropyl-3-((S)-2-(4-(5-fluoro-2-methoxypyridin-4-yl)-3-formylphenyl)chroman-7-yl)-2-methylpropanoate (2S, 3R)-methyl 3-cyclopropyl-3-((RS)-2-(4-(5-fluoro-2-methoxypyridin-4-yl)-3-formylphenyl)chroman-7-yl)-2-methylpropanoate (3.60 g, 7.15 mmol) was separated into separate isomers via SFC separation to give: Peak 1: (2S, 3R)-methyl 3-cyclopropyl-3-((R)-2-(4-(5-fluoro-2-methoxypyridin-4-yl)-3-formylphenyl)chroman-7-yl)-2-methylpropanoate; and Peak 2: (2S, 3R)-methyl 3-cyclopropyl-3-((S)-2-(4-(5-fluoro-2-methoxypyridin-4-yl)-3-formylphenyl)chroman-7-yl)-2-methylpropanoate. The absolute configuration at the chroman stereocenter of the Peak 1 isomer and the Peak 2 isomer was established by VCD (Instrument: Berger MultiGram™ SFC, Mettler Toledo Co, Ltd; Column: AS (250 mm*50 mm, 10 um); Mobile phase: 35% Neutral-MeOH; Column Temp: 38° C.; Nozzle Pressure: 100 Bar; Nozzle Temp: 60° C.; Wavelength: 220 nm).

Step 7: (2S, 3R)-methyl 3-cyclopropyl-3-((S)-2-(4-(5-fluoro-2-methoxypyridin-4-yl)-3-(((S)-2-(methoxymethyl)pyrrolidin-1-yl)methyl)phenyl)chroman-7-yl)-2-methylpropanoate To a solution of (2S, 3R)-methyl 3-cyclopropyl-3-((S)-2-(4-(5-fluoro-2-methoxypyridin-4-yl)-3-formylphenyl)chroman-7-yl)-2-methylpropanoate (150 mg, 0.298 mmol) and (S)-2-(methoxymethyl)pyrrolidine (68.6 mg, 0.596 mmol) in MeOH (3.0 mL) was added titanium (iv) isopropoxide (169 mg, 0.596 mmol). The reaction mixture was stirred at 80° C. for 1 h, then cooled to 0° C. Sodium borohydride (135 mg, 3.57 mmol) was added to the mixture in one portion, and the reaction was stirred at 25° C. for 30 min. The reaction was then quenched by the slow addition of 1N HCl (2 mL). The resulting mixture was extracted with EtOAc (3×10 mL). The combined organic layers were washed with sodium bicarbonate (5%, 2×5 mL), dried (Na$_2$SO$_4$), filtered and the filtrate was evaporated under reduced pressure to give the title compound, which was used to next step without further purification.

Step 8: (2S, 3R)-3-cyclopropyl-3-((S)-2-(4-(5-fluoro-2-methoxypyridin-4-yl)-3-(((S)-2-(methoxymethyl)pyrrolidin-1-yl)methyl)phenyl)chroman-7-yl)-2-methylpropanoic acid To a solution of (2S, 3R)-methyl 3-cyclopropyl-3-((S)-2-(4-(5-fluoro-2-methoxypyridin-4-yl)-3-(((S)-2-(methoxymethyl)pyrrolidin-1-yl)methyl)phenyl)chroman-7-yl)-2-methylpropanoate (175 mg, 0.290 mmol) in a co-solvent of THF/MeOH/H$_2$O (2 mL/2 mL/2 mL) was added lithium hydroxide monohydrate (244 mg, 5.81 mmol). The reaction mixture was stirred at 50° C. for 16 hours. Then the reaction mixture was acidified with HC (1 M, aqueous) to pH 2 and the mixture was extracted with ethyl acetate (3 mL×3). The combined organic layers were concentrated in vacuo. The resulting residue was purified by preparative HPLC (on a GILSON 281 instrument fitted with a YMC-Actus Triart C18 (150*30 mm*5 μm) eluting with Mobile phase A: water (containing 0.1% TFA, v/v), mobile phase B: acetonitrile. Gradient: 25-55% B, 0-10 min; 100% B, 10.5-12.5 min; 5% B, 13-15 min) to give the title compound. $^1$H NMR (400 MHz, CDCl$_3$): δ=8.03 (s, 1H), 7.63 (s, 1H), 7.41 (d, J=7.6 Hz, 1H), 7.22 (d, J=7.6 Hz, 1H), 7.05 (d, J=7.6 Hz, 1H), 6.77 (s, 1H), 6.74 (d, J=8.0 Hz, 1H), 6.69 (d, J=4.8 Hz, 1H), 5.14 (d, J=9.6 Hz, 1H), 4.06 (d, J=14.0 Hz, 1H), 3.96 (s, 3H), 3.33 (d, J=14.0 Hz, 1H), 3.26 (s, 3H), 3.20-2.96 (m, 2H), 3.05-2.92 (m, 1H), 2.90-2.75 (m, 3H), 2.65-2.54 (m, 1H), 2.30-1.95 (m, 5H), 1.67-1.50 (m, 3H), 1.18-1.10 (m, 1H), 1.04 (d, J=7.2 Hz, 3H), 0.68-0.60 (m, 1H), 0.42-0.33 (m, 2H), 0.11-0.01 (m, 1H).

TABLE 10

Examples 135-170 were prepared in a similar manner to Example 134 using the appropriate intermediates and commercially available starting materials.

| Example | Structure | M.W. | LC/MS (ESI) observed [M + 1]$^+$ |
|---|---|---|---|
| 135 | 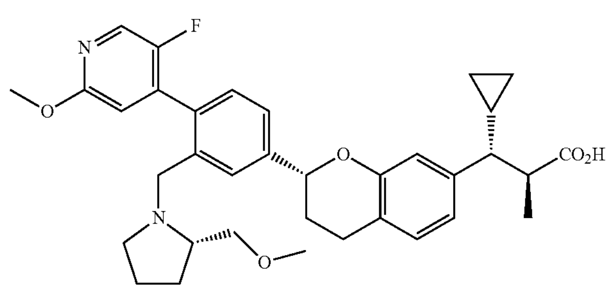 [SMILES: COC[C@@H]1CCCN1Cc1cc([C@H]2CCc3ccc([C@H](C4CC4)[C@H](C)C(=O)O)cc3O2)ccc1-c1cc(OC)ncc1F] | 588.7 | 589.3 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---|---|---|---|
| 136 | 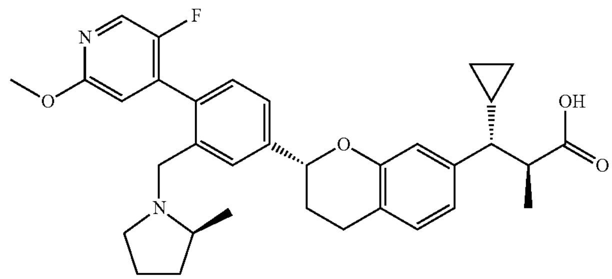 [SMILES: COc1cc(-c2ccc([C@H]3CCc4ccc([C@H](C5CC5)[C@H](C)C(=O)O)cc4O3)cc2CN2CCC[C@@H]2C)c(F)cn1] | 558.7 | 559.3 |
| 137 | 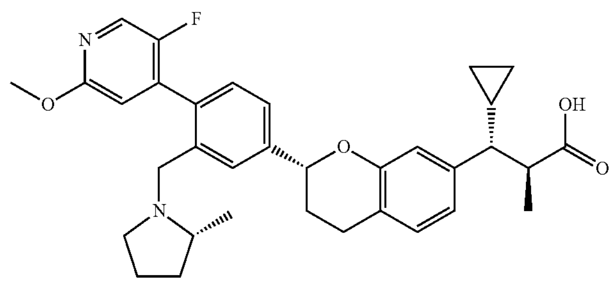 [SMILES: COc1cc(-c2ccc([C@H]3CCc4ccc([C@H](C5CC5)[C@H](C)C(=O)O)cc4O3)cc2CN2CCC[C@H]2C)c(F)cn1] | 558.7 | 559.3 |
| 138 | 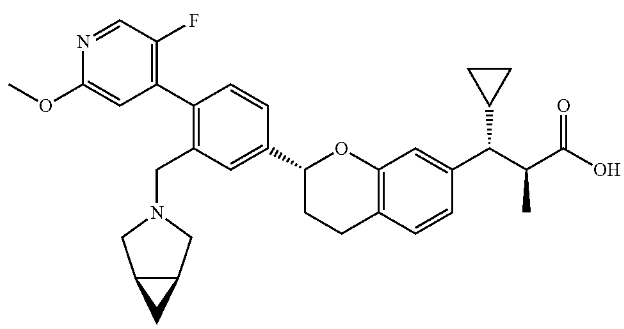 [SMILES: COc1cc(-c2ccc([C@H]3CCc4ccc([C@H](C5CC5)[C@H](C)C(=O)O)cc4O3)cc2CN2C[C@H]3C[C@H]3C2)c(F)cn1] | 556.7 | 557.4 |
| 139 | 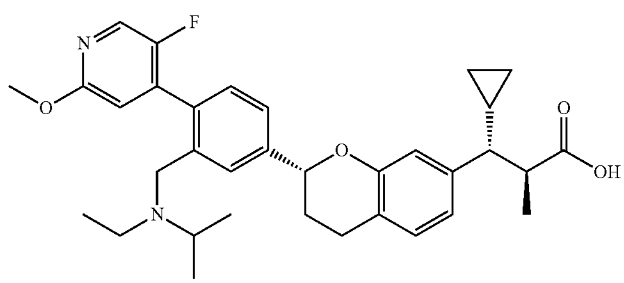 [SMILES: CCN(Cc1cc([C@H]2CCc3ccc([C@H](C4CC4)[C@H](C)C(=O)O)cc3O2)ccc1-c1cc(OC)ncc1F)C(C)C] | 560.7 | 561.4 |
| 140 | 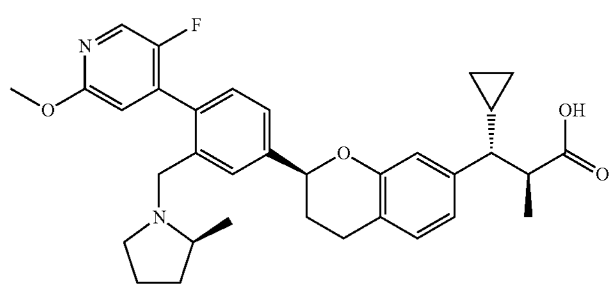 [SMILES: COc1cc(-c2ccc([C@@H]3CCc4ccc([C@H](C5CC5)[C@H](C)C(=O)O)cc4O3)cc2CN2CCC[C@@H]2C)c(F)cn1] | 558.7 | 559.3 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---|---|---|---|
| 141 | 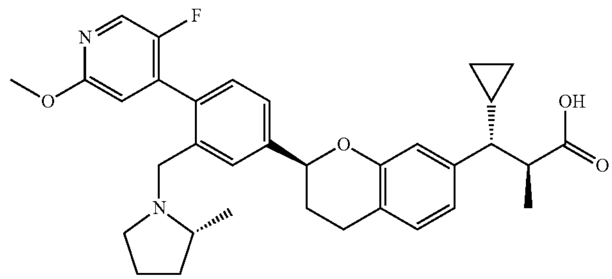 [SMILES: COc1cc(-c2ccc([C@@H]3CCc4ccc([C@H](C5CC5)[C@H](C)C(=O)O)cc4O3)cc2CN2CCC[C@H]2C)c(F)cn1] | 558.7 | 559.3 |
| 142 | 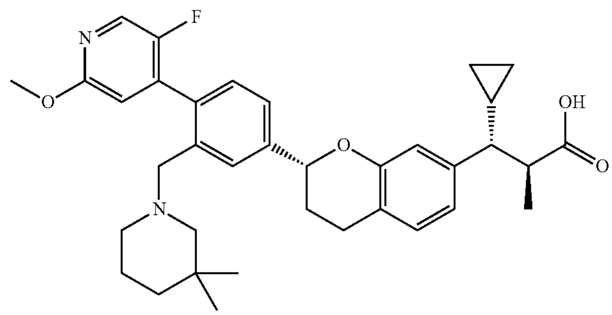 [SMILES: COc1cc(-c2ccc([C@H]3CCc4ccc([C@H](C5CC5)[C@H](C)C(=O)O)cc4O3)cc2CN2CCCC(C)(C)C2)c(F)cn1] | 586.7 | 587.3 |
| 143 | 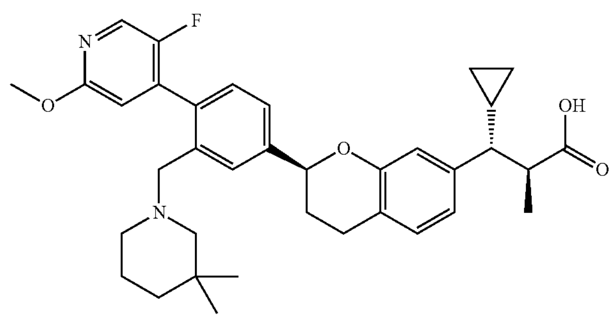 [SMILES: COc1cc(-c2ccc([C@@H]3CCc4ccc([C@H](C5CC5)[C@H](C)C(=O)O)cc4O3)cc2CN2CCCC(C)(C)C2)c(F)cn1] | 586.7 | 587.3 |
| 144 | 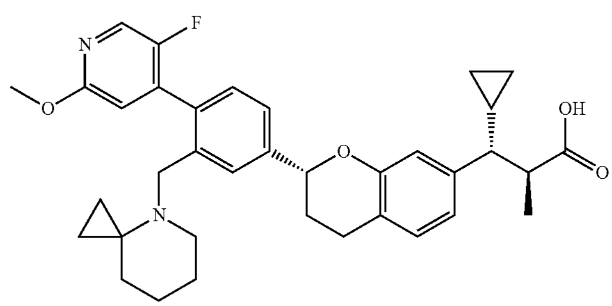 [SMILES: COc1cc(-c2ccc([C@H]3CCc4ccc([C@H](C5CC5)[C@H](C)C(=O)O)cc4O3)cc2CN2CCCCC23CC3)c(F)cn1] | 584.7 | 585.3 |
| 145 | 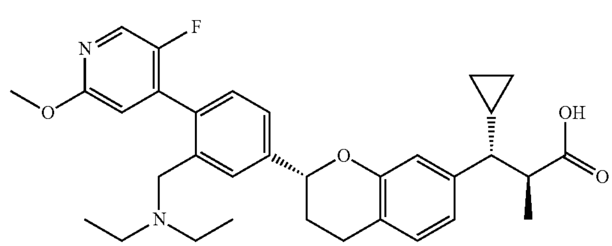 [SMILES: CCN(CC)Cc1cc([C@H]2CCc3ccc([C@H](C4CC4)[C@H](C)C(=O)O)cc3O2)ccc1-c1cc(OC)ncc1F] | 546.7 | 547.3 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---|---|---|---|
| 146 | 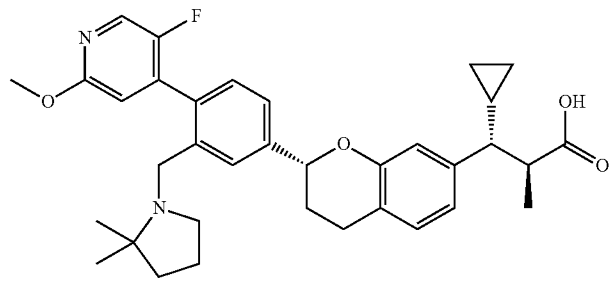 [SMILES: COc1cc(-c2ccc([C@H]3CCc4ccc([C@H](C5CC5)[C@H](C)C(=O)O)cc4O3)cc2CN2CCCC2(C)C)c(F)cn1] | 572.7 | 573.3 |
| 147 | 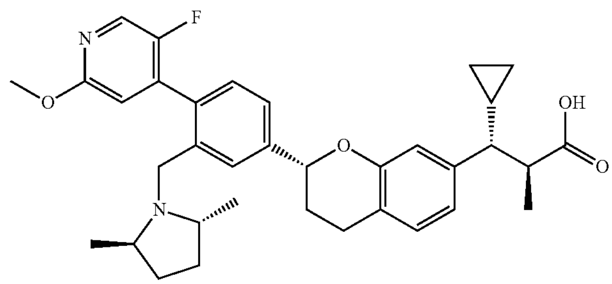 [SMILES: COc1cc(-c2ccc([C@H]3CCc4ccc([C@H](C5CC5)[C@H](C)C(=O)O)cc4O3)cc2CN2[C@H](C)CC[C@H]2C)c(F)cn1] | 572.7 | 573.3 |
| 148 | 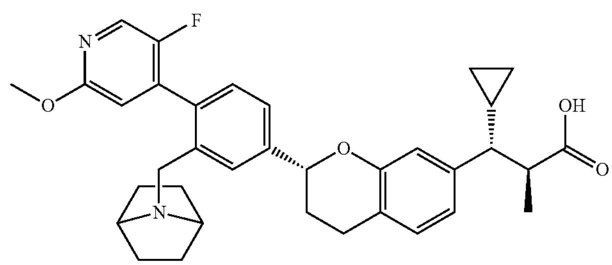 [SMILES: COc1cc(-c2ccc([C@H]3CCc4ccc([C@H](C5CC5)[C@H](C)C(=O)O)cc4O3)cc2CN2C3CCC2CC3)c(F)cn1] | 570.7 | 571.3 |
| 149 | 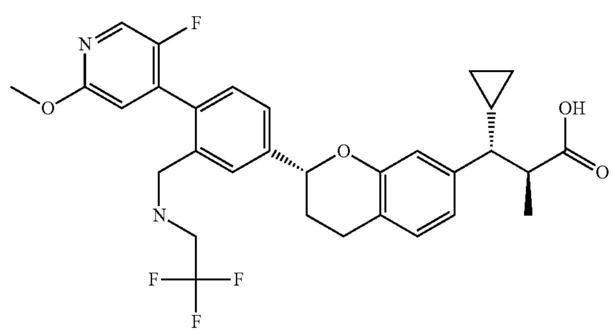 [SMILES: COc1cc(-c2ccc([C@H]3CCc4ccc([C@H](C5CC5)[C@H](C)C(=O)O)cc4O3)cc2CNCC(F)(F)F)c(F)cn1] | 572.6 | 573.2 |
| 150 | 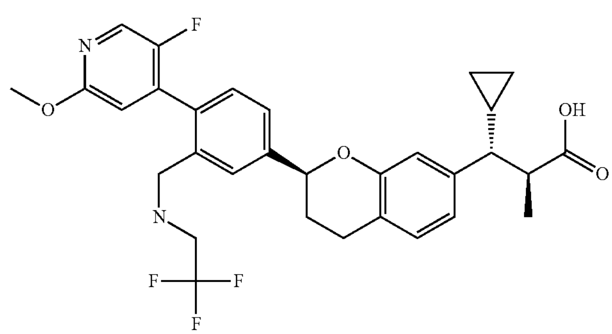 [SMILES: COc1cc(-c2ccc([C@@H]3CCc4ccc([C@H](C5CC5)[C@H](C)C(=O)O)cc4O3)cc2CNCC(F)(F)F)c(F)cn1] | 572.6 | 573.2 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---------|-----------|------|-------------------------------|
| 151 | 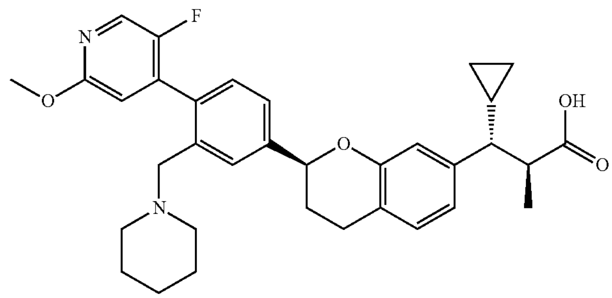 [SMILES: COc1cc(-c2ccc([C@@H]3CCc4ccc([C@H](C5CC5)[C@H](C)C(=O)O)cc4O3)cc2CN2CCCCC2)c(F)cn1] | 558.7 | 559.3 |
| 152 | 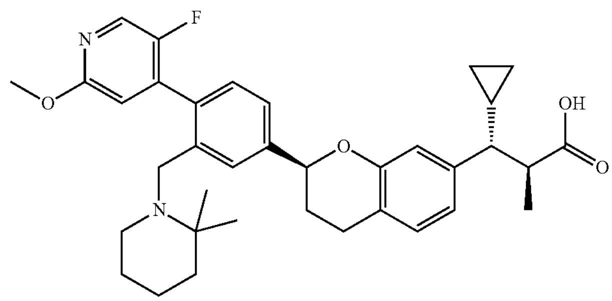 [SMILES: COc1cc(-c2ccc([C@@H]3CCc4ccc([C@H](C5CC5)[C@H](C)C(=O)O)cc4O3)cc2CN2CCCCC2(C)C)c(F)cn1] | 586.7 | 587.3 |
| 153 | 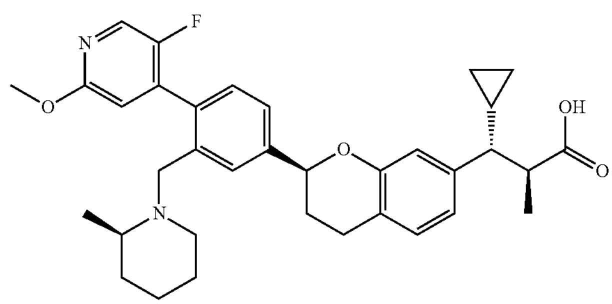 [SMILES: COc1cc(-c2ccc([C@@H]3CCc4ccc([C@H](C5CC5)[C@H](C)C(=O)O)cc4O3)cc2CN2CCCC[C@H]2C)c(F)cn1] | 572.7 | 573.3 |
| 154 | 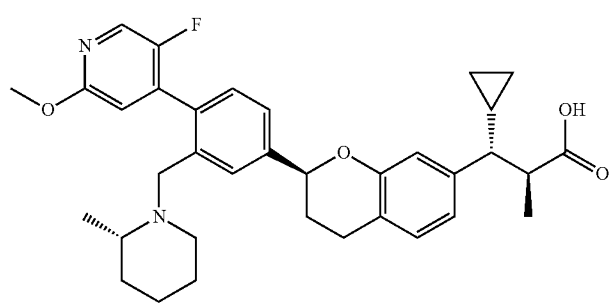 [SMILES: COc1cc(-c2ccc([C@@H]3CCc4ccc([C@H](C5CC5)[C@H](C)C(=O)O)cc4O3)cc2CN2CCCC[C@@H]2C)c(F)cn1] | 572.7 | 573.3 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---|---|---|---|
| 155 | 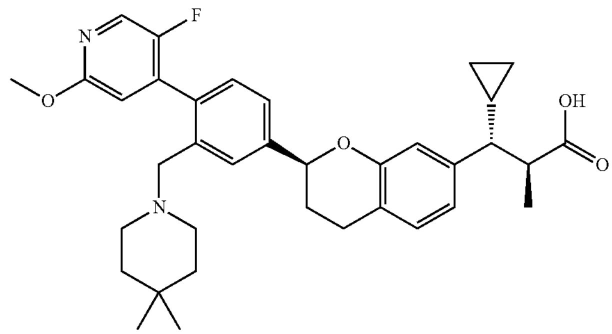 [SMILES: COc1cc(-c2ccc([C@@H]3CCc4ccc([C@H](C5CC5)[C@H](C)C(=O)O)cc4O3)cc2CN2CCC(C)(C)CC2)c(F)cn1] | 586.7 | 587.3 |
| 156 | 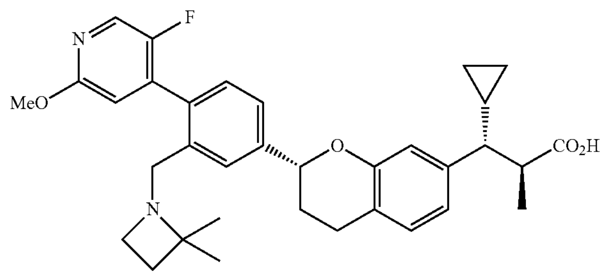 [SMILES: COc1cc(-c2ccc([C@H]3CCc4ccc([C@H](C5CC5)[C@H](C)C(=O)O)cc4O3)cc2CN2CCC2(C)C)c(F)cn1] | 558.7 | 559.3 |
| 157 | 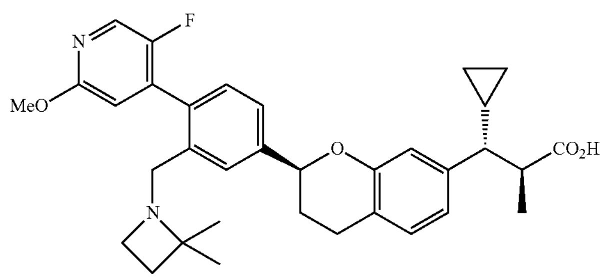 [SMILES: COc1cc(-c2ccc([C@@H]3CCc4ccc([C@H](C5CC5)[C@H](C)C(=O)O)cc4O3)cc2CN2CCC2(C)C)c(F)cn1] | 558.7 | 559.3 |
| 158 | 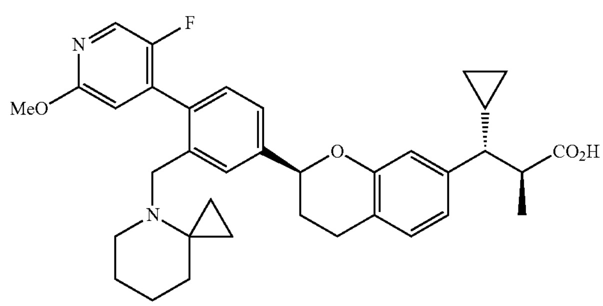 [SMILES: COc1cc(-c2ccc([C@@H]3CCc4ccc([C@H](C5CC5)[C@H](C)C(=O)O)cc4O3)cc2CN2CCCCC23CC3)c(F)cn1] | 457.6 | 458.1 |
| 159 | 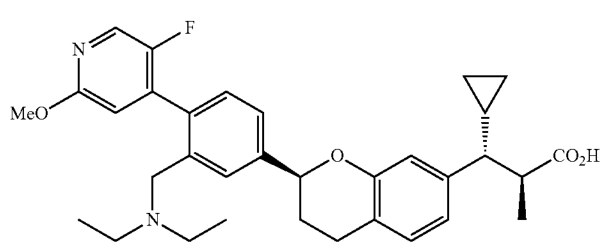 [SMILES: CCN(CC)Cc1cc([C@@H]2CCc3ccc([C@H](C4CC4)[C@H](C)C(=O)O)cc3O2)ccc1-c1cc(OC)ncc1F] | 546.7 | 547.1 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---|---|---|---|
| 160 | 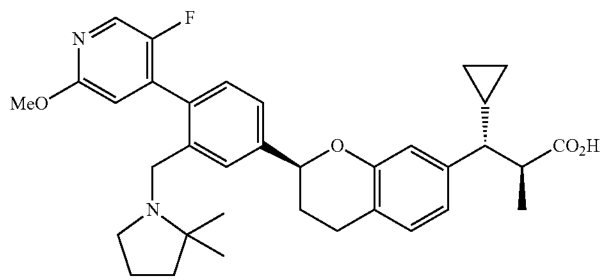 [SMILES: COc1cc(-c2ccc([C@@H]3CCc4ccc([C@H](C5CC5)[C@H](C)C(=O)O)cc4O3)cc2CN2CCCC2(C)C)c(F)cn1] | 572.7 | 573.1 |
| 161 | 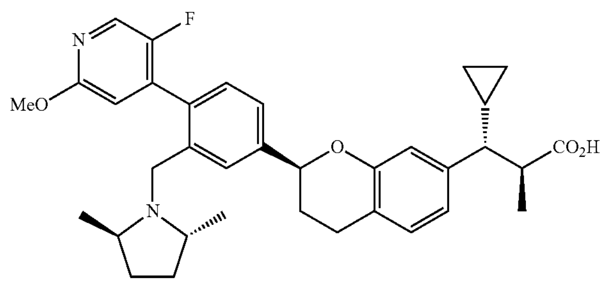 [SMILES: COc1cc(-c2ccc([C@@H]3CCc4ccc([C@H](C5CC5)[C@H](C)C(=O)O)cc4O3)cc2CN2[C@H](C)CC[C@H]2C)c(F)cn1] | 572.7 | 573.3 |
| 162 | 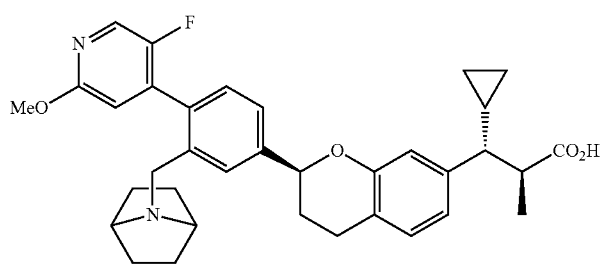 [SMILES: COc1cc(-c2ccc([C@@H]3CCc4ccc([C@H](C5CC5)[C@H](C)C(=O)O)cc4O3)cc2CN2C3CCC2CC3)c(F)cn1] | 570.7 | 571.4 |
| 163 | 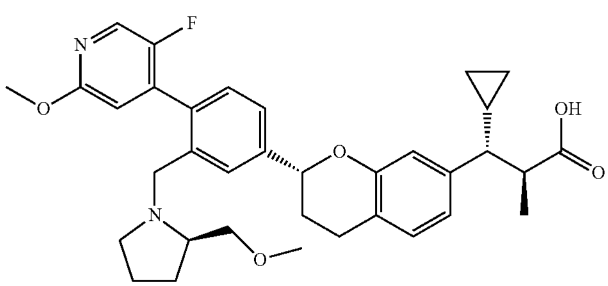 [SMILES: COC[C@H]1CCCN1Cc1cc([C@H]2CCc3ccc([C@H](C4CC4)[C@H](C)C(=O)O)cc3O2)ccc1-c1cc(OC)ncc1F] | 588.7 | 589.3 |
| 164 | 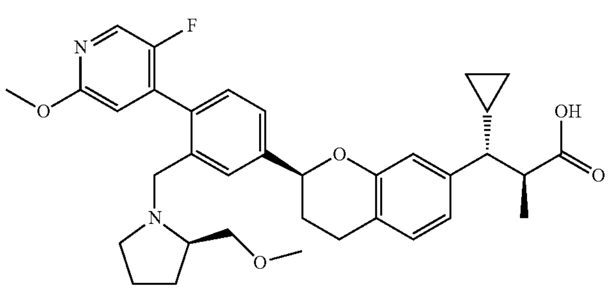 [SMILES: COC[C@H]1CCCN1Cc1cc([C@@H]2CCc3ccc([C@H](C4CC4)[C@H](C)C(=O)O)cc3O2)ccc1-c1cc(OC)ncc1F] | 588.7 | 589.3 |

TABLE 10-continued

Examples 135-170 were prepared in a similar manner to Example 134 using the appropriate intermediates and commercially available starting materials.

| Example | Structure | M.W. | LC/MS (ESI) observed [M + 1]+ |
|---|---|---|---|
| 165 | 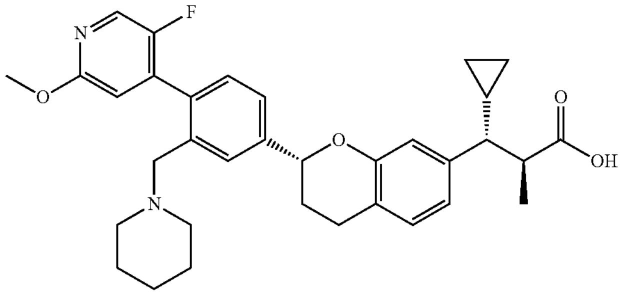 [SMILES: COc1cc(-c2ccc([C@H]3CCc4ccc([C@H](C5CC5)[C@H](C)C(=O)O)cc4O3)cc2CN2CCCCC2)c(F)cn1] | 558.7 | 559.3 |
| 166 | 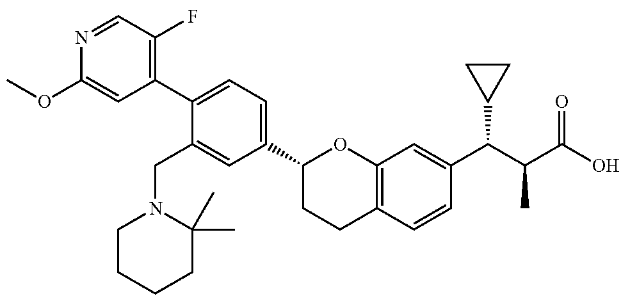 [SMILES: COc1cc(-c2ccc([C@H]3CCc4ccc([C@H](C5CC5)[C@H](C)C(=O)O)cc4O3)cc2CN2CCCCC2(C)C)c(F)cn1] | 586.7 | 587.3 |
| 167 | 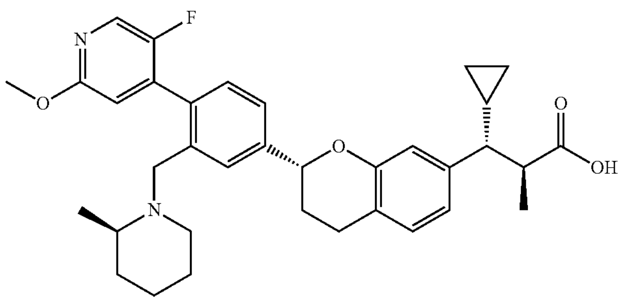 [SMILES: COc1cc(-c2ccc([C@H]3CCc4ccc([C@H](C5CC5)[C@H](C)C(=O)O)cc4O3)cc2CN2CCCC[C@H]2C)c(F)cn1] | 572.7 | 573.3 |
| 168 | 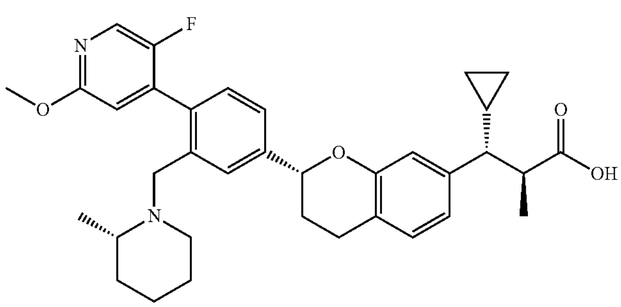 [SMILES: COc1cc(-c2ccc([C@H]3CCc4ccc([C@H](C5CC5)[C@H](C)C(=O)O)cc4O3)cc2CN2CCCC[C@@H]2C)c(F)cn1] | 572.7 | 573.3 |

TABLE 10-continued

Examples 135-170 were prepared in a similar manner to Example 134 using the appropriate intermediates and commercially available starting materials.

| Example | Structure | M.W. | LC/MS (ESI) observed [M + 1]⁺ |
|---|---|---|---|
| 169 | 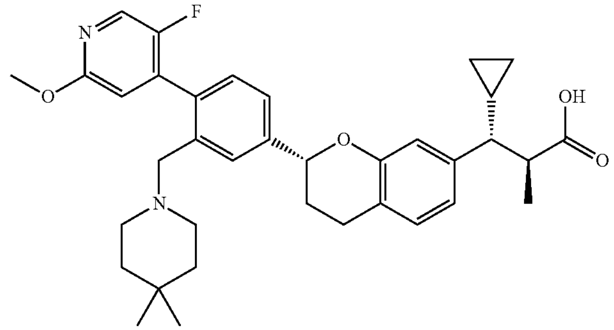 [SMILES: COc1cc(-c2ccc([C@H]3CCc4ccc([C@H](C5CC5)[C@H](C)C(=O)O)cc4O3)cc2CN2CCC(C)(C)CC2)c(F)cn1] | 586.7 | 587.3 |
| 170 | 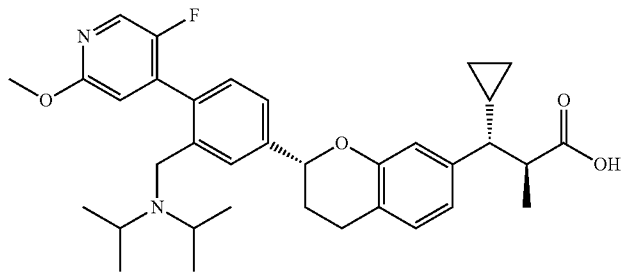 [SMILES: COc1cc(-c2ccc([C@H]3CCc4ccc([C@H](C5CC5)[C@H](C)C(=O)O)cc4O3)cc2CN(C(C)C)C(C)C)c(F)cn1] | 574.7 | 575.4 |

Examples 171 and 172

(2S, 3R)-3-cyclopropyl-3-(2-(3-(diethylamino)methyl)-4-(2-ethoxy-5-fluoropyridin-4-yl)phenyl)chroman-7-yl)-2-methylpropanoic acid

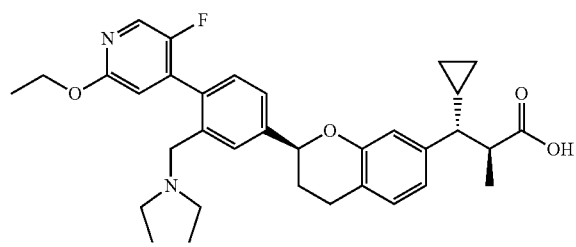 [SMILES: CCOc1cc(-c2ccc([C@@H]3CCc4ccc([C@H](C5CC5)[C@H](C)C(=O)O)cc4O3)cc2CN(CC)CC)c(F)cn1]

Step 1: (2S, 3R)-methyl 3-cyclopropyl-3-(2-(4-(2-ethoxy-5-fluoropyridin-4-yl)-3-formylphenyl)chroman-7-yl)-2-methylpropanoate To a solution of (2S, 3R)-methyl 3-cyclopropyl-3-(2-(3-formyl-4-(tosyloxy)phenyl)chroman-7-yl)-2-methylpropanoate (110 mg, 0.200 mmol) in 1,4-dioxane (2 mL) and Water (0.5 mL) were added chloro(2-dicyclohexylphosphino-2',6'-dimethoxy-1,1'-biphenyl)[2-(2'-amino-1,1'-biphenyl)]palladium(II), (15.0 mg, 0.021 mmol) and (2-ethoxy-5-fluoropyridin-4-yl)boronic acid (74 mg, 0.401 mmol) under nitrogen. The reaction mixture was stirred at 80° C. for 2 h, and then cooled to room temperature. Water (10 mL) was added to the mixture. The aqueous phase was extracted with EtOAc (15 mL×3). The combined organic layers were washed with brine (20 mL), dried over anhydrous Na₂SO₄ and filtered. The filtrate was concentrated under reduced pressure to give a residue, which was purified by prep-TLC (SiO₂, PE/EA=5:1, v/v) to give the title compound. MS (ESI) m/z: 518.3 [M+H]⁺

Step 2: (2S, 3R)-methyl 3-cyclopropyl-3-(2-(3-((diethylamino)methyl)-4-(2-ethoxy-5-fluoropyridin-4-yl)phenyl)chroman-7-yl)-2-methylpropanoate To a solution of (2S, 3R)-methyl 3-cyclopropyl-3-(2-(4-(2-ethoxy-5-fluoropyridin-4-yl)-3-formylphenyl)chroman-7-yl)-2-methylpropanoate (100 mg, 0.193 mmol) and diethylamine (70.6 mg, 0.966 mmol) in MeOH (2.0 mL) was added titanium (IV) isopropoxide (109.7 mg, 0.386 mmol). The resulting mixture was stirred at 80° C. for 1 h, then cooled to 0° C. Sodium borohydride (87.7 mg, 2.32 mmol) was added to the mixture in one portion, and the mixture was stirred at 20° C. for 30 min. The reaction was then quenched by the slow addition of 1N HCl (2 mL). The resulting mixture was extracted with ethyl acetate (15 mL×3). The combined organic layers were washed with brine (10 mL), dried (Na₂SO₄), filtered and the filtrate was evaporated under reduced pressure to give the title compound, which was used in the next step without further purification. MS (ESI) m/z: 575.3 [M+H]⁺

Step 3: (2S, 3R)-3-cyclopropyl-3-((RS)-2-(3-((diethylamino)methyl)-4-(2-ethoxy-5-fluoropyridin-4-yl)phenyl)chroman-7-yl)-2-methylpropanoic acid To a solution of compound (2S, 3R)-methyl 3-cyclopropyl-3-(2-(3-((diethylamino)methyl)-4-(2-ethoxy-5-fluoropyridin-4-yl)phenyl)chroman-7-yl)-2-methylpropanoate (115 mg, 0.193 mmol) in a co-solvent of THF/MeOH/H$_2$O (1 mL/1 mL/1 mL) was added lithium hydroxide (46.3 mg, 1.93 mmol). The reaction mixture was stirred at 50° C. for 40 hours, then acidified with citric acid to pH 5-6 and extracted with ethyl acetate (15 mL×3). The combined organic layers were concentrated in vacuo. The resulting crude product was purified by preparative HPLC (reverse phase C-18 eluting with water and 1% formic acid in CH$_3$CN) to give the title compound. MS (ESI) m/z: 561.3 [M+H]$^+$ Step 4: SFC Separation of (2S, 3R)-3-cyclopropyl-3-((R or S)-2-(3-((diethylamino)methyl)-4-(2-ethoxy-5-fluoropyridin-4-yl)phenyl)chroman-7-yl)-2-methylpropanoic acid The diastereomers at the carbon alpha to the chroman oxygen of (2S, 3R)-3-cyclopropyl-3-(2-(3-((diethylamino)methyl)-4-(2-ethoxy-5-fluoropyridin-4-yl)phenyl)chroman-7-yl)-2-methylpropanoic acid (75 mg, 0.134 mmol) were separated via SFC separation to give: Isomer 1 (faster eluting): (2S, 3R)-3-cyclopropyl-3-((R or S)-2-(3-((diethylamino)methyl)-4-(2-ethoxy-5-fluoropyridin-4-yl)phenyl)chroman-7-yl)-2-methylpropanoic acid; and Isomer 2 (slower eluting): (2S, 3R)-3-cyclopropyl-3-((S or R)-2-(3-((diethylamino)methyl)-4-(2-ethoxy-5-fluoropyridin-4-yl)phenyl)chroman-7-yl)-2-methylpropanoic acid.

Step 5: Formation of the Sodium Salt

To a separate solution of each diastereomer (Isomer 1 or Isomer 2) in MeCN (1.0 mL) and water (1.0 mL) was added an aqueous solution of NaOH (1 eq, 0.5 M). The mixture was stirred for 1 hour at rt, then lyophilized to give the sodium salt of (2S, 3R)-3-cyclopropyl-3-((S or R)-2-(3-((diethylamino)methyl)-4-(2-ethoxy-5-fluoropyridin-4-yl)phenyl)chroman-7-yl)-2-methylpro-panoic acid. EXAMPLE 171 (Isomer 1 faster eluting): MS (ESI) m/z: 561.3 [M+H]$^+$ $^1$H NMR (400 MHz, MeOD): δ=8.07 (s, 1H), 7.75 (s, 1H), 7.54 (d, J=7.6 Hz, 1H), 7.33 (d, J=8.0 Hz, 1H), 7.02 (d, J=8.0 Hz, 1H), 6.77 (d, J=4.8 Hz, 1H), 6.74-6.69 (m, 2H), 5.22-5.14 (m, 1H), 4.35 (q, J=7.2 Hz, 2H), 3.87-3.79 (m, 2H), 3.04-2.96 (m, 1H), 2.82-2.71 (m, 2H), 2.69-2.61 (m, 4H), 2.32-2.25 (m, 1H), 2.13-2.05 (m, 1H), 1.93 (t, J=9.6 Hz, 1H), 1.39 (t, J=7.2 Hz, 3H), 1.15-1.08 (m, 1H), 0.96 (t, J=7.2 Hz, 6H), 0.91 (m, 3H), 0.64-0.53 (m, 1H), 0.42-0.34 (m, 1H), 0.33-0.21 (m, 1H), 0.04-0.09 (m, 1H); EXAMPLE 172 (Isomer 2, slower eluting): MS (ESI) m/z: 561.3 [M+H]$^+$ $^1$H NMR (400 MHz, MeOD): δ=8.06 (s, 1H), 7.74 (s, 1H), 7.53 (d, J=8.0 Hz, 1H), 7.32 (d, J=7.6 Hz, 1H), 7.02 (d, J=7.6 Hz, 1H), 6.76 (d, J=4.8 Hz, 1H), 6.74-6.68 (m, 2H), 5.17 (d, J=8.8 Hz, 1H), 4.35 (q, J=7.2 Hz, 2H), 3.80 (s, 2H), 3.04-2.96 (m, 1H), 2.82-2.70 (m, 2H), 2.62 (q, J=7.2 Hz, 4H), 2.33-2.25 (m, 1H), 2.12-2.03 (m, 1H), 1.96-1.88 (m, 1H), 1.39 (t, J=7.2 Hz, 3H), 1.13-1.06 (m, 1H), 0.96 (t, J=7.2 Hz, 6H), 0.91 (d, J=6.8 Hz, 3H), 0.63-0.54 (m, 1H), 0.43-0.33 (m, 1H), 0.33-0.23 (m, 1H), 0.08-0.03 (m, 1H)

TABLE 11

Examples 173 and 174 were prepared in a similar manner to Examples 171 and 172 using the appropriate intermediates and commercially available starting materials.

| Example | Structure | M.W. | LC/MS (ESI) observed [M + 1]$^+$ |
|---|---|---|---|
| 173 | 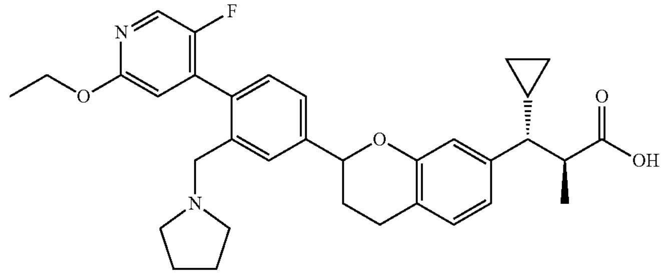 [SMILES: CCOc1cc(-c2ccc(C3CCc4ccc([C@H](C5CC5)[C@H](C)C(=O)O)cc4O3)cc2CN2CCCC2)c(F)cn1] | 558.3 | 559.3 |
| 174 | 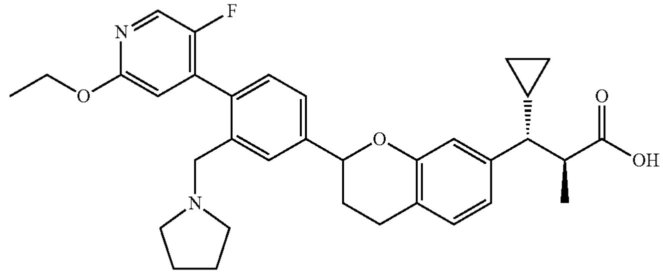 [SMILES: CCOc1cc(-c2ccc(C3CCc4ccc([C@H](C5CC5)[C@H](C)C(=O)O)cc4O3)cc2CN2CCCC2)c(F)cn1] | 558.3 | 559.3 |

Example 175

(2S, 3R)-3-cyclopropyl-3-(2-(4-(2-methoxypyridin-4-yl)-5-fluoro)-3-(pyrrolidin-1-ylmethyl)phenyl)-chroman-7-yl)-2-methylpropanoic acid

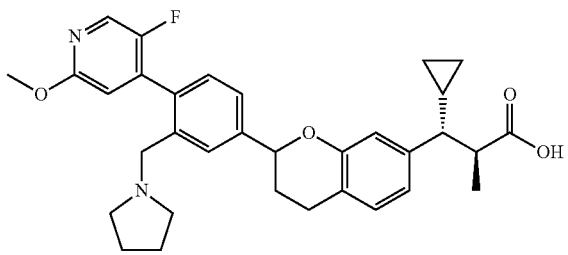 [SMILES: COc1cc(-c2ccc(C3CCc4ccc([C@H](C5CC5)[C@H](C)C(=O)O)cc4O3)cc2CN2CCCC2)c(F)cn1]

Step 1:
4-((tert-butyldimethylsilyl)oxy)benzaldehyde

TBSCl (7.41 g, 49.1 mmol) was added portionwise to a stirred, cooled 0° C. mixture of 4-hydroxybenzaldehyde (5.00 g, 40.9 mmol) and imidazole (5.57 g, 82.0 mmol) in DMF (50 mL). The resulting mixture was stirred at 0° C. for 1 hour and then warmed to 25° C. for another 12 hours. The mixture was then cooled, and water (100 mL) was added. The resulting mixture was extracted with EtOAc (100 mL×3). The combined organic layers were washed with water (100 mL×3), dried (Na$_2$SO$_4$), filtered and the filtrate was evaporated under reduced pressure. The resulting residue was purified by column chromatography on silica gel (eluting with PE/EtOAc (v/v)=100:1-50:1) to give the title compound. MS (ESI) m/z: 237.2[M+H]$^+$ Step 2: 1-(4-((tert-butyldimethylsilyl)oxy)phenyl)prop-2-en-1-ol Vinylmagnesium bromide (68.5 ml, 68.5 mmol) was added dropwise over 20 min to a stirred, cooled 0° C. solution of 4-((tert-butyldimethylsilyl)oxy)benzaldehyde (8.10 g, 34.3 mmol) in THF (90 mL) under nitrogen atmosphere. The resulting mixture was stirred at 0° C. for 40 minutes, then cooled, and aqueous ammonium chloride (saturated, 100 mL) was added. The resulting mixture was extracted with ethyl acetate (100 mL×3). The combined organic fractions were washed with brine (saturated, 200 mL), dried (Na$_2$SO$_4$), filtered and the filtrate was evaporated under reduced pressure to give the title compound, which was used in the next step without further purification. MS (ESI) m/z: 247.1 [M–OH]$^+$ Step 3: (2S, 3R)-methyl 3-cyclopropyl-3-(3-hydroxy-4-(3-(4-hydroxyphenyl)-3-oxopropyl) phenyl)-2-methylpropanoate To a mixture of lithium acetate (3.50 g, 53.0 mmol), 1-(4-((tert-butyldimethylsilyl)oxy) phenyl)prop-2-en-1-ol (9.10 g, 26.5 mmol), (2S, 3R) methyl 3-cyclopropyl-3-(3-hydroxy-4-iodophenyl)-2-methylpropanoate (8.59 g, 23.9 mmol), tetra-n-butylammonium chloride (4.42 g, 15.9 mmol) and lithium chloride (2.25 g, 53.0 mmol) in DMF (90 mL) was added PdOAc$_2$ (0.595 g, 2.65 mmol) under a N$_2$ atmosphere. The resulting mixture was heated to 80° C. for 2 h, then cooled to room temperature, poured into water (100 mL), and extracted with ethyl acetate (100 mL×3). The combined organic layers were washed with water (100 mL×3), brine (200 mL), dried (Na$_2$SO$_4$) and concentrated in vacuo. The resulting crude product was purified by silica gel column chromatography (petroleum ether:EtOAc=10:1 to petroleum ether:EtOAc=2:1) to give the title compound.

Step 4: (2S, 3R)-methyl 3-cyclopropyl-3-(3-hydroxy-4-(3-hydroxy-3-(4-hydroxyphenyl) propyl) phenyl)-2-methylpropanoate NaBH$_4$ (1.37 g, 36.1 mmol) was added to a stirred, cooled 0° C. mixture of (2S, 3R)-methyl 3-cyclopropyl-3-(3-hydroxy-4-(3-(4-hydroxyphenyl)-3-oxopropyl)phenyl)-2-methylpropanoate (6.90 g, 18.0 mmol) and THF (70 mL). The resulting mixture was stirred at 0° C. for 1 h, then warmed to 25° C. for 12 h. The mixture was then poured into water (100 mL), and extracted with ethyl acetate (100 mL×3). The combined organic layers were washed with water (100 mL×3), brine (200 mL), dried (Na$_2$SO$_4$) and concentrated in vacuo to afford the title compound, which was used in the next step without purification. MS (ESI) m/z: 407.3 [M+Na]$^+$ Step 5: (2S, 3R)-methyl 3-cyclopropyl-3-(2-(4-hydroxyphenyl)chroman-7-yl)-2-methylpropanoate DIAD (5.31 ml, 27.3 mmol) was added dropwise to a solution of (2S, 3R)-methyl 3-cyclopropyl-3-(3-hydroxy-4-(3-hydroxy-3-(4-hydroxyphenyl)propyl)phenyl)-2-methylpropanoate (7.00 g, 18.2 mmol) and triphenylphosphine (7.16 g, 27.3 mmol) in DCM (90 mL) in an ice bath. The resulting mixture was stirred at 0° C. for 1 h, then warmed to 25° C. and stirred for 12 h. The mixture was then concentrated in vacuo to give a residue, which was purified by silica gel column chromatography (petroleum ether: EtOAc=30:1 to petroleum ether:EtOAc=4:1, v/v) to give the title compound. MS (ESI) m/z: 367.1 [M+H]$^+$ Step 6: (2S, 3R)-methyl 3-cyclopropyl-3-(2-(3-formyl-4-hydroxyphenyl)chroman-7-yl)-2-methylpropanoate A mixture of (2S, 3R)-methyl 3-cyclopropyl-3-(2-(4-hydroxyphenyl)-chroman-7-yl)-2-methylpropanoate (6.00 g, 16.4 mmol), magnesium chloride (9.35 g, 98.0 mmol), TEA (31.9 ml, 229 mmol) and paraformaldehyde (9.83 g, 327 mmol) in MeCN (70 mL) was heated to reflux (90° C.) for 5 h. The mixture was then cooled, and 1N HCl (35 mL) was added. The mixture was then stirred at rt for 30 min, and extracted with EtOAc (100 mL×2). The combined organic layers were washed with brine (saturated, 200 mL), dried (Na$_2$SO$_4$), filtered and the filtrate was evaporated under reduced pressure. The resulting residue was purified by flash silica gel chromatography (PE:EtOAc=20:1 to PE:EtOAc=10:1, v/v) to give the title compound. MS (ESI) m/z: 417.0 [M+Na]$^+$ Step 7: (2S, 3R)-methyl 3-cyclopropyl-3-(2-(3-formyl-4-(tosyloxy)phenyl)chroman-7-yl)-2-methylpropanoate To a solution of (2S, 3R)-methyl 3-cyclopropyl-3-(2-(3-formyl-4-hydroxyphenyl)chroman-7-yl)-2-methylpropanoate (2.60 g, 6.59 mmol) in DCM (30 mL) was added TEA (2.76 ml, 19.8 mmol) and TsCl (1.51 g, 7.91 mmol). The reaction was stirred at 25° C. for 1 h, then poured into water (100 mL), and extracted with DCM (100 mL×2). The combined organic layers were washed with brine (saturated, 200 mL), dried ($Na_2SO_4$), filtered and the filtrate was evaporated under reduced pressure. The resulting crude residue was purified by column chromatography ($SiO_2$, PE:EtOAc=30:1 to PE:EtOAc=6:1, v/v) to give the title compound. MS (ESI) m/z: 549.2[M+H]$^+$ Step 8: (2S, 3R)-methyl 3-cyclopropyl-3-(2-(3-formyl-4-(2-methoxypyridin-4-yl)phenyl) chroman-7-yl)-2-methylpropanoate To a solution of (2S, 3R)-methyl 3-cyclopropyl-3-(2-(3-formyl-4-(tosyloxy)phenyl) chroman-7-yl)-2-methylpropanoate (500 mg, 0.911 mmol) in 1, 4-dioxane (10 mL) and water (2.5 mL) were added potassium phosphate tribasic (580 mg, 2.73 mmol), 2nd Generation SPhos precatalyst (32.8 mg, 0.046 mmol) and (2-methoxypyridin-4-yl)boronic acid (279 mg, 1.82 mmol) under nitrogen. The reaction mixture was stirred at 80° C. for 2 h, then poured into water (50 mL), extracted with EtOAc (50 mL×2). The combined organic layers were washed with brine (saturated, 50 mL), dried ($Na_2SO_4$), filtered and the filtrate was evaporated under reduced pressure. The resulting residue was purified by column chromatography ($SiO_2$, PE:EtOAc=30:1 to PE:EtOAc=6:1, v/v) to give the title compound. MS (ESI) m/z: 486.3[M+H]$^+$ Step 9: (2S, 3R)-methyl 3-cyclopropyl-3-(2-(4-(2-methoxypyridin-4-yl)-3-(pyrrolidin-1-ylmethyl)phenyl)chroman-7-yl)-2-methylpropanoate To a solution of (2S, 3R)-methyl 3-cyclopropyl-3-(2-(3-formyl-4-(2-methoxypyridin-4-yl) phenyl)chroman-7-yl)-2-methylpropanoate (200 mg, 0.412 mmol) in MeOH (10 mL) were added pyrrolidine (0.068 ml, 0.824 mmol) and titanium (IV) isopropoxide (0.241 ml, 0.824 mmol) under nitrogen. The reaction mixture was stirred at 80° C. for 1 h, then cooled to 0° C. Sodium borohydride (187 mg, 4.94 mmol) was added to the reaction in one portion, and the resulting mixture was stirred at 25° C. for 30 min. The reaction was then quenched by the slow addition of 1N HCl (15 mL), and the mixture was extracted with EtOAc (20 mL×3). The combined EtOAc layers were washed with sodium bicarbonate (5%, 15 mL×2), dried ($Na_2SO_4$), filtered and the filtrate was evaporated under reduced pressure to give the title compound, which was used in the next step without further purification. MS (ESI) m/z: 541.4[M+H]$^+$ Step 10: (2S, 3R)-3-cyclopropyl-3-((S)-2-(4-(2-methoxypyridin-4-yl)-3-(pyrrolidin-1-ylmethyl) phenyl)chroman-7-yl)-2-methylpropanoic acid To a solution of (2S, 3R)-methyl 3-cyclopropyl-3-(2-(4-(2-methoxypyridin-4-yl)-3-(pyrrolidin-1-ylmethyl)phenyl)chroman-7-yl)-2-methylpropanoate (260 mg, 0.481 mmol) in a co-solvent of water (3 mL), THF (3 mL) and MeOH (3 mL) was added LiOH (115 mg, 4.81 mmol). The reaction mixture was stirred at 50° C. for 16 h, then acidified with aqueous solution of HCl (1 M) to pH=5-6, and extracted with ethyl acetate (10 mL×3). The combined organic layers were concentrated in vacuo. The resulting crude product was purified by preparative HPLC to give the title compound. $^1$H NMR (400 MHz, $CDCl_3$) δ=8.22 (d, J=5.2 Hz, 1H), 7.79 (s, 1H), 7.36 (t, J=7.9 Hz, 1H), 7.22 (dd, J=3.1, 7.7 Hz, 1H), 6.95 (d, J=7.2 Hz, 1H), 6.85-6.75 (m, 2H), 6.74-6.63 (m, 2H), 5.14-5.04 (m, 1H), 4.09-3.84 (m, 5H), 2.97-2.85 (m, 1H), 2.85-2.55 (m, 6H), 2.34-2.12 (m, 2H), 2.08-1.73 (m, 5H), 1.16 (d, J=13.8 Hz, 1H), 0.86 (t, J=7.5 Hz, 3H), 0.58 (s, 1H), 0.45-0.21 (m, 2H), 0.12-0.09 (m, 1H); MS (ESI) m/z: 527.4[M+H]$^+$

TABLE 12

Example 176 was prepared in a similar manner to Example 175 using the appropriate intermediates and commercially available starting material.

| Example | Structure | M.W. | LC/MS (ESI) observed [M + 1]+ |
|---|---|---|---|
| 176 | 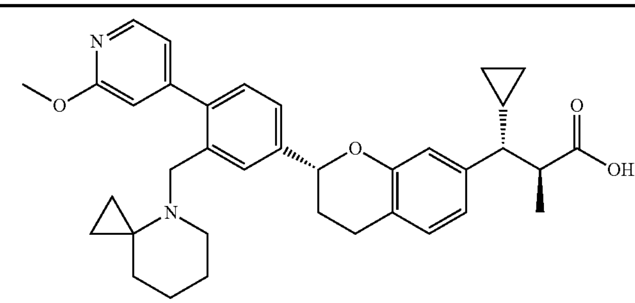 | 566.7 | 567.4 |

Example 177

(2S, 3R)-3-cyclopropyl-3-((R or S)-2-(3-((R or S)-1-methoxy-2-(pyrrolidin-1-yl)ethyl)-4-(2-methoxypyridin-4-yl)phenylchroman-7-yl)-2-methylpropanoic acid

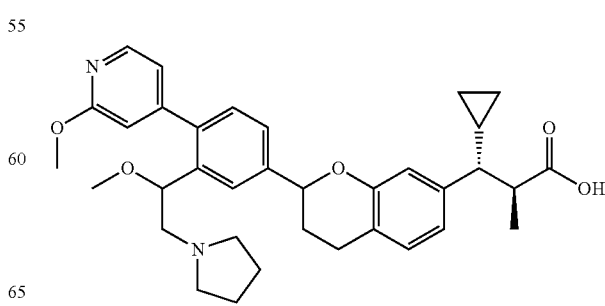

Step 1: (2S, 3R)-methyl 3-cyclopropyl-3-((R or S)-2-(4-(2-methoxypyridin-4-yl)-3-vinylphenyl)chroman-7-yl)-2-methylpropanoate To a solution of potassium trifluoro(vinyl)borate (272 mg, 2.032 mmol) and (2S, 3R)-methyl 3-((R or S)-2-(3-chloro-4-(2-methoxypyridin-4-yl)phenyl)chroman-7-yl)-3-cyclopropyl-2-methylpropanoate (500 mg, 1.02 mmol) in THF (10 mL) and water (2.0 mL) was added potassium phosphate tribasic (647 mg, 3.05 mmol). The mixture was degassed and purged with $N_2$, then 2nd generation Xphos precatalyst (80.0 mg, 0.102 mmol) was added, and the reaction was warmed to 80° C. for 5 h. The reaction was then quenched with water (10 mL) and the aqueous layers were extracted with EtOAc (20 mL×3). The combined organic layers were dried over $Na_2SO_4$ and filtered. The filtrate was concentrated in vacuo and purified by column chromatography (silica gel, PE:EtOAc=3:1, v/v) to give the title compound. MS (ESI) m/z: 484.4[M+H]$^+$

Step 2: (2S, 3R)-methyl 3-cyclopropyl-3-((2R or 2S)-2-(4-(2-methoxypyridin-4-yl)-3-(oxiran-2-yl)phenyl)chroman-7-yl)-2-methylpropanoate To a solution of (2S, 3R)-methyl 3-cyclopropyl-3-((R or S)-2-(4-(2-methoxypyridin-4-yl)-3-vinylphenyl)chroman-7-yl)-2-methylpropanoate (290 mg, 0.600 mmol) in DCM (5.0 mL) was added m-CPBA (345 mg, 1.20 mmol). The mixture was stirred at 25° C. for 5 h, then quenched with saturated $NaHCO_3$ (10 mL) and the aqueous layers were extracted was DCM (10 mL×3). The combined organic layers were washed with saturated $Na_2S_2O_3$ (10 mL), dried over $Na_2SO_4$ and filtered. The filtrate was concentrated in vacuo. The resulting residue was purified by column chromatography (silica gel, PE:EtOAc=5:1, v/v) to give the title compound. MS (ESI) m/z: 500.1 [M+H]$^+$

Step 3: (2S, 3R)-methyl 3-cyclopropyl-3-((2R or 2S)-2-(3-(2-hydroxy-1-methoxyethyl)-4-(2-methoxypyridin-4-yl)phenyl)chroman-7-yl)-2-methylpropanoate To a solution of (2S, 3R)-methyl 3-cyclopropyl-3-((2R or 2S)-2-(4-(2-methoxypyridin-4-yl)-3-(oxiran-2-yl)phenyl)chroman-7-yl)-2-methylpropanoate (150 mg, 0.300 mmol) in MeOH (2 mL) was added TsOH (5.71 mg, 0.0300 mmol). The mixture was stirred at 80° C. for 5 h, then concentrated in vacuo. The resulting crude residue was diluted with saturated $NaHCO_3$ (5 mL) and DCM (20 mL). The mixture was extracted with DCM (15 mL×2), dried over $Na_2SO_4$ and filtered. The filtrate was concentrated in vacuo. The resulting residue, was purified by prep-TLC (silica gel, PE:EtOAc=1:1, v/v) to give the title compound. MS (ESI) m/z: 532.4[M+H]$^+$

Step 4: (2S, 3R)-methyl 3-cyclopropyl-3-((2R or 2S)-2-(3-(1-methoxy-2-((methylsulfonyl)-oxy)ethyl)-4-(2-methoxypyridin-4-yl)phenyl)chroman-7-yl)-2-methylpropanoate To a solution of (2S, 3R)-methyl 3-cyclopropyl-3-((2R or 2S)-2-(3-(2-hydroxy-1-methoxyethyl)-4-(2-methoxy-pyridin-4-yl)phenyl)chroman-7-yl)-2-methylpropanoate (110 mg, 0.207 mmol) and $Et_3N$ (0.087 ml, 0.621 mmol) in DCM (1 mL) was added dropwise Ms-Cl (0.024 mL, 0.310 mmol) at 0° C. The mixture was stirred at 25° C. for 1 h, then concentrated in vacuo to give a residue, which was diluted with saturated $NaHCO_3$ (5 mL) and DCM (20 mL). The mixture was extracted with DCM (15 mL×2), and the combined organic layers were dried over $Na_2SO_4$ and filtered. The filtrate was concentrated in vacuo to give the title compound, which was used in the next step directly. MS(ESI) m/z: 610.1[M+H]$^+$

Step 5: (2S, 3R)-methyl 3-cyclopropyl-3-((2R)-2-(3-(1-methoxy-2-(pyrrolidin-1-yl)ethyl)-4-(2-methoxypyridin-4-yl)phenyl)chroman-7-yl)-2-methylpropanoate To a mixture of the product of Step 4 (126 mg, 0.207 mmol) and pyrrolidine (73.5 mg, 1.03 mmol) in MeCN (3 mL) were added potassium carbonate (171 mg, 1.24 mmol) and sodium iodide (186 mg, 1.24 mmol). The resulting mixture was stirred at 90° C. for 2 h and then allowed to reach rt. The precipitate was filtered off and the filtrate was concentrated in vacuo. The mixture was re-dissolved with ethyl acetate (20 mL). The organic layer was washed with water (6 mL×2), dried ($Na_2SO_4$), filtered and the filtrate was evaporated under reduced pressure to give the title compound, which was used in the next step without further purification. MS (ESI) m/z: 585.3[M+H]$^+$

Step 6: (2S, 3R)-3-cyclopropyl-3-((2R or 2S)-2-(3-(1-methoxy-2-(pyrrolidin-1-yl)ethyl)-4-(2-methoxypyridin-4-yl)phenyl)chroman-7-yl)-2-methylpropanoic acid To a solution of (2S, 3R)-methyl 3-cyclopropyl-3-((2R or 2S)-2-(3-(1-methoxy-2-(pyrrolidin-1-yl)ethyl)-4-(2-methoxypyridin-4-yl)phenyl)chroman-7-yl)-2-methylpropanoate (136 mg, 0.233 mmol) in MeOH (1 mL) and THF (1 mL) and water (1 mL) was added LiOH (55.7 mg, 2.33 mmol). The mixture was stirred at 50° C. for 7 h, then filtered and the filtrate was concentrated to give the title compound, which was used for the next step directly. MS(ESI) m/z: 571.4[M+H]$^+$

Step 7: SFC Separation of (2S, 3R)-3-cyclopropyl-3-((R or S)-2-(3-((R or S)-1-methoxy-2-(pyrrolidin-1-yl)ethyl)-4-(2-methoxypyridin-7-yl)-2-methylpropanoic acid A mixture of 2 diastereomers at the benzylic methoxy carbon of (2S, 3R)-3-cyclopropyl-3-((2R or 2S)-2-(3-(1-methoxy-2-(pyrrolidin-1-yl)ethyl)-4-(2-methoxypyridin-4-yl)phenyl)chroman-7-yl)-2-methylpropanoic acid (60 mg, 0.105 mmol) was separated by SFC (Column: AD (250 mm*30 mm, 5 um); Mobile phase: A: Supercritical $CO_2$, B: MeOH 0.1% $NH_3H_2O$, A:B=45:55 at 60 ml/min; Column Temp: 38° C.; Nozzle Pressure: 100 Bar; Nozzle Temp: 60° C.; Evaporator Temp: 20° C.; Trimmer Temp: 25° C.) to give (2S, 3R)-3-cyclopropyl-3-((R or S)-2-(3-((R or S)-1-methoxy-2-(pyrrolidin-1-yl)ethyl)-4-(2-methoxypyridin-4-yl)phenyl)chroman-7-yl)-2-methylpropanoic acid. Faster Eluting Isomer: MS(ESI) m/z: 571.3[M+H]$^+$ $^1$H NMR (400 MHz, MeOD) δ=8.23 (d, J=5.2 Hz, 1H), 7.71 (s, 1H), 7.54 (d, J=7.6 Hz, 1H), 7.31 (d, J=8.0 Hz, 1H), 7.00-6.92 (m, 2H), 6.79 (s, 1H), 6.71-6.68 (m, 2H), 5.17 (d, J=8.8 Hz, 1H), 4.60 (d, J=8.8 Hz, 1H), 3.97 (s, 3H), 3.45-3.35 (m, 1H), 3.20 (s, 3H), 3.16-2.96 (m, 6H), 2.78 (d, J=16.0 Hz, 1H), 2.65-2.63 (m, 1H), 2.26-2.23 (m, 1H), 2.11-2.01 (m, 1H), 1.99-1.89 (m, 5H), 1.08-1.07 (m, 1H), 0.88 (d, J=6.8 Hz, 3H), 0.56-0.54 (m, 1H), 0.40-0.39 (m, 1H), 0.25-0.24 (m, 1H), 0.06-0.04 (m, 1H)

TABLE 13

Example 178 was prepared in a similar manner to Example 177 using the appropriate intermediates and commercially available starting material.

| Example | Structure | M.W. | LC/MS (ESI) observed [M + H]+ |
|---|---|---|---|
| 178 | | 570.7 | 571.3 | slower eluting isomer

Example 179

(2S, 3R)-3-cyclopropyl-3-((2R)-2-(3-(2-methoxy-1-(pyrrolidin-1-yl)ethyl)-4-(2-methoxypyridin-4-yl)phenyl)chroman-7-yl)-2-methylpropanoic acid

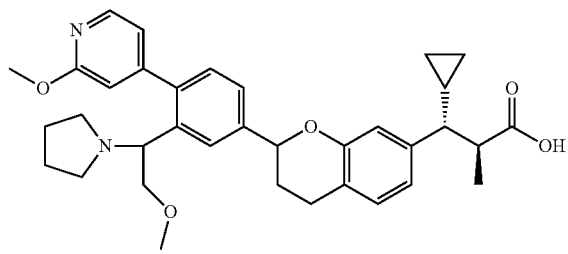 [SMILES: COCC(c1cc(C2CCc3ccc([C@H](C4CC4)[C@H](C)C(=O)O)cc3O2)ccc1-c1ccnc(OC)c1)N1CCCC1]

Step 1: (2S, 3R)-methyl 3-cyclopropyl-3-(2-(4-(2-methoxypyridin-4-yl)-3-(oxiran-2-yl)phenyl)chroman-7-yl)-2-methylpropanoate A dry flask was charged with DMSO (5.0 mL) at 20° C. under a nitrogen atmosphere. The flask was evacuated and backfilled with nitrogen three times. NaH (28.8 mg, 0.721 mmol) was added, followed by THF (5.0 mL) was added. The reaction was cooled to −10° C. in an ice salt bath, and a solution of trimethylsulfonium iodide (147 mg, 0.721 mmol) in DMSO (5 mL) was added dropwise to the reaction over 5 min. THF (5 mL) was added to the reaction, and the reaction was stirred for 3 min. Then a solution of (2S, 3R)-methyl 3-cyclopropyl-3-(2-(3-formyl-4-(2-methoxypyridin-4-yl)phenyl)chroman-7-yl)-2-methylpropanoate (350 mg, 0.721 mmol) in THF (20 mL) was added dropwise over 5 min. The reaction mixture was stirred at −10° C. for 30 min, then quenched with water (10 mL). The reaction mixture was extracted with EtOAc (20 mL×3). The combined organic layers were washed with saturated brine (20 mL), dried over anhydrous Na$_2$SO$_4$ and filtered. The filtrate was concentrated and the resulting residue was purified by prep-TLC (PE:EtOAc=2:1, v/v) to give the title compound. MS (ESI) m/z: 500.3[M+H]+

Step 2: (2S, 3R)-methyl 3-cyclopropyl-3-(2-(3-(1-hydroxy-2-methoxyethyl)-4-(2-methoxypyridin-4-yl)phenyl)chroman-7-yl)-2-methylpropanoate To a solution of (2S, 3R)-methyl 3-cyclopropyl-3-(2-(4-(2-methoxypyridin-4-yl)-3-(oxiran-2-yl)phenyl)chroman-7-yl)-2-methylpropanoate (100 mg, 0.200 mmol) in MeOH (2.0 mL) was added sodium methoxide (21.6 mg, 0.400 mmol). The mixture was stirred at 50° C. for 5.5 h. The mixture was concentrated to give a residue, which was purified by prep-TLC (PE:EtOAc=2:1, v/v) to give the title compound. MS (ESI) m/z: 532.4[M+H]+

Step 3: (2S, 3R)-methyl 3-cyclopropyl-3-(2-(3-(2-methoxy-1-((methylsulfonyl)oxy)ethyl)-4-(2-methoxypyridin-4-yl)phenyl)chroman-7-yl)-2-methylpropanoate To a solution of (2S, 3R)-methyl 3-cyclopropyl-3-(2-(3-(1-hydroxy-2-methoxyethyl)-4-(2-methoxypyridin-4-yl)phenyl)chroman-7-yl)-2-methylpropanoate (40.0 mg, 0.075 mmol) and Et$_3$N (0.0310 mL, 0.226 mmol) in DCM (1.0 mL) was added dropwise MsCl (8.79 µl, 0.113 mmol) at 0° C. The mixture was stirred at 25° C. for 1 h, then concentrated in vacuo to give a residue, which was diluted with saturated NaHCO$_3$ (10 mL) and DCM (20 mL). The resulting mixture was extracted with DCM (15 mL×2), dried over Na$_2$SO$_4$ and filtered. The filtrate was concentrated to give the title compound. MS (ESI) m/z: 610.3[M+H]+

Step 4: (2S, 3R)-methyl 3-cyclopropyl-3-((2R)-2-(3-(2-methoxy-1-(pyrrolidin-1-yl)ethyl)-4-(2-methoxypyridin-4-yl)phenyl)chroman-7-yl)-2-methylpropanoate To a mixture of (2S, 3R)-methyl 3-cyclopropyl-3-((2R)-2-(3-(2-methoxy-1-((methylsulfonyl)oxy)ethyl)-4-(2-methoxypyridin-4-yl)phenyl)chroman-7-yl)-2-methylpropanoate (40.0 mg, 0.066 mmol) and pyrrolidine (23.3 mg, 0.328 mmol) in MeCN (2.0 mL) were added potassium carbonate (54.4 mg, 0.394 mmol) and sodium iodide (59.0 mg, 0.394 mmol). The resulting mixture was stirred at 90° C. for 12 h and then allowed to reach room temperature. The precipitate was filtered off and the filtrate was concentrated.

The resulting mixture was re-dissolved with ethyl acetate (20 mL). The organic layer was washed with water (3.0 mL×3), dried over Na$_2$SO$_4$ and filtered. The filtrate was evaporated under reduced pressure to give the title compound, which was used to next step without further purification. MS (ESI) m/z: 585.4 [M+H]$^+$ Step 5: (2S, 3R)-3-cyclopropyl-3-((2R)-2-(3-(2-methoxy-1-(pyrrolidin-1-yl)ethyl)-4-(2-methoxypyridin-4-yl)phenyl)chroman-7-yl)-2-methylpropanoic acid To a solution of (2S, 3R)-methyl 3-cyclopropyl-3-((2R)-2-(3-(2-methoxy-1-(pyrrolidin-1-yl)ethyl)-4-(2-methoxypyridin-4-yl)phenyl)chroman-7-yl)-2-methylpropanoate (25.0 mg, 0.043 mmol) in MeOH (1 mL) and THF (1 mL) and water (1 mL) was added LiOH (10.2 mg, 0.428 mmol). The mixture was stirred at 50° C. for 7 h, then concentrated to give a residue. The residue was dissolved in water (10 mL) and EtOAc (20 mL). The pH of the resulting mixture was adjusted to pH 6 with solid citric acid. The mixture was extracted with EtOAc (15 mL×3), dried over Na$_2$SO$_4$ and filtered. The filtrate was concentrated to give a residue, which was purified by prep-HPLC (neutral) to give (2S, 3R)-3-cyclopropyl-3-((2R)-2-(3-(2-methoxy-1-(pyrrolidin-1-yl)ethyl)-4-(2-methoxypyridin-4-yl)phenyl)chroman-7-yl)-2-methylpropanoic acid. MS (ESI) m/z: 571.4[M+H]$^+$ 1H NMR (400 MHz, CDCl$_3$) δ=8.19 (d, J=4.8 Hz, 1H), 7.79~7.5 (m, 1H), 7.35 (s, 1H), 7.18 (d, J=7.4 Hz, 1H), 6.99-6.91 (m, 1H), 6.91-6.58 (m, 4H), 5.14-5.03 (m, 1H), 4.00 (s, 3H), 3.84-3.67 (m, 2H), 3.42 (s., 1H), 3.36-3.13 (m, 3H), 2.97-2.39 (m, 7H), 2.32-1.85 (m, 4H), 1.73 (s, 3H), 1.24-1.09 (m, 1H), 1.06-0.80 (m, 3H), 0.59 (s, 1H), 0.35 (d, J=4.2 Hz, 2H), 0.07-0.06 (m, 1H).

Example 180

1RS, (2S, 3R)-3-cyclopropyl-3-(2-(2-fluoro-4-(2-methoxypyridin-4-yl)-5-(pyrrolidin-1-ylmethyl)phenyl)chroman-7-yl)-2-methylpropanoic acid

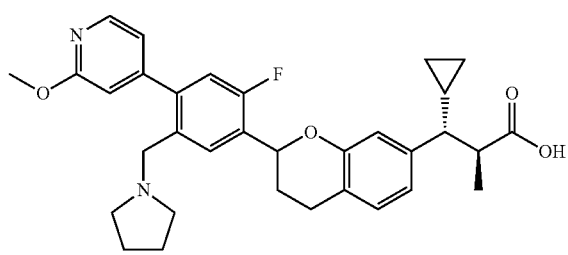 [SMILES: COc1cc(-c2cc(F)c(C3CCc4ccc([C@H](C5CC5)[C@H](C)C(=O)O)cc4O3)cc2CN2CCCC2)ccn1]

Step 1: 4-((tert-butyldimethylsilyl)oxy)-2-fluorobenzaldehyde

To a solution of 2-fluoro-4-hydroxybenzaldehyde (8.50 g, 60.7 mmol) in DCM (130 mL) was added 1H-imidazole (8.26 g, 121 mmol) and tert-butylchlorodimethylsilane (18.3 g, 121 mmol) in portions at 0° C. The mixture was stirred for 10 min at 0° C., then at 25° C. for 16 h. The reaction mixture was then diluted with water (100 mL) and extracted with DCM (100 ml×2). The combined organic layers were washed with brine (100 mL), dried over Na$_2$SO$_4$, filtered and concentrated under reduced pressure to afford crude product, which was purified by column chromatography (SiO$_2$, PE/EtOAc=100:1, v/v) to give the title compound. MS (ESI) m/z: 255.2[M+H]$^+$ Step 2: 1-(4-(((tert-butyldimethylsilyl)oxy)-2-fluorophenyl)prop-2-en-1-ol To a solution of 4-((tert-butyldimethylsilyl)oxy)-2-fluorobenzaldehyde (13.0 g, 51.1 mmol) in THF (150 mL) was added vinylmagnesium bromide (92.0 mL, 92.0 mmol) dropwise at 0° C. under a N$_2$ atmosphere. The mixture was stirred for 1 h at 0° C., then quenched with saturated aqueous NH$_4$Cl (50 mL) and extracted with EtOAc (200 mL×2). The combined organic layers were washed with brine (200 mL), dried over Na$_2$SO$_4$, filtered and concentrated under reduced pressure to give the title compound. MS (ESI) m/z: 265.1 [M-OH]$^+$ Step 3: (2S, 3R)-methyl 3-cyclopropyl-3-(4-(3-(2-fluoro-4-hydroxyphenyl-3-oxopropyl)-3-hydroxyphenyl-2-methylpropanoate To a solution of (2S, 3R)-methyl 3-cyclopropyl-3-(3-hydroxy-4-iodophenyl)-2-methylpropanoate (10.0 g, 27.8 mmol) in DMF (200 mL) were added tetra-butylammonium chloride (7.72 g, 27.8 mmol), lithium acetate (5.50 g, 83.0 mmol), lithium chloride (3.53 g, 83.0 mmol), diacetoxypalladium (0.623 g, 2.78 mmol) and 1-(4-((tert-butyl-dimethylsilyl)oxy)-2-fluorophenyl)prop-2-en-1-ol (11.8 g, 41.6 mmol). The mixture was stirred for 2 h at 80° C. under a N$_2$ atmosphere, then diluted with water (400 mL) and extracted with EtOAc (300 mL×3). The combined organic layers were washed with brine (200 mL), dried over Na$_2$SO$_4$, filtered and concentrated under reduced pressure to afford the crude product, which was purified by column chromatography (SiO$_2$, PE:EtOAc=20:1 to 5:1, v/v) to give the title compound. MS (ESI) m/z: 423.2 [M+Na]$^+$ Step 4: (2S, 3R)-methyl 3-cyclopropyl-3-(4-(3-(2-fluoro-4-hydroxyphenyl)-3-hydroxypropyl)-3-hydroxyphenyl)-2-methylpropanoate To a solution of (2S, 3R)-methyl 3-cyclopropyl-3-(4-(3-(2-fluoro-4-hydroxyphenyl)-3-oxopropyl)-3-hydroxyphenyl)-2-methylpropanoate (6.40 g, 16.0 mmol) in MeOH (80 mL) was added NaBH$_4$ (1.81 g, 47.9 mmol) at 25° C. The mixture was stirred for 48 h at 25° C., then quenched with saturated aqueous NH$_4$Cl (10 mL) and extracted with EtOAc (30 mL×3). The combined organic layers were washed with brine (20 mL), dried over Na$_2$SO$_4$, filtered and concentrated under reduced pressure to the title compound. MS (ESI) m/z: 425.2 [M+H]$^+$ Step 5: (2S, 3R)-methyl 3-cyclopropyl-3-(2-(2-fluoro-4-hydroxyphenyl)chroman-7-yl)-2-methylpropanoate To a solution of (2S, 3R)-methyl 3-cyclopropyl-3-(4-(3-(2-fluoro-4-hydroxyphenyl)-3-hydroxypropyl)-3-hydroxyphenyl)-2-methylpropanoate (4.50 g, 11.2 mmol) in DCM (90 mL) were added dropwise at dropwise dropwise triphenylphosphine (4.40 g, 16.8 mmol) and diisopropyl hydrazine-1, 2-dicarboxylate (3.29 ml, 16.8 mmol) at 0° C. The resulting mixture was stirred for 1 h at 0° C. Then the mixture was purified by column chromatography (SiO$_2$, PE:EtOAc=50:1 to 2:1, v/v) to give the crude product, which was purified again by preparative HPLC (MS trigger/Gilson 281/Gilson 215 instrument fitted with YMC-Actus Pro C18 150*30 Sum using Mobile phase A: water (containing 0.1% TFA, v/v), mobile phase B: acetonitrile. Gradient: 43-73% B, 0-1 min; 100% B, 10.1-11.2 min; 10% B, 11.2-12.5 min Flow rate: 25 ml/min) to give the title compound. MS (ESI) m/z: 385.2 [M+H]$^+$

Step 6: (2S, 3R)-methyl 3-cyclopropyl-3-(2-(2-fluoro-5-formyl-4-hydroxyphenyl) chroman-7-yl)-2-methylpropanoate To a solution of (2S, 3R)-methyl 3-cyclopropyl-3-(2-(2-fluoro-4-hydroxyphenyl) chroman-7-yl)-2-methylpropanoate (550 mg, 1.43 mmol) in acetonitrile (30 mL) were added magnesium chloride (1.64 g, 17.2 mmol), triethylamine (4.05 g, 40.1 mmol) and paraformaldehyde (2.23 g, 57.2 mmol). The mixture was stirred for 24 h at 90° C. under a $N_2$ atmosphere, then quenched with saturated aqueous $NH_4Cl$ (10 mL), diluted with water (10 mL) and extracted with EtOAc (10 mL×3). The combined organic layers were washed with brine (10 mL), dried over $Na_2SO_4$, filtered and the filtrate was concentrated under reduced pressure. The resulting crude product was purified by preparative TLC ($SiO_2$, PE:EtOAc=2:1, v/v) to give the title compound. MS (ESI) m/z: 413.2 [M+H]$^+$.

Step 7: (2S, 3R)-methyl 3-cyclopropyl-3-(2-(2-fluoro-5-formyl-4-(tosyloxy)phenyl) chroman-7-yl)-2-methylpropanoate To a solution of (2S, 3R)-methyl 3-cyclopropyl-3-(2-(2-fluoro-5-formyl-4-hydroxyphenyl) chroman-7-yl)-2-methylpropanoate (60.0 mg, 0.145 mmol) in DCM (1 mL) were added $Et_3N$ (0.0410 ml, 0.291 mmol) and 4-methylbenzene-1-sulfonyl chloride (33.3 mg, 0.175 mmol). The mixture was stirred for 1 h at 25° C., then diluted with water (1 mL) and extracted with DCM (1 ml×2). The combined organic layers were washed with brine (2 mL), dried over $Na_2SO_4$, filtered and the filtrate was concentrated under reduced pressure. The resulting crude product was purified by preparative TLC ($SiO_2$, PE:EtOAc=5:1, v/v) to give the title compound. MS (ESI) m/z: 567.3[M+H]+

Step 8: (2S, 3R)-methyl 3-cyclopropyl-3-(2-(2-fluoro-5-formyl-4-(2-methoxypyridin-4-yl)phenyl) chroman-7-yl)-2-methylpropanoate To a solution of (2S, 3R)-methyl 3-cyclopropyl-3-(2-(2-fluoro-5-formyl-4-(tosyloxy)phenyl)chroman-7-yl)-2-methylpropanoate (50.0 mg, 0.0880 mmol) in 1, 4-dioxane (2.0 mL) and water (0.5 mL) were added potassium phosphate tribasic (56.2 mg, 0.265 mmol), 2$^{nd}$ generation SPhos pre catalyst (3.18 mg, 4.41 µmol) and (2-methoxypyridin-4-yl) boronic acid (27.0 mg, 0.176 mmol) under nitrogen. The reaction mixture was stirred at 80° C. for 2 h, then water (5 mL) was added. The aqueous phase was extracted with EtOAc (10 mL×3). The combined organic layers were washed with water (15 mL) and brine (15 mL), dried over anhydrous $MgSO_4$ and filtered. The filtrate was concentrated under reduced pressure. The resulting residue was purified by preparative TLC ($SiO_2$, PE:EtOAc=4:1, v/v) to give the title compound. MS (ESI) m/z: 504.3 [M+H]$^+$

Step 9: (2S, 3R)-methyl 3-cyclopropyl-3-(2-(2-fluoro-4-(2-methoxypyridin-4-yl)-5-(pyrrolidin-1-ylmethyl)phenyl)chroman-7-yl)-2-methylpropanoate To a solution of (2S, 3R)-methyl 3-cyclopropyl-3-(2-(2-fluoro-5-formyl-4-(2-methoxypyridin-4-yl)phenyl)chroman-7-yl)-2-methylpropanoate (30.0 mg, 0.0600 mmol) in MeOH (2.0 mL) were added pyrrolidine (9.85 µl, 0.119 mmol) and titanium (iv) isopropoxide (0.035 mL, 0.119 mmol) under nitrogen. The reaction mixture was stirred at 80° C. for 1 h, then cooled to 0° C. Sodium borohydride (27.0 mg, 0.715 mmol) was added to the mixture in one portion, and the mixture was stirred at 25° C. for 30 min. The reaction was then quenched by the slow addition of 1N HCl (3 mL). The resulting mixture was extracted with EtOAc (3 mL×3). The combined EtOAc layers were washed with sodium bicarbonate (5%, 3 mL×2), dried ($Na_2SO_4$), filtered and the filtrate was evaporated under reduced pressure to give the title compound, which was used to next step without further purification. MS (ESI) m/z: 559.4 [M+H]$^+$

Step 10: 1RS, (2S, 3R)-3-cyclopropyl-3-(2-fluoro-4-(2-methoxypyridin-4-yl)-5-(pyrrolidin-1-ylmethyl) phenyl)chroman-7-yl)-2-methylpropanoic acid (2S, 3R)-methyl3-cyclopropyl-3-(2-(2-fluoro-4-(2-methoxypyridin-4-yl)-5-(pyrrolidin-1-ylmethyl)phenyl) chroman-7-yl)-2-methylpropanoate (30.0 mg, 0.0540 mmol) was dissolved in a mixed solvent of THF (1 mL), MeOH (1 mL) and of water (1 mL). Then lithium hydroxide (12.9 mg, 0.537 mmol) was added, and the reaction was stirred at 50° C. for 12 h. The reaction mixture was acidified with aqueous HCl solution to pH 3 and concentrated. The residue was dissolved in water (10 mL) and EtOAc (20 mL). The mixture was extracted with EtOAc (15 mL×3), dried over $Na_2SO_4$ and filtered. The filtrate was concentrated to give a residue, which was purified by preparative HPLC (GILSON 281 instrument fitted with a Waters xselect C18 150*30 mm*5 um using Mobile phase A: water (containing 0.1% TFA, v/v), mobile phase B: acetonitrile. Gradient: 39-69% B, 0-10 min; 100% B, 10.5-12.5 min; 5% B, 13-15 min) to give 1RS, (2S, 3R)-3-cyclopropyl-3-(2-(2-fluoro-4-(2-methoxypyridin-4-yl)-5-(pyrrolidin-1-ylmethyl) phenyl)chroman-7-yl)-2-methylpropanoic acid. MS (ESI) m/z: 545.4 [M+H]$^+$ $^1$H NMR (400 MHz, CDCl$_3$): δ=8.28 (d, J=5.30 Hz, 1H), 7.97 (t, J=6.40 Hz, 1H), 7.25 (d, J=10.6 Hz, 1H), 7.08 (d, J=7.72 Hz, 1H), 6.99 (d, J=5.06 Hz, 1H), 6.87 (s, 1H), 6.72-6.78 (m, 2H), 5.42 (d, J=10.6 Hz, 1H), 4.45 (s, 2H), 3.98 (s, 3H), 3.40 (s, 2H), 3.01-3.15 (m, 1H), 2.71-2.96 (m, 4H), 2.29-2.39 (m, 1H), 1.85-2.12 (m, 6H), 1.10-1.09 (m, 1H), 0.94 (d, J=6.84 Hz, 3H), 0.56-0.67 (m, 1H), 0.27-0.40 (m, 2H), −0.06-0.08 (m, 1H)

TABLE 14

Examples 181-188 were prepared in a similar manner to Example 180 using the
appropriate intermediates and commercially available starting materials.

| Example | Structure | M.W. | Isomer | LC/MS (ESI) observed [M + 1]+ |
|---------|-----------|------|--------|-------------------------------|
| 181 | 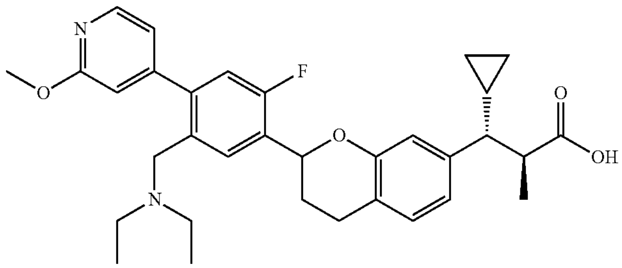 [SMILES: CCN(CC)Cc1cc(C2CCc3ccc([C@H](C4CC4)[C@H](C)C(=O)O)cc3O2)c(F)cc1-c1ccnc(OC)c1] | 546.7 | Isomer A | 548.3 |
| 182 | 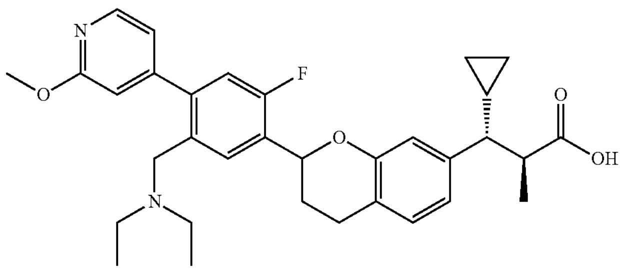 [SMILES: CCN(CC)Cc1cc(C2CCc3ccc([C@H](C4CC4)[C@H](C)C(=O)O)cc3O2)c(F)cc1-c1ccnc(OC)c1] | 546.7 | Isomer B | 548.3 |
| 183 | 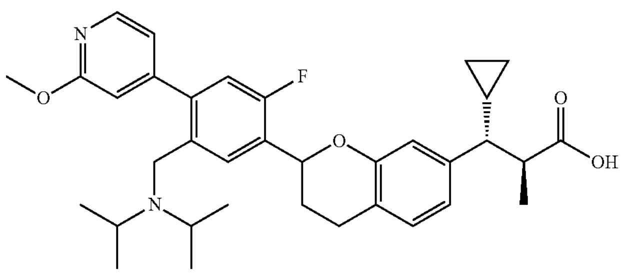 [SMILES: COc1cc(-c2cc(F)c(C3CCc4ccc([C@H](C5CC5)[C@H](C)C(=O)O)cc4O3)cc2CN(C(C)C)C(C)C)ccn1] | 574.7 | Isomer A | 575.4 |
| 184 | 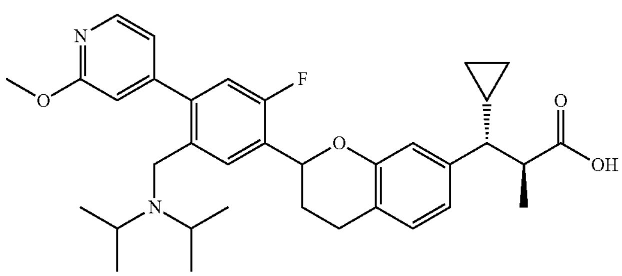 [SMILES: COc1cc(-c2cc(F)c(C3CCc4ccc([C@H](C5CC5)[C@H](C)C(=O)O)cc4O3)cc2CN(C(C)C)C(C)C)ccn1] | 574.7 | Isomer B | 575.4 |
| 185 | 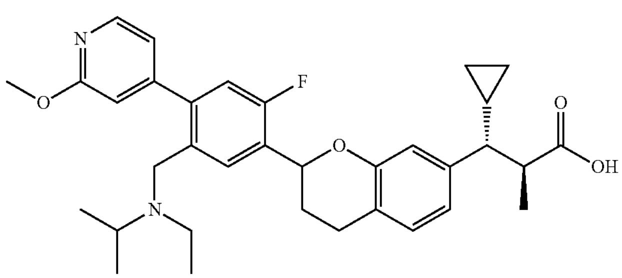 [SMILES: CCN(Cc1cc(C2CCc3ccc([C@H](C4CC4)[C@H](C)C(=O)O)cc3O2)c(F)cc1-c1ccnc(OC)c1)C(C)C] | 560.7 | Isomer A | 561.2 |

TABLE 14-continued

Examples 181-188 were prepared in a similar manner to Example 180 using the appropriate intermediates and commercially available starting materials.

| Example | Structure | M.W. | Isomer | LC/MS (ESI) observed [M + 1]+ |
|---|---|---|---|---|
| 186 | 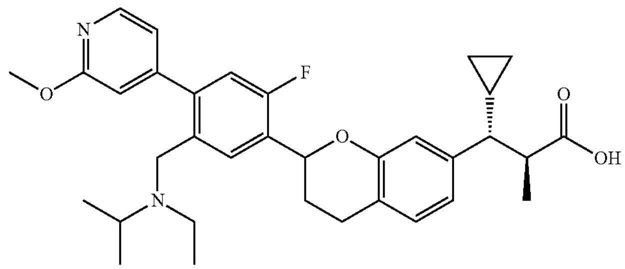 [SMILES: CCN(Cc1cc(C2CCc3ccc([C@H](C4CC4)[C@H](C)C(=O)O)cc3O2)c(F)cc1-c1ccnc(OC)c1)C(C)C] | 560.7 | Isomer B | 561.2 |
| 187 | 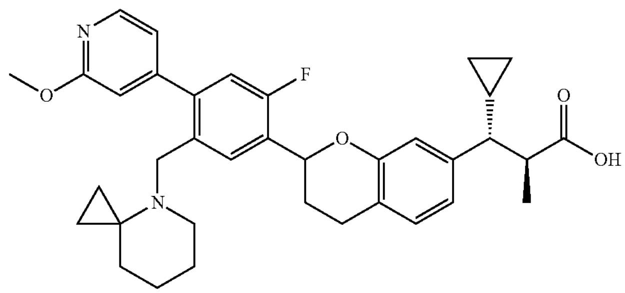 [SMILES: COc1cc(-c2cc(F)c(C3CCc4ccc([C@H](C5CC5)[C@H](C)C(=O)O)cc4O3)cc2CN2CCCCC23CC3)ccn1] | 584.7 | Isomer A | 585.4 |
| 188 | 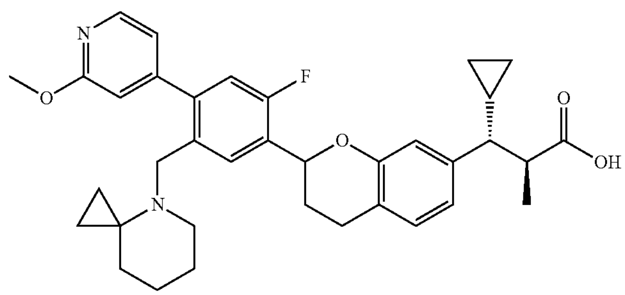 [SMILES: COc1cc(-c2cc(F)c(C3CCc4ccc([C@H](C5CC5)[C@H](C)C(=O)O)cc4O3)cc2CN2CCCCC23CC3)ccn1] | 584.7 | Isomer B | 585.4 |

Example 189

(2S, 3R)-3-((R or S)-2-(3-(4-azaspiro[2.5]octan-4-ylmethyl)-4-(3-fluoro-6-methoxypyridin-2-yl)phenyl)chroman-7-yl-3-cyclopropyl-2-methylpropanoic acid

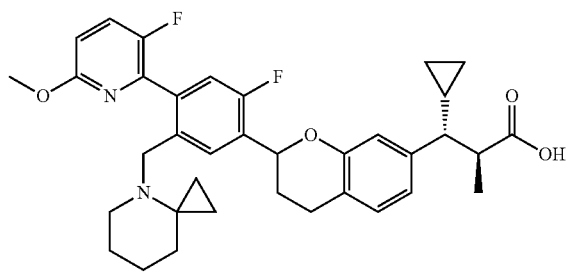 [SMILES: COc1ccc(F)c(-c2cc(F)c(C3CCc4ccc([C@H](C5CC5)[C@H](C)C(=O)O)cc4O3)cc2CN2CCCCC23CC3)n1]

Step 1: 3-cyclopropyl-3-(2-(3-formyl-4-(((trifluoromethyl)sulfonyl)oxy)phenyl)-chroman-7-yl)-2-methylpropanoate To a solution of (2S, 3R)-methyl 3-cyclopropyl-3-(2-(3-formyl-4-hydroxyphenyl)-chroman-7-yl)-2-methylpropanoate (2.10 g, 5.32 mmol) in DCM (20 mL) was successively added Et$_3$N (5.94 ml, 42.6 mmol) and Tf$_2$O (3.60 mL, 21.3 mmol) at 0° C. Then the reaction was warmed to 15° C. After stirring for 2 h at 15° C., saturated aqueous NaHCO$_3$ (50 mL) was added and the reaction mixture was extracted with DCM (50 mL×3). The combined organic extracts were washed with brine (50 mL), dried over Na$_2$SO$_4$, and concentrated in vacuo. The resulting residue was purified by flash column chromatography (silica gel, PE:EtOAc=30:1, v/v) to give the title compound. LCMS: m/z 549.0 [M+Na]$^+$ Step 2: (2S, 3R)-methyl 3-cyclopropyl-3-(2-(3-formyl-4-(4, 4, 5, 5-tetramethyl-1, 3, 2-dioxaborolan-2-yl)phenyl)chroman-7-yl)-2-methylpropanoate To a flask was added bis(pinacolato)diboron (B$_2$Pin$_2$, 4.82 g, 19.0 mmol), (2S, 3R)-methyl 3-cyclopropyl-3-(2-(3- formyl-4-(((trifluoromethyl)sulfonyl)oxy)phenyl)chroman-7-yl)-2-methylpropanoate (2.50 g, 4.75 mmol), [1, 1'-bis(diphenylphosphino)ferrocene]-dichloropalladium(II) (0.347 g, 0.475 mmol) and potassium acetate (3.73 g, 38.0 mmol). The flask was evacuated and refilled with nitrogen three times. Then degassed 1, 4-dioxane (60 mL) was added. The reaction mixture was heated to 100° C. for 2 h, then diluted with 30 mL of brine and extracted with EtOAc (50 mL×3). The combined organic layers were dried over Na$_2$SO$_4$ and filtered. The filtrate was concentrated by rotary evaporation. The resulting residue was purified by flash column chromatography (silica gel, PE:EtOAc=50:1~30:1, v/v) to give the title compound. LCMS: m/z 505.2 [M+H]$^+$ Step 3: (2S, 3R)-methyl 3-cyclopropyl-3-(2-(4-(3-fluoro-6-methoxypyridin-2-yl)-3-formylphenyl)chroman-7-yl)-2-methylpropanoate To a flask was added (2S, 3R)-methyl 3-cyclopropyl-3-(2-(3-formyl-4-(4,4,5,5-tetramethyl-1,3,2-dioxaborolan-2-yl)phenyl)chroman-7-yl)-2-methylpropanoate (380 mg, 0.753 mmol), 2-bromo-3-fluoro-6-methoxypyridine (163 mg, 0.791 mmol), [1,1'-bis(diphenylphosphino)ferrocene]dichloropalladium(II) (27.6 mg, 0.0380 mmol) and K$_2$CO$_3$ (219 mg, 1.58 mmol). Then 1,4-dioxane (8 mL) was added and the flask was evacuated and backfilled with nitrogen three times. The reaction mixture was heated to 80° C. for 2 h, and then concentrated by rotary evaporation. The resulting residue was purified by preparative TLC (silica gel, PE:EtOAc=3:1, v/v) to give the title compound. LCMS: m/z 504.3 [M+Na]$^+$ Step 4: (2S, 3R)-methyl 3-cyclopropyl-3-(2-(4-(3-fluoro-6-methoxypyridin-2-yl)-3-(hydroxymethyl)phenyl)chroman-7-yl)-2-methylpropanoate To a solution of (2S, 3R)-methyl 3-cyclopropyl-3-(2-(4-(3-fluoro-6-methoxypyridin-2-yl)-3-formylphenyl)chroman-7-yl)-2-methylpropanoate (240 mg, 0.477 mmol) in MeOH (1 mL) was added NaBH$_4$ (36.1 mg, 0.953 mmol) under a nitrogen atmosphere at 0° C. The resulting mixture was stirred for 10 min and then warmed to 20° C. After stirring for 1 h, saturated aqueous NH$_4$Cl (10 mL) was added. The resulting mixture was extracted with EtOAc (20 mL×3). The combined organic layers were washed with saturated brine (10 mL), dried over anhydrous Na$_2$SO$_4$ and filtered. The filtrate was concentrated by rotary evaporation to give the title compound, which was used directly in the next step. LCMS: m/z 506.3 [M+H]$^+$ Step 5: (2S, 3R)-methyl 3-(2-(3-(chloromethyl)-4-(3-fluoro-6-methoxypyridin-2-yl)phenyl)chroman-7-yl)-3-cyclopropyl-2-methylpropanoate To a solution of (2S, 3R)-methyl 3-cyclopropyl-3-(2-(4-(3-fluoro-6-methoxypyridin-2-yl)-3-(hydroxymethyl)phenyl)chroman-7-yl)-2-methylpropanoate (185 mg, 0.366 mmol) in DCM (5 mL) at 0° C. was added SOCl$_2$ (80.0 μL, 1.10 mmol) under a nitrogen atmosphere. The reaction was stirred for 1 h at 0° C., then saturated aqueous NaHCO$_3$ solution was added to neutralize the reaction mixture to pH 7. The organic layer was separated. The water layer was extracted with DCM (10 mL×3). The combined organic layers were washed with brine (20 mL), dried over Na$_2$SO$_4$ and filtered. The filtrate was concentrated by rotary evaporation. The resulting residue was purified by preparative TLC (silica gel, PE:EtOAc=3:1, v/v) to give the title compound. LCMS: m/z 524.3 [M+H]$^+$ Step 6: (2S, 3R)-methyl 3-(2-(3-(4-azaspiro[2.5]octan-4-ylmethyl)-4-(3-fluoro-6-methoxypyridin-2-yl)phenyl)chroman-7-yl)-3-cyclopropyl-2-methylpropanoate To a mixture of (2S, 3R)-methyl 3-(2-(3-(chloromethyl)-4-(3-fluoro-6-methoxy-pyridin-2-yl)phenyl)chroman-7-yl)-3-cyclopropyl-2-methylpropanoate (192 mg, 0.366 mmol) and 4-azaspiro[2.5]octane hydrochloride (162 mg, 1.099 mmol) in MeCN (0.5 mL) was added K$_2$CO$_3$ (304 mg, 2.20 mmol) and sodium iodide (330 mg, 2.20 mmol). The resulting mixture was stirred at 80° C. for 1 h and then allowed to cool to room temperature. To the reaction was added 10 mL of water. The mixture was extracted with EtOAc (10 mL×3). The combined organic layers were washed with 10 mL of brine, dried over Na$_2$SO$_4$ and filtered. The filtrate was concentrated. The resulting residue was purified by preparative HPLC (0.1% TFA-MeCN) to give the title compound. LCMS: m/z 599.4 [M+H]$^+$ Step 7: (2S, 3R)-3-(2-(3-(4-azaspiro[2.5]octan-4-ylmethyl)-4-(3-fluoro-6-methoxy-pyridin-2-yl)phenyl)chroman-7-yl)-3-cyclopropyl-2-methylpropanoic acid To a suspension of (2S, 3R)-methyl 3-(2-(3-(4-azaspiro[2.5]octan-4-ylmethyl)-4-(3-fluoro-6-methoxypyridin-2-yl)phenyl)chroman-7-yl)-3-cyclopropyl-2-methylpropanoate (53.0 mg, 89.0 μmol) in MeOH (1 mL), THF (1 mL) and water (1 mL) was added lithium hydroxide monohydrate (55.7 mg, 1.33 mmol). The reaction was heated to 50° C. for 18 h, and then cooled to rt. Concentrated HCl was added to adjust the reaction pH to pH 7, and the reaction mixture was extracted with EtOAc (10 mL×3). The combined organic layers were washed with brine (10 mL), dried over Na$_2$SO$_4$ and filtered. The filtrate was concentrated by rotary evaporation to give (2S,3R)-3-(2-(3-(4-azaspiro[2.5]octan-4-ylmethyl)-4-(3-fluoro-6-methoxypyridin-2-yl)phenyl)chroman-7-yl)-3-cyclopropyl-2-methylpropanoic acid, which was used directly in the next step. LCMS: m/z 585.3 [M+H]$^+$ Step 8: (2S, 3R)-3-((R or S)-2-(3-(4-azaspiro[2.5]octan-4-ylmethyl)-4-(3-fluoro-6-methoxy-pyridin-2-yl)phenyl)chroman-7-yl)-3-cyclopropyl-2-methylpropanoic acid and (2S, 3R)-3-((S or R)-2-(3-(4-azaspiro[2.5]octan-4-ylmethyl)-4-(3-fluoro-6-methoxypyridin-2-yl)phenyl)chroman-7-yl)-3-cyclopropyl-2-methylpropanoic acid A mixture of 2 diastereomers at the carbon alpha to the chroman oxygen (2S, 3R)-3-(2-(3-(4-azaspiro[2.5]octan-4-ylmethyl)-4-(3-fluoro-6-methoxypyridin-2-yl)phenyl)chroman-7-yl)-3-cyclopropyl-2-methylpropanoic acid (52.0 mg, 89.0 μmol) was separated by SFC (Column AD (250 mm*30 mm, 5 μm); Condition Base-EtOH Begin B 20%; End B 20% Gradient Time (min); 100% B Hold Time (min) Flow-Rate (ml/min) 60) to give (2S, 3R)-3-((R or S)-2-(3-(4-azaspiro[2.5]octan-4-ylmethyl)-4-(3-fluoro-6-methoxypyridin-2-yl)phenyl)chroman-7-yl)-3-cyclopropyl-2-methylpropanoic acid, and (2S, 3R)-3-((S or R)-2-(3-(4-azaspiro[2.5]octan-4-ylmethyl)-4-(3-fluoro-6-methoxypyridin-2-yl)phenyl)chroman-7-yl)-3-cyclopropyl-2-methylpropanoic acid.

Step 9: Conversion to Sodium Salt

To a solution of each isomer in acetonitrile (2 ml)/water (1 ml) was added 1 equivalent of 1 M aqueous sodium hydroxide at ambient temperature. The resulting solution was sonicated for 2 minutes, frozen in a dry ice bath, and then lyophilized for 19 h to give the title compound. LCMS: m/z 585.3 [M+H]+ 1H NMR (400 MHz, MeOD): δ=7.64-7.56 (m, 2H), 7.47 (d, J=7.4 Hz, 1H), 7.39 (d, J=7.8 Hz, 1H), 7.01 (d, J=7.4 Hz, 1H), 6.86 (dd, J=2.7, 9.0 Hz, 1H), 6.74-6.67 (m, 2H), 5.15 (d, J=8.2 Hz, 1H), 4.11 (s, 2H), 3.91 (s, 3H), 3.05-2.91 (m, 1H), 2.71 (d, J=5.5 Hz, 4H), 2.32-2.21 (m, 1H), 2.14-2.00 (m, 1H), 1.92 (t, J=10.2 Hz, 1H), 1.67-1.57 (m, 2H), 1.39-1.26 (m, 4H), 1.16-1.04 (m, 1H), 0.91 (d, J=6.7 Hz, 3H), 0.64-0.52 (m, 1H), 0.45-0.24 (m, 6H), 0.04-0.07 (m, 1H).

mmol), 2nd generation XPhos precatalyst (94.0 mg, 0.119 mmol) and tripotassium phosphate (1.26 g, 5.95 mmol). Then 1, 4-dioxane (16 mL) and water (4 mL) were added under a nitrogen atmosphere. The flask was evacuated and backfilled with nitrogen three times. The reaction mixture was heated to 80° C. for 2 h, then cooled to room temperature. EtOAc (30 mL) was added to the reaction mixture. The organic layer was separated, and the water layer was extracted with EtOAc (30 mL×2). The combined organic layers were washed with brine (50 mL), dried over anhydrous $Na_2SO_4$ and filtered. The filtrate was concentrated by rotary evaporation. The resulting residue was purified by flash column chromatography (silica gel, PE:EtOAc=30: 1~10:1, v/v) to give the title compound. LCMS: m/z 511.1 [M+H]+

TABLE 15

Example 190 was prepared in a similar manner to EXAMPLE 189 using the appropriate and commercially available starting materials and intermediates.

| Example | Structure | M.W. | LC/MS (ESI) observed [M + 1]+ |
|---|---|---|---|
| 190 | 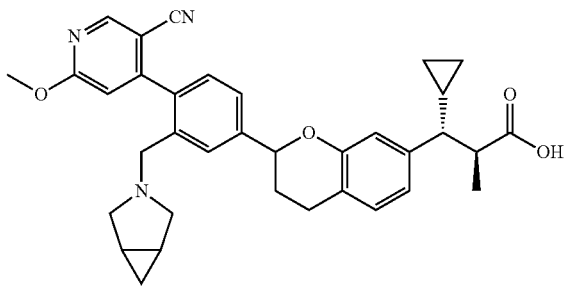 [SMILES: COc1cc(-c2ccc(C3CCc4ccc([C@H](C5CC5)[C@H](C)C(=O)O)cc4O3)cc2CN2CC3CC3C2)c(C#N)cn1] | 584.7 | 585.3 |

Example 191

(2S, 3R)-3-(2-(3-(3-azabicyclo[3.1.0]hexan-3-ylmethyl)-4-(5-cyano-2-methoxypyridin-4-yl)phenyl-chroman-7-yl)-3-cyclopropyl-2-methylpropanoic acid

Step 1: (2S, 3R)-methyl 3-(2-(4-(5-cyano-2-methoxypyridin-4-yl)-3-formylphenyl)-chroman-7-yl)-3-cyclopropyl-2-methylpropanoate To a flask were added 4-chloro-6-methoxynicotinonitrile (0.421 g, 2.50 mmol), (2S, 3R)-methyl 3-cyclopropyl-3-(2-(3-formyl-4-(4, 4, 5, 5-tetramethyl-1, 3, 2-dioxaborolan-2-yl)phenyl)chroman-7-yl)-2-methylpropanoate (1.20 g, 2.38

Step 2: (2S, 3R)-methyl 3-(2-(4-(5-cyano-2-methoxypyridin-4-yl)-3-(hydroxymethyl)-phenyl-chroman-7-yl)-3-cyclopropyl-2-methylpropanoate To a solution of (2S, 3R)-methyl 3-(2-(4-(5-cyano-2-methoxypyridin-4-yl)-3-formyl-phenyl)chroman-7-yl)-3-cyclopropyl-2-methyl-propanoate (680 mg, 1.33 mmol) in MeOH (14 mL) was added $NaBH_4$ (101 mg, 2.66 mmol) under a nitrogen atmosphere at 0° C. The resulting mixture was stirred for 10 min at 0° C., and then warm to 20° C. After stirring for 1 h, saturated aqueous $NH_4Cl$ aqueous solution (10 mL) was added to the reaction. The reaction mixture was extracted with EtOAc (20 mL×3). The combined organic layers were washed with saturated brine (10 mL), dried over anhydrous $Na_2SO_4$ and filtered. The filtrate was concentrated by rotary evaporation to give the title compound, which was used directly in the next step. LCMS: m/z 513.2 [M+H]+

Step 3: (2S, 3R)-methyl 3-(2-(4-(5-cyano-2-methoxypyridin-4-yl)-3-(((methyl-sulfonyl)-oxy)methyl)phenyl)chroman-7-yl)-3-cyclopropyl-2-methylpropanoate To a solution of (2S, 3R)-methyl 3-(2-(4-(5-cyano-2-methoxypyridin-4-yl)-3-(hydroxy-methyl)phenyl)chroman-7-yl)-3-cyclopropyl-2-methylpropanoate (450 mg, 0.878 mmol) in DCM (7 mL) was added $Et_3N$ (0.367 mL, 2.63 mmol) and MsCl (0.103 mL, 1.32 mmol) at 0° C. The reaction was stirred for 1 h, then diluted with 10 mL of water. The organic layer was separated. The water layer was extracted with DCM (10 mL×3). The combined organic layers were washed with brine (10 mL), dried over $Na_2SO_4$ and filtered. The filtrate was concentrated by rotary evaporating to give the title compound, which was used in the next step without further purification. LCMS: m/z 591.1 $[M+H]^+$ Step 4: (2S, 3R)-methyl 3-(2-(3-(3-azabicyclo [3.1.0]hexan-3-ylmethyl)-4-(5-cyano-2-methoxypyridin-4-yl)phenyl)chroman-7-yl)-3-cyclopropyl-2-methylpropanoate To a mixture of (2S, 3R)-methyl 3-(2-(4-(5-cyano-2-methoxypyridin-4-yl)-3-(((methylsulfonyl)oxy)methyl)-phenyl)chroman-7-yl)-3-cyclopropyl-2-methylpropan-oate (150 mg, 0.254 mmol) and 3-azabicyclo[3.1.0]hexane hydrochloride (152 mg, 1.27 mmol) in MeCN (2 mL) were added $K_2CO_3$ (421 mg, 3.05 mmol) and sodium iodide (457 mg, 3.05 mmol). The reaction was stirred at 50° C. for 3 h and then allowed to cool to room temperature. The reaction mixture was then diluted with 20 mL of water, extracted with EtOAc (20 mL×3), dried over $Na_2SO_4$ and filtered. The filtrate was concentrated by rotary evaporation to give the title compound, which was used directly in the next step. LCMS: m/z 578.4 $[M+H]^+$ Step 5: (2S, 3R)-3-(2-(3-(3-azabicyclo[3.1.0]hexan-3-ylmethyl)-4-(5-cyano-2-methoxypyridin-4-yl)phenyl)chroman-7-yl)-3-cyclopropyl-2-methylpropanoic acid To a solution of (2S, 3R)-methyl 3-(2-(3-(3-azabicyclo [3.1.0]hexan-3-ylmethyl)-4-(5-cyano-2-methoxypyridin-4-yl)phenyl)chroman-7-yl)-3-cyclopropyl-2-methylpropano-ate (156 mg, 0.270 mmol) in MeOH (0.5 mL), THF (0.5 mL) and water (0.5 mL) was added lithium hydroxide monohydrate (170 mg, 4.05 mmol). The reaction was heated to 50° C. for 18 h, and then cooled to room temperature. Then concentrated HCl was added to adjust the reaction pH to pH 6. The reaction mixture was filtered, and the filtrate was purified by preparative HPLC (10 mM $NH_4HCO_3$-MeCN) to give (2S, 3R)-3-(2-(3-(3-azabicyclo[3.1.0]-hexan-3-ylm-ethyl)-4-(5-cyano-2-methoxypyridin-4-yl)phenyl)chroman-7-yl)-3-cyclopropyl-2-methylpropanoic acid. LCMS: m/z 564.4 $[M+H]^+$ Step 6: (2S, 3R)-3-((2R or 2S)-2-(3-(3-azabicyclo [3.1.0]hexan-3-ylmethyl)-4-(5-cyano-2-methoxypyridin-4-yl)phenyl)chroman-7-yl)-3-cyclopropyl-2-methylpropanoic acid and (2S, 3R)-3-((2S or 2R)-2-(3-(3-azabicyclo[3.1.0]hexan-3-ylmethyl)-4-(5-cyano-2-methoxypyridin-4-yl)phenyl)chroman-7-yl)-3-cyclopropyl-2-methylpropanoic acid A mixture of 2 diastereomers at the carbon alpha to the chroman oxygen of (2S, 3R)-3-(2-(3-(3-azabicyclo[3.1.0] hexan-3-ylmethyl)-4-(5-cyano-2-methoxypyridin-4-yl)phe-nyl)chroman-7-yl)-3-cyclopropyl-2-methylpropanoic acid (66.0 mg, 0.117 mmol) was separated by SFC (Column: AS (250 mm*30 mm, 10 μm); Conditions: Base-EtOH Begin B 30% End B 30%; Gradient Time (min); 100% B Hold Time (min) FlowRate (ml/min) 70) to give (2S, 3R)-3-((2R or 2S)-2-(3-(3-azabicyclo[3.1.0]-hexan-3-ylmethyl)-4-(5-cyano-2-methoxypyridin-4-yl)phenyl)-chroman-7-yl)-3-cyclopropyl-2-methylpropanoic acid, and (2S, 3R)-3-((2S or 2R)-2-(3-(3-azabicyclo[3.1.0]hexan-3-ylmethyl)-4-(5-cyano-2-methoxypyridin-4-yl)phenyl)chroman-7-yl)-3-cyclopropyl-2-methylpropanoic acid. LCMS: m/z 564.2 $[M+H]^+$ Step 7: Conversion to Sodium Salt To a solution of each isomer in acetonitrile (2 ml)/water (1 ml) was added 1 equivalent of 1 M aqueous sodium hydroxide at ambient temperature. The resulting solution was sonicated for 2 minutes, frozen on a dry ice bath, and then lyophilized for 19 h to give the sodium salt of Example 191. $^1H$ NMR (400 MHz, MeOD): δ=8.60 (s, 1H), 7.53 (s, 1H), 7.48 (d, J=8.2 Hz, 1H), 7.26 (d, J=8.2 Hz, 1H), 7.03 (d, J=7.8 Hz, 1H), 6.89 (s, 1H), 6.74-6.68 (m, 2H), 5.15 (d, J=8.2 Hz, 1H), 4.04 (s, 3H), 3.68-3.52 (m, 2H), 3.06-2.94 (m, 1H), 2.82-2.70 (m, 2H), 2.69-2.60 (m, 2H), 2.32-2.22 (m, 3H), 2.14-2.00 (m, 1H), 1.92 (t, J=9.4 Hz, 1H), 1.33-1.22 (m, 2H), 1.17-1.04 (m, 1H), 0.93 (d, J=7.0 Hz, 3H), 0.64-0.54 (m, 1H), 0.39-0.28 (m, 2H), 0.28-0.20 (m, 2H), 0.05-−0.05 (m, 1H)

TABLE 16

Examples 192-197 were prepared in a similar manner to Example 191 using the appropriate and commercially available intermediates and starting materials.

| Example | Structure | M.W. | Isomer | LC/MS (ESI) observed $[M + 1]^+$ |
|---|---|---|---|---|
| 192 | 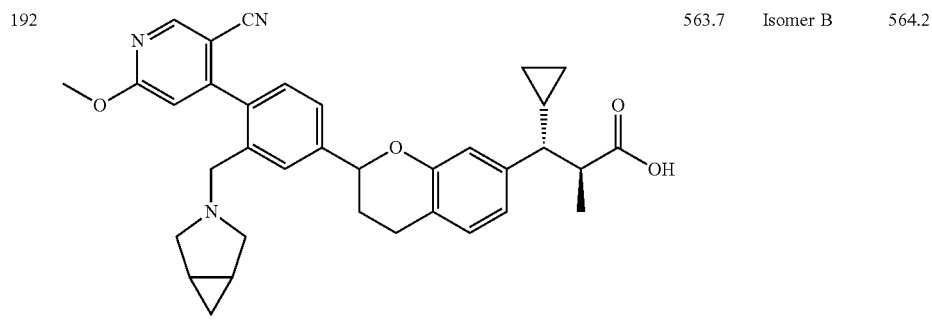 | 563.7 | Isomer B | 564.2 |

TABLE 16-continued

Examples 192-197 were prepared in a similar manner to Example 191 using the appropriate and commercially available intermediates and starting materials.

| Example | Structure | M.W. | Isomer | LC/MS (ESI) observed [M + 1]+ |
|---------|-----------|------|--------|-------------------------------|
| 193 | 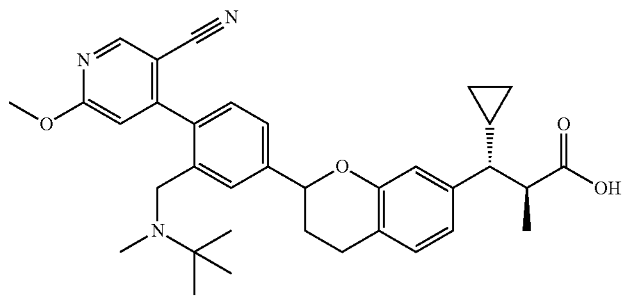 [SMILES: COc1cc(-c2ccc(C3CCc4ccc([C@H](C5CC5)[C@H](C)C(=O)O)cc4O3)cc2CN(C)C(C)(C)C)c(C#N)cn1] | 567.7 | Isomer A | 568.3 |
| 194 | 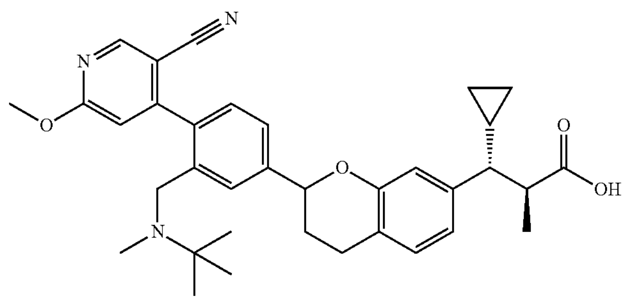 [SMILES: COc1cc(-c2ccc(C3CCc4ccc([C@H](C5CC5)[C@H](C)C(=O)O)cc4O3)cc2CN(C)C(C)(C)C)c(C#N)cn1] | 567.7 | Isomer B | 568.3 |
| 195 | 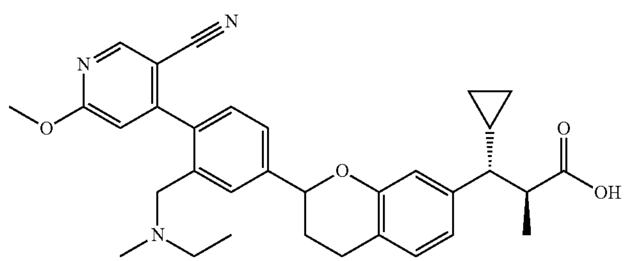 [SMILES: CCN(C)Cc1cc(C2CCc3ccc([C@H](C4CC4)[C@H](C)C(=O)O)cc3O2)ccc1-c1cc(OC)ncc1C#N] | 539.7 | Isomer A | 540.2 |
| 196 | 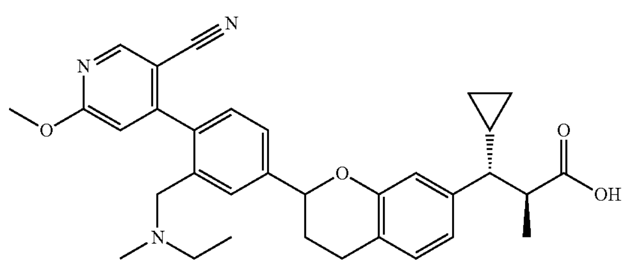 [SMILES: CCN(C)Cc1cc(C2CCc3ccc([C@H](C4CC4)[C@H](C)C(=O)O)cc3O2)ccc1-c1cc(OC)ncc1C#N] | 539.7 | Isomer B | 540.2 |
| 197 | 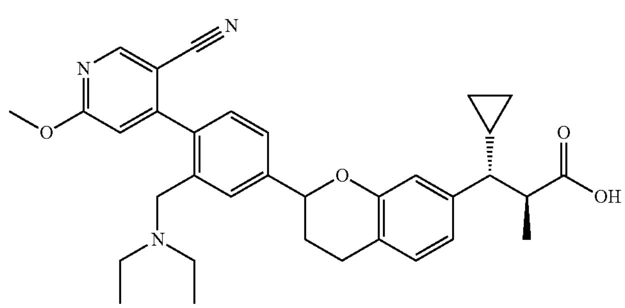 [SMILES: CCN(CC)Cc1cc(C2CCc3ccc([C@H](C4CC4)[C@H](C)C(=O)O)cc3O2)ccc1-c1cc(OC)ncc1C#N] | 553.7 | Mixture of 2 Diastereomers | 554.2 |

Examples 198 and 199

(2S, 3R)-3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoic acid

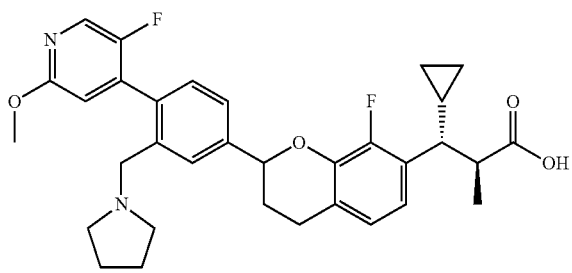 [SMILES: COc1cc(-c2ccc(C3CCc4ccc([C@H](C5CC5)[C@H](C)C(=O)O)c(F)c4O3)cc2CN2CCCC2)c(F)cn1]

Step 1: 4-((tert-butyldimethylsilyl)oxy)benzaldehyde 4-hydroxybenzaldehyde (10.0 g, 82.0 mmol) was dissolved in DCM (150 mL). Then imidazole (6.13 g, 90.0 mmol), TBDMS-Cl (13.6 g, 90.0 mmol), DMAP (1.50 g, 12.3 mmol) were added and the mixture was stirred at 15° C. for 3 h. The reaction mixture was then washed with saturated aqueous NH$_4$Cl (200 mL), and extracted with DCM (150 mL×2). The combined organic layers were washed with brine (200 mL), and dried over anhydrous Na$_2$SO$_4$. The mixture was filtered and the filtrate was concentrated. The resulting crude product was purified via silica gel chromatography (SiO$_2$, eluent of PE:EA=10:1) to give the title compound.

Step 2: 1-(4-((tert-butyldimethylsilyl)oxy)phenyl)prop-2-en-1-ol

Vinylmagnesium bromide (13.2 g, 100 mmol) was added dropwise over 20 minutes to a stirred, 0° C. solution of 4-((tert-butyldimethylsilyl)-oxy)-benzaldehyde (15.8 g, 66.8 mmol) in THF (200 mL). The mixture was stirred at 0° C. for 2 h, then concentrated. Saturated aqueous NH$_4$Cl (150 mL) was added and the mixture was extracted with ethyl acetate (150 mL×3). The combined organic layers were washed with brine (200 mL), dried (Na$_2$SO$_4$), and filtered. The filtrate was evaporated under reduced pressure to give the title compound.

Step 3: (2S, 3R)-methyl 3-cyclopropyl-3-(2-fluoro-3-hydroxy-4-(3-(4-hydroxyphenyl)-3-oxopropyl)phenyl)-2-methylpropanoate To a mixture of lithium acetate (1.05 g, 15.9 mmol), 1-(4-((tert-butyldimethylsilyl)-oxy)phenyl)prop-2-en-1-ol (2.10 g, 7.93 mmol), (2S, 3R)-methyl 3-cyclopropyl-3-(2-fluoro-3-hydroxy-4-iodophenyl)-2-methylpropanoate (Intermediate 7, 2.00 g, 5.29 mmol), tetra-n-butylammonium chloride (4.41 g, 15.9 mmol) and lithium chloride (0.673 g, 15.9 mmol) in DMF (80 mL) was added Pd(OAc)$_2$ (0.119 g, 0.529 mmol). The reaction was heated to 80° C. for 16 h, then cooled to room temperature, and concentrated. Water (50 mL) was added, and the reaction mixture extracted with ethyl acetate (80 mL×3). The combined organic layers were washed with water (100 mL×1), brine (120 mL), dried (Na$_2$SO$_4$), filtered and concentrated in vacuo. The resulting crude product was purified by flash silica gel chromatography (ISCO®; 120 g SepaFlash® Silica Flash Column, Eluent of 0~40% EA/PE gradient at 85 mL/min) to give the title compound.

Step 4: (2S, 3R)-methyl 3-cyclopropyl-3-(2-fluoro-3-hydroxy-4-(3-hydroxy-3-(4-hydroxyphenyl)propyl)phenyl)-2-methylpropanoate NaBH$_4$ (0.340 g, 8.99 mmol) was added to a stirred, 0° C. mixture of (2S, 3R)-methyl 3-cyclopropyl-3-(2-fluoro-3-hydroxy-4-(3-(4-hydroxyphenyl)-3-oxopropyl)phenyl)-2-methylpropanoate in EtOH (30 mL). The reaction was stirred at 0° C. for 1 h, then warmed to 30° C. for 20 h. Water (1.0 mL) was added, and the reaction mixture was stirred at 30° C. for 30 minutes. Then the reaction mixture was concentrated and aqueous ammonium chloride (saturated, 30 mL) was added. The resulting mixture was extracted with ethyl acetate (50 mL×2). The combined organic layers were washed with brine (saturated, 80 mL), dried (Na$_2$SO$_4$), and filtered. The filtrate was evaporated under reduced pressure to give the title compound, which was used in the next step without further purification.

Step 5: (2S, 3R)-methyl 3-cyclopropyl-3-(8-fluoro-2-(4-hydroxyphenyl)chroman-7-yl)-2-methyl-propanoate DIAD (103 mg, 0.447 mmol) was added dropwise to a solution of (2S, 3R)-methyl 3-cyclo-propyl-3-(2-fluoro-3-hydroxy-4-(3-hydroxy-3-(4-hydroxyphenyl)propyl)phenyl)-2-methylpropanoate (150 mg, 0.373 mmol) and triphenylphosphine (117 mg, 0.447 mmol) in DCM (4.0 mL) cooled in an ice bath. The reaction was stirred at 10° C. for 16 h, then concentrated in vacuo. The resulting residue which was purified by flash silica gel chromatography (ISCO®; 4 g SepaFlash® Silica Flash Column, Eluent of 0~30% EA/PE gradient at 30 mL/min) to give the title compound.

Step 6: (2S, 3R)-methyl 3-cyclopropyl-3-(8-fluoro-2-(3-formyl-4-hydroxyphenyl) chroman-7-yl)-2-methylpropanoate To a mixture of (2S, 3R)-methyl 3-cyclopropyl-3-(8-fluoro-2-(4-hydroxyphenyl)chroman-7-yl)-2-methylpropanoate (240 mg, 0.624 mmol) in acetonitrile (8.0 mL) were added magnesium chloride (357 mg, 3.75 mmol), formaldehyde (375 mg, 12.49 mmol) and TEA (1.305 ml, 9.36 mmol). The reaction mixture was refluxed (95° C.) for 16 h, then cooled to rt. EtOAc (20 mL) was added, and the mixture was filtered. The filtrate was concentrated under reduced pressure, diluted with EtOAc (20 mL×2), and the resulting mixture was washed with aqueous HCl (1 N, 10 mL). The organic layer was separated, dried over anhydrous Na$_2$SO$_4$ and filtered. The filtrate was concentrated under reduced pressure. The resulting crude product was purified by flash silica gel chromatography (ISCO®; 4 g SepaFlash® Silica Flash Column, Eluent of 0~10% EA/PE gradient at 30 mL/min) to give the title compound.

Step 7: (2S, 3R)-methyl 3-cyclopropyl-3-(8-fluoro-2-(3-formyl-4-(tosyloxy)phenyl) chroman-7-yl)-2-methylpropanoate To a solution of (2S, 3R)-methyl 3-cyclopropyl-3-(8-fluoro-2-(3-formyl-4-hydroxylphenyl)chroman-7-yl)-2- methylpropanoate (200 mg, 0.485 mmol) in DCM (8.0 mL) were added TEA (0.203 mL, 1.46 mmol) and TsCl (111 mg, 0.582 mmol). The reaction was stirred at 10° C. for 2 h, then saturated aqueous NH$_4$Cl (30 mL) was added. The reaction mixture was then extracted with DCM (30 mL×2). The combined organic layers were washed with saturated brine (50 mL), dried over anhydrous Na$_2$SO$_4$, filtered and the filtrate was evaporated under reduced pressure. The resulting crude product was purified by preparative TLC (SiO$_2$, PE:EtOAc=3:1, v/v) to give the title compound.

Step 8: (2S, 3R)-methyl 3-cyclopropyl-3-(8-fluoro-2-(4-(5-fluoro-2-methoxypyridin-4-yl)-3-formylphenyl)chroman-7-yl)-2-methylpropanoate To a solution of (2S, 3R)-methyl 3-cyclopropyl-3-(8-fluoro-2-(3-formyl-4-(tosyloxy)phenyl)chroman-7-yl)-2-methylpropanoate (390 mg, 0.688 mmol) in 1,4-dioxane (12 mL) and water (3 mL) were added potassium phosphate tribasic (438 mg, 2.06 mmol), 2nd Generation XPhos precatalyst (54.2 mg, 0.069 mmol) and (5-fluoro-2-methoxypyridin-4-yl)boronic acid (235 mg, 1.377 mmol) under a nitrogen atmosphere. The reaction mixture was stirred at 80° C. for 2 h, and then cooled to room temperature. Water (20 mL) was added to the mixture, and the aqueous phase was extracted with EtOAc (50 mL×2). The combined organic layers were washed with brine (80 mL), dried over anhydrous Na$_2$SO$_4$ and filtered. The filtrate was concentrated under reduced pressure. The resulting crude product was purified by flash silica gel chromatography (ISCO®; 40 g SepaFlash® Silica Flash Column, Eluent of 0~30% EA/PE gradient at 40 mL/min) to give the title compound.

Step 9: (2S, 3R)-methyl 3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoate To a solution of (2S, 3R)-methyl 3-cyclopropyl-3-(8-fluoro-2-(4-(5-fluoro-2-methoxypyridin-4-yl)-3-formylphenyl)chroman-7-yl)-2-methylpropanoate (120 mg, 0.230 mmol) in MeOH (5.0 mL) were added pyrrolidine (0.038 ml, 0.460 mmol), and titanium (IV) isopropoxide (0.135 ml, 0.460 mmol). The reaction mixture was stirred at 80° C. for 1 h, and then cooled to 0° C. Sodium borohydride (104 mg, 2.76 mmol) was added to the mixture in one portion. The reaction was stirred at 10° C. for 30 minutes, then water (10 mL) was added, and the reaction was quenched by the slow addition of 1N HCl (8 mL). The reaction mixture was extracted with EtOAc (20 mL×3). The combined EtOAc layers were washed with sodium bicarbonate (5%, 30 mL), dried (Na$_2$SO$_4$), filtered and the filtrate was evaporated under reduced pressure to give the title compound, which was used in the next step without further purification.

Step 10: (2S, 3R)-3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoic acid Lithium hydroxide monohydrate (160 mg, 3.81 mmol) was added to the mixture of (2S, 3R)-methyl 3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoate (220 mg, 0.381 mmol) in a co-solvent of MeOH (3 mL), THF (2 mL) and water (2 mL). The reaction was stirred at 60° C. for 26 h. Then the reaction mixture was concentrated, water (10 mL) was added, and the mixture was neutralized with HCl (aqueous, 1 N) to pH 5~6. The reaction mixture was then extracted with ethyl acetate (20 mL×3). The combined organic layers were washed with brine (30 mL), dried over Na$_2$SO$_4$, filtered and concentrated. The resulting residue was purified by reverse preparative HPLC (EI instrument fitted with a Phenomenex Synergi C18 100*21.2 mm*4 um; Mobile phase A: water (containing 0.1% TFA, v/v), B: acetonitrile. Gradient: 44-64% B, 0-10 min; 100% B, 10.5-12.5 min; 5% B, 13-15 min) to give (2S, 3R)-3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoic acid. $^1$H NMR (400 MHz, MeOD) δ=8.18 (s, 1H), 7.88 (br. s., 1H), 7.71 (d, J=7.72 Hz, 1H), 7.48 (d, J=7.94 Hz, 1H), 6.84-6.94 (m, 2H), 6.78 (t, J=7.17 Hz, 1H), 5.24 (d, J=10.58 Hz, 1H), 4.40 (br. s., 2H), 3.95 (s, 3H), 3.47 (br. s., 2H), 3.02-3.16 (m, 2H), 2.80-2.96 (m, 4H), 2.27-2.41 (m, 2H), 1.89-2.16 (m, 5H), 1.17 (br. s., 1H), 0.94 (d, J=6.84 Hz, 3H), 0.61 (br. s., 1H), 0.28-0.40 (m, 2H), −0.06-0.02 (m, 1H). MS (ESI) m/z: 563.2 [M+H]$^+$ Step 11: (2S, 3R)-3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoic acid

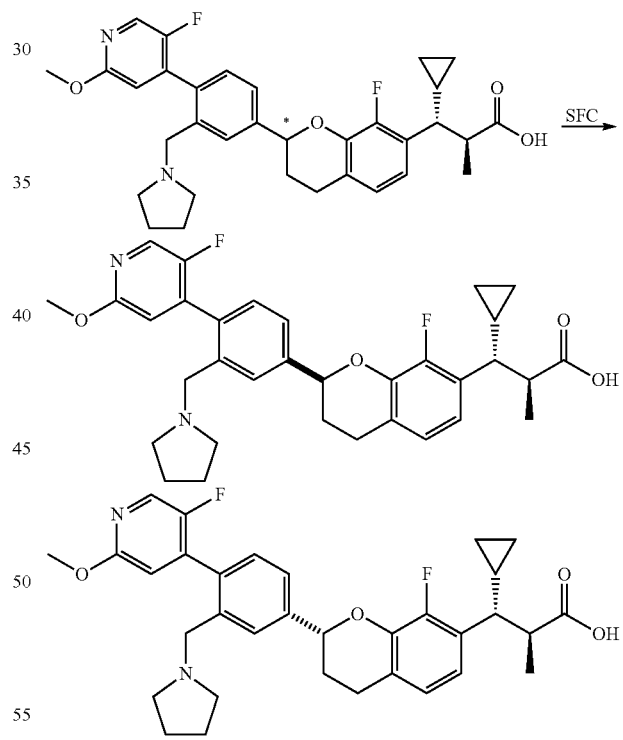

A mixture of 2 diastereomers at the * carbon alpha to the chroman oxygen of (2S, 3R)-3-cyclopropyl-3-(8-fluoro-2-(4-(5-fluoro-2-methoxypyridin-4-yl)-3-(pyrrolidin-1-ylmethyl)-phenyl)chroman-7-yl)-2-methylpropanoic acid (100 mg, 0.178 mmol) was resolved by SFC (Column: Chiralpak AD-3 50*4.6 mm I.D., 3 um Mobile phase: A: CO$_2$ B: ethanol (0.05% DEA), Gradient: from 5% to 40% of B in 1.4 min and hold 40% for 1.05 min, then 5% of B for 0.35 min Flow rate: 4 mL/min Column temp.: 40 deg. C. Wavelength: 254 nm") to give Isomer 1 (faster eluting with a shorter retention time in chiral HPLC): (2S, 3R)-3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoic acid ($t_R$=1.382 min), and Isomer 2 (slower eluting with a longer retention time in chiral HPLC): (2S, 3R)-3-cyclopropyl-3-(8-fluoro-2-(4-(5-fluoro-2-methoxypyridin-4-yl)-3-(pyrrolidin-1-ylmethyl)phenyl)-chroman-7-yl)-2-methylpropanoic acid ($t_R$=1.608 min).

Step 12: Conversion to Sodium Salt

To a solution of each isomer in acetonitrile (2 ml)/water (1 ml) was added 1 equivalent of 1 M aqueous sodium hydroxide at ambient temperature. The resulting solution was sonicated for 2 minutes, frozen on a dry ice bath, and then lyophilized for 19 h to give the sodium salt of (2S, 3R)-3-cyclopropyl-3-(8-fluoro-2-(4-(5-fluoro-2-methoxypyridin-4-yl)-3-(pyrrolidin-1-ylmethyl)phenyl)chroman-7-yl)-2-methylpropanoic acid. EXAMPLE 198 (Isomer 1): $^1$H NMR (400 MHz, MeOD) δ=8.12 (s, 1H), 7.84 (br. s., 1H), 7.55 (d, J=7.72 Hz, 1H), 7.36 (d, J=7.94 Hz, 1H), 6.79-6.87 (m, 2H), 6.68-6.77 (m, 1H), 5.20 (d, J=9.70 Hz, 1H), 4.10 (d, J=13.45 Hz, 1H), 3.94 (s, 4H), 2.99-3.10 (m, 1H), 2.83 (br. s., 5H), 2.70 (br. s., 1H), 2.40 (t, J=9.70 Hz, 1H), 2.28 (br. s., 1H), 2.08-2.21 (m, 1H), 1.86 (br. s., 4H), 1.29 (br. s., 1H), 1.11 (br. s., 1H), 0.82 (d, J=6.84 Hz, 3H), 0.55 (br. s., 1H), 0.41 (d, J=4.41 Hz, 1H), 0.25 (br. s., 1H), −0.05 (br. s., 1H). MS (ESI) m/z: 563.2 [M+H]$^+$; EXAMPLE 199 (Isomer 2): $^1$H NMR (400 MHz, MeOD) δ=8.11 (s, 1H), 7.84 (s, 1H), 7.61-7.69 (m, 1H), 7.39 (d, J=7.94 Hz, 1H), 6.78-6.88 (m, 2H), 6.67-6.75 (m, 1H), 5.16 (d, J=9.92 Hz, 1H), 4.31 (br. s., 2H), 3.90 (s, 3H), 3.12 (br. s., 3H), 2.96-3.08 (m, 1H), 2.74-2.86 (m, 2H), 2.22-2.34 (m, 2H), 2.00-2.12 (m, 1H), 1.91 (br. s., 3H), 1.22-1.35 (m, 1H), 1.05-1.16 (m, 1H), 0.83-0.95 (m, 4H), 0.50-0.59 (m, 1H), 0.29-0.38 (m, 1H), 0.18-0.29 (m, 1H), −0.08 (dd, J=4.63, 9.04 Hz, 1H). MS (ESI) m/z: 563.2 [M+H]$^+$.

TABLE 17

Examples 200-213 were prepared in a similar manner to Example 198 using the appropriate intermediates and commercially available starting materials.

| Example | Structure | M.W. | Isomer | LC/MS (ESI) observed [M + 1]+ |
|---|---|---|---|---|
| 200 | 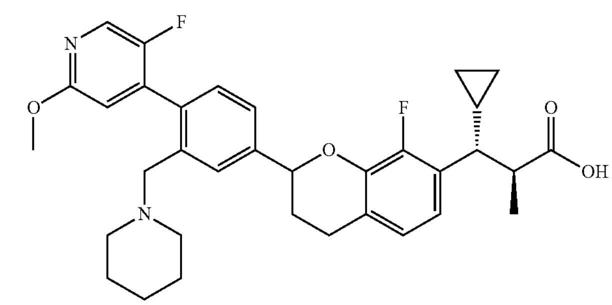 [SMILES: COc1cc(-c2ccc(C3CCc4ccc([C@H](C5CC5)[C@H](C)C(=O)O)c(F)c4O3)cc2CN2CCCCC2)c(F)cn1] | 576.3 | Isomer A | 577.3 |
| 201 | 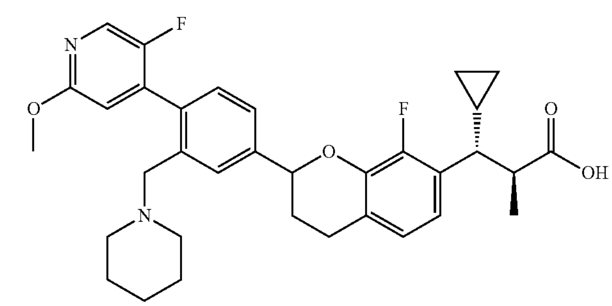 [SMILES: COc1cc(-c2ccc(C3CCc4ccc([C@H](C5CC5)[C@H](C)C(=O)O)c(F)c4O3)cc2CN2CCCCC2)c(F)cn1] | 576.3 | Isomer B | 577.3 |
| 202 | 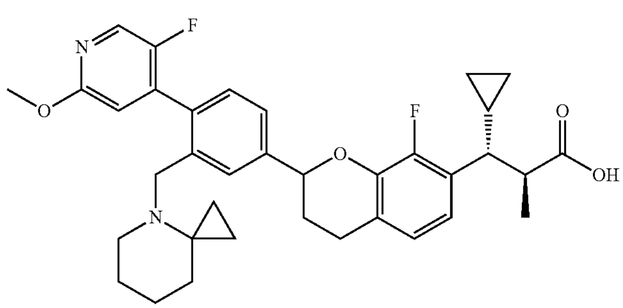 [SMILES: COc1cc(-c2ccc(C3CCc4ccc([C@H](C5CC5)[C@H](C)C(=O)O)c(F)c4O3)cc2CN2CCCCC23CC3)c(F)cn1] | 602.3 | Isomer A | 603.3 |

TABLE 17-continued

Examples 200-213 were prepared in a similar manner to Example 198 using the appropriate intermediates and commercially available starting materials.

| Example | Structure | M.W. | Isomer | LC/MS (ESI) observed [M + 1]+ |
|---------|-----------|------|--------|-------------------------------|
| 203 | 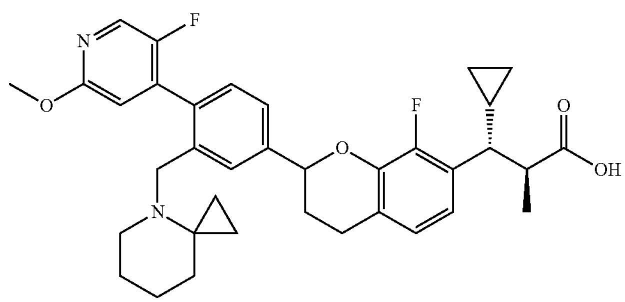 [SMILES: COc1cc(-c2ccc(C3CCc4ccc([C@H](C5CC5)[C@H](C)C(=O)O)c(F)c4O3)cc2CN2CCCCC23CC3)c(F)cn1] | 602.3 | Isomer B | 603.3 |
| 204 | 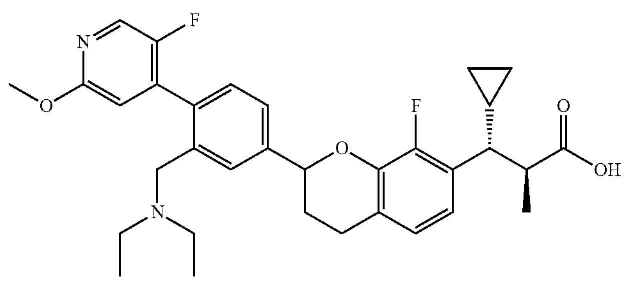 [SMILES: CCN(CC)Cc1cc(C2CCc3ccc([C@H](C4CC4)[C@H](C)C(=O)O)c(F)c3O2)ccc1-c1cc(OC)ncc1F] | 564.3 | Isomer A | 565.3 |
| 205 | 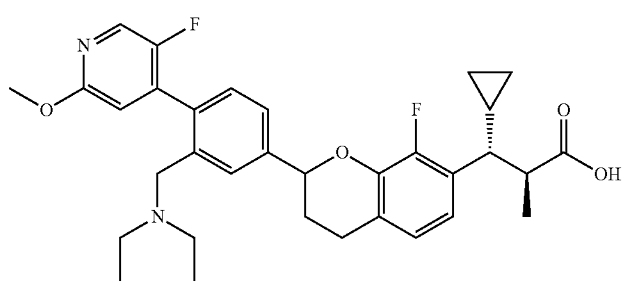 [SMILES: CCN(CC)Cc1cc(C2CCc3ccc([C@H](C4CC4)[C@H](C)C(=O)O)c(F)c3O2)ccc1-c1cc(OC)ncc1F] | 564.3 | Isomer B | 565.3 |
| 206 | 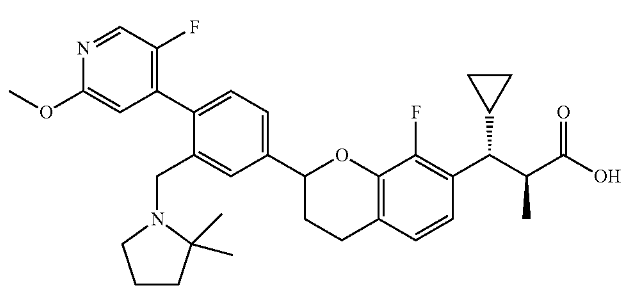 [SMILES: COc1cc(-c2ccc(C3CCc4ccc([C@H](C5CC5)[C@H](C)C(=O)O)c(F)c4O3)cc2CN2CCCC2(C)C)c(F)cn1] | 590.3 | Isomer A | 591.3 |
| 207 | 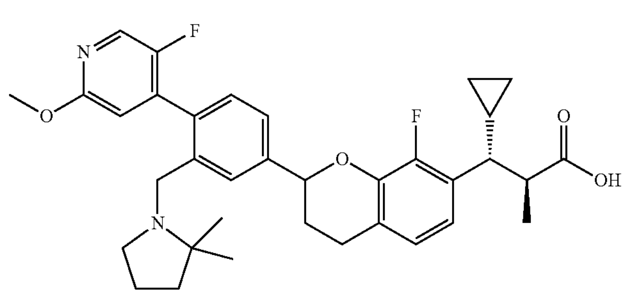 [SMILES: COc1cc(-c2ccc(C3CCc4ccc([C@H](C5CC5)[C@H](C)C(=O)O)c(F)c4O3)cc2CN2CCCC2(C)C)c(F)cn1] | 590.3 | Isomer B | 591.3 |

TABLE 17-continued

Examples 200-213 were prepared in a similar manner to Example 198 using the appropriate intermediates and commercially available starting materials.

| Example | Structure | M.W. | Isomer | LC/MS (ESI) observed [M + 1]+ |
|---|---|---|---|---|
| 208 | 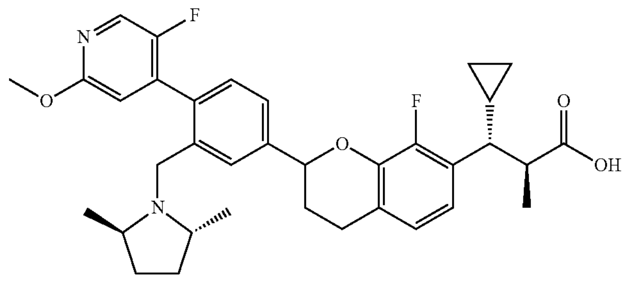 [SMILES: COc1cc(-c2ccc(C3CCc4ccc([C@H](C5CC5)[C@H](C)C(=O)O)c(F)c4O3)cc2CN2[C@H](C)CC[C@H]2C)c(F)cn1] | 590.3 | Isomer A | 591.3 |
| 209 | 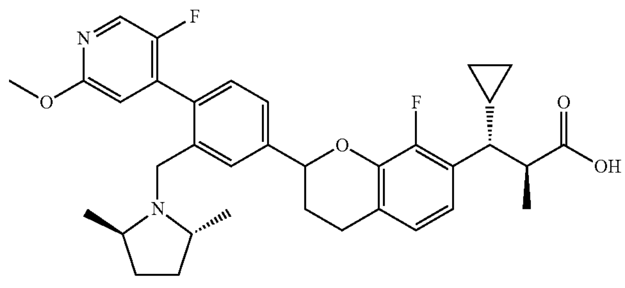 [SMILES: COc1cc(-c2ccc(C3CCc4ccc([C@H](C5CC5)[C@H](C)C(=O)O)c(F)c4O3)cc2CN2[C@H](C)CC[C@H]2C)c(F)cn1] | 590.3 | Isomer B | 591.3 |
| 210 | 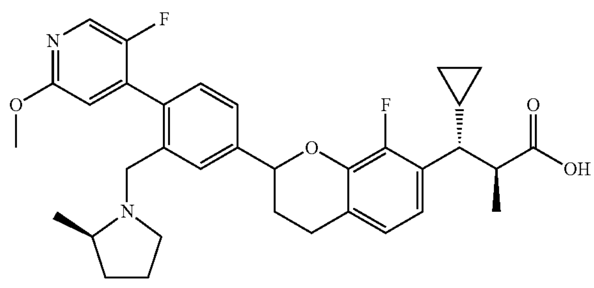 [SMILES: COc1cc(-c2ccc(C3CCc4ccc([C@H](C5CC5)[C@H](C)C(=O)O)c(F)c4O3)cc2CN2CCC[C@H]2C)c(F)cn1] | 576.6 | Isomer A | 577.3 |
| 211 | 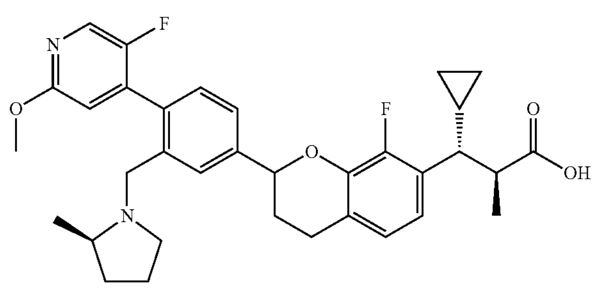 [SMILES: COc1cc(-c2ccc(C3CCc4ccc([C@H](C5CC5)[C@H](C)C(=O)O)c(F)c4O3)cc2CN2CCC[C@H]2C)c(F)cn1] | 576.6 | Isomer B | 577.3 |
| 212 | 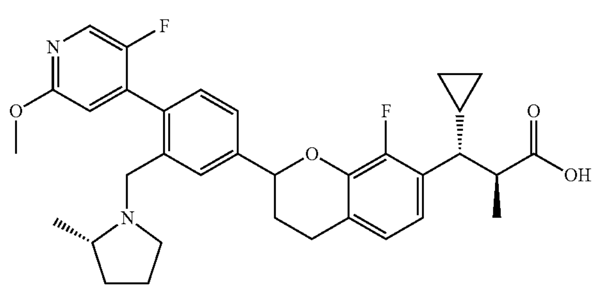 [SMILES: COc1cc(-c2ccc(C3CCc4ccc([C@H](C5CC5)[C@H](C)C(=O)O)c(F)c4O3)cc2CN2CCC[C@@H]2C)c(F)cn1] | 576.6 | Isomer A | 577.3 |

TABLE 17-continued

Examples 200-213 were prepared in a similar manner to Example 198 using the appropriate intermediates and commercially available starting materials.

| Example | Structure | M.W. | Isomer | LC/MS (ESI) observed [M + 1]+ |
|---|---|---|---|---|
| 213 | 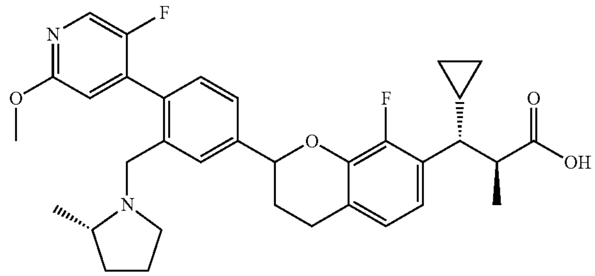 [SMILES: COc1cc(-c2ccc(C3CCc4ccc([C@H](C5CC5)[C@H](C)C(=O)O)c(F)c4O3)cc2CN2CCC[C@@H]2C)c(F)cn1] | 576.6 | Isomer B | 577.3 |

Examples 214 and 215

(2S, 3R)-3-(2-(4-(5-chloro-2-ethoxypyridin-4-yl)-3-((diethylamino)methyl)phenyl)chroman-7-yl)-3-cyclopropyl-2-methylpropanoic acid

Step 1: 5-chloro-2-ethoxypyridine

A mixture of 2, 5-dichloropyridine (5.00 g, 33.8 mmol) and sodium ethanolate (4.60 g, 67.6 mmol) in EtOH (60 mL) was stirred at 90° C. for 20 h. Then the mixture was concentrated, saturated aqueous NH$_4$Cl (150 mL) was added, and the mixture was extracted with EtOAc (100 ml×3). The combined organic layers were washed with brine (150 mL), dried over anhydrous Na$_2$SO$_4$, filtered and the filtrate was concentrated to give the title compound.

Step 2: (5-chloro-2-ethoxypyridin-4-yl)boronic acid

To a solution of 5-chloro-2-ethoxypyridine (1 g, 6.35 mmol) in THF (30 mL), cooled in a dry ice/acetone bath, was added LDA (3.81 ml, 7.61 mmol) in one portion. The mixture was stirred for 2 h, then triisopropyl borate (2.95 ml, 12.69 mmol) was added. The reaction was stirred for 3 h at −70° C., and then quenched with water (20 mL) at −70° C. The pH of the reaction mixture was adjusted to pH 6 with 1N HCl, and the mixture was extracted with EtOAc (50 ml×3). The combined organic layers were washed with brine (80 mL), dried over Na$_2$SO$_4$, filtered and concentrated. The resulting solid was washed with EtOAc (5 mL) and PE (30 mL) to give the title compound.

Step 3: (2S, 3R)-methyl 3-(2-(4-(5-chloro-2-ethoxypyridin-4-yl)-3-formylphenyl)chroman-7-yl)-3-cyclopropyl-2-methylpropanoate To a solution of (2S, 3R)-methyl 3-cyclopropyl-3-(2-(3-formyl-4-(tosyloxy)phenyl)chroman-7-yl)-2-methylpropanoate (550 mg, 1.002 mmol) in 1, 4-dioxane (10 mL) and water (2.5 mL) were added potassium phosphate tribasic (638 mg, 3.01 mmol), 2$^{nd}$ Generation Xphos precatalyst (79 mg, 0.100 mmol), and (5-chloro-2-ethoxypyridin-4-yl)boronic acid (606 mg, 3.01 mmol). The mixture was stirred at 90° C. for 2 h under N$_2$ protection. Then water (30 mL) was added, and the mixture was extracted with ethyl acetate (3×50 mL). The combined organic layers were washed with brine (saturated, 100 mL), dried over Na$_2$SO$_4$, filtered and concentrated. The resulting residue was purified by flash silica gel chromate-graphy (ISCO®; 24 g SepaFlash® Silica Flash Column, Eluent of 0~20% EA/PE gradient at 40 mL/min) to give the title compound.

Step 4: (2S, 3R)-methyl 3-(2-(4-(5-chloro-2-ethoxypyridin-4-yl)-3-((diethylamino) methyl)phenyl)chroman-7-yl)-3-cyclopropyl-2-methylpropanoate To a solution of (2S, 3R)-methyl 3-(2-(4-(5-chloro-2-ethoxypyridin-4-yl)-3-formylphenyl)chroman-7-yl)-3-cyclopropyl-2-methylpropanoate (125 mg, 0.234 mmol) in DCE (5.0 mL), cooled in an ice bath, were added diethylamine (171 mg, 2.341 mmol) and acetic acid (14.1 mg, 0.234 mmol). The mixture was stirred at 30° C. for 1 h, then sodium triacetoxyborohydride (149 mg, 0.702 mmol) was added. The reaction was stirred at 50° C. for 16 h, then saturated aqueous saturated aqueous NH$_4$Cl (30 mL) was added, and the mixture was extracted with EtOAc (30 mL×3). The combined EtOAc layers were washed with sodium bicarbonate (5%, 50 mL), dried (Na$_2$SO$_4$), filtered and the filtrate was evaporated under reduced pressure to give the title compound, was used in the next step without purification.

Step 5: (2S, 3R)-3-(2-(4-(5-chloro-2-ethoxypyridin-4-yl)-3-((diethylamino)methyl) phenyl)chroman-7-yl)-3-cyclopropyl-2-methylpropanoic acid A solution of (2S, 3R)-methyl 3-(2-(4-(5-chloro-2-ethoxypyridin-4-yl)-3-((diethylamino)methyl)phenyl)chroman-7-yl)-3-cyclopropyl-2-methylpropanoate (130 mg, 0.220 mmol) in a co-solvent of MeOH (1 mL), THF (1 mL) and water (1 mL) was stirred at 50° C. for 1 h in a microwave. Then the reaction mixture was concentrated, and water (10 mL) was added. The mixture was neutralized with HCl (1N, aqueous) to pH 5~6, and extracted with ethyl acetate (3×20 mL). The combined organic layers were washed with brine (saturated, 30 mL), dried over $Na_2SO_4$, filtered and concentrated. The resulting residue was purified by reverse preparative HPLC (on a EB instrument fitted with a Phenomenex Synergi C18 150*30 mm*4 um, Mobile phase A: water (containing 0.1% TFA, v/v), B: acetonitrile. Gradient: 44-59% B, 0-10 min; 100% B, 10.5-12.5 min; 5% B, 13-15 min) to give (2S, 3R)-3-(2-(4-(5-chloro-2-ethoxypyridin-4-yl)-3-((diethylamino)methyl)phenyl)-chroman-7-yl)-3-cyclopropyl-2-methylpropanoic acid. MS (ESI) m/z: 577.3 [M+H]$^+$. $^1$H NMR (400 MHz, MeOD) δ=8.30 (s, 1H), 7.87 (br. s., 1H), 7.69 (d, J=7.94 Hz, 1H), 7.40 (d, J=8.16 Hz, 1H), 7.06 (d, J=7.72 Hz, 1H), 6.88 (s, 1H), 6.69-6.76 (m, 2H), 5.17-5.23 (m, 1H), 4.36-4.46 (m, 3H), 4.07-4.16 (m, 1H), 2.99-3.22 (m, 4H), 2.72-2.88 (m, 2H), 2.33 (d, J=11.03 Hz, 1H), 2.00-2.14 (m, 1H), 1.91 (t, J=9.81 Hz, 1H), 1.40 (t, J=7.06 Hz, 3H), 1.05-1.27 (m, 8H), 0.93 (d, J=6.84 Hz, 3H), 0.56-0.64 (m, 1H), 0.27-0.38 (m, 2H), −0.04-0.04 (m, 1H)

Step 6: (2S, 3R)-3-(2-(4-(5-chloro-2-ethoxypyridin-4-yl)-3-((diethylamino)methyl)phenyl) chroman-7-yl)-3-cyclopropyl-2-methylpropanoic acid A mixture of 2 diastereomers at the carbon alpha to the chroman oxygen of (2S, 3R)-3-(2-(4-(5-chloro-2-ethoxypyridin-4-yl)-3-((diethyl-amino)methyl)phenyl)chroman-7-yl)-3-cyclopropyl-2-methylpropanoic acid (90 mg, 0.156 mmol) was resolved by SFC (Column: Chiralpak AD-3 50×4.6 mm I.D., 3 um Mobile phase: A: $CO_2$ B: methanol (0.05% DEA) Gradient: from 5% to 40% of B in 1.4 min and hold 40% for 1.05 min, then 5% of B for 0.35 min Flow rate: 2.5 mL/min Column temp.: 40 deg. C. Wavelength: 254 nm") to give Isomer 1 (faster eluting with a shorter retention time ($t_R$=1.356 min) in chiral HPLC): (2S, 3R)-3-(2-(4-(5-chloro-2-ethoxypyridin-4-yl)-3-((diethylamino)methyl)-phenyl)chroman-7-yl)-3-cyclopropyl-2-methylpropanoic acid; and Isomer 2 (slower eluting with a longer retention time ($t_R$=1.467 min) in chiral HPLC): (2S, 3R)-3-(2-(4-(5-chloro-2-ethoxypyridin-4-yl)-3-((diethylamino)methyl)phenyl)-chroman-7-yl)-3-cyclopropyl-2-methylpropanoic acid. EXAMPLE 214 (Isomer 1 faster eluting): MS (ESI) m/z: 577.3 [M+H]$^+$. $^1$H NMR (400 MHz, MeOD) δ=8.30 (br. s., 1H), 7.86 (br. s., 1H), 7.69 (d, J=7.50 Hz, 1H), 7.40 (d, J=7.72 Hz, 1H), 7.06 (d, J=7.28 Hz, 1H), 6.88 (br. s., 1H), 6.69-6.77 (m, 2H), 5.20 (br. s., 1H), 4.35-4.47 (m, 3H), 4.12 (dd, J=6.50, 13.56 Hz, 1H), 2.97-3.23 (m, 5H), 2.70-2.89 (m, 2H), 2.33 (d, J=12.35 Hz, 1H), 2.08 (d, J=9.26 Hz, 1H), 1.91 (t, J=9.59 Hz, 1H), 1.40 (t, J=6.51 Hz, 3H), 1.05-1.25 (m, 7H), 0.93 (d, J=6.17 Hz, 3H), 0.60 (br. s., 1H), 0.33 (d, J=5.51 Hz, 2H), 0.00 (br. s., 1H). EXAMPLE 215 (Isomer 2 slower eluting): MS (ESI) m/z: 577.3 [M+H]$^+$. $^1$H NMR (400 MHz, MeOD) δ 8.30 (s, 1H), 7.86 (br. s., 1H), 7.69 (d, J=7.94 Hz, 1H), 7.40 (d, J=7.94 Hz, 1H), 7.06 (d, J=7.50 Hz, 1H), 6.88 (s, 1H), 6.71-6.76 (m, 2H), 5.20 (d, J=5.51 Hz, 1H), 4.36-4.46 (m, 3H), 4.12 (dd, J=6.84, 13.89 Hz, 1H), 2.98-3.21 (m, 6H), 2.73-2.87 (m, 3H), 2.33 (d, J=11.25 Hz, 1H), 2.08 (d, J=11.03 Hz, 1H), 1.90 (t, J=9.81 Hz, 1H), 1.39 (t, J=7.06 Hz, 3H), 1.20 (t, J=6.95 Hz, 3H), 1.10 (d, J=7.28 Hz, 4H), 0.93 (d, J=6.84 Hz, 3H), 0.60 (t, J=8.60 Hz, 1H), 0.28-0.38 (m, 2H), −0.01 (d, J=5.07 Hz, 1H).

TABLE 18

Examples 216-218 were prepared in a similar manner to Example 214 using the appropriate intermediates and commercially available starting material.

| Example | Structure | M.W. | Isomer | LC/MS (ESI) observed [M + 1]+ |
|---|---|---|---|---|
| 216 | 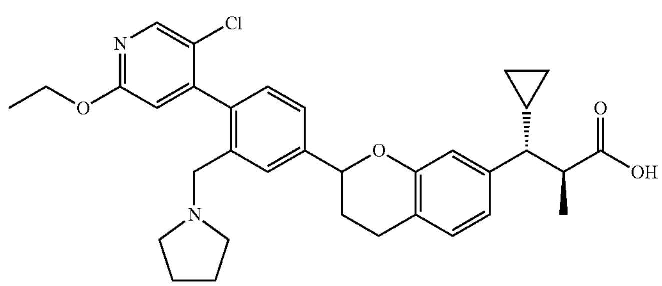 [SMILES: CCOc1cc(-c2ccc(C3CCc4ccc([C@H](C5CC5)[C@H](C)C(=O)O)cc4O3)cc2CN2CCCC2)c(Cl)cn1] | 562.3 | Mixture of Diastereomers | 575.3 |
| 217 | 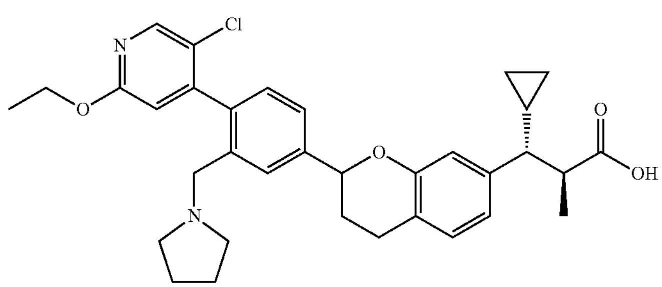 [SMILES: CCOc1cc(-c2ccc(C3CCc4ccc([C@H](C5CC5)[C@H](C)C(=O)O)cc4O3)cc2CN2CCCC2)c(Cl)cn1] | 562.3 | Isomer A | 575.2 |

TABLE 18-continued

Examples 216-218 were prepared in a similar manner to Example 214 using the appropriate intermediates and commercially available starting material.

| Example | Structure | M.W. | Isomer | LC/MS (ESI) observed [M + 1]+ |
|---|---|---|---|---|
| 218 | (structure shown) | 562.3 | Isomer B | 575.2 |

Examples 219 and 220

(2S, 3R)-3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoic acid

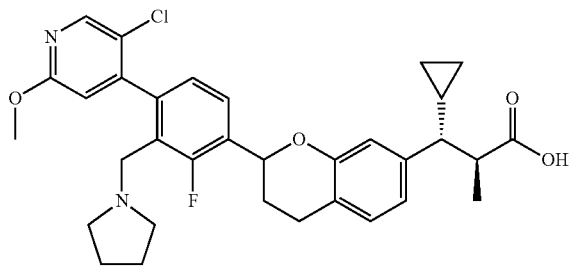

Step 1: tert-butyl((2-chloro-6-fluorobenzyl)oxy)dimethylsilane (2-chloro-6-fluorophenyl)-methanol (2.00 g, 12.5 mmol) was dissolved in DCM (40 mL). Then Imidazole (0.933 g, 13.7 mmol), TBDMS-Cl (2.07 g, 13.7 mmol), DMAP (0.228 g, 1.87 mmol) were added and the reaction was stirred at 20° C. for 3 h. The reaction mixture was then washed with saturated aqueous NH₄Cl (80 mL), and extracted with DCM (100 mL×2). The combined organic layers were washed with brine (100 mL), and dried over anhydrous Na₂SO₄. The mixture was filtered and the filtrate was concentrated to give the crude product, which was purified via silica gel chromatography (SiO₂, eluent: PE:EA=30:1) to give the title compound.

Step 2: 3-(((tert-butyldimethylsilyl)oxy)methyl)-4-chloro-2-fluorobenzaldehyde To a solution of tert-butyl((2-chloro-6-fluorobenzyl)oxy)dimethylsilane(1.80 g, 6.55 mmol) in THF (25 mL) was added s-BuLi (5.61 ml, 7.86 mmol) at −70° C. The mixture was stirred at −70° C. for 2 h, then DMF (2.54 ml, 32.7 mmol) was added and the reaction was stirred at −70° C. for 2 h. Saturated aqueous NH₄Cl (50 mL) was added, and the reaction mixture was extracted with EtOAc (80 mL×3). The combined organic layers were washed with brine (100 mL), and dried over anhydrous Na₂SO₄. The mixture was filtered and the filtrate was concentrated to give the crude product, which was purified by flash silica gel chromatography (ISCO®; 40 g SepaFlash® Silica Flash Column, Eluent of 0~20% EA/PE gradient at 45 mL/min) to give the title compound.

Step 3: 1-(3-(((tert-butyldimethylsilyl)oxy)methyl)-4-chloro-2-fluorophenyl)prop-2-en-1-ol Vinylmagnesium bromide (1.073 g, 8.17 mmol) was added dropwise over 5 minutes to a stirred, 0° C. solution of 3-(((tert-butyldimethylsilyl)oxy)methyl)-4-chloro-2-fluorobenzaldehyde (1.65 g, 5.45 mmol) in THF (20 mL) under a nitrogen atmosphere. The reaction was stirred at 0° C. for 2 h, then concentrated. Saturated aqueous NH₄Cl (50 mL) was added and the mixture was extracted with ethyl acetate (3×80 mL). The combined organic layers were washed with brine (100 mL), dried (Na₂SO₄), and filtered. The filtrate was evaporated under reduced pressure to give the crude product, which was purified by flash silica gel chromatography (ISCO®; 40 g SepaFlash® Silica Flash Column, Eluent of 0~20% EA/PE gradient at 40 mL/min) to give the title compound.

Step 4: (2S, 3R)-methyl 3-(4-(3-(4-chloro-2-fluoro-3-(hydroxymethyl)phenyl)-3-oxopropyl)-3-hydroxyphenyl)-3-cyclopropyl-2-methylpropanoate, and (2S, 3R)-methyl 3-(4-((E)-3-(4-chloro-2-fluoro-3-(hydroxymethyl)phenyl)-3-hydroxyprop-1-en-1-yl)-3-hydroxyphenyl)-3-cyclopropyl-2-methylpropanoate To a mixture of lithium acetate (0.605 g, 9.16 mmol), 1-(3-(((tert-butyldimethylsilyl)oxy)-methyl)-4-chloro-2-fluorophenyl)prop-2-en-1-ol (1.21 g, 3.66 mmol), (2S, 3R)-methyl 3-cyclopropyl-3-(3-hydroxy-4-iodophenyl)-2-methylpropanoate (1.1 g, 3.05 mmol, Intermediate 5), tetra-n-butylammonium chloride (2.22 g, 9.16 mmol) and lithium chloride (0.388 g, 9.16 mmol) in DMF (40 mL) was added Pd(OAc)₂ (690 mg, 0.305 mmol) under a N₂ atmosphere. Then the resulting mixture was heated to 80° C. for 2 h, then cooled to rt and concentrated. Water (50 mL) was added, and the reaction mixture was extracted with ethyl acetate (80 mL×2). The combined organic layers were washed with water (50 mL), brine (100 mL), dried (Na₂SO₄), filtered and concentrated in vacuo to afford crude product, which was purified by flash silica gel chromatography (ISCO®; 40 SepaFlash® Silica Flash Column, Eluent of 0~40% EA/PE gradient at 45 mL/min) to give (2S, 3R)-methyl 3-(4-(3-(4-chloro-2-fluoro-3-(hydroxymethyl)-phenyl)-3-oxopropyl)-3-hydroxyphenyl)-3-cyclopropyl-2-methylpropanoate, and (2S, 3R)-methyl 3-(4-((E)-3-(4-chloro-2-fluoro-3-(hydroxymethyl)phenyl)-3-hydroxyprop-1-en-1-yl)-3-hydroxyphenyl)-3-cyclopropyl-2-methylpropanoate.

Step 5: (2S, 3R)-methyl 3-(4-(3-(3-(((tert-butyldimethylsilyl)oxy)methyl)-4-chloro-2-fluorophenyl)-3-hydroxypropyl)-3-hydroxyphenyl-3-cyclopropyl-2-methylpropanoate To a solution of (2S, 3R)-methyl 3-(4-(3-(3-(((tert-butyldimethylsilyl)oxy)methyl)-4-chloro-2-fluorphenyl) 3-oxopropyl)-3-hydroxyphenyl)-3-cyclopropyl-2-methylpropanoate (1.00 g, 1.78 mmol) in MeOH (15 mL) cooled in an ice bath was added NaBH$_4$ (0.134 g, 3.55 mmol). The reaction was stirred at 18° C. for 2 h, and then concentrated. Water (20 mL) was added, and their reaction mixture was extracted with EtOAc (20 mL×2). The combined organic layers were washed with brine (30 mL), and dried over anhydrous Na$_2$SO$_4$. The mixture was filtered and the filtrate was concentrated to give the crude product, which was purified by flash silica gel chromatography (ISCO®; 20 g SepaFlash® Silica Flash Column, Eluent of 0~25% EA/PE gradient at 40 mL/min) to give the title compound.

Step 6: (2S, 3R)-methyl 3-(4-(3-(3-(((tert-butyldimethylsilyl)oxy)methyl)-4-chloro-2-fluorophenyl)-3-hydroxypropyl)-3-hydroxyphenyl)-3-cyclopropyl-2-methylpropanoate To a solution of (2S, 3R)-methyl 3-(4-((E)-3-(3-(((tert-butyldimethylsilyl)oxy)methyl)-4-chloro-2-fluorophenyl)-3-hydroxyprop-1-en-1-yl)-3-hydroxyphenyl)-3-cyclopropyl-2-methylpropanoate (570 mg, 1.01 mmol) in MeOH (50 mL) was added platinum (IV) oxide (80.0 mg, 0.352 mmol). The reaction was stirred at 18° C. for 1 h under H$_2$ (15 psi). The mixture was then filtered and concentrated to give the title compound, which was used in the next step directly.

Step 7: (2S, 3R)-methyl 3-(2-(3-(((tert-butyldimethylsilyl)oxy)methyl)-4-chloro-2-fluorophenyl)chroman-7-yl)-3-cyclopropyl-2-methylpropanoate DIAD (0.289 mL, 1.49 mmol) was added dropwise to a solution of (2S, 3R)-methyl 3-(4-(3-(3-(((tert-butyldimethylsilyl)-oxy)methyl)-4-chloro-2-fluorophenyl)-3-hydroxypropyl)-3-hydroxyphenyl)-3-cyclopropyl-2-methylpropanoate (700 mg, 1.24 mmol) and Ph$_3$P (390 mg, 1.49 mmol) in DCM (10 mL) cooled in an ice bath. The reaction was stirred at 0° C. for 1 h, then warmed to 18° C. and stirred for 15 h. The reaction mixture was then concentrated in vacuo to give a residue, which was purified by flash silica gel chromatography (ISCO®; 12 g SepaFlash® Silica Flash Column, Eluent of 0~5% EA/PE gradient at 30 mL/min) to give the title compound.

Step 8: (2S, 3R)-methyl 3-(2-(3-(((tert-butyldimethylsilyl)oxy)methyl)-2-fluoro-4-(5-fluoro-2-methoxypyridin-4-yl)phenyl)chroman-7-yl)-3-cyclopropyl-2-methylpropanoate To a solution of (2S, 3R)-methyl 3-(2-(3-(((tert-butyldimethylsilyl)oxy)methyl)-4-chloro-2-fluorophenyl)chroman-7-yl)-3-cyclopropyl-2-methylpropanoate (900 mg, 1.65 mmol), ((5-fluoro-2-methoxypyridin-4-yl)boronic acid (562 mg, 3.29 mmol) and potassium phosphate tribasic (1.05 g, 4.93 mmol) in 1,4-dioxane (12 mL) and water (4.0 mL) was added 2nd Generation XPhos precatalyst (129 mg, 0.164 mmol). The reaction was stirred at 80° C. for 2 h under N$_2$, and then concentrated. Water (30 mL) was added, and the reaction mixture was extracted with EtOAc (50 mL×3). The combined organic layers were washed with brine (80 mL), and dried over anhydrous Na$_2$SO$_4$. The mixture was filtered and the filtrate was concentrated to give the title compound, which was used to the next step without further purification.

Step 9: (2S, 3R)-methyl 3-cyclopropyl-3-(2-(2-fluoro-4-(5-fluoro-2-methoxypyridin-4-yl)-3-(hydroxymethyl)phenyl)chroman-7-yl)-2-methylpropanoate To a solution of (2S, 3R)-methyl 3-(2-(3-(((tert-butyldimethylsilyl)oxy)methyl)-2-fluoro-4-(5-fluoro-2-methoxypyridin-4-yl)-phenyl)chroman-7-yl)-3-cyclopropyl-2-methylpropanoate (1.00 g, 0.972 mmol) in DCM (20 mL) was added TBAF (1.94 mL, 1.94 mmol). The reaction was stirred at 18° C. for 20 h, then water (50 mL) was added, and the reaction mixture was extracted with DCM (50 mL×2). The combined organic layers were washed with brine (100 mL), and dried over anhydrous Na$_2$SO$_4$. The mixture was filtered and the filtrate was concentrated. The resulting crude product was purified by flash silica gel chromatography (ISCO®; 20 g SepaFlash® Silica Flash Column, Eluent of 0~20% EA/PE gradient at 40 mL/min) to give the title compound.

Step 10: (2S, 3R)-methyl 3-cyclopropyl-3-(2-(2-fluoro-4-(5-fluoro-2-methoxypy-ridin-4-yl)-3-(((methylsulfonyl)oxy)methyl)phenyl)chroman-7-yl)-2-methylpropanoate To a solution of (2S, 3R)-methyl 3-cyclopropyl-3-(2-(2-fluoro-4-(5-fluoro-2-methoxypyridin-4-yl)-3-(hydroxymethyl)phenyl)-chroman-7-yl)-2-methylpropanoate (300 mg, 0.573 mmol) and TEA (0.120 ml, 0.859 mmol) in DCM (15 mL) was added MsCl (0.054 mL, 0.688 mmol) at 0° C. The mixture was stirred at 0° C. for 2 h, then concentrated and poured into water (30 mL). The reaction mixture was extracted with EtOAc (50 mL×3). The combined organic layers were washed with brine (saturated, 50 mL), dried (Na$_2$SO$_4$), filtered and the filtrate was evaporated under reduced pressure to give the title compound, which was used to the next step without purification.

Step 11: (2S, 3R)-methyl 3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoate To a mixture of pyrrolidine (106 mg, 1.50 mmol) and (2S, 3R)-methyl 3-cyclopropyl-3-(2-(2-fluoro-4-(5-fluoro-2-methoxypyridin-4-yl)-3-(((methylsulfonyl)oxy)methyl)phenyl)chroman-7-yl)-2-methyl-propanoate (300 mg, 0.499 mmol) in MeCN (10 mL) were added K$_2$CO$_3$ (413 mg, 2.99 mmol) and sodium iodide (448 mg, 2.99 mmol). The reaction was stirred at 50° C. for 12 h and then allowed to reach room temperature. Then the reaction mixture was concentrated, and water (30 mL) was added. The reaction mixture was extracted with EtOAc (30 mL×3). The combined organic layers were washed with brine (50 mL), and dried over anhydrous Na$_2$SO$_4$. The mixture was filtered and the filtrate was concentrated to give the title compound, which was used in the next step directly.

Step 12: (2S, 3R)-3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoic acid To (2S, 3R)-methyl 3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoate (280 mg, 0.486 mmol) in a co-solution of MeOH (4 mL), THF (4 mL) and Water (2 mL) was added LiOH (233 mg, 9.71 mmol). The reaction was stirred at 50° C. for 64 h, then concentrated and neutralized with aqueous HCl (1 M) to pH 4~5. Water (30 mL) was added, and the reaction mixture was extracted with ethyl acetate (50 mL×3). The combined organic layers were washed with brine (saturated, 80 mL), dried over $Na_2SO_4$, filtered and concentrated. The resulting residue was purified by reverse preparative HPLC (EB instrument fitted with a Phenomenex Synergi C18 150*30 mm*4 um, Mobile phase A: water (containing 0.1% TFA, v/v), B: acetonitrile. Gradient: 35-55% B, 0-10 min; 100% B, 10.5-12.5 min; 5% B, 13-15 min) to give (2S, 3R)-3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoic acid. $^1$H NMR (400 MHz, MeOD) δ=8.21 (s, 1H), 7.85 (t, J=7.61 Hz, 1H), 7.34 (d, J=7.94 Hz, 1H), 7.07 (d, J=7.72 Hz, 1H), 6.90 (d, J=4.63 Hz, 1H), 6.75 (d, J=7.94 Hz, 1H), 6.70 (s, 1H), 5.46 (d, J=9.92 Hz, 1H), 4.31-4.63 (m, 2H), 3.96 (s, 3H), 3.50 (br. s., 2H), 2.97-3.10 (m, 2H), 2.64-2.92 (m, 3H), 2.35 (d, J=13.45 Hz, 1H), 2.06-2.18 (m, 1H), 1.87-2.05 (m, 5H), 1.09 (d, J=4.63 Hz, 1H), 0.93 (d, J=6.84 Hz, 3H), 0.55-0.64 (m, 1H), 0.33 (d, J=5.07 Hz, 2H), −0.01 (d, J=4.19 Hz, 1H).

Step L: (2S, 3R)-3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoic acid

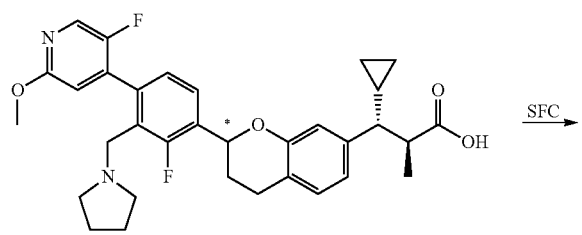

SFC

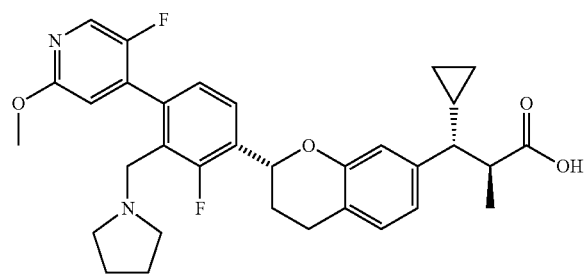 [SMILES: COc1cc(-c2ccc(C3CCc4ccc([C@H](C5CC5)[C@H](C)C(=O)O)cc4O3)c(F)c2CN2CCCC2)c(Cl)cn1]

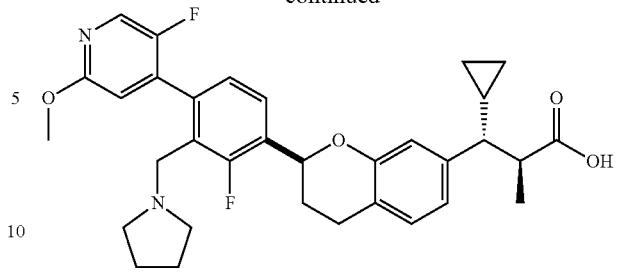

A mixture of 2 diastereomers at the * carbon alpha to the chroman oxygen of (2S, 3R)-3-cyclopropyl-3-(2-(2-fluoro-4-(5-fluoro-2-methoxypyridin-4-yl)-3-(pyrrolidin-1-ylmethyl)phenyl)-chroman-7-yl)-2-methylpropanoic acid (180 mg, 0.320 mmol) was separated via SFC (Column: Chiralpak AD-3 50*4.6 mm I.D., 3 um Mobile phase: A: $CO_2$ B: ethanol (0.05% TEA), Gradient: from 5% to 40% of B in 1.4 min and hold 40% for 1.05 min, then 5% of B for 0.35 min Flow rate: 4 mL/min Column temp.: 40 deg. C. Wavelength: 254 nm) to give: Isomer 1 (faster eluting/shorter retention time in chiral HPLC): (2S, 3R)-3-cyclopropyl-3-(2-(2-fluoro-4-(5-fluoro-2-methoxy-pyridin-4-yl)-3-(pyrrolidin-1-ylmethyl)phenyl)chroman-7-yl)-2-methylpropanoic acid ($t_R$=1.480 min); and Isomer 2 (slower eluting/longer retention time in chiral HPLC): (2S, 3R)-3-cyclopropyl-3-(2-(2-fluoro-4-(5-fluoro-2-methoxypyridin-4-yl)-3-(pyrrolidin-1-ylmethyl)phenyl)chroman-7-yl)-2-methylpropanoic acid ($t_R$=1.818 min).

Step M: Sodium Salt Formation

To a separate solution of each isomer in MeCN (5 mL) and water (10 mL) was added a solution of NaOH (1.0 eq, 0.5 M). Each reaction mixture was stirred for 1 h at room temperature, then lyophilized to give the sodium salt of (2S, 3R)-3-cyclopropyl-3-(2-(2-fluoro-4-(5-fluoro-2-methoxypyridin-4-yl)-3-(pyrrolidin-1-ylmethyl)-phenyl)chroman-7-yl)-2-methylpropanoic acid. EXAMPLE 219 (Isomer 1): MS (ESI) m/z: 563.2 [M+H]$^+$ $^1$H NMR (400 MHz, MeOD) δ=8.04 (s, 1H), 7.58 (t, J=7.63 Hz, 1H), 7.12 (d, J=8.22 Hz, 1H), 6.98 (d, J=7.43 Hz, 1H), 6.87 (d, J=4.70 Hz, 1H), 6.66-6.71 (m, 2H), 5.38 (d, J=9.00 Hz, 1H), 3.90 (s, 3H), 3.65 (br. s., 2H), 2.93-3.05 (m, 1H), 2.76 (d, J=16.04 Hz, 1H), 2.54-2.64 (m, 1H), 2.24-2.38 (m, 5H), 1.96-2.08 (m, 1H), 1.90 (t, J=9.98 Hz, 1H), 1.62 (br. s., 4H), 0.99-1.11 (m, 1H), 0.82 (d, J=7.04 Hz, 3H), 0.48-0.57 (m, 1H), 0.40 (dd, J=4.70, 9.39 Hz, 1H), 0.15-0.25 (m, 1H), −0.10 (dd, J=4.50, 8.80 Hz, 1H); EXAMPLE 220 (Isomer 2): MS (ESI) m/z: 563.3 [M+H]$^+$ $^1$H NMR (400 MHz, MEOD) δ=8.05 (s, 1H), 7.59 (t, J=7.63 Hz, 1H), 7.13 (d, J=7.83 Hz, 1H), 6.98 (d, J=7.83 Hz, 1H), 6.87 (d, J=4.70 Hz, 1H), 6.66-6.73 (m, 2H), 5.38 (d, J=9.00 Hz, 1H), 3.91 (s, 3H), 3.65 (br. s., 2H), 2.94-3.05 (m, 1H), 2.76 (d, J=16.43 Hz, 1H), 2.55-2.65 (m, 1H), 2.24-2.38 (m, 5H), 1.97-2.09 (m, 1H), 1.91 (t, J=9.98 Hz, 1H), 1.63 (br. s., 4H), 0.98-1.11 (m, 1H), 0.83 (d, J=7.04 Hz, 3H), 0.48-0.57 (m, 1H), 0.41 (dd, J=4.89, 9.19 Hz, 1H), 0.16-0.25 (m, 1H), −0.09 (dd, J=4.70, 9.00 Hz, 1H)

Example 221

(2S, 3R)-3-cyclopropyl-3-(2-(3-((diethylamino)methyl)-4-(2-methoxypyridin-4-yl)phenyl)chroman-7-yl)-2-methylpropanoic acid

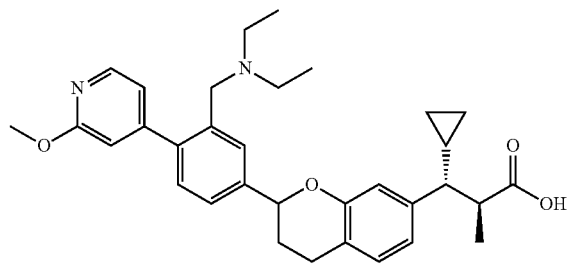 [SMILES: CCN(CC)Cc1cc(C2CCc3ccc([C@H](C4CC4)[C@H](C)C(=O)O)cc3O2)ccc1-c1ccnc(OC)c1]

Step 1: (5-bromo-2-chlorophenyl)methanol 5-bromo-2-chlorobenzoic acid (31.9 mL, 31.9 mmol) was added dropwise to a solution of 2-bromo-5-chlorobenzoic acid (5.00 g, 21.2 mmol) in THF (50 mL) at 0° C. The mixture was stirred at 10° C. for 16 h, then quenched with MeOH (30 mL) and evaporated. The resulting residue was purified by flash silica gel chromatography (ISCO®; 40 g Silica Column, eluent: 0~20% EA/PE gradient at 40 ml/min) to give the title compound.

Step 2: ((5-bromo-2-chlorobenzyl)oxy)(tert-butyl)dimethylsilane

A solution of (5-bromo-2-chlorophenyl)methanol (3.80 g, 17.2 mmol), tert-butylchlorodimethylsilane (2.84 g, 18.9 mmol), and 1H-imidazole (2.34 g, 34.3 mmol) in DMF (30 mL) was maintained with stirring at 10° C. for 16 hours. Then the reaction mixture was poured into diethyl ether (10 mL) and washed three times with 5% LiCl (15 mL). The organic layer was separated, dried over sodium sulfate, filtered, taken to a residue under reduced pressure. The residue was purified by column chromatography (SiO$_2$, petroleum ether=100%) to give the title compound.

Step 3: 3-(((tert-butyldimethylsilyl)oxy)methyl)-4-chlorobenzaldehyde

A solution of ((5-bromo-2-chlorobenzyl)oxy)(tert-butyl)dimethylsilane (4.20 g, 12.5 mmol) in THF (30 mL) was cooled to −78° C., and n-butyllithium (7.51 mL, 18.8 mmol) was added dropwise. The mixture was stirred at −78° C. for 30 min, and N,N-dimethylformamide (1.828 g, 25.02 mmol) was added dropwise. The reaction mixture was stirred at 0° C. for 1 hour under nitrogen, then quenched with saturated NH$_4$Cl (60 mL). The organic layer was washed with brine (60 mL), filtered, and the filtrate was evaporated to give the title compound.

Step 4: 1-(3-(((tert-butyldimethylsilyl)oxy)methyl)-4-chlorophenyl)prop-2-en-1-ol Vinyl magnesium bromide (10.5 ml, 10.53 mmol) was added dropwise over 20 min to a stirred, cooled 0° C. solution of 3-(((tert-butyldimethylsilyl)oxy)methyl)-4-chlorobenzaldehyde (2 g, 7.02 mmol) in THF (20 mL) under a nitrogen atmosphere. The reaction was stirred at 0° C. for 0.5 h, then concentrated, followed by the addition of saturated aqueous NH$_4$Cl (50 mL). The mixture was extracted with ethyl acetate (3×50 mL). The combined organic layers were washed with brine (100 mL), dried over Na$_2$SO$_4$, filtered. The filtrate was evaporated under reduced pressure to give the title compound.

Step 5: (2S, 3R)-methyl 3-(4-(3-(3-(((tert-butyldimethylsilyl)oxy)methyl)-4-chlorophenyl)-3-oxopropyl)-3-hydroxyphenyl-3-cyclopropyl-2-methylpropanoate To a mixture of lithium acetate (0.594 g, 9.00 mmol), 1-(3-(((tert-butyldimethylsilyl)oxy)-methyl)-4-chlorophenyl)prop-2-en-1-ol (1.40 g, 4.50 mmol), Intermediate 5 (1.08 g, 3.00 mmol), tetra-n-butylammonium chloride (2.50 g, 9.00 mmol) and lithium chloride (0.381 g, 9.00 mmol) in DMF (25 mL) was added Pd(OAc)$_2$ (0.0670 g, 0.300 mmol) under N$_2$ atmosphere. The reaction was heated to 80° C. for 16 h, then cooled to 10° C., and concentrated. Water (50 mL) was added, and the reaction mixture was extracted with ethyl acetate (100 ml×3). The combined organic layers were washed with water (100 mL), brine (200 mL), dried (Na$_2$SO$_4$), filtered and concentrated in vacuo. The resulting crude product was purified by flash silica gel chromatography (ISCO®; 40 g SepaFlash® Silica Flash Column, Eluent of 0~20% EA/PE gradient at 55 ml/min) to give the title compound.

Step 6: (2S, 3R)-methyl 3-(4-(3-(3-(((tert-butyldimethylsilyl)oxy)methyl)-4-chlorophenyl)-3-hydroxypropyl)-3-hydroxyphenyl-3-cyclopropyl-2-methylpropanoate Sodium borohydride (0.416 g, 11.0 mmol) was added to a stirred, cooled 0° C. mixture of (2S, 3R)-methyl 3-(4-(3-(3-(((tert-butyldimethylsilyl)oxy)methyl)-4-chlorophenyl)-3-oxopropyl)-3-hydroxyphenyl)-3-cyclopropyl-2-methylpropanoate (1.20 g, 2.20 mmol) in MeOH (30 mL). The reaction was stirred at 0° C. for 1 h, and then was warmed to 30° C. for 16 h. Then the reaction was quenched with aqueous ammonium chloride (saturated, 30 mL), and the reaction mixture was extracted with ethyl acetate (3×50 mL). The combined organic layers were washed with brine (saturated, 80 mL), dried (Na$_2$SO$_4$), filtered and the filtrate was evaporated under reduced pressure to give the title compound.

Step 7: (2S, 3R)-methyl 3-(2-(3-(((tert-butyldimethylsilyl)oxy)methyl)-4-chlorophenyl)-chroman-7-yl)-3-cyclopropyl-2-methylpropanoate To a solution of (2S, 3R)-methyl 3-(4-(3-(3-(((tert-butyldimethyl-silyl)oxy)methyl)-4-chlorophenyl)-3-hydroxypropyl)-3-hydroxyphenyl)-3-cyclopropyl-2-methylpropanoate (950 mg, 1.736 mmol) and triphenylphosphine (546 mg, 2.083 mmol) in DCM (30 mL) was slowly added di-isopropyl azodicarboxylate (421 mg, 2.083 mmol). The resulting mixture was stirred at 10° C. for 16 h, then concentrated in vacuo. The resulting residue was purified by preparative TLC (SiO$_2$, petroleum ether:EtOAc=3:1) to give the title compound. MS (ESI) m/z: 529[M+H]$^+$.

Step 8: (2S, 3R)-methyl 3-cyclopropyl-3-(2-(3-(hydroxymethyl)-4-(2-methoxypyridin-4-yl)phenyl)chroman-7-yl)-2-methylpropanoate To a solution of (2S, 3R)-methyl 3-(2-(3-(((tert-butyldimethylsilyl)oxy)methyl)-4-chlorophenyl)chroman-7-yl)-3- cyclopropyl-2-methylpropanoate (650 mg, 1.228 mmol) in 1, 4-dioxane (25 mL) and water (5.0 mL) were added potassium phosphate tribasic (782 mg, 3.68 mmol), 2$^{nd}$ Generation Xphos precatalyst (97.0 mg, 0.123 mmol) and 2-methoxypyridine-4-boronic acid (376 mg, 2.457 mmol) under nitrogen. The reaction mixture was stirred at 90° C. for 16 h, then water (50 mL) was added to the reaction mixture. The aqueous phase was extracted with EtOAc (150 ml×3). The combined organic layers were washed with brine (300 mL), dried over anhydrous $Na_2SO_4$ and filtered. The filtrate was concentrated under reduced pressure. The resulting crude product was purified on a SepaFlash® Silica Flash Column (Eluent of 0~50% EA/PE gradient at 40 ml/min) to give the title compound. MS (ESI) m/z: 488[M+H]$^+$ Step 9: (2S, 3R)-methyl 3-cyclopropyl-3-(2-(4-(2-methoxypyridin-4-yl)-3-(((methylsulfonyl)-oxy)methyl)phenyl)chroman-7-yl)-2-methylpropanoate Methanesulfonyl chloride (0.0720 ml, 0.923 mmol) was added in one portion to a stirred, 0° C. solution of (2S, 3R)-methyl 3-cyclopropyl-3-(2-(3-(hydroxymethyl)-4-(2-methoxypyridin-4-yl)phenyl)chroman-7-yl)-2-methylpropanoate (300 mg, 0.615 mmol) and triethylamine (0.257 ml, 1.85 mmol) in DCM (10 mL). The reaction mixture was stirred at 0° C. for 30 min, then diluted with DCM (50 mL), washed with water (3×30 mL), dried ($Na_2SO_4$), filtered. The filtrate was evaporated under reduced pressure to give the title compound, which was used to next step without further purification. LCMS (ESI) m/z: 566[M+H]$^+$ Step 10 (2S, 3R)-methyl 3-cyclopropyl-3-(2-(3-((diethylamino)methyl)-4-(2-methoxypyridin-4-yl)phenyl)chroman-7-yl)-2-methylpropanoate To a mixture of diethylamine (38.8 mg, 0.530 mmol) and (2S, 3R)-methyl 3-cyclopropyl-3-(2-(4-(2-methoxypyridin-4-yl)-3-(((methylsulfonyl)oxy)-methyl)phenyl)chroman-7-yl)-2-methylpropanoate (100 mg, 0.177 mmol) in MeCN (5.0 mL) were added $K_2CO_3$ (293 mg, 2.121 mmol) and sodium iodide (132 mg, 0.884 mmol). The reaction was stirred at 90° C. for 2 h and then allowed to reach room temperature. The precipitate was filtered off and the filtrate was concentrated. The resulting mixture was re-dissolved with ethyl acetate (15 mL). The ethyl acetate layer was washed with water (3×10 mL), dried ($Na_2SO_4$), filtered and the filtrate was evaporated under reduced pressure to give the title compound, which was used in the next step without further purification.

Step 11: (2S, 3R)-3-cyclopropyl-3-(2-(3-((diethylamino)methyl)-4-(2-methoxypyridin-4-yl)phenyl)chroman-7-yl)-2-methylpropanoic acid To a solution of (2S, 3R)-methyl 3-cyclopropyl-3-(2-(3-((diethylamino)methyl)-4-(2-methoxypyridin-4-yl)phenyl)chroman-7-yl)-2-methylpropanoate (110 mg, 0.203 mmol) in a co-solvent of MeOH (3 mL) and water (2 mL) was added lithium hydroxide (97.0 mg, 4.05 mmol). The reaction was stirred at 50° C. for 16 h under nitrogen, then concentrated. Water (10 mL) was added, and the reaction mixture was neutralized with HCl (aqueous, 1 N) to pH=5~6. The reaction mixture was extracted with ethyl acetate (3×20 mL). The combined organic layers were washed with brine (saturated, 30 mL), dried over $Na_2SO_4$, filtered and concentrated to give a residue. The residue was purified by reverse prep-HPLC (Column Phenomenex Synergi C18 250×21.2 mm×4 um Condition 0.1% TFA-ACN Begin B 30 End B 60 Gradient Time (min) 11 100% B Hold Time (min) 1.1 Flow Rate (ml/min) 40) to give (2S, 3R)-3-cyclopropyl-3-(2-(3-((diethylamino)methyl)-4-(2-methoxypyridin-4-yl)phenyl)chroman-7-yl)-2-methylpropanoic acid. MS (ESI) m/z: 529.3 [M+H]$^+$ $^1$H NMR (400 MHz, CDCl$_3$): δ=8.13 (d, J=5.3 Hz, 1H), 7.51 (s, 1H), 7.41 (d, J=7.7 Hz, 1H), 7.21 (d, J=7.7 Hz, 1H), 7.00 (d, J=7.9 Hz, 1H), 6.93 (d, J=5.1 Hz, 1H), 6.78 (s, 1H), 6.64-6.72 (m, 2H), 5.12 (d, J=7.9 Hz, 1H), 3.87-3.98 (m, 5H), 2.95 (ddd, J=16.3, 10.5, 5.6 Hz, 1H), 2.68-2.78 (m, 2H), 2.64 (t, J=5.2 Hz, 2H), 2.22 (d, =13.5 Hz, 1H), 1.98-2.11 (m, 1H), 1.89 (t, J=9.9 Hz, 1H), 1.54-1.65 (m, 2H), 1.28 (br. s., 3H), 1.02-1.13 (m, 1H), 0.91 (d, J=6.8 Hz, 3H), 0.51-0.62 (m, 1H), 0.22-0.39 (m, 6H), −0.07-0.01 (m, 1H).

Example 222

(2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid

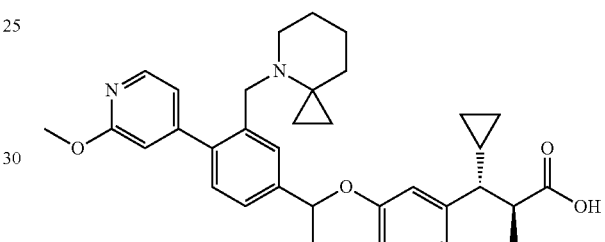

Step 1: (2S, 3R)-methyl 3-(2-(3-(4-azaspiro[2.5]octan-4-ylmethyl)-4-(2-methoxypyridin-4-yl)phenyl-chroman-7-yl)-3-cyclopropyl-2-methylpropanoate To a mixture of 4-azaspiro[2.5]octane hydrochloride (172.66 mg, 1.167 mmol) and (2S, 3R)-methyl 3-cyclopropyl-3-(2-(4-(2-methoxypyridin-4-yl)-3-(((methylsulfonyl)oxy)methyl)-phenyl)chroman-7-yl)-2-methylpropanoate (220 mg, 0.389 mmol) in MeCN (12.0 mL) were added $K_2CO_3$ (645 mg, 4.66 mmol) and sodium iodide (292 mg, 1.94 mmol). The resulting mixture was stirred at 90° C. for 2 h and then allowed to reach room temperature. The precipitate was filtered off and the filtrate was concentrated. The resulting mixture was re-dissolved with ethyl acetate (30 mL). The ethyl acetate layer was washed with water (3×10 mL), dried ($Na_2SO_4$), filtered and the filtrate was evaporated under reduced pressure to give the title compound, which was used in the next step without further purification. LCMS (ESI) m/z: 581[M+H]$^+$ Step 2: (2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid To a solution of (2S, 3R)-methyl 3-(2-(3-(4-azaspiro[2.5]octan-4-ylmethyl)-4-(2-methoxypyridin-4-yl)phenyl)chroman-7-yl)-3-cyclopropyl-2-methylpropanoate (185 mg, 0.319 mmol) in a co-solvent of MeOH (3 mL), water (2 mL) was added lithium hydroxide (153 mg, 6.37 mmol). The mixture was stirred at 50° C. for 16 h under nitrogen. The reaction was concentrated, and water (10 mL) was added.

The resulting mixture was neutralized with HCl (aqueous, 1 N) to pH 5~6, and extracted with ethyl acetate (3×20 mL). The combined organic layers were washed with brine (saturated, 30 mL), dried over Na$_2$SO$_4$, filtered and the filtrate was concentrated. The resulting residue was purified by reverse prep-HPLC (Column Agela ASB 150×25 mm×5 um Condition 0.1% TFA-ACN Begin B 36 End B 66 Gradient Time (min) 11 100% B Hold Time (min) 2 Flow Rate (ml/min)) to give the title compound.

Step 3: (2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid

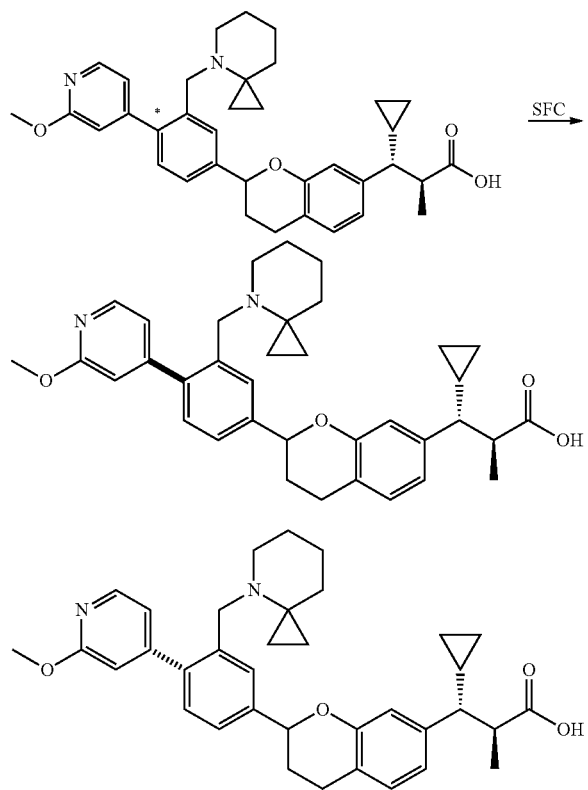

A mixture of 2 diastereomers at the * carbon alpha to the chroman oxygen of (2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid was purified via SFC to give: Isomer 1 (faster eluting) of (2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid, and Isomer 2 (slower eluting) of (2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid. EXAMPLE 222 (Isomer 2 slower eluting): MS (ESI) m/z: 567.3 [M+H]$^+$ $^1$H NMR (400 MHz, DMSO-d$_6$) δ=8.18 (d, J=5.07 Hz, 1H), 7.46 (s, 1H), 7.39 (d, J=7.94 Hz, 1H), 7.20 (d, J=7.72 Hz, 1H), 7.01 (d, J=7.72 Hz, 1H), 6.96 (d, J=5.07 Hz, 1H), 6.78 (s, 1H), 6.70 (d, J=7.72 Hz, 1H), 6.66 (s, 1H), 5.14 (d, J=8.60 Hz, 1H), 3.89 (s, 3H), 3.74 (s, 2H), 2.93 (ddd, J=5.95, 10.36, 16.32 Hz, 1H), 2.62-2.76 (m, 2H), 2.33 (br. s., 1H), 2.12-2.21 (m, 1H), 2.02 (d, J=9.26 Hz, 1H), 1.89 (t, J=9.59 Hz, 1H), 1.53 (d, J=5.29 Hz, 2H), 1.23 (br. s., 4H), 1.08 (br. s., 1H), 0.83 (d, J=6.84 Hz, 3H), 0.51 (d, J=6.84 Hz, 1H), 0.16-0.32 (m, 6H), −0.06 (d, J=4.41 Hz, 1H).

Examples 223 and 224

(2S, 3R)-3-(2-(3-(4-azaspiro[2.5]octan-4-ylmethyl)-4-(2-methoxypyridin-4-yl)phenyl)chroman-7-yl)-3-cyclopropyl-2-methylpropanoic acid

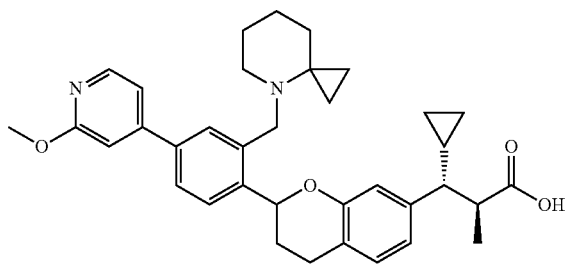 [SMILES: COc1cc(-c2ccc(C3CCc4ccc([C@H](C5CC5)[C@H](C)C(=O)O)cc4O3)c(CN3CCCCC34CC4)c2)ccn1]

Step 1: ((2-bromo-5-chlorobenzyl)oxy)(tert-butyl)dimethylsilane

A solution of (2-bromo-5-chlorophenyl)methanol (15.0 g, 67.7 mmol), tert-butylchlorodimethylsilane (11.2 g, 74.5 mmol), and 1H-imidazole (9.22 g, 135 mmol) in DCM (150 mL) was stirred at 10° C. for 16 hours. Then the reaction mixture was poured into diethyl ether (10 mL) and washed 3 times with 5% LiCl (15 mL). The organic layer was separated, dried over sodium sulfate, filtered, taken to a residue under reduced pressure. The residue was purified by column chromatography (SiO$_2$, 100% petroleum ether) to give the title compound. $^1$H NMR (400 MHz, CDCl$_3$) δ=7.70 (s, 1H), 7.32 (dd, J=1.98, 8.38 Hz, 1H), 7.17 (d, J=8.38 Hz, 1H), 4.75 (s, 2H), 0.98 (s, 9H), 0.15 (s, 6H).

Step 2: 2-(((tert-butyldimethylsilyloxy)methyl)-4-chlorobenzaldehyde

A solution of ((2-bromo-5-chlorobenzyl)oxy)(tert-butyl)dimethylsilane (11 g, 32.8 mmol) in THF (150 mL) was cooled to −78° C., and n-butyllithium (19.66 ml, 49.1 mmol) was added dropwise. The mixture was stirred at −78° C. for 30 min, and N,N-dimethylformamide (4.79 g, 65.5 mmol) was added dropwise. The reaction mixture was stirred at 0° C. for 1 hour under nitrogen, then quenched with saturated NH$_4$Cl (10 mL). The organic layer was separated, washed with brine (20 mL), filtered, and the filtrate was evaporated to give the title compound, which was used directly in next step without further purification.

Step 3: 1-(2-(((tert-butyldimethylsilyl)oxy)methyl)-4-chlorophenyl)prop-2-en-1-ol Vinylmagnesium bromide (21.6 ml, 21.6 mmol) was added dropwise over 20 minutes to a stirred, cooled 0° C. solution of 2-(((tert-butyl-dimethylsilyl)oxy)methyl)-4-chlorobenzaldehyde (4.1 g, 14.39 mmol) in THF (40 mL) under a nitrogen atmosphere. The mixture was stirred at 0° C. for 0.5 h, then concentrated. Saturated aqueous NH$_4$Cl (50 mL) was added and the mixture was extracted with ethyl acetate (3×50 mL). The combined organic layers were washed with brine (100 mL), dried over Na$_2$SO$_4$, filtered and the filtrate was evaporated under reduced pressure to give the title compound, which was used directly in next without further purification.

Step 4: (2S, 3R)-methyl 3-(4-(3-(2-(((tert-butyldimethylsilyl)oxy)methyl-4-chlorophenyl)-3-oxopropyl)-3-hydroxyphenyl)-3-cyclopropyl-2-methylpropanoate To a mixture of lithium acetate (1.10 g, 16.7 mmol), 1-(2-(((tert-butyldimethylsilyl)oxy)methyl)-4-chlorophenyl)prop-2-en-1-ol (2.61 g, 8.33 mmol), (2S, 3R)-methyl 3-cyclopropyl-3-(3-hydroxy-4-iodophenyl)-2-methyl propanoate (2 g, 5.55 mmol), tetra-n-butylammonium chloride (4.63 g, 16.66 mmol) and lithium chloride (0.706 g, 16.66 mmol) in DMF (50 mL) was added PdOAc$_2$ (0.125 g, 0.555 mmol) under a N$_2$ atmosphere. Then the resulting mixture was heated at 80° C. for 16 hours. After cooling to 10° C., the mixture was concentrated and water (50 mL) was added. The mixture was extracted with ethyl acetate (100 mL×3). The combined organic layers were washed with water (100*1), brine (200 mL), dried (Na$_2$SO$_4$), filtered and concentrated in vacuo to afford the crude product, which was purified by flash silica gel chromatography (ISCO®; 40 g SepaFlash® Silica Flash Column, Eluent of 0~20% EA/PE gradient at 55 mL/min) to give (2S, 3R)-methyl 3-(4-((E)-3-(2-(((tert-butyldimethylsilyl)-oxy)methyl)-4-chlorophenyl)-3-hydroxyprop-1-en-1-yl)-3-hydroxyphenyl)-3-cyclopropyl-2-methylpropanoate and (2S, 3R)-methyl 3-(4-(3-(2-(((tert-butyldimethylsilyl)oxy)-methyl)-4-chlorophenyl)-3-oxopropyl)-3-hydroxyphenyl)-3-cyclopropyl-2-methylpropanoate.

Step 5: (2S, 3R)-methyl 3-(4-(3-(2-(((tert-butyldimethyl)-4-chlorophenyl)-3-hydroxypropyl)-3-hydroxyphenyl)-3-cyclopropyl-2-methylpropanoate Sodium borohydride (0.867 g, 22.93 mmol) was added to a stirred, cooled 0° C. mixture of (2S, 3R)-methyl 3-(4-(3-(2-(((tert-butyldimethylsilyl)oxy)methyl)-4-chlorophenyl)-3-oxopropyl)-3-hydroxyphenyl)-3-cyclopropyl-2-methylpropanoate (2.50 g, 4.59 mmol) in MeOH (60 mL). The resulting mixture was stirred at 0° C. for 1 h, then warmed to 30° C. for 16 hours. The reaction was quenched with aqueous ammonium chloride (saturated, 30 mL), and the resulting mixture was extracted with ethyl acetate (3×50 mL). The combined organic layers were washed with brine (saturated, 80 mL), dried (Na$_2$SO$_4$), filtered and the filtrate was evaporated under reduced pressure to give the title compound, which was used directly in next step. MS (ESI) m/z: 569.0 [M+Na$^+$].

Step 6: (2S, 3R)-methyl 3-(2-(2-(((tert-butyldimethylsilyl)oxy)methyl)-4-chlorophenyl)chroman-7-yl)-3-cyclopropyl-2-methylpropanoate Triphenylphosphine (1.150 g, 4.39 mmol) was added dropwise to a solution of (2S, 3R)-methyl 3-(4-(3-(2-(((tert-butyldimethylsilyl)oxy)methyl)-4-chlorophenyl)-3-hydroxypropyl)-3-hydroxyphenyl)-3-cyclopropyl-2-methylpropanoate (2 g, 3.65 mmol) and diisopropyl azodicarboxylate (0.887 g, 4.39 mmol) in DCM (60 mL) cooled in an ice bath under nitrogen atmosphere. The resulting mixture was stirred at 10° C. for 16 h, then concentrated in vacuo to give a residue, which was purified by silica gel chromatograph (SiO$_2$, petroleum ether: EtOAc=3:1) to give the title compound. MS (ESI) m/z: 551.2 [M+Na]+

Step 7: (2S, 3R)-methyl 3-cyclopropyl-3-(2-(2-(hydroxymethyl)-4-(2-methoxypyridin-4-yl)phenyl) chroman-7-yl)-2-methylpropanoate To a solution of (2S, 3R)-methyl 3-(2-(2-(((tert-butyldimethylsilyl)oxy)methyl)-4-chlorophenyl)chroman-7-yl)-3-cyclopropyl-2-methylpropanoate (1.30 g, 2.46 mmol) in 1,4-dioxane (25 mL) and water (5.0 mL) were added potassium phosphate tribasic (1.56 g, 7.37 mmol), 2$^{nd}$ Generation XPhos precatalyst (0.193 g, 0.246 mmol) and (2-methoxypyridin-4-yl)boronic acid (0.751 g, 4.91 mmol) under nitrogen. The reaction mixture was stirred at 90° C. for 16 h, then concentrated in vacuo and purified via silica gel chromatography (SiO$_2$, PE/EA=10:1) to give the title compound.

Step 8: (2S, 3R)-methyl 3-cyclopropyl-3-(2-(2-(hydroxymethyl)-4-(2-methoxypyridin-4-yl)phenyl) chroman-7-yl)-2-methylpropanoate To a solution of (2S, 3R)-methyl 3-(2-(2-(((tert-butyldimethylsilyl)oxy)methyl)-4-(2-methoxypyridin-4-yl)phenyl) chroman-7-yl)-3-cyclopropyl-2-methylpropanoate (500 mg, 0.831 mmol) in THF (20 mL) was added TBAF (2.492 ml, 2.492 mmol). The reaction mixture was stirred at 15° C. for 16 hour under nitrogen, then concentrated in vacuo. DCM (20 mL) was added to the residue and the mixture was washed with water (20 ml×2) and purified via silica gel chromatography (SiO$_2$, PE/EA=5:1) to give the title compound.

Step 9: (2S, 3R)-methyl 3-cyclopropyl-3-(2-(4-(2-methoxypyridin-4-yl)-2-(((methylsulfonyl)-oxy) methyl)phenyl)chroman-7-yl)-2-methylpropanoate Methanesulfonyl chloride (0.120 mL, 1.54 mmol) was added to a stirred, cooled 0° C. solution of (2S, 3R)-methyl 3-cyclopropyl-3-(2-(2-(hydroxymethyl)-4-(2-methoxypyridin-4-yl)phenyl)chroman-7-yl)-2-methylpropanoate (500 mg, 1.025 mmol) and trimethylamine (0.429 ml, 3.08 mmol) in DCM (20 mL) as one portion, and the mixture was stirred at 0° C. for 30 min. Then the reaction mixture was diluted with DCM (50 mL), washed with water (3×30 mL), dried (Na$_2$SO$_4$), filtered and the solvent was evaporated under reduced pressure to give the title compound, which was used in the next step without further purification. MS (ESI) m/z: 506.2[M+H]$^+$ Step 10: (2S, 3R)-methyl 3-(2-(2-(4-azaspiro[2.5] octan-4-ylmethyl)-4-(2-methoxypyridin-4-yl)phenyl) chroman-7-yl)-3-cyclopropyl-2-methylpropanoate To a mixture of 4-azaspiro[2.5]octane hydrochloride (201 mg, 1.364 mmol) and (2S, 3R)-methyl 3-(2-(2-(chloromethyl)-4-(2-methoxypyridin-4-yl)phenyl)chroman-7-yl)-3-cyclopropyl-2-methylpropanoate (230 mg, 0.455 mmol) in MeCN (15.0 mL) were added K$_2$CO$_3$ (565 mg, 4.09 mmol) and sodium iodide (68.1 mg, 0.455 mmol). The resulting mixture was stirred at 90° C. for 2 h and then allowed to reach room temperature. The precipitate was filtered off and the filtrate was concentrated. The resulting mixture was re-dissolved with ethyl acetate (30 mL). The ethyl acetate layer was washed with water (3×10 mL), dried (Na$_2$SO$_4$), filtered and the filtrate was evaporated under reduced pressure to give the title compound, which was used in the next step without further purification. LC/MS (ESI) m/z: 581.0 [M+H]$^+$ Step 11: (2S, 3R)-3-(2-(2-(4-azaspiro[2.5]octan-4-ylmethyl)-4-(2-methoxypyridin-4-yl)phenyl)chroman-7-yl)-3-cyclopropyl-2-methylpropanoic acid To a solution of (2S, 3R)-methyl 3-(2-(2-(4-azaspiro[2.5]octan-4-ylmethyl)-4-(2-methoxypyridin-4-yl)phenyl)chroman-7-yl)-3-cyclopropyl-2-methylpropanoate (250 mg, 0.430 mmol) in a co-solvent of MeOH (10 mL), water (6 mL) and THF (10.00 mL) was added lithium hydroxide (206 mg, 8.61 mmol). The mixture was stirred at 50° C. for 16 h under nitrogen. Then the reaction mixture was concentrated. Water (10 mL) was added, and the resulting mixture was neutralized with HCl (1 N) to pH=5~6, and extracted with ethyl acetate (3×20 mL). The combined organic layers were washed with brine (saturated, 30 mL), dried over Na$_2$SO$_4$, filtered and concentrated to give a (2S, 3R)-3-(2-(2-(4-azaspiro[2.5]octan-4-ylmethyl)-4-(2-methoxypyridin-4-yl)phenyl)chroman-7-yl)-3-cyclopropyl-2-methylpropanoic acid.

Step 12: (2S, 3R)-3-(2-(2-(4-azaspiro[2.5]octan-4-ylmethyl)-4-(2-methoxypyridin-4-yl)phenyl)chroman-7-yl)-3-cyclopropyl-2-methylpropanoic acid

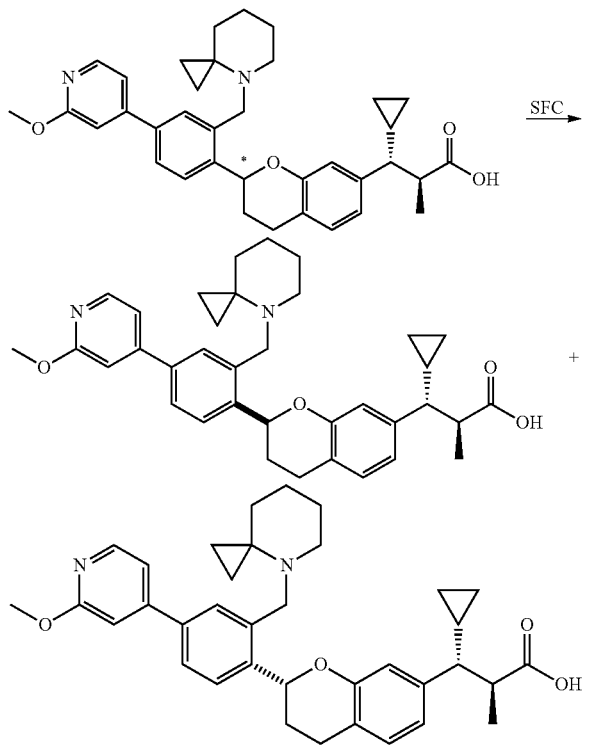

A mixture of 2 diastereomers at the * carbon alpha to the chroman oxygen of (2S, 3R)-3-(2-(2-(4-azaspiro[2.5]octan-4-ylmethyl)-4-(2-methoxypyridin-4-yl)phenyl)chroman-7-yl)-3-cyclopropyl-2-methylpropanoic acid (230 mg, 0.406 mmol) was separated via SFC (Column: Chiralpak AD-3 50*4.6 mm I.D., 3 um Mobile phase: A: CO$_2$ B: ethanol (0.05% DEA), Gradient: from 5% to 40% of B in 4.5 min and hold 40% for 2.5 min, then 5% of B for 1 min Flow rate: 2.8 mL/min Column temp.: 40 deg. C. Wavelength: 254 nm") to give Isomer 1 (faster eluting with a shorter retention time in chiral HPLC): (2S, 3R)-3-(2-(2-(4-azaspiro[2.5]octan-4-ylmethyl)-4-(2-methoxypyridin-4-yl)phenyl)chroman-7-yl)-3-cyclopropyl-2-methylpropanoic acid; and Isomer 2 (slower eluting with a longer retention time in chiral HPLC): ((2S, 3R)-3-(2-(2-(4-azaspiro[2.5]octan-4-ylmethyl)-4-(2-methoxypyridin-4-yl)phenyl)chroman-7-yl)-3-cyclopropyl-2-methylpropanoic acid. EXAMPLE 223 (Peak 1 isomer): LCMS (MS (ESI) m/z: 567.3 [M+H]$^+$ $^1$H NMR (400 MHz, MeOD) δ=8.17 (d, J=5.29 Hz, 1H), 7.61-7.70 (m, 3H), 7.25 (d, J=5.29 Hz, 1H), 7.01-7.09 (m, 2H), 6.71 (d, J=7.72 Hz, 1H), 6.65 (s, 1H), 5.36 (d, J=10.36 Hz, 1H), 4.61 (br. s., 1H), 4.06-4.16 (m, 2H), 3.96 (s, 3H), 2.67-2.92 (m, 5H), 2.19 (br. s., 1H), 1.87-1.97 (m, 2H), 1.75 (br. s., 3H), 1.48 (br. s., 1H), 1.28 (br. s., 1H), 1.04-1.19 (m, 2H), 0.93 (d, J=6.84 Hz, 3H), 0.54-0.68 (m, 3H), 0.42 (s, 2H), 0.32 (d, =5.73 Hz, 2H), 0.00 (br. s., 1H). EXAMPLE 224 (Peak 2 isomer): LCMS (MS (ESI) m/z: 567.3 [M+H]$^+$ $^1$H NMR (400 MHz, MeOD) δ 7.86 (d, J=5.29 Hz, 1H), 7.31-7.41 (m, 3H), 6.94 (d, J=4.41 Hz, 1H), 6.70-6.77 (m, 2H), 6.40 (d, J=7.50 Hz, 1H), 6.34 (s, 1H), 5.04 (d, J=10.14 Hz, 1H), 3.77-3.90 (m, 2H), 3.64 (s, 3H), 3.29 (q, J=7.06 Hz, 1H), 2.60-2.70 (m, 1H), 2.38-2.53 (m, 4H), 1.88 (d, J=7.94 Hz, 1H), 1.58-1.67 (m, 2H), 1.44 (br. s., 3H), 1.17 (d, J=6.84 Hz, 2H), 0.97 (br. s., 2H), 0.84-0.88 (m, 1H), 0.77 (d, J=5.07 Hz, 1H), 0.57-0.65 (m, 4H), 0.35 (d, J=9.92 Hz, 1H), 0.26 (d, J=6.39 Hz, 2H), 0.12 (s, 2H), −0.03-0.05 (m, 2H), −0.32 (d, J=5.29 Hz, 1H).

Example 225

Sodium (2S,3R)-3-cyclopropyl-3-((S)-2-(3-((diisopropylamino)methyl)-4-(5-fluoro-2-methoxypyridin-4-yl)phenyl)chroman-7-yl)-2-methylpropanoate

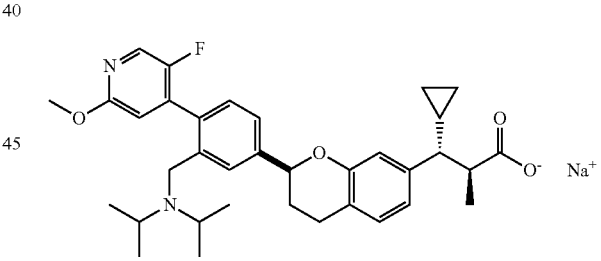

Step 1: Methyl (2S,3R)-3-cyclopropyl-3-((S)-2-(4-(5-fluoro-2-methoxypyridin-4-yl)-3-(hydroxymethyl)phenyl)chroman-7-yl)-2-methylpropanoate To a solution of (2S,3R)-methyl 3-cyclopropyl-3-((S)-2-(4-(5-fluoro-2-methoxypyridin-4-yl)-3-formylphenyl)chroman-7-yl)-2-methylpropanoate (11 g, 21.84 mmol, Intermediate 4b) in MeOH (218 mL) at 0° C. was added sodium borohydride (3.31 g, 87 mmol). The resulting solution was warmed to r.t. After 30 minutes, the reaction was recooled to 0° C. and quenched slowly with water. The MeOH was removed and the mixture was partitioned between EtOAc and brine. The organic layer was separated, dried over MgSO$_4$ and concentrated in vacuo to give the title compound. LC/MS (m/z): 506.6 (M+H)$^+$.

Step 2: Methyl (2S,3R)-3-cyclopropyl-3-((S)-2-(4-(5-fluoro-2-methoxypyridin-4-yl)-3-(((methylsulfonyl)oxy)methyl)phenyl)chroman-7-yl)-2-methylpropanoate To a solution of (2S,3R)-methyl 3-cyclopropyl-3-((S)-2-(4-(5-fluoro-2-methoxypyridin-4-yl)-3-(hydroxyl-methyl)phenyl)-chroman-7-yl)-2-methylpropanoate (11.17 g, 22.09 mmol) in CH$_2$Cl$_2$ (110 mL) at 0° C. was added TEA (6.16 ml, 44.2 mmol), followed by methanesulfonyl chloride (1.808 ml, 23.20 mmol). The resulting mixture was stirred at 0° C. for 1 h, then partitioned between CH$_2$Cl$_2$ and water. The organic layer was dried over MgSO$_4$, concentrated, and purified by ISCO (220 g, 0-30% EtOAc/hexanes) to give the title compound. LC/MS (m/z): 584.5 (M+H)$^+$.

Step 3: Methyl (2S,3R)-3-cyclopropyl-3-((S)-2-(3-((diisopropylamino)methyl)-4-(5-fluoro-2-methoxypyridin-4-yl)phenyl)chroman-7-yl)-2-methylpropanoate A solution of (2S,3R)-methyl 3-cyclopropyl-3-((S)-2-(4-(5-fluoro-2-methoxypyridin-4-yl)-3-(((methylsulfonyl)oxy)methyl)-phenyl)chroman-7-yl)-2-methylpropanoate (8.35 g, 14.31 mmol), diisopropylamine (4.04 ml, 28.6 mmol), sodium iodide (1.072 g, 7.15 mmol) and Cs$_2$CO$_3$ (6.99 g, 21.46 mmol) in acetonitrile (143 ml) was heated at 50° C. overnight. The reaction mixture was diluted with H$_2$O, extracted with EtOAc (3×), washed with brine, dried over MgSO$_4$, filtered, concentrated and purified by ISCO (220 g, 0-30% EtOAc/hexanes) to give the title compound. LC/MS (m/z): 589.6 (M+H)$^+$.

Step 4: (2S,3R)-3-Cyclopropyl-3-((S)-2-(3-((diisopropylamino)methyl)-4-(5-fluoro-2-methoxypyridin-4-yl)phenyl)chroman-7-yl)-2-methylpropanoic acid To (2S,3R)-methyl 3-cyclopropyl-3-((S)-2-(3-((diisopropylamino)methyl)-4-(5-fluoro-2-methoxypyridin-4-yl)phenyl)chroman-7-yl)-2-methylpropanoate (6.69 g, 11.36 mmol) in THF (50 ml)/MeOH (50 ml)/water (33 ml) at rt was added lithium hydroxide hydrate (1.907 g, 45.5 mmol). The resulting mixture was stirred at 52° C. for 3 days. The reaction mixture was diluted with H$_2$O, and acidified with 1N HCl to pH-7. Then pH 7 buffer was added to further adjust the pH to pH 7. The MeOH and THF were removed under vacuum, and the resulting mixture was extracted with EtOAc (3×). The combined organic layers were washed with brine, dried over MgSO$_4$, filtered, concentrated, and purified by ISCO (120 g, 0-100% EtOAc/hexanes) to give the title compound. LC/MS (m/z): 575.7 (M+H)$^+$. SFC Separation: The above acid was further purified by AD-H column (4.6×150 mm; 25% IPA+(DEA)/CO$_2$. Retention time=1.8 min. The product after SFC purification was dissolved in EtOAc, washed with pH 7 buffer (2×), dried over MgSO$_4$, filtered and concentrated to give the title compound.

Step 5: Conversion to Sodium Salt

To a solution of (2S,3R)-3-Cyclopropyl-3-((S)-2-(3-((diisopropylamino)methyl)-4-(5-fluoro-2-methoxypyridin-4-yl)phenyl)chroman-7-yl)-2-methylpropanoic acid (6.6 g, 11.5 mmol) in acetonitrile (40 ml)/Water (40 ml) was added 1 M aqueous sodium hydroxide (11.5 ml, 11.5 mmol) at ambient temperature. The resulting solution was sonicated, then lyophilized to dryness to give the title compound. $^1$H NMR (500 MHz, CD$_3$OD) δ: 8.09 (s, 1H); 7.83 (s, 1H); 7.44 (d, J=7.8 Hz, 1H); 7.23 (d, J=7.8 Hz, 1H); 7.03 (d, J=7.6 Hz, 1H); 6.75 (d, J=6.5 Hz, 3H); 5.23 (d, J=9.0 Hz, 1H); 3.98 (s, 3H); 3.61 (s, 2H); 3.00 (s, 1H); 2.94 (dt, J=13.2, 6.7 Hz, 2H); 2.78 (d, J=16.4 Hz, 1H); 2.70 (s, 1H); 2.30 (br s, 1H); 2.12 (br s, 1H); 1.99 (t, J=8.9 Hz, 1H); 1.13 (br s, 1H); 0.92 (d, J=6.6 Hz, 15H); 0.61 (br s, 1H); 0.48 (br s, 1H); 0.29 (br s, 1H); 0.01 (br s, 1H). LC/MS (m/z): 575.60 (M+H)$^+$.

Example 226

Sodium (2S,3R)-3-((S)-2-(3-((tert-butyl(methyl)amino)methyl)-4-(5-fluoro-2-methoxypyridin-4-yl)phenyl)chroman-7-yl)-3-cyclopropyl-2-methylpropanoate

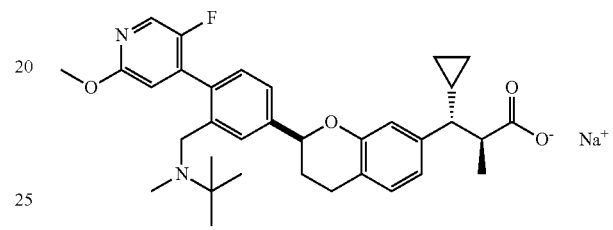

Step 1: Methyl (2S,3R)-3-((S)-2-(3-((tert-butyl(methyl)amino)methyl)-4-(5-fluoro-2-methoxypyridin-4-yl)phenyl)chroman-7-yl)-3-cyclopropyl-2-methylpropanoate A solution of (2S,3R)-methyl 3-cyclopropyl-3-((S)-2-(4-(5-fluoro-2-methoxypyridin-4-yl)-3-(((methyl-sulfonyl)oxy)methyl)-phenyl)chroman-7-yl)-2-methylpropanoate (the product of Step 2 of Example 225, 8.35 g, 14.31 mmol), N,2-dimethylpropan-2-amine (564 mg, 6.6 mmol), sodium iodide (108 mg, 0.72 mmol) and Cs$_2$CO$_3$ (700 mg, 21.46 mmol) in acetonitrile (1 ml) was heated at 50° C. for 3 days. The reaction mixture was diluted with H$_2$O, and the aqueous layer was extracted with EtOAc (3×), washed with brine, and dried over MgSO$_4$. The mixture was filtered and the filtrate was concentrated. The resulting residue was purified by gradient flash chromatography (24 g SiO$_2$ column, 0-30% EtOAc/hexanes), and purified again by gradient flash chromatography (24 g SiO$_2$ column, 0-30% EtOAc/DCM) to provide the title compound. LC/MS (m/z): 575.6 (M+H)$^+$.

Step 2: (2S,3R)-3-((S)-2-(3-((tert-butyl(methyl)amino)methyl)-4-(5-fluor-2-methoxypyridin-4-yl)phenyl)chroman-7-yl)-3-cyclopropyl-2-methylpropanoic acid To (2S,3R)-methyl 3-((S)-2-(3-((tert-butyl(methyl)amino)methyl)-4-(5-fluoro-2-methoxypyridin-4-yl)phenyl)chroman-7-yl)-3-cyclopropyl-2-methylpropanoate (664 mg, 1.2 mmol) in THF (4.5 ml)/MeOH (4.5 ml)/water (3 ml) at 25° C. was added lithium hydroxide hydrate (194 mg, 4.62 mmol). The reaction mixture was stirred at 52° C. for two days. Then the mixture was diluted with H$_2$O and acidified with 1N HCl (aqueous) to pH 7. The mixture was extracted with EtOAc, and the EtOAc layer was washed with brine, dried over MgSO$_4$, and filtered. The filtrate was concentrated, and the resulting residue was purified by gradient flash chromatography (24 g SiO$_2$ column, 0-100% EtOAc/hexanes. The product fractions were purified again using the same conditions (12 g SiO₂ column) to give (2S,3R)-3-((S)-2-(3-((tert-butyl(methyl)amino)methyl)-4-(5-fluoro-2-methoxypyridin-4-yl)phenyl)chroman-7-yl)-3-cyclopropyl-2-methylpropanoic acid. LC/MS (m/z): 561.7 (M+H)⁺.

Step 3: Sodium (2S,3R)-3-((S)-2-(3-((tert-butyl(methyl)amino)methyl)-4-(5-fluoro-2-methoxypyridin-4-yl)phenyl)chroman-7-yl)-3-cyclopropyl-2-methylpropanoate (2S,3R)-3-((S)-2-(3-((tert-butyl(methyl)amino)methyl)-4-(5-fluoro-2-methoxypyridin-4-yl)phenyl)chroman-7-yl)-3-cyclopropyl-2-methylpropanoic acid was dissolved in MeCN/H₂O (4 ml, 1:1) and treated with 1N NaOH (1.04 ml). After stirring for 30 minutes, the solution was lyophilized to dryness to give sodium (2S,3R)-3-((S)-2-(3-((tert-butyl(methyl)amino)methyl)-4-(5-fluoro-2-methoxypyridin-4-yl)phenyl)chroman-7-yl)-3-cyclopropyl-2-methylpropanoate. LC/MS (m/z): 561.7 (M+H)⁺. ¹H NMR (500 MHz, CD₃OD) δ 8.05 (s, 1H), 7.72 (s, 1H), 7.50 (d, 1H), 7.28 (d, 1H), 7.04 (d, 1H), 6.80 (m, 3H), 5.20 (d, 1H), 4.00 (s, 3H), 3.59 (br, 2H), 3.05 (m, 1H), 2.82 (m, 1H), 2.70 (m, 1H), 2.35 (m, 1H), 2.14 (m, 1H), 2.02 (s, 3H), 2.00 (t, 1H), 1.14 (m, 1H), 1.02 (s, 9H), 0.95 (d, 3H), 0.61 (m, 1H), 0.50 (m, 1H), 0.30 (m, 1H), 0.01 (m, 1H).

TABLE 19

Examples 227-249 were prepared in a similar manner to Example 225 using the appropriate starting materials.

| Example | Structure | LC/MS (M + H)⁺ |
|---|---|---|
| 227 | 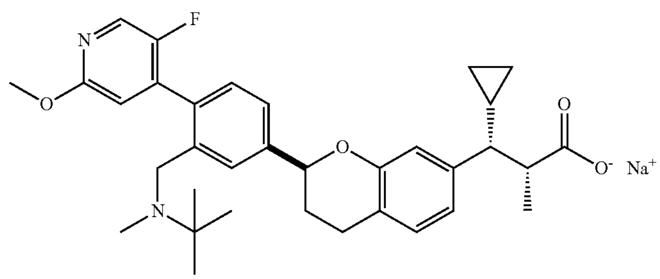 | 561.7 |
| 228 | 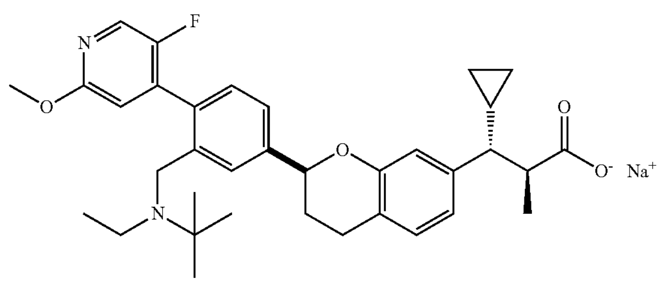 | 575.7 |
| 229 | 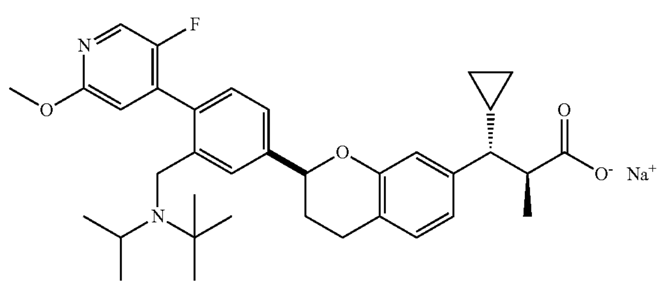 | 589.7 |
| 230 | 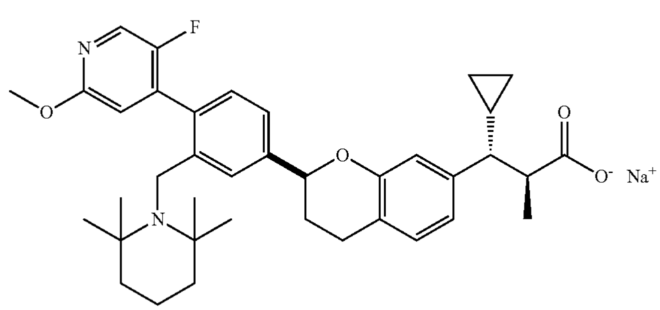 | 615.8 |

TABLE 19-continued

Examples 227-249 were prepared in a similar manner to Example 225 using the appropriate starting materials.

| Example | Structure | LC/MS (M + H)+ |
|---|---|---|
| 231 | 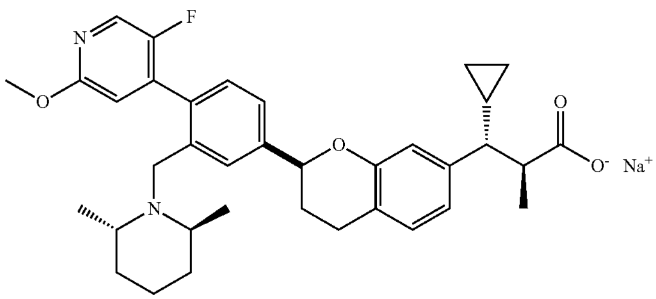 | 587.7 |
| 232 | 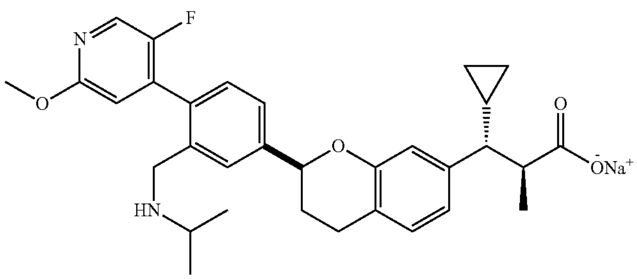 | 533.5 |
| 233 | 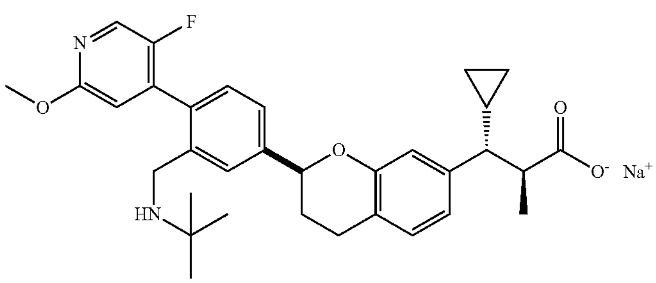 | 547.6 |
| 234 | 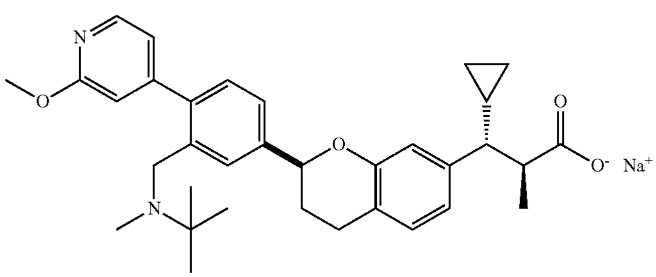 | 543.6 |
| 235 | 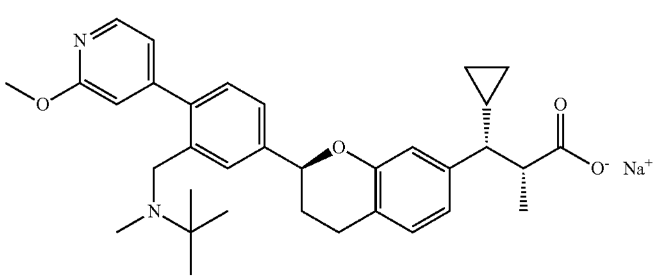 [SMILES: COc1cc(-c2ccc([C@@H]3CCc4ccc([C@H](C5CC5)[C@@H](C)C(=O)[O-])cc4O3)cc2CN(C)C(C)(C)C)ccn1 ; [Na+]] | 543.6 |

TABLE 19-continued

Examples 227-249 were prepared in a similar manner to Example 225 using the appropriate starting materials.

| Example | Structure | LC/MS (M + H)+ |
|---------|-----------|----------------|
| 236 | 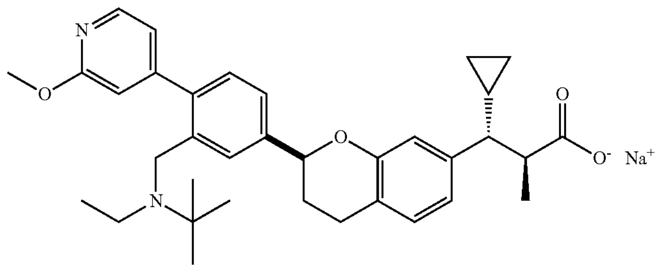 | 557.7 |
| 237 | 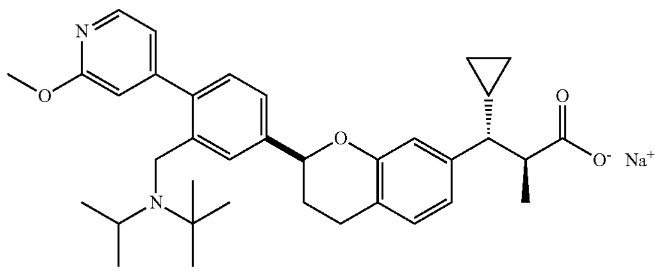 | 571.7 |
| 238 | 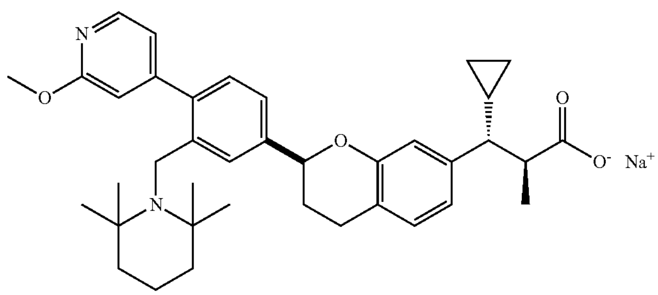 | 597.8 |
| 239 | 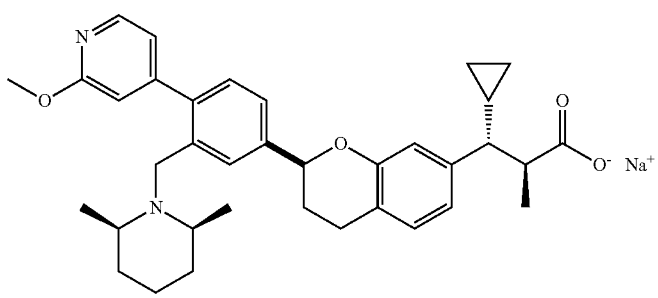 | 569.5 |
| 240 | 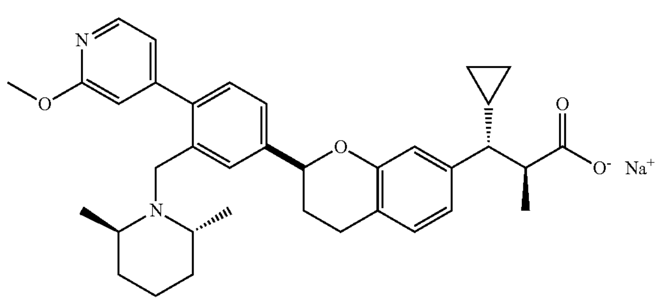 | 569.7 |

TABLE 19-continued

Examples 227-249 were prepared in a similar manner to Example 225 using the appropriate starting materials.

| Example | Structure | LC/MS (M + H)+ |
|---|---|---|
| 241 | 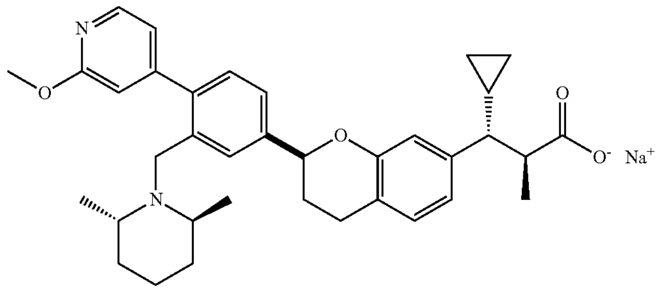 | 569.7 |
| 242 | 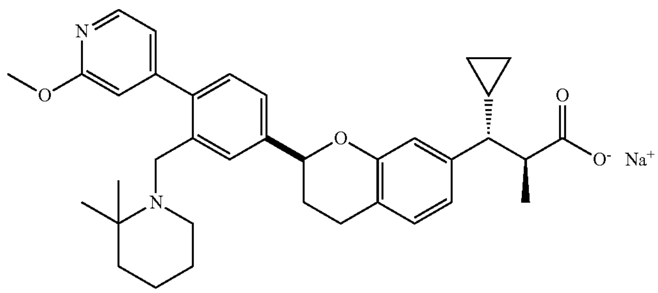 | 569.7 |
| 243 | 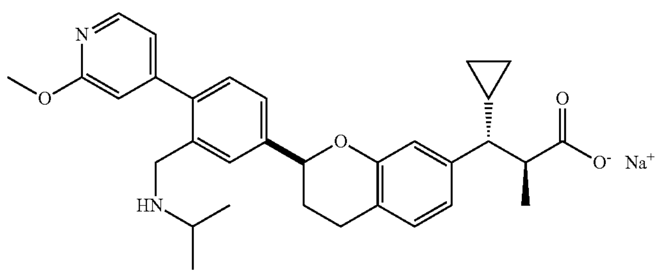 | 515.6 |
| 244 | Isomer A | 561.6 |
| 245 | Isomer B | 561.6 |

TABLE 19-continued

Examples 227-249 were prepared in a similar manner to Example 225 using the appropriate starting materials.

| Example | Structure | LC/MS (M + H)+ |
|---------|-----------|----------------|
| 246 | 2 Isomers | 547.5 |
| 247 | Isomer A | 557.7 |
| 248 | Isomer B | 557.6 |
| 249 | 2 Isomers | 541.5 |

Example 250

Sodium (2S,3R)-3-((2S)-2-(3-((3-azabicyclo[3.1.0]hexan-3-yl)methyl)-4-(5-fluoro-2-methoxypyridin-4-yl)phenyl)chroman-7-yl)-3-cyclopropyl-2-methylpropanoate

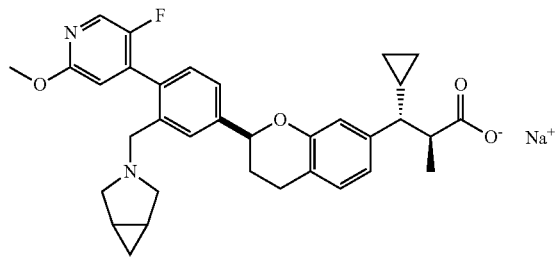 [SMILES: COc1cc(-c2ccc([C@@H]3CCc4ccc([C@H](C5CC5)[C@H](C)C(=O)[O-])cc4O3)cc2CN2CC3CC3C2)c(F)cn1 ; [Na+]]

Step 1: Methyl (2S,3R)-3-((2S)-2-(3-((3-azabicyclo[3.1.0]hexan-3-yl)methyl)-4-(5-fluoro-2-methoxypyridin-4-yl)phenyl)chroman-7-yl)-3-cyclopropyl-2-methylpropanoate To a solution of (2S,3R)-methyl 3-cyclopropyl-3-((S)-2-(4-(5-fluoro-2-methoxypyridin-4-yl)-3-formylphenyl)-chroman-7-yl)-2-methylpropanoate (70 mg, 0.139 mmol) and 3-azabicyclo[3.1.0]hexane hydrochloride (24.94 mg, 0.209 mmol) in DCE (1390 μL) at r.t was added triethylamine (58.1 μL, 0.417 mmol), followed by sodium triacetoxyborohydride (44.2 mg, 0.209 mmol) and AcOH (one drop). The resulting mixture was stirred at r.t. overnight, then partitioned between EtOAc and saturated NaHCO₃, and extracted with EtOAc. The organic layer was washed with brine, dried over MgSO₄, and concentrated in vacuo. The resulting residue was purified by Isco (12 g. 0-50% EtOAc/hexanes) to give the title compound. LC/MS (m/z): 571.50 (M+H)⁺.

Step 2: (2S,3R)-3-((2S)-2-(3-((3-azabicyclo[3.1.0]hexan-3-yl)methyl)-4-(5-fluoro-2-methoxypyridin-4-yl)phenyl)chroman-7-yl)-3-cyclopropyl-2-methylpropanoic acid Methyl (2S,3R)-3-((2S)-2-(3-((3-azabicyclo[3.1.0]hexan-3-yl)methyl)-4-(5-fluoro-2-methoxypyridin-4-yl)phenyl)chroman-7-yl)-3-cyclopropyl-2-methylpropanoate was converted to its sodium salt following the same procedure as described in Example 1 to give the title compound. LC/MS (m/z): 557.5 (M+H)⁺.

TABLE 20

Examples 251-283 were prepared in a similar manner to Example 250 using appropriate starting materials.

| Example | Structure | LC/MS |
|---|---|---|
| 251 | 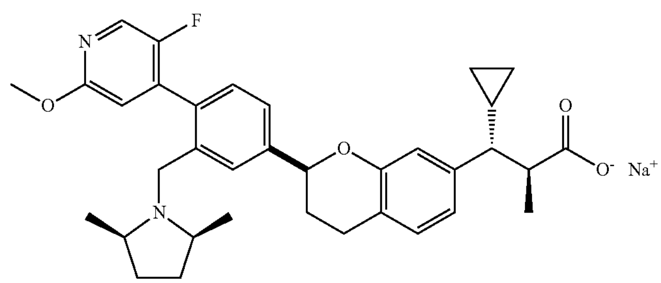 | 573.6 |
| 252 | 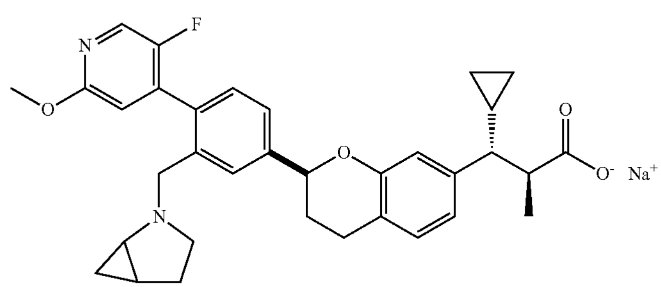 | 2 Isomers 557.5 |
| 253 | 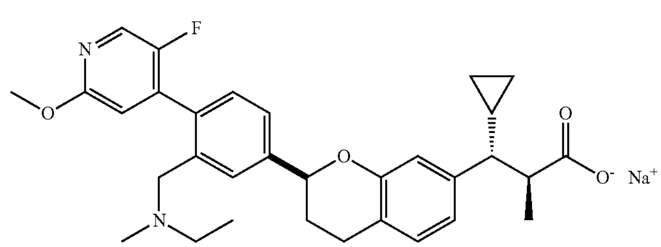 | 533.5 |

TABLE 20-continued

Examples 251-283 were prepared in a similar manner to Example 250 using appropriate starting materials.

| Example | Structure | LC/MS |
|---|---|---|
| 254 | 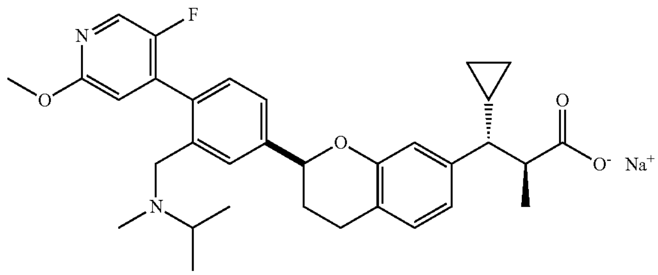 | 547.5 |
| 255 | 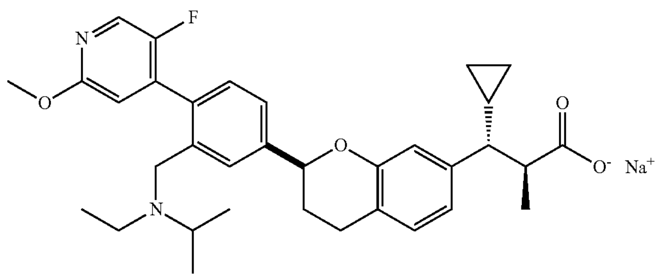 | 561.6 |
| 256a 256b | | Faster isomer 557.5 Slower isomer 557.5 OZ-H |
| 257 | 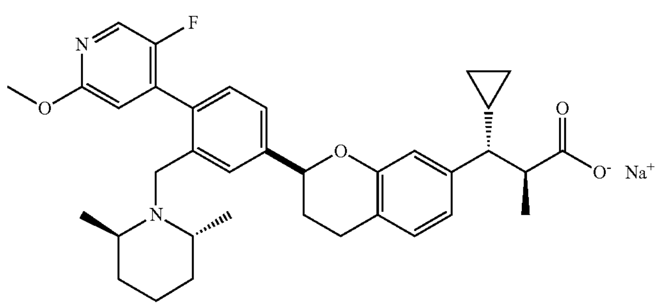 | 587.7 |
| 258a 258b | | Faster isomer 569.8 Slower isomer 569.7 OZ |

TABLE 20-continued

Examples 251-283 were prepared in a similar manner to Example 250 using appropriate starting materials.

| Example | Structure | LC/MS |
|---------|-----------|-------|
| 259 | 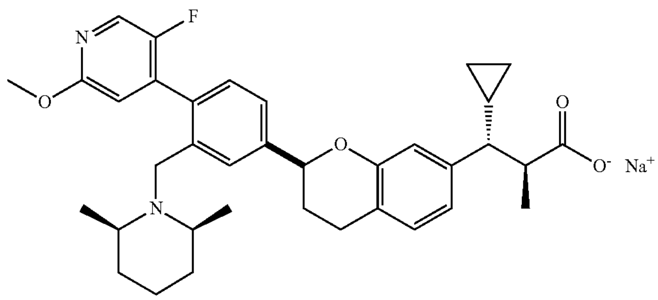 | 587.6 |
| 260 | 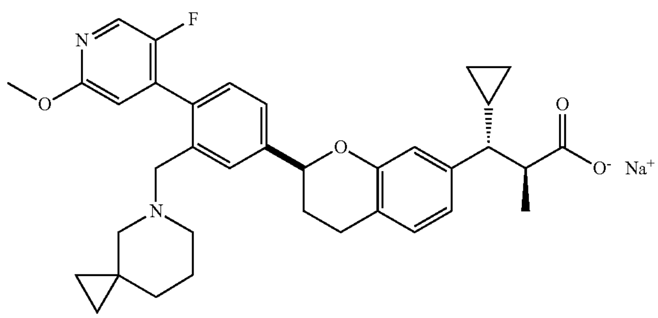 | 585.7 |
| 261 | 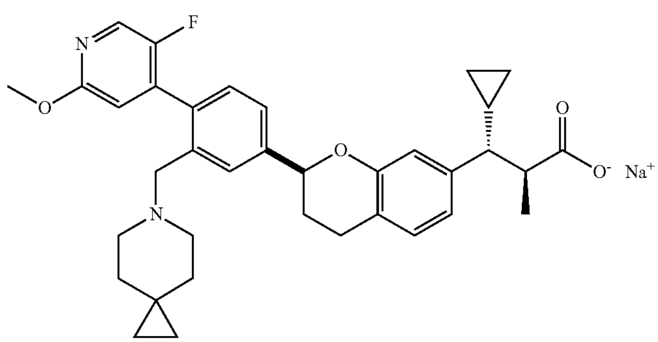 | 585.6 |
| 262 | 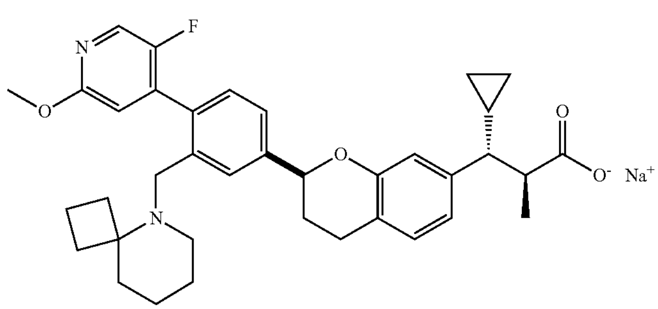 | 599.6 |

TABLE 20-continued

Examples 251-283 were prepared in a similar manner to Example 250 using appropriate starting materials.

| Example | Structure | LC/MS |
|---|---|---|
| 263 | 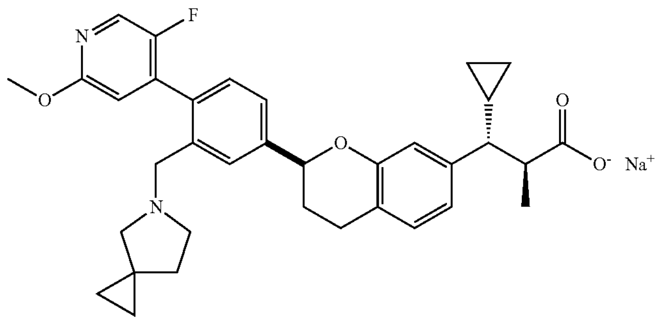 | 571.5 |
| 264 | 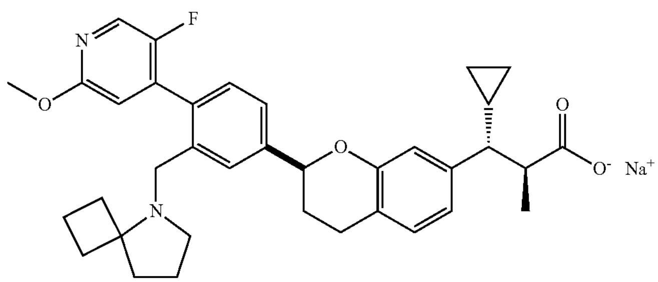 | 585.6 |
| 265 | 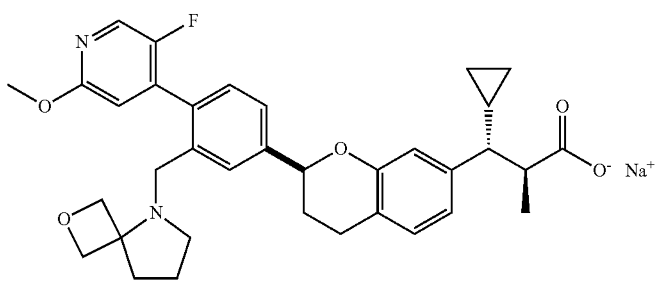 | 587.5 |
| 266 | 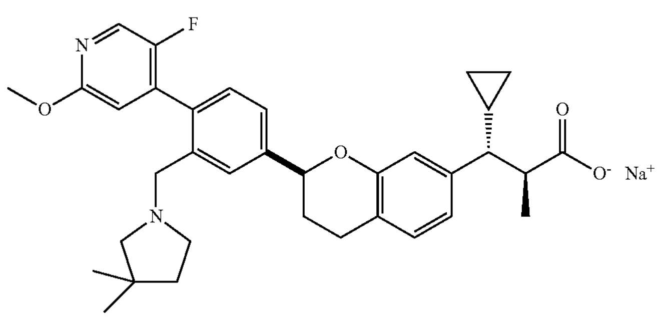 | 573.6 |
| 267a<br>267b | 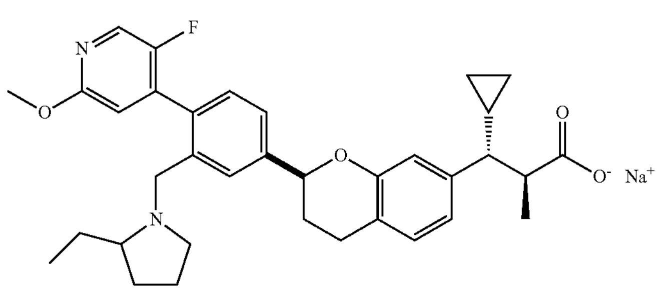 | Faster isomer<br>573.6<br>Slower isomer<br>573.6<br>AD-H |

TABLE 20-continued

Examples 251-283 were prepared in a similar manner to Example 250 using appropriate starting materials.

| Example | Structure | LC/MS |
|---|---|---|
| 268a | | Faster isomer 575.5 |
| 268b | | Slower isomer 575.5 IC column |
| 269 | 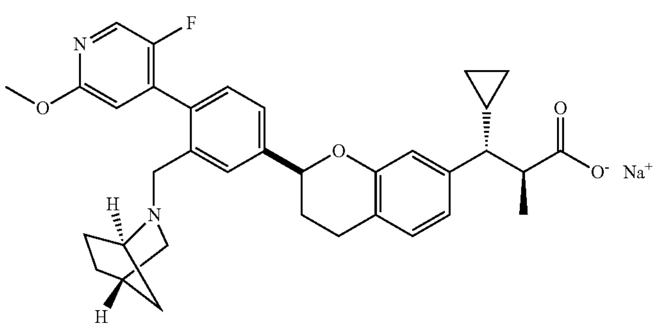 | 571.6 |
| 270 | 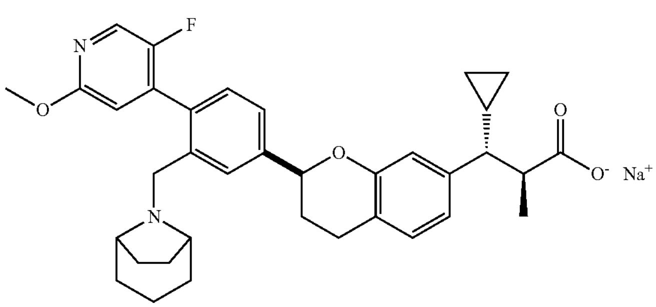 | 585.7 |
| 271 | 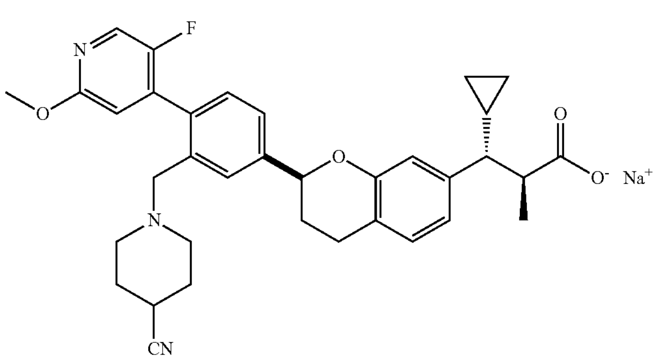 | 584.5 |

TABLE 20-continued
Examples 251-283 were prepared in a similar manner to Example 250 using appropriate starting materials.
| Example | Structure | LC/MS |
|---|---|---|
| 272 | 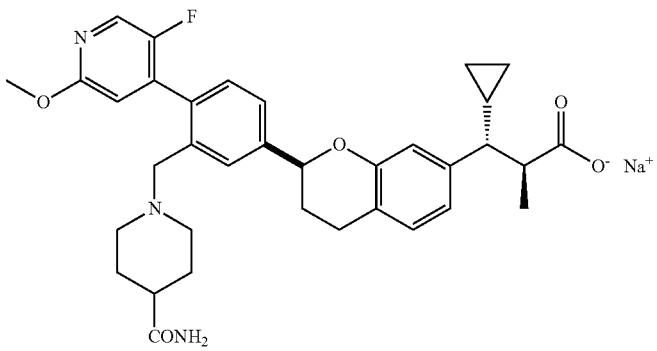 | 602.6 |
| 273a<br>273b | 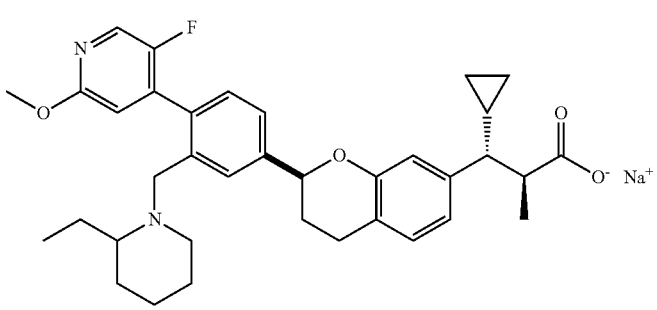 | Faster isomer<br>587.6<br>Slower isomer<br>587.6<br>OZ column |
| 274 | 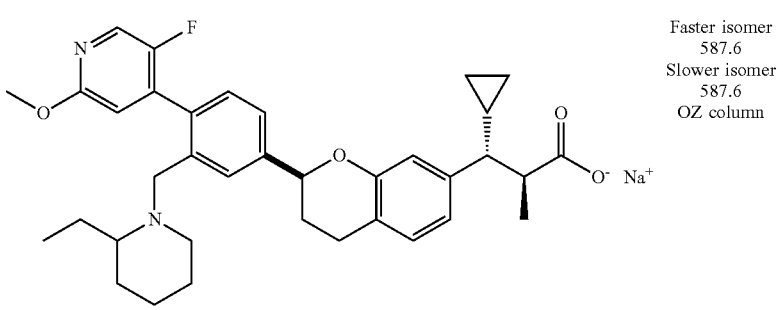 | 555.6 |
| 275 | 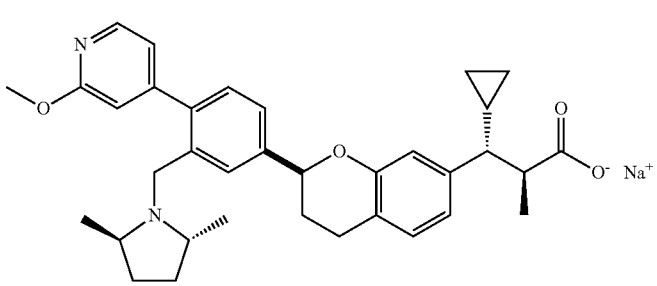 | 555.6 |
| 276 | 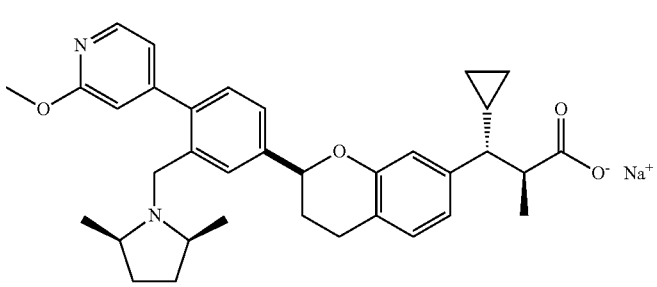 | 567.6 |

TABLE 20-continued

Examples 251-283 were prepared in a similar manner to Example 250 using appropriate starting materials.

| Example | Structure | LC/MS |
|---|---|---|
| 277 | 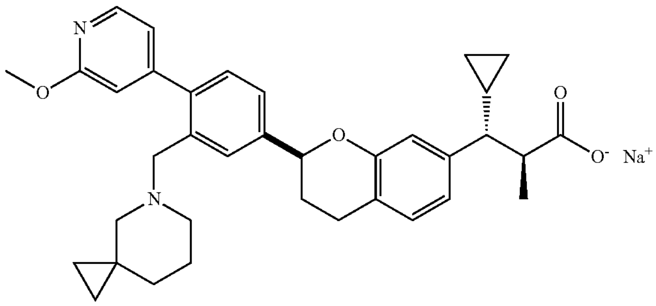 | 567.7 |
| 278 | 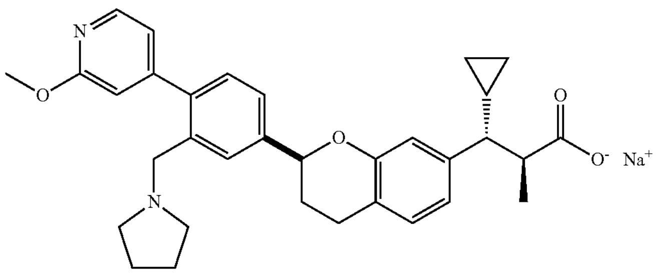 | 527.5 |
| 279 | 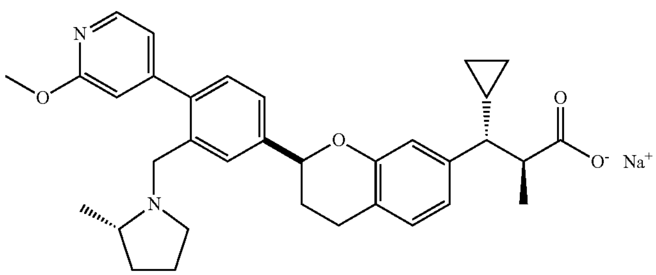 | 541.6 |
| 280 | 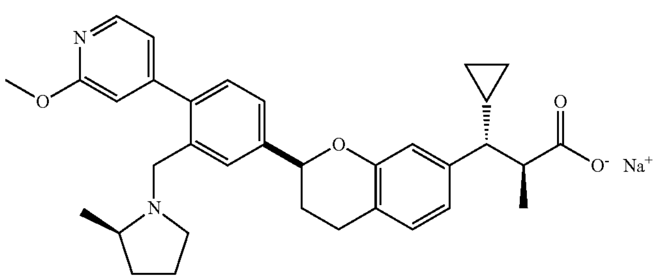 | 541.6 |
| 281 | 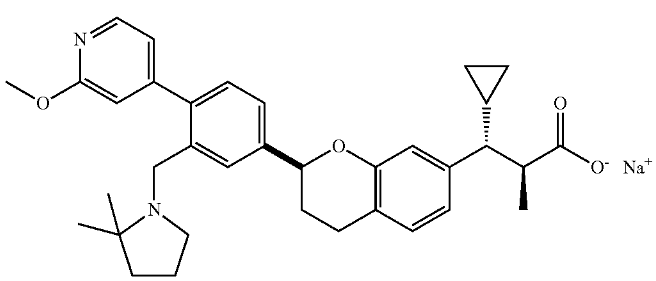 | 555.6 |

TABLE 20-continued

Examples 251-283 were prepared in a similar manner to Example 250 using appropriate starting materials.

| Example | Structure | LC/MS |
|---|---|---|
| 282 | 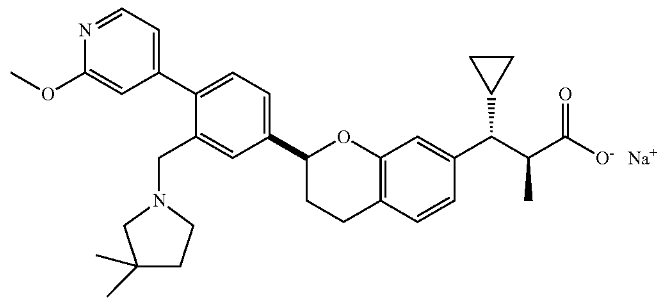 | 555.5 |
| 283 | 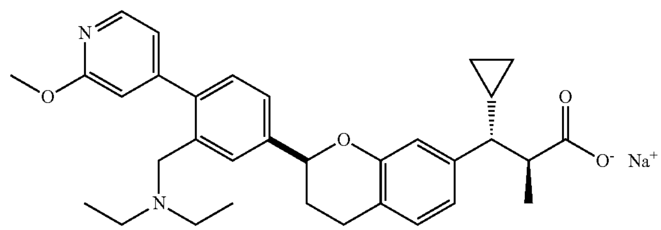 | 529.5 |

Example 284

Sodium (2S,3R)-3-cyclopropyl-3-((S)-2-(3-((diisopropylamino)methyl)-4-(2-methoxypyridin-4-yl)phenyl)chroman-7-yl)-2-methylpropanoate

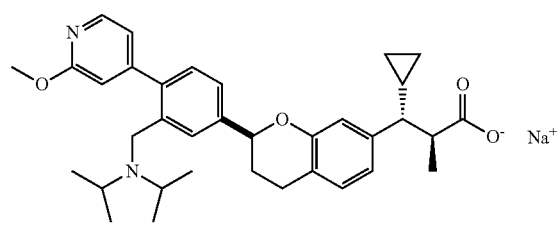 [SMILES: COc1cc(-c2ccc([C@@H]3CCc4ccc([C@H](C5CC5)[C@H](C)C(=O)[O-])cc4O3)cc2CN(C(C)C)C(C)C)ccn1 ; [Na+]]

Step 1: (2S,3R)-methyl 3-cyclopropyl-3-(2-(3-formyl-4-hydroxyphenyl)chroman-7-yl)-2-methylpropanoate To a xylenes (1 mL) solution of (2S,3R)-methyl 3-(4-(acetoxymethyl)-3-hydroxyphenyl)-3-cyclopropyl-2-methylpropanoate (3 g, 9.79 mmol) was added 2-hydroxy-5-vinylbenzaldehyde (2.176 g, 14.69 mmol). The mixture was degassed and then heated to 170° C. in a sealed vial. After 45 minutes, the reaction mixture was cooled to room temp. The reaction mixture was loaded directly onto an ISCO™ cartridge and purified by HPLC (ISCO 40 gram, 0 to 50% EtOAc/Hex) to give the title compound. (m/z): 395.22 $(M+H)^+$.

Step 2

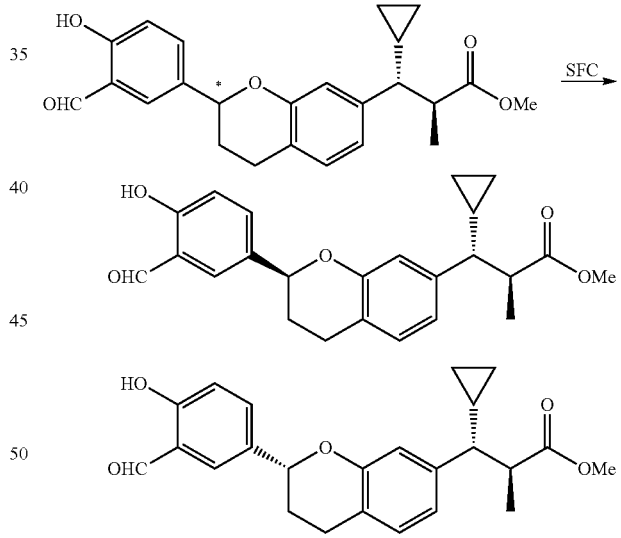

(2S,3R)-methyl 3-cyclopropyl-3-((S)-2-(3-formyl-4-hydroxyphenyl)chroman-7-yl)-2-methylpropanoate (peak 1) and (2S,3R)-methyl 3-cyclopropyl-3-((R)-2-(3-formyl-4-hydroxyphenyl)chroman-7-yl)-2-methylpropanoate (peak 2)

A mixture of 2 diastereomers at the * carbon alpha to the chroman oxygen of (2S,3R)-methyl 3-cyclopropyl-3-(−2-(3-formyl-4-hydroxyphenyl)chroman-7-yl)-2-methylpropanoate were separated by SFC (Column: AD-H, 250 mm*50 mm, 10 um; Mobile phase: 45% IPA; Column Temp: 40° C.;

Nozzle Pressure: 120 Bar). The absolute configuration at the chroman center for each isomer was established by VCD.

Step 3: (2S,3R)-methyl 3-cyclopropyl-3-((S)-2-(3-formyl-4-(tosyloxy)phenyl)chroman-7-yl)-2-methylpropanoate To a DCM (50 mL) solution of (2S,3R)-methyl 3-cyclopropyl-3-((S)-2-(3-formyl-4-hydroxyphenyl)chroman-7-yl)-2-methylpropanoate (4.2 g, 10.65 mmol) and TEA (1.781 ml, 12.78 mmol) was added p-toluenesulfonic anhydride (3.82 g, 11.71 mmol) in a single portion. After 16 h, the reaction was poured into water (200 mL) and extracted with DCM (2×200 mL). The combined organic layers were dried (Na$_2$SO$_4$) and concentrated. The resulting residue was purified by gradient flash chromatography (220 gram SiO$_2$ column, 0 to 50% EtOAc/Hex) to give the title compound. LC/MS (m/z): 549.4 (M)$^+$.

Step 4: Methyl (2S,3R)-3-cyclopropyl-3-((S)-2-(3-formyl-4-(2-methoxypyridin-4-yl)phenyl)chroman-7-yl)-2-methylpropanoate To a nitrogen-sparged THF (18.5 ml) solution of methyl (2S,3R)-3-cyclopropyl-3-((S)-2-(3-formyl-4-(tosyloxy)phenyl)chroman-7-yl)-2-methylpropanoate (2.04 g, 3.72 mmol), (2-methoxypyridin-4-yl)boronic acid (0.853 g, 5.58 mmol) and Chloro(2-dicyclohexylphosphino-2',6'-dimethoxy-1,1'-biphenyl)[2-(2'-amino-1,1'-biphenyl)]palladium (II) (0.134 g, 0.186 mmol) was added potassium phosphate tribasic (2.34 g, 11 mmol) (1 M aqueous solution). The reaction was heated at 70° C. for 16 h, then cooled to room temp and poured into NH$_4$Cl (aqueous, 100 mL, saturated). The mixture was extracted with EtOAc (2×100 mL). The combined organic layers were dried (MgSO$_4$), filtered, and concentrated. The resulting residue was purified by gradient flash chromatography (120 gram SiO$_2$ column, 0 to 50% EtOAc/Hexane) to give the title compound. LC/MS (m/z): 485.5 (M)+.

Step 5: Methyl (2S,3R)-3-cyclopropyl-3-((S)-2-(3-((diisopropylamino)methyl)-4-(2-methoxypyridin-4-yl)phenyl)chroman-7-yl)-2-methylpropanoate (2S,3R)-Methyl 3-cyclopropyl-3-((S)-2-(3-formyl-4-(2-methoxypyridin-4-yl)phenyl)chroman-7-yl)-2-methylpropanoate (70 mg, 0.14 mmol) and di-isopropylamine (61.1 µL, 0.43 mmol) were taken up in 1,2-dichloroethane (1.4 ml) at 25° C. Triethylamine (60.3 µL, 0.43 mmol), sodium triacetoxyborohydride (46 mg, 0.22 mmol), and AcOH (3 µL, 0.052 mmol) were added to the reaction mixture. The reaction was stirred at 25° C. for 10 hours, then additional di-isopropylamine (61.1 µL, 0.43 mmol), triethylamine (60.3 µL, 0.43 mmol), sodium triacetoxyborohydride (46 mg, 0.22 mmol), and AcOH (3 µL, 0.052 mmol) were added. The reaction was stirred for 10 hours, then partitioned between EtOAc and saturated NaHCO$_3$ (aqueous). The aqueous layer was extracted with EtOAc. The combined organic layers were washed with brine and dried over MgSO$_4$. The mixture was filtered and the filtrate was concentrated in vacuo. The resulting residue was purified by gradient flash chromatography (12 g SiO$_2$ column. 0-20% EtOAc/hexanes) to give the title compound. LC/MS (m/z): 571.6 (M+H)$^+$.

Step 6: (2S,3R)-3-Cyclopropyl-3-((S)-2-(3-((diisopropylamino)methyl)-4-(2-methoxypyridin-4-yl)phenyl)chroman-7-yl)-2-methylpropanoic acid (2S,3R)-Methyl 3-cyclopropyl-3-((S)-2-(3-((diisopropylamino)methyl)-4-(2-methoxypyridin-4-yl)phenyl)chroman-7-yl)-2-methylpropanoate (69 mg, 0.12 mmol) was taken up in THF (0.75 ml)/MeOH (0.75 ml)/water (0.5 ml) at 25° C. Lithium hydroxide hydrate (20 mg, 0.48 mmol) was added, and the resulting mixture was stirred at 52° C. for two days. The reaction mixture was then diluted with H$_2$O and acidified with 1N HCl (aqueous) to pH 5-6. The mixture was extracted with EtOAc (3×). The combined organic layers were washed with brine and dried over MgSO$_4$. The solution was filtered and the filtrate was concentrated. The resulting residue was purified by gradient flash chromatography (4 g SiO$_2$ column, 0-100% EtOAc/hexanes) to give (2S,3R)-3-cyclopropyl-3-((S)-2-(3-((diisopropylamino)methyl)-4-(2-methoxypyridin-4-yl)phenyl)chroman-7-yl)-2-methylpropanoic acid. LC/MS (m/z): 557.6 (M+H)$^+$.

Step 7: Sodium (2S,3R)-3-cyclopropyl-3-((S)-2-(3-((diisopropylamino)methyl)-4-(2-methoxypyridin-4-yl)phenyl)chroman-7-yl)-2-methylpropanoate (2S,3R)-3-Cyclopropyl-3-((S)-2-(3-((diisopropylamino)methyl)-4-(2-methoxypyridin-4-yl)phenyl)chroman-7-yl)-2-methylpropanoic acid (64.7 mg) was dissolved in MeCN/H$_2$O (1 ml, 1:1). The solution was treated with 1N NaOH (0.12 ml) and stirred for 30 minutes. The solution was then lyophilized to give sodium (2S,3R)-3-cyclopropyl-3-((S)-2-(3-((diisopropylamino)methyl)-4-(2-methoxypyridin-4-yl)phenyl)chroman-7-yl)-2-methylpropanoate. LC/MS (m/z): 557.6 (M+H)$^+$. $^1$H NMR (500 MHz, CD$_3$OD) δ 8.10 (s, 1H), 7.84 (s, 1H), 7.40 (d, 1H), 7.12 (d, 1H), 7.02 (d, 1H), 7.00 (d, 1H), 6.80 (s, 1H), 6.76 (m, 2H), 5.21 (d, 1H), 4.01 (s, 3H), 3.66 (s, 2H), 3.00 (m, 3H), 2.80 (m, 1H), 2.68 (m, 1H), 2.30 (m, 1H), 2.10 (m, 1H), 2.00 (t, 1H), 1.15 (m, 1H), 0.96 (d, 12H), 0.95 (d, 3H), 0.61 (m, 1H), 0.50 (m, 1H), 0.30 (m, 1H), 0.00 (m, 1H).

TABLE 21

Examples 285-295 were prepared in a similar manner to Example 250 using appropriate starting materials.

| Example | Structure | LC/MS |
|---|---|---|
| 285 | ![structure] | 557.7 |

TABLE 21-continued

Examples 285-295 were prepared in a similar manner to Example 250 using appropriate starting materials.

| Example | Structure | LC/MS |
|---------|-----------|-------|
| 286 | 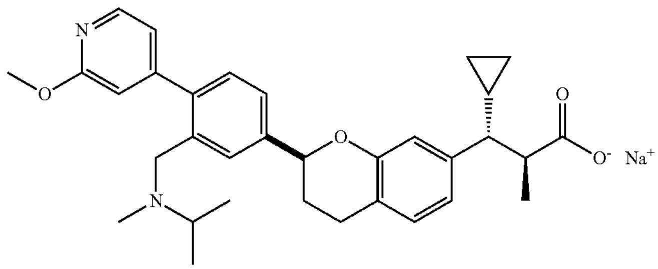 | 529.55 |
| 287 | 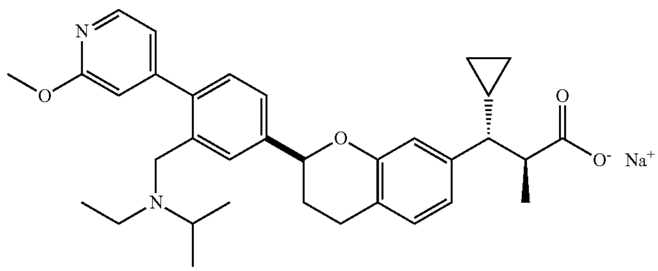 | 543.57 |
| 288 | 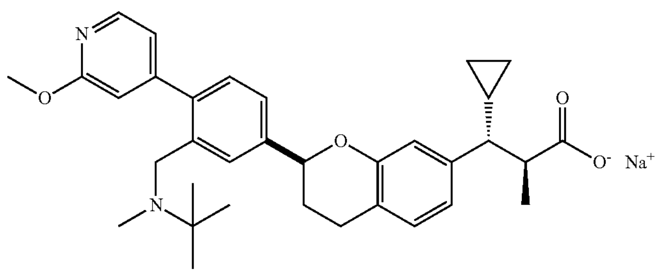 | 543.6 |
| 289 | 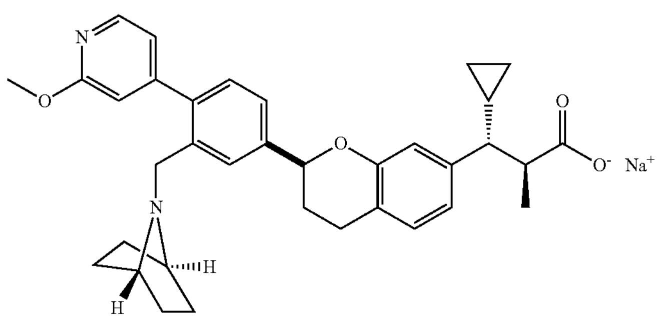 | 553.6 |
| 290 | 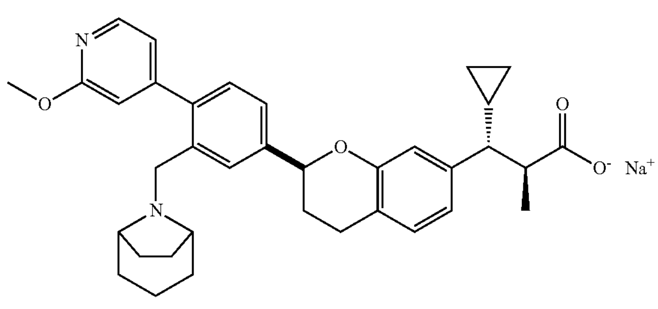 | 567.6 |

TABLE 21-continued

Examples 285-295 were prepared in a similar manner to Example 250 using appropriate starting materials.

| Example | Structure | LC/MS |
|---------|-----------|-------|
| 291 | 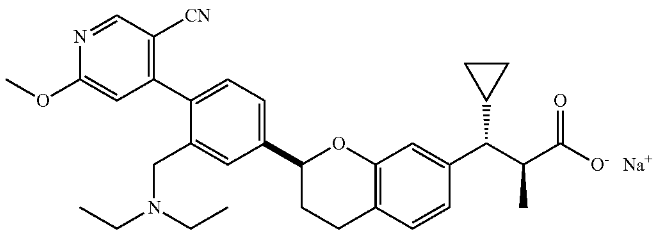 | 554.6 |
| 292 | 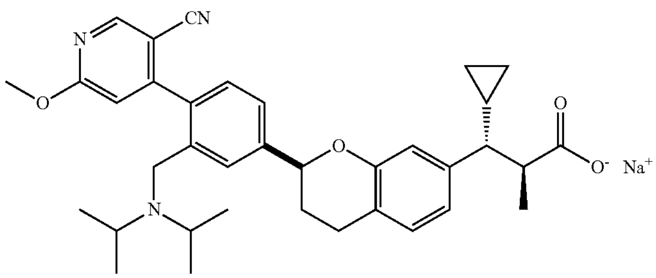 | 582.6 |
| 293 | 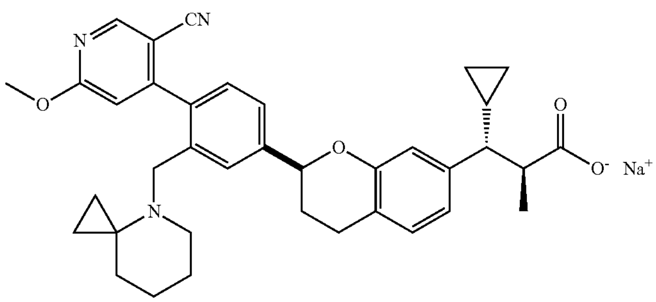 | 592.6 |
| 294 | 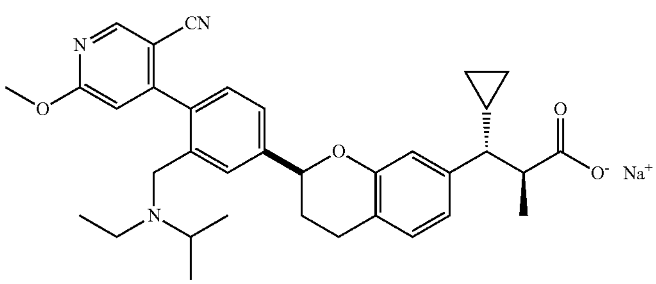 | 568.6 |
| 295 | 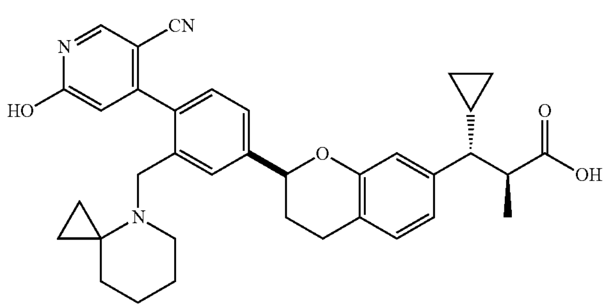 | 578.5 |

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

Inositol Phosphate Turnover (IP1) Assay 1:

The assay was performed in 384-well format. HEK cells stably expressing human GPR40 were plated at 15,000 cells per well in growth medium (DMEM/10% fetal calf serum). Cell plates were then incubated 16 hours at 37 degrees in a 5% $CO_2$ incubator.

Measurement of Inositol Phosphate Turnover (IP1) was performed using the CisBio IP-One kit (Part number 62IPA-PEB). After the 16 hour incubation, the cells were washed with HEPES buffer and 10 ul of stimulation buffer (prepared as described in the kit) is added to each well. In a separate plate, compounds were diluted in DMSO (400-fold over the final concentration in the assay well) and 25 nl was transferred via pocket tip to the appropriate well in the assay cell plate. The plates were then incubated for 60 minutes at 37 degrees. 10 ul of detection buffer (also prepared as described in the IP-One kit) was added to each well and the plates were incubated for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Inositol Phosphate Turnover (IP1) Assay 1 $EC_{50}$ values for specific compounds are listed in Table 1.

Inositol Phosphate Turnover (IP1) Assay 2:

The assay was performed in 384-well format. HEK cells stably expressing human GPR40 were plated at 15,000 cells per well in growth medium (DMEM/10% fetal calf serum). Cell plates were then incubated 16 hours at 37 degrees in a 5% $CO_2$ incubator.

Measurement of Inositol Phosphate Turnover (IP1) was performed using the CisBio IP-One kit (Part number 62IPA-PEB). After the 16 hour incubation, the cells were washed with HEPES buffer and 10 ul of stimulation buffer (prepared as described in the kit) was added to each well. In a separate plate, compounds were diluted in DMSO (400-fold over the final concentration in the assay well) and 25 nl was acoustically transferred to the appropriate well in the assay cell plate. The plates were then incubated for 60 minutes at 37 degrees. 10 ul of detection buffer (also prepared as described in the IP-One kit) was added to each well and the plates were incubated for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Inositol Phosphate Turnover (IP1) Assay 2 $EC_{50}$ values for specific compounds are listed in Table II.

Inositol Phosphate Turnover (IP1) Assay 3:

The assay was performed in 384-well format. HEK cells stably expressing human GPR40 were plated at 7500 cells per well in growth medium (DMEM/10% fetal calf serum). Cell plates were then incubated 16 hours at 37 degrees in a 5% $CO_2$ incubator.

Measurement of Inositol Phosphate Turnover (IP) was performed using the CisBio IP-One kit (Part number 62IPA-PEB). After the 16 hour incubation, the growth media was removed by centrifugation using the BlueWasher (AusWasher GUI Ver. v1.0.1.8) Protocol #21—"Light Dry" and 10 ul of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% CO2 incubator. 10 ul of detection buffer (also prepared as described in the IP-One kit) was added to each well and the plates were incubated at rt for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Data is normalized to % activity using a reference compound and $EC_{50}$s determined using a standard 4-parameter fit. Inositol Phosphate Turnover (IP1) Assay 3 $EC_{50}$ values for specific compounds are listed in Table III.

The compounds of the present invention, including the compounds in Examples 1-295, have $EC_{50}$ values less than 6500 nanomolar (nM) in either the Inositol Phosphate Turnover (IP) Assay 1, 2, or 3 described above.

TABLE I

Inositol Phosphate Turnover (IP1) Assay 1

| Example No. | Inositol Phosphate Turnover Assay 1, EC50 (nM) | Isomer* |
|---|---|---|
| 1 | 8.6 | Mixture of 2 isomers |
| 2 | 2986 | Mixture of 2 isomers |
| 3 | 18 | Mixture of 2 isomers |
| 10 | 193 | Mixture of 2 isomers |

TABLE II

Inosito Phosphate Turnover (IP1) Assay 2

| Example No. | Inositol Phosphate Turnover Assay 2, EC50 (nM) | Isomer* |
|---|---|---|
| 1a | 2.3 | single isomer |
| 1b | 2.9 | single isomer |
| 4 | 310 | Mixture of 2 isomers |
| 5 | 660 | Mixture of 2 isomers |
| 6 | 227 | Mixture of 2 isomers |
| 7 | 118 | Mixture of 2 isomers |
| 8 | 238 | Mixture of 2 isomers |
| 9 | 4.3 | Mixture of 2 isomers |
| 9a | 3.9 | single isomer |
| 9b | 3.4 | single isomer |
| 11 | 4.6 | Mixture of 2 isomers |
| 11a | 1.7 | single isomer |
| 11b | 2.4 | single isomer |
| 12 | 60 | Mixture of 2 isomers |
| 13 | 210 | Mixture of 2 isomers |
| 14 | 0.87 | Mixture of 4 isomers |

TABLE II-continued

Inosito Phosphate Turnover (IP1) Assay 2

| Example No. | Inositol Phosphate Turnover Assay 2, EC50 (nM) | Isomer* |
|---|---|---|
| 15 | 1.1 | Mixture of 2 isomers |
| 16 | 2.3 | Mixture of 2 isomers |
| 17 | 0.7 | Mixture of 2 isomers |
| 18 | 11 | Mixture of 2 isomers |
| 19 | 6.4 | Mixture of 2 isomers |
| 33 | 573 | Mixture of 2 isomers |
| 20 | 0.84 | single isomer |
| 21 | 0.76 | single isomer |
| 22 | 0.46 | single isomer |
| 23 | 1.7 | single isomer |
| 24 | 2.2 | single isomer |
| 25 | 2.3 | single isomer |
| 26 | 2.5 | single isomer |
| 27 | 1.5 | single isomer |
| 28 | 1.4 | single isomer |
| 29 | 0.8 | single isomer |
| 30 | 1.5 | single isomer |
| 34 | 1.9 | single isomer |
| 35 | 22 | Mixture of 2 isomers |
| 36 | 2.1 | Mixture of 2 isomers |
| 37 | 4.7 | Mixture of 2 isomers |
| 38 | 1.8 | Mixture of 2 isomers |
| 39 | 2.1 | Mixture of 2 isomers |
| 40 | 184 | Mixture of 2 isomers |
| 41 | 13 | Mixture of 2 isomers |
| 42 | 3.1 | Mixture of 2 isomers |
| 43 | 2.1 | Mixture of 2 isomers |
| 44 | 1.8 | Mixture of 2 isomers |
| 45 | 12 | Mixture of 2 isomers |
| 46 | 1.0 | Mixture of 2 isomers |
| 47 | 3.5 | Mixture of 2 isomers |
| 48 | 3.6 | Mixture of 2 isomers |
| 49 | 4.0 | Mixture of 2 isomers |
| 50 | 1.3 | Mixture of 2 isomers |
| 51 | 1.0 | Mixture of 2 isomers |
| 52 | 0.35 | Mixture of 2 isomers |
| 53 | 1.7 | Mixture of 2 isomers |
| 54 | 13 | Mixture of 2 isomers |
| 55 | 0.73 | Mixture of 2 isomers |
| 56 | 7.0 | Mixture of 2 isomers |
| 57 | 0.18 | Mixture of 2 isomers |
| 58 | 1.1 | Mixture of 2 isomers |
| 59 | 0.98 | Mixture of 2 isomers |
| 60 | 0.59 | Mixture of 2 isomers |
| 61 | 2.0 | Mixture of 2 isomers |
| 62 | 0.20 | Mixture of 2 isomers |
| 63 | 2.3 | Mixture of 2 isomers |
| 62 | 0.99 | Mixture of 2 isomers |
| 65 | 2.0 | Mixture of 2 isomers |
| 66 | 0.65 | Mixture of 2 isomers |
| 67 | 15 | Mixture of 2 isomers |
| 68 | 0.7 | Mixture of 2 isomers |
| 69 | 2.6 | Mixture of 2 isomers |
| 70 | 0.5 | Mixture of 2 isomers |
| 71 | 0.7 | Mixture of 2 isomers |
| 72 | 1.2 | Mixture of 2 isomers |
| 73 | 8.2 | Mixture of 2 isomers |
| 31 | 0.95 | Single isomer |
| 32 | 0.84 | Single isomer |
| 74 | 9.3 | Mixture of 2 isomers |
| 75 | 17 | Mixture of 2 isomers |
| 78 | 8.0 | Mixture of 2 isomers |
| 76 | 8.2 | Mixture of 2 isomers |
| 77 | 29 | Single isomer |
| 79 | 4843 | Single isomer |
| 80 | 11 | Single isomer |
| 81 | 4.0 | Single isomer |
| 82 | 13 | Single isomer |
| 83 | 3.0 | Single isomer |
| 84 | 2.0 | Mixture of 4 isomers |
| 92 | 4.0 | Single isomer |
| 93 | 2.9 | Single isomer |
| 94 | 1.8 | Single isomer |
| 95 | 1.8 | Single isomer |
| 110 | 824 | Mixture of 2 isomers |
| 110a | 446 | Single isomer |
| 110b | 139 | Single isomer |
| 134 | 0.8 | Single isomer |
| 135 | 5.0 | Single isomer |
| 136 | 4.6 | Single isomer |
| 137 | 4.6 | Single isomer |
| 140 | 1.8 | Single isomer |
| 141 | 1.1 | Single isomer |
| 142 | 1.1 | Single isomer |
| 143 | 0.3 | Single isomer |
| 144 | 0.3 | Single isomer |
| 145 | 2.7 | Single isomer |
| 146 | 1.8 | Single isomer |
| 147 | 0.7 | Single isomer |
| 148 | 4.2 | Single isomer |
| 149 | 2.5 | Single isomer |
| 150 | 1.0 | Single isomer |
| 151 | 2.0 | Single isomer |
| 152 | 0.5 | Single isomer |
| 153 | 1.1 | Single isomer |
| 154 | 1.3 | Single isomer |
| 155 | 1.8 | Single isomer |
| 156 | 8.3 | Single isomer |
| 157 | 4.2 | Single isomer |
| 158 | 0.2 | Single isomer |
| 159 | 3.3 | Single isomer |
| 160 | 2.5 | Single isomer |
| 161 | 0.6 | Single isomer |
| 162 | 5.4 | Single isomer |
| 163 | 3.3 | Single isomer |
| 164 | 1.6 | Single isomer |
| 165 | 3.9 | Single isomer |
| 166 | 0.3 | Single isomer |
| 167 | 2.2 | Single isomer |
| 168 | 2.9 | Single isomer |
| 169 | 1.7 | Single isomer |
| 180 | 41 | Single isomer |
| 216 | 86 | Mixture of 2 isomers |
| 112 | 5.6 | Mixture of 2 isomers |

TABLE III

Inositol Phosphate Turnover (IP1) Assay 3

| Example No. | Inositol Phosphate Turnover Assay 3, EC50 (nM) | Isomer* |
|---|---|---|
| 85 | 1.7 | Mixture of 2 isomers |
| 86 | 1.4 | Single isomer |
| 87 | 6.6 | Single isomer |
| 88 | 6.7 | Single isomer |
| 89 | 0.9 | Single isomer |
| 90 | 9.5 | Mixture of 2 isomers |
| 91 | 467 | Mixture of 2 isomers |
| 96 | 0.06 | Single isomer |
| 97 | 0.19 | Single isomer |
| 98 | 0.09 | Single isomer |
| 99 | 0.18 | Single isomer |
| 100 | 0.14 | Single isomer |
| 101 | 0.25 | Single isomer |
| 102 | 0.07 | Single isomer |
| 103 | 0.09 | Single isomer |
| 104 | 1.1 | Single isomer |
| 105 | 0.1 | Single isomer |
| 106 | 0.2 | Single isomer |
| 107 | 0.1 | Single isomer |
| 108 | 0.1 | Single isomer |
| 109 | 0.1 | Single isomer |
| 138 | 0.3 | Single isomer |
| 139 | 0.5 | Single isomer |
| 170 | 0.07 | Single isomer |
| 171 | 2.5 | Single isomer |

TABLE III-continued

Inositol Phosphate Turnover (IP1) Assay 3

| Example No. | Inositol Phosphate Turnover Assay 3, EC50 (nM) | Isomer* |
|---|---|---|
| 172 | 2.3 | Single isomer |
| 173 | 50 | Single isomer |
| 174 | 27 | Single isomer |
| 175 | 53 | Mixture of 2 isomers |
| 176 | 0.2 | Single isomer |
| 177 | 231 | Single isomer |
| 178 | 136 | Single isomer |
| 179 | 17 | Mixture of 2 isomers |
| 181 | 14 | Single isomer |
| 182 | 16 | Single isomer |
| 183 | 0.35 | Single isomer |
| 184 | 0.73 | Single isomer |
| 185 | 4.4 | Single isomer |
| 186 | 7.9 | Single isomer |
| 187 | 0.4 | Single isomer |
| 188 | 0.7 | Single isomer |
| 189 | 5.1 | Single isomer |
| 190 | 3.9 | Single isomer |
| 191 | 1.9 | Single isomer |
| 192 | 0.3 | Single isomer |
| 193 | 1.5 | Single isomer |
| 194 | 1.1 | Single isomer |
| 195 | 12 | Single isomer |
| 196 | 7.2 | Single isomer |
| 197 | 2.9 | Mixture of 2 isomers |
| 198 | 4.7 | Single isomer |
| 199 | 5.7 | Single isomer |
| 200 | 1.5 | Single isomer |
| 201 | 4.4 | Single isomer |
| 202 | 0.16 | Single isomer |
| 203 | 0.16 | Single isomer |
| 204 | 2.1 | Single isomer |
| 205 | 2.4 | Single isomer |
| 206 | 1.3 | Single isomer |
| 207 | 1.3 | Single isomer |
| 208 | 0.73 | Single isomer |
| 209 | 0.5 | Single isomer |
| 210 | 3.1 | Single isomer |
| 211 | 2.1 | Single isomer |
| 212 | 3.1 | Single isomer |
| 213 | 1.4 | Single isomer |
| 214 | 12 | Single isomer |
| 215 | 6.0 | Single isomer |
| 217 | 57 | Single isomer |
| 218 | 10 | Single isomer |
| 219 | 2.0 | Single isomer |
| 220 | 7.2 | Single isomer |
| 221 | 14 | Single isomer |
| 222 | 1.3 | Single isomer |
| 223 | 0.05 | Single isomer |
| 224 | 11 | Single isomer |
| 225 | 0.07 | Single isomer |
| 226 | 1.1 | Single isomer |
| 227 | 14 | Single isomer |
| 228 | 0.12 | Single isomer |
| 229 | 0.07 | Single isomer |
| 230 | 0.09 | Single isomer |
| 231 | 0.16 | Single isomer |
| 232 | 36 | Single isomer |
| 233 | 42 | Single isomer |
| 234 | 21 | Single isomer |
| 236 | 1.3 | Single isomer |
| 237 | 0.17 | Single isomer |
| 238 | 0.14 | Single isomer |
| 239 | 1.1 | Single isomer |
| 240 | 1.4 | Single isomer |
| 241 | 1.1 | Single isomer |
| 242 | 3.1 | Single isomer |
| 243 | 810 | Single isomer |
| 244 | 0.43 | Single isomer |
| 245 | 5.4 | Single isomer |
| 246 | 2.2 | Mixture of 2 isomers |
| 247 | 1.3 | Single isomer |
| 248 | 11.5 | Single isomer |
| 249 | 14.2 | Mixture of 2 isomers |
| 250 | 0.19 | Single isomer |
| 251 | 0.3 | Single isomer |
| 252 | 0.7 | Mixture of 2 isomers |
| 253 | 0.9 | Single isomer |
| 254 | 1.0 | Single isomer |
| 255 | 0.3 | Single isomer |
| 256a | 0.6 | Single isomer |
| 256b | 0.9 | Single isomer |
| 257 | 0.4 | Single isomer |
| 258a | 1.7 | Single isomer |
| 258b | 2.2 | Single isomer |
| 259 | 0.2 | Single isomer |
| 260 | 0.9 | Single isomer |
| 261 | 0.6 | Single isomer |
| 262 | 0.2 | Single isomer |
| 263 | 0.8 | Single isomer |
| 264 | 0.2 | Single isomer |
| 265 | 0.2 | Single isomer |
| 266 | 0.1 | Single isomer |
| 267a | 0.7 | Single isomer |
| 267b | 0.1 | Single isomer |
| 268a | 0.6 | Single isomer |
| 268b | 0.5 | Single isomer |
| 269 | 6.2 | Single isomer |
| 270 | 0.9 | Single isomer |
| 271 | 2.6 | Single isomer |
| 272 | 278 | Single isomer |
| 273a | 0.08 | Single isomer |
| 273b | 0.3 | Single isomer |
| 274 | 4.3 | Single isomer |
| 275 | 2.8 | Single isomer |
| 276 | 0.2 | Single isomer |
| 277 | 1.9 | Single isomer |
| 278 | 19 | Single isomer |
| 279 | 30 | Single isomer |
| 280 | 16 | Single isomer |
| 281 | 5.7 | Single isomer |
| 282 | 7.4 | Single isomer |
| 283 | 4.4 | Single isomer |
| 284 | 0.3 | Single isomer |
| 285 | 4.0 | Single isomer |
| 286 | 11 | Single isomer |
| 287 | 3.3 | Single isomer |
| 288 | 21 | Single isomer |
| 289 | 72 | Single isomer |
| 290 | 22 | Single isomer |
| 291 | 3.1 | Single isomer |
| 292 | 0.1 | Single isomer |
| 293 | 0.08 | Single isomer |
| 294 | 0.5 | Single isomer |
| 295 | 85 | Single isomer |
| 111 | 0.7 | Mixture of 2 isomers |
| 111a | 3.2 | Single isomer |
| 111b | 0.4 | Single isomer |
| 112a | 2.3 | Single isomer |
| 112b | 273 | Single isomer |
| 113 | 0.7 | Mixture of 2 isomers |
| 113a | 0.4 | Single isomer |
| 113b | 14 | Single isomer |
| 114 | 5.0 | Mixture of 2 isomers |
| 114a | 1.5 | Single isomer |
| 114b | 250 | Single isomer |
| 115 | 0.1 | Mixture of 2 isomers |
| 115a | 0.1 | Single isomer |
| 115b | 5.3 | Single isomer |
| 116 | 104 | Mixture of 4 isomers |
| 116a | 1.7 | Single isomer |
| 116b | 1.0 | Single isomer |
| 116c | 1000 | Single isomer |
| 116d | 387 | Single isomer |
| 117 | 0.6 | Mixture of 2 isomers |
| 117a | 0.4 | Single isomer |
| 117b | 24 | Single isomer |
| 118a | 0.6 | Single isomer |
| 118b | 109 | Single isomer |

TABLE III-continued

Inositol Phosphate Turnover (IP1) Assay 3

| Example No. | Inositol Phosphate Turnover Assay 3, EC50 (nM) | Isomer* |
|---|---|---|
| 119a | 308 | Single isomer |
| 119b | 4.2 | Single isomer |
| 120 | 0.7 | Mixture of 2 isomers |
| 120a | 0.4 | Single isomer |
| 120b | 41 | Single isomer |
| 121 | 0.4 | Mixture of 2 isomers |
| 122 | 0.7 | Mixture of 2 isomers |
| 122a | 3.3 | Single isomer |
| 122b | 190 | Single isomer |
| 123a | 91 | Single isomer |
| 123b | 1.4 | Single isomer |
| 124 | 0.3 | Mixture of 2 isomers |
| 124a | 0.09 | Single isomer |
| 124b | 16 | Single isomer |
| 125 | 2.2 | Mixture of 2 isomers |
| 125a | 0.3 | Single isomer |
| 125b | 12 | Single isomer |
| 126 | 0.1 | Mixture of 2 isomers |
| 126a | 0.05 | Single isomer |
| 126b | 2.7 | Single isomer |
| 127 | 0.2 | Mixture of 4 isomers |
| 128 | 0.16 | Mixture of 2 isomers |
| 128a | 0.07 | Single isomer |
| 128b | 1.2 | Single isomer |
| 129a | 0.25 | Single isomer |
| 129b | 36 | Single isomer |
| 130a | 8.7 | Single isomer |
| 130b | 0.06 | Single isomer |
| 131 | 0.09 | Mixture of 2 isomers |
| 132 | 4.8 | Mixture of 2 isomers |
| 132a | 1.8 | Single isomer |
| 132b | 106 | Single isomer |
| 133 | 0.8 | Single isomer |

*Single Isomer refers to one isomer at the chroman stereocenter.
*Mixture of 2 isomers refers to a 1:1 diastereomeric ratio at the chroman stereocenter.
*Mixture of 4 isomers refers to a 1:1 diastereomeric ratio at the chroman stereocenter and diastereomers at the benzylic amine center.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:
1. A compound of structural formula I:

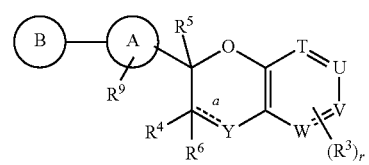

or a pharmaceutically acceptable salt thereof; wherein
"a" is a single bond;
Y is —CR$^g$R$^g$;
T is CH;
U is CR$^1$;
V is CR$^2$;
W is CH;
A is selected from the group consisting of:
  (1) aryl, and
  (2) heteroaryl,
wherein each aryl and heteroaryl is unsubstituted or substituted with one to five substituents selected from R$^a$;
B is selected from the group consisting of:
  (1) aryl, and
  (2) heteroaryl,
wherein each aryl and heteroaryl is unsubstituted or substituted with one to five substituents selected from R$^b$;
R$^1$ and R$^2$ are each independently selected from:
  (1) hydrogen, and
  (2) C$_{1-6}$alkyl,
wherein alkyl is unsubstituted or substituted with one to three substituents selected from R$^L$, and wherein one of R$^1$ and R$^2$ is C$_{1-6}$alkyl substituted with R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with R$^7$;
R$^3$ is absent or when present is selected from the group consisting of:
  (1) hydrogen,
  (2) halogen,
  (3) —OR$^e$,
  (4) —CN,
  (5) —C$_{1-6}$alkyl,
  (6) —C$_{3-6}$cycloalkyl, and
  (7) C$_{3-6}$cycloalkyl-C$_{1-3}$alkyl-,
wherein each alkyl and cycloalkyl is unsubstituted or substituted with one to three substituents selected from R$^i$;

$R^4$ is selected from the group consisting of:
(1) hydrogen,
(2) halogen,
(3) $OR^e$,
(4) $C_{1-6}$alkyl,
(5) $C_{1-6}$alkyl-O—,
(6) $C_{3-6}$cycloalkyl,
(7) $C_{3-6}$cycloalkyl-O—,
(8) $C_{3-6}$cycloalkyl-$C_{1-10}$alkyl-,
(9) $C_{3-6}$cycloalkyl-$C_{1-10}$alkyl-O—,
(10) $C_{2-5}$cycloheteroalkyl,
(11) $C_{2-5}$cycloheteroalkyl-O—,
(12) $C_{2-5}$cycloheteroalkyl-$C_{1-10}$alkyl-,
(13) $C_{2-5}$cycloheteroalkyl-$C_{1-10}$alkyl-O—,
(14) aryl,
(15) aryl-O—,
(16) aryl-$C_{1-10}$alkyl-,
(17) heteroaryl,
(18) heteroaryl-O—, and
(19) heteroaryl-$C_{1-10}$alkyl-,
wherein each alkyl, cycloalkyl, cycloheteroalkyl, aryl and heteroaryl is unsubstituted or substituted with one to three substituents selected from $R^j$;
$R^5$ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
$R^6$ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
$R^7$ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$alkyl-$SO_2NHCOR^m$,
(5) —$C_{1-6}$alkyl-tetrazolyl, and
(6) a cycloheteroalkyl selected from the group consisting of:

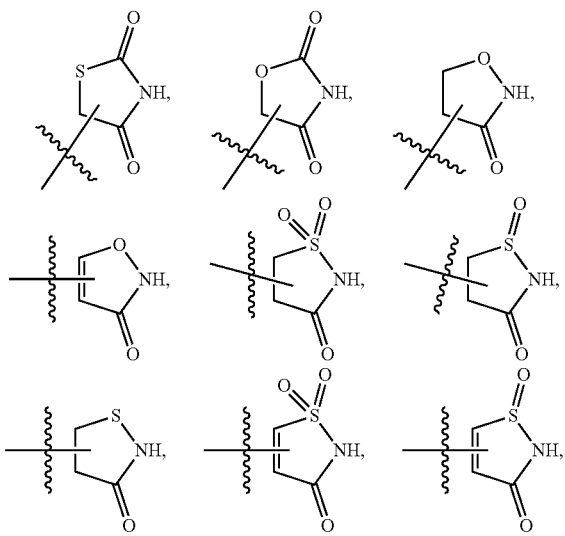

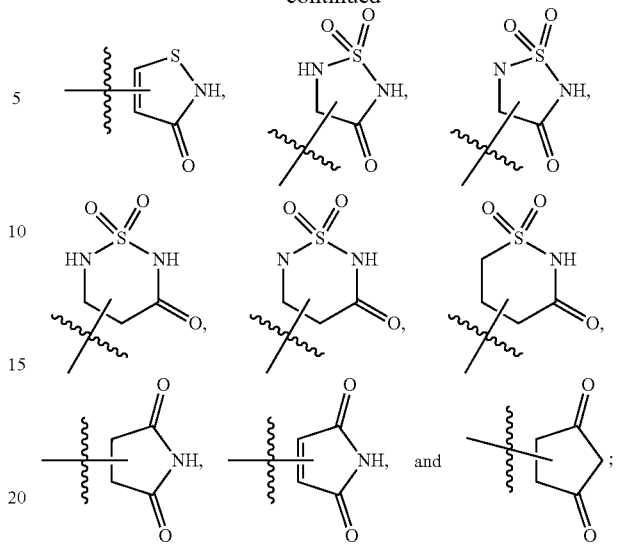

$R^8$ is selected from the group consisting of:
(1) hydrogen,
(2) —$C_{1-6}$alkyl,
(3) —$C_{3-6}$cycloalkyl, and
(4) aryl-$C_{1-6}$alkyl,
wherein each alkyl, cycloalkyl and aryl is unsubstituted or substituted with one to three substituents selected from $R^j$;
$R^9$ is selected from the group consisting of:
(1) —$C_{1-6}$alkyl-$NR^cR^d$, and
(2) —$C_{1-6}$alkyl-$C_{2-5}$cycloheteroalkyl,
wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;
$R^a$ is selected from the group consisting of:
(1) —$C_{1-6}$alkyl,
(2) halogen,
(3) —$C_{0-6}$alkyl-$OR^e$,
(4) —$C_{0-6}$alkyl-$NR^cS(O)_nR^e$,
(5) —$C_{0-6}$alkyl-$S(O)_nR^e$,
(6) —$C_{0-6}$alkyl-$S(O)_nNR^cR^d$,
(7) —$C_{0-6}$alkyl-$NR^cR^d$,
(8) —$C_{0-6}$alkyl-$C(O)R^e$,
(9) —$C_{0-6}$alkyl-$OC(O)R^e$,
(10) —$C_{0-6}$alkyl-$CO_2R^e$,
(11) —$C_{0-6}$alkyl-CN,
(12) —$C_{0-6}$alkyl-$C(O)NR^cR^d$,
(13) —$C_{0-6}$alkyl-$NR^cC(O)R^e$,
(14) —$C_{0-6}$alkyl-$NR^cC(O)OR^e$,
(15) —$C_{0-6}$alkyl-$NR^cC(O)NR^cR^d$,
(16) —$CF_3$,
(17) —$OCF_3$,
(18) —$OCHF_2$,
(19) —$C_{0-6}$alkyl-aryl,
(20) —$C_{0-6}$alkyl-heteroaryl,
(21) —$C_{0-6}$alkyl-$C_{3-10}$cycloalkyl,
(22) —$C_{0-6}$alkyl-$C_{3-10}$cycloalkenyl, and
(23) —$C_{0-6}$alkyl-$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-}$ ₆alkyl, —S(O)₂—C₁₋₄alkyl, —CN, —OCHF₂, —OCF₃, —CF₃, and —C₀₋₆alkyl-NR$^c$R$^d$;

R$^b$ is independently selected from the group consisting of:
(1) —C$_{1-10}$alkyl,
(2) —C$_{2-10}$alkenyl,
(3) —CF₃,
(4) halogen,
(5) —CN,
(6) —OH,
(7) —OC$_{1-10}$alkyl,
(8) —OC$_{2-10}$alkenyl,
(9) —O(CH₂)$_p$OC$_{1-10}$alkyl,
(10) —O(CH₂)$_p$C$_{3-6}$cycloalkyl,
(11) —O(CH₂)$_p$C$_{3-6}$ cycloalkyl-C$_{1-10}$alkyl,
(12) —O(CH₂)$_p$C$_{2-5}$cycloheteroalkyl,
(13) —O(CH₂)$_p$C$_{2-5}$cycloheteroalkyl-C$_{1-10}$alkyl,
(14) —O-aryl,
(15) —O-heteroaryl,
(16) —O-aryl-C$_{1-10}$alkyl,
(17) —O-heteroaryl-C$_{1-10}$alkyl,
(18) —O(CH₂)$_p$NR$^c$S(O)$_m$R$^e$,
(19) —O(CH₂)$_p$S(O)$_m$R$^e$,
(20) —O(CH₂)$_p$S(O)$_m$NR$^c$R$^d$,
(21) —O(CH₂)$_p$NR$^c$R$^d$,
(22) —C(O)R$^e$,
(23) —OC(O)R$^e$,
(24) —CO₂R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH₂)$_p$O—C$_{3-6}$cycloalkyl,
(30) —O(CH₂)$_p$O—C$_{2-5}$cycloheteroalkyl,
(31) —OCF₃,
(32) —OCHF₂,
(33) —(CH₂)$_p$C$_{3-6}$cycloalkyl,
(34) —(CH₂)$_p$C$_{2-5}$cycloheteroalkyl,
(35) aryl,
(36) heteroaryl,
(37) aryl-C$_{1-10}$alkyl-, and
(38) heteroaryl-C$_{1-10}$alkyl-,
wherein each CH, CH₂, alkyl, alkenyl, cycloalkyl, cycloheteroalkyl, aryl and heteroaryl is unsubstituted or substituted with one to five substituents selected from —C$_{1-6}$alkyl, halogen, —O—C$_{1-6}$alkyl and —CF₃;

R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$cycloheteroalkyl,
(7) C$_{2-5}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^f$,
or R$^c$ and R$^d$ together with the atom(s) to which they are attached form a C$_{2-10}$ cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$;

each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) C$_{3-6}$ cycloalkyl-C$_{1-10}$alkyl-,
(6) —C$_{2-5}$cycloheteroalkyl,
(7) C$_{2-5}$cycloheteroalkyl-C$_{1-10}$alkyl-,
(8) aryl,
(9) aryl-C$_{1-10}$alkyl-,
(10) heteroaryl, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents selected from R$^h$;

each R$^f$ is selected from the group consisting of:
(1) halogen,
(2) —C$_{1-10}$alkyl,
(3) —C$_{0-6}$alkyl —OH,
(4) —O—C$_{1-6}$alkyl,
(5) oxo,
(6) —S(O)$_m$—C$_{1-4}$alkyl,
(7) —CN,
(8) —CF₃,
(9) —OCHF₂, and
(10) —OCF₃,
wherein each alkyl is unsubstituted or substituted with one to three substituents independently selected from: —OH, halogen, C$_{1-6}$alkyl, cyano and S(O)₂C$_{1-6}$alkyl;

each R$^g$ is selected from the group consisting of:
(1) hydrogen,
(2) —C(O)R$^e$, and
(3) —C$_{1-10}$alkyl,
wherein alkyl is unsubstituted or substituted with one to five halogens;

each R$^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF₃,
(8) —OCHF₂, and
(9) —OCF₃,
wherein each alkyl is unsubstituted or substituted with one to three substituents independently selected from: —OH, halogen, C$_{1-6}$alkyl, cyano and —S(O)₂C$_{1-6}$alkyl;

R$^i$ is selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO₂R$^e$,
(11) —CN,
(12) —C(O)NR$^c$R$^d$,
(13) —NR$^c$C(O)R$^e$,
(14) —NR$^c$C(O)OR$^e$,

(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

each R$^j$ is selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

R$^k$ is selected from the group consisting of:
(1) hydrogen,
(2) —C$_{1-6}$ alkyl,
(3) —C$_{1-6}$alkyl-SO$_2$C$_{1-6}$alkyl,
(4) —CF$_3$, and
(5) —CHF$_2$, wherein each alkyl is unsubstituted or substituted with one to three substituents independently selected from: —OH, —OC$_{1-6}$alkyl, halogen, cyano, and —S(O)$_2$C$_{1-6}$alkyl;

each R$^L$ is independently selected from the group consisting of:
(1) —CO$_2$C$_{1-6}$alkyl,
(2) —C$_{1-10}$alkyl,
(3) —C$_{2-10}$ alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl, wherein each alkyl, alkenyl, alkynyl, cycloalkyl, cycloheteroalkyl, aryl and heteroaryl is unsubstituted or substituted with 1-4 substituents selected from C$_{1-6}$alkyl, halogen, and —OC$_{1-6}$alkyl;

each R$^m$ is independently selected from the group consisting of:
(1) —C$_{1-10}$alkyl,
(2) —C$_{2-10}$ alkenyl,
(3) —C$_{3-6}$ cycloalkyl,
(4) C$_{3-6}$ cycloalkyl-C$_{1-10}$alkyl-,
(5) —C$_{2-5}$cycloheteroalkyl,
(6) C$_{2-5}$cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;

each n is independently selected from: 0, 1 or 2;
each m is independently selected from: 0, 1 or 2;
each p is independently selected from: 0, 1, 2, 3, 4, 5 or 6; and
each r is independently selected from: 0, 1, 2 or 3.

2. The compound according to claim 1, wherein R$^1$ and R$^2$ are each independently selected from:
(1) hydrogen, and
(2) —C$_{1-6}$alkyl,
wherein one of R$^1$ and R$^2$ is —C$_{1-6}$alkyl substituted with R$^7$, and wherein alkyl is unsubstituted or substituted with one to three substituents independently selected from R$^L$; or a pharmaceutically acceptable salt thereof.

3. The compound according to claim 1, wherein R$^1$ is —C$_{1-6}$alkyl, wherein alkyl is unsubstituted or substituted with one to three substituents selected from R$^L$, and wherein R$^1$ is substituted with R$^7$; and R$^2$ is hydrogen; or a pharmaceutically acceptable salt thereof.

4. The compound according to claim 1 wherein
R$^3$ is absent or when present R$^3$ is hydrogen;
R$^4$ is hydrogen;
R$^5$ is hydrogen; and
R$^6$ is hydrogen;
or a pharmaceutically acceptable salt thereof.

5. The compound according to claim 1 wherein R$^7$ is —CO$_2$R$^8$; or a pharmaceutically acceptable salt thereof.

6. The compound according to claim 1 wherein R$^8$ is hydrogen; or a pharmaceutically acceptable salt thereof.

7. The compound according to claim 1 of structural formula Ik:

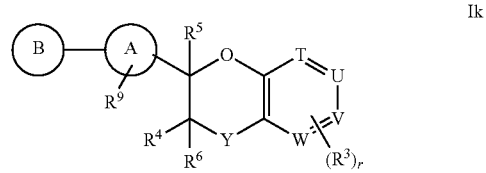

or a pharmaceutically acceptable salt thereof,
wherein
T is CH;
U is CR$^1$;
V is CR$^2$;
W is CH;
Y is —CR$^g$R$^g$;
A is selected from the group consisting of:
(1) aryl, and
(2) heteroaryl,
wherein each aryl and heteroaryl is unsubstituted or substituted with one to five substituents selected from R$^a$;
B is selected from the group consisting of:
(1) aryl, and
(2) heteroaryl,
wherein each aryl and heteroaryl is unsubstituted or substituted with one to five substituents selected from R$^b$;
R$^1$ and R$^2$ are each independently selected from:
(1) hydrogen, and
(2) —C$_{1-6}$alkyl,
wherein one of R$^1$ and R$^2$ is —C$_{1-6}$alkyl substituted with R$^7$, and wherein alkyl is unsubstituted or substituted with one to three substituents independently selected from R$^L$;
R$^3$ is hydrogen;
R$^4$ is hydrogen;
R$^5$ is hydrogen;

$R^6$ is hydrogen;
$R^7$ is —$CO_2R^8$;
$R^8$ is hydrogen;
$R^9$ is selected from the group consisting of:
  (1) —$C_{1-6}$alkyl-$NR^cR^d$, and
  (2) —$C_{1-6}$alkyl-$C_{2-5}$cycloheteroalkyl,
wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;
$R^g$ is hydrogen; and
r is 0.

8. The compound according to claim 1 of structural formula Ik:

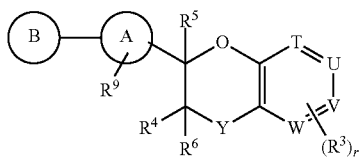

Ik or a pharmaceutically acceptable salt thereof,
wherein
T is CH,
U is $CR^1$,
V is $CR^2$,
W is CH,
Y is —$CR^gR^g$;
A is selected from the group consisting of:
  (1) aryl, and
  (2) heteroaryl,
wherein each aryl and heteroaryl is unsubstituted or substituted with one to five substituents selected from $R^a$;
B is selected from the group consisting of:
  (1) aryl, and
  (2) heteroaryl,
wherein each aryl and heteroaryl is unsubstituted or substituted with one to five substituents selected from $R^b$;
$R^1$ and $R^2$ are each independently selected from:
  (1) hydrogen, and
  (2) —$C_{1-6}$alkyl,
wherein each alkyl is substituted with one to three substituents selected from $R^L$, and wherein one of $R^1$ and $R^2$ is substituted with $R^7$;
$R^3$ is selected from the group consisting of:
  (1) hydrogen, and
  (2) halogen;
$R^4$ is hydrogen;
$R^5$ is hydrogen;
$R^6$ is hydrogen;
$R^7$ is —$CO_2R^8$;
$R^8$ is hydrogen;
$R^9$ is selected from the group consisting of:
  (1) —$C_{1-6}$alkyl-$NR^cR^d$, and
  (2) —$C_{1-6}$alkyl-$C_{2-5}$cycloheteroalkyl,
wherein each alkyl and cycloheteroalkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;

$R^g$ is hydrogen; and
r is 0, 1, 2 or 3.

9. The compound according to claim 1 of structural formula Ik:

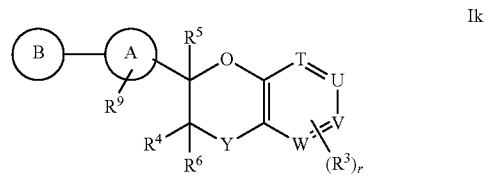

Ik or a pharmaceutically acceptable salt thereof,
wherein
T is CH;
U is $CR^1$;
V is CH;
W is CH;
Y is —$CH_2$;
A is selected from the group consisting of:
  (1) phenyl, and
  (2) pyridine,
wherein each phenyl and pyridine is unsubstituted or substituted with one to five substituents selected from $R^a$;
B is heteroaryl, wherein heteroaryl is unsubstituted or substituted with one to five substituents selected from $R^b$;
$R^1$ is —$C_{1-6}$alkyl, wherein alkyl is substituted with one to three substituents selected from $R^L$, and wherein alkyl is substituted with one substituent selected from $R^7$;
$R^3$ is hydrogen;
$R^4$ is hydrogen;
$R^5$ is hydrogen;
$R^6$ is hydrogen;
$R^7$ is —$CO_2R^8$;
$R^8$ is hydrogen;
$R^9$ is selected from the group consisting of:
  (1) —$CH_2NH(CH(CH_3)_2)$,
  (2) —$CH_2N(CH_2CH_3)_2$,
  (3) —$CH_2N(CH_3)(CH_2CH_3)$,
  (4) —$CH_2N(CH(CH_3)_2)_2$,
  (5) —$CH_2N(CH_2CH_3)(CH(CH_3)_2)$,
  (6) —$CH_2N(CH_3)(C(CH_3)_3)$,
  (7) —$CH_2$-pyrrolidine,
  (8) —$CH_2$-piperidine,
  (9) —$CH_2$-(4-azaspiro[2.5]octane), and
  (10) —$CH_2$-(3-azabicyclo[3.1.0]hexane),
wherein each —$CH_2$, alkyl, and cycloheteroalkyl is unsubstituted or substituted with one to five substituents independently selected from: —$C_{1-6}$alkyl, and —$CH_3$;
r is 0.

10. The compound according to claim 9 selected from:

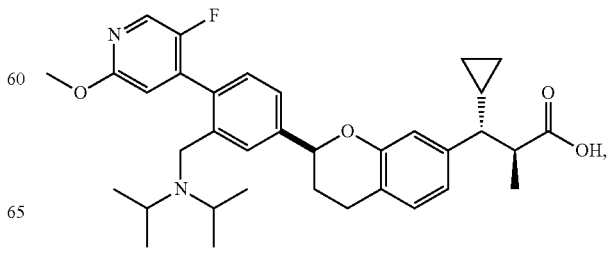

305
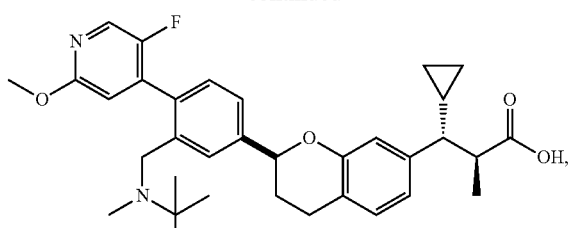
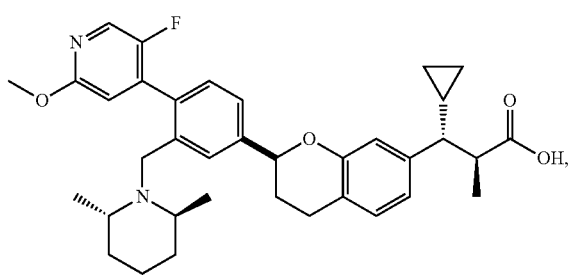
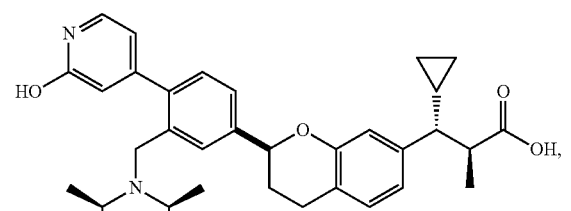
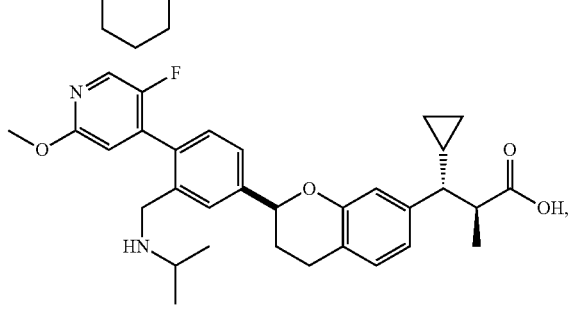
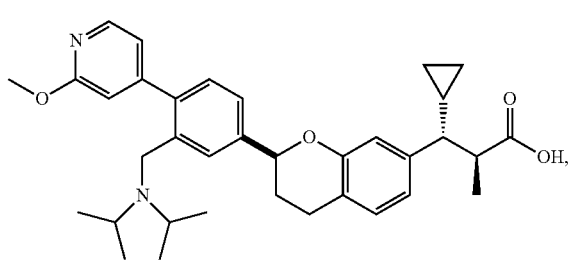
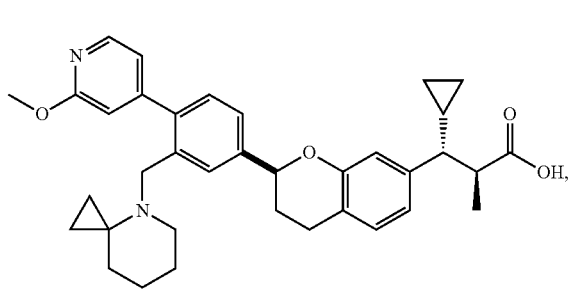
306
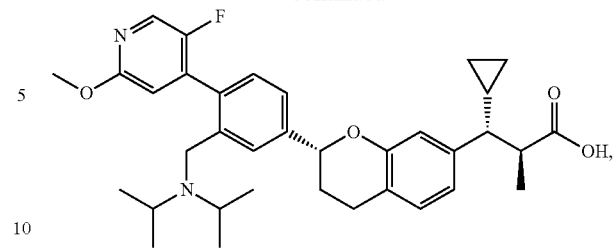
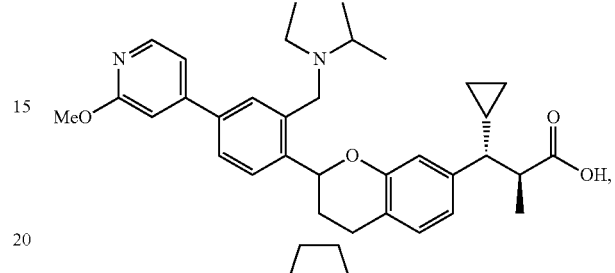
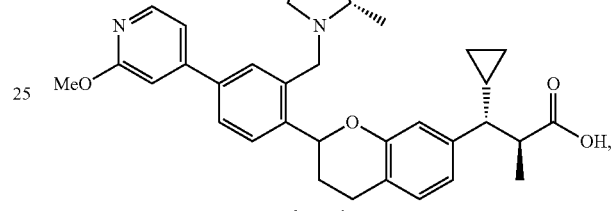
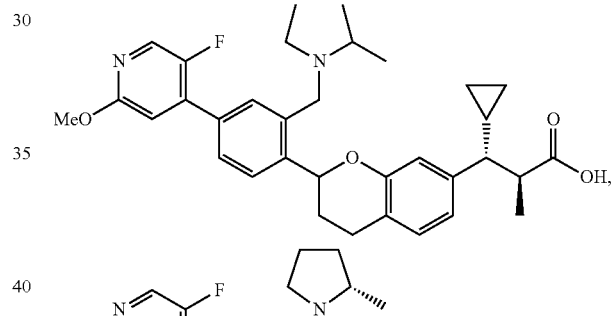
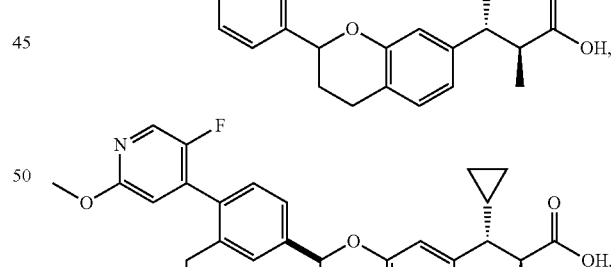
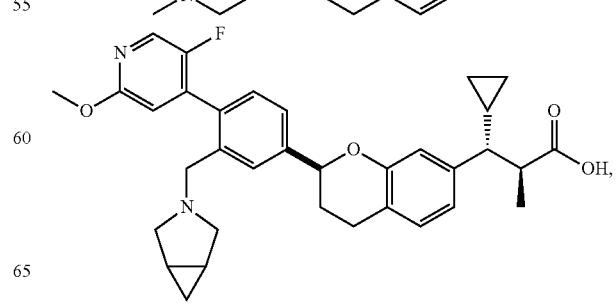

307
-continued
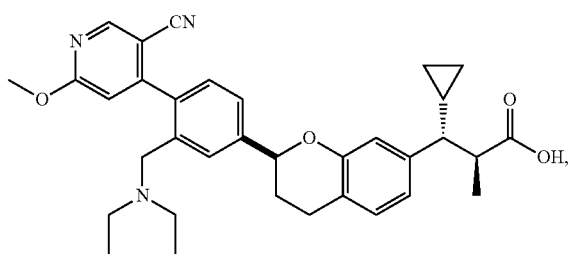
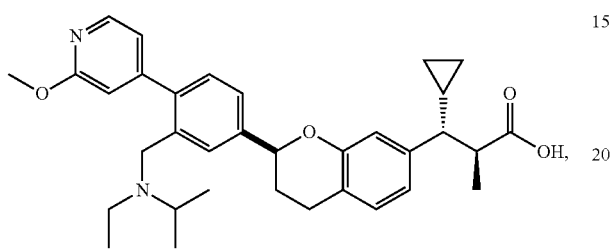
308
-continued
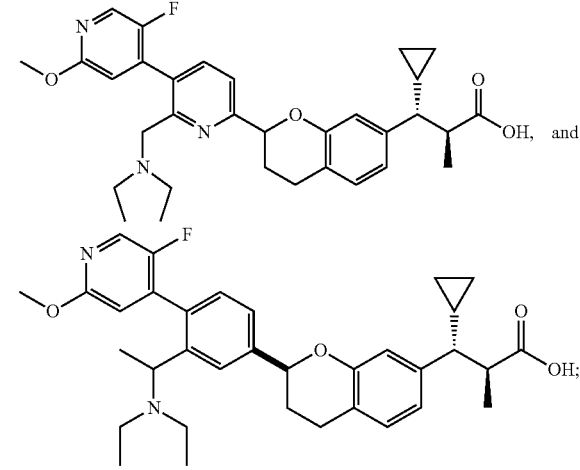
or pharmaceutically acceptable salt thereof.
11. A pharmaceutical composition comprising a compound of claim 1, or a pharmaceutically acceptable salt thereof, and a pharmaceutically acceptable carrier.
* * * * *